United States Patent
Romines, III et al.

(10) Patent No.: US 6,833,456 B2
(45) Date of Patent: Dec. 21, 2004

(54) INDOLYL-UREA DERIVATIVES OF THIENOPYRIDINES USEFUL AS ANTIANGIOGENIC AGENTS, AND METHODS FOR THEIR USE

(75) Inventors: William Henry Romines, III, San Diego, CA (US); Robert Steven Kania, San Diego, CA (US); Jihong Lou, San Diego, CA (US); Stephan Cripps, San Diego, CA (US); Ru Zhou, Carlsbad, CA (US); Mingying He, San Diego, CA (US)

(73) Assignee: Agouron Pharmaceuticals, Inc., San Diego, CA (US)

(*) Notice: Subject to any disclaimer, the term of this patent is extended or adjusted under 35 U.S.C. 154(b) by 0 days.

(21) Appl. No.: 10/371,337

(22) Filed: Feb. 21, 2003

(65) Prior Publication Data

US 2004/0019065 A1 Jan. 29, 2004

Related U.S. Application Data

(60) Provisional application No. 60/360,952, filed on Mar. 1, 2002.

(51) Int. Cl.[7] .................. C07D 495/04; C07D 521/00; A61K 31/4365
(52) U.S. Cl. ...................... 546/114; 514/301
(58) Field of Search .......................... 546/114; 514/301

(56) References Cited

U.S. PATENT DOCUMENTS

| | | | |
|---|---|---|---|
| 5,792,783 A | 8/1998 | Tang et al. | 514/397 |
| 5,834,504 A | 11/1998 | Tang et al. | 514/418 |
| 5,861,510 A | 1/1999 | Piscopio et al. | 544/131 |
| 5,883,113 A | 3/1999 | Tang et al. | 514/418 |
| 5,886,020 A | 3/1999 | Tang et al. | 514/418 |
| 6,071,935 A | 6/2000 | Lyssikatos | 514/333 |

FOREIGN PATENT DOCUMENTS

| | | |
|---|---|---|
| WO | 90/05719 | 5/1990 |
| WO | 95/21613 | 8/1995 |
| WO | 95/23141 | 8/1995 |
| WO | 96/27583 | 9/1996 |
| WO | 96/30347 | 10/1996 |
| WO | 96/33172 | 10/1996 |
| WO | 96/40142 | 12/1996 |
| WO | 97/13771 | 4/1997 |
| WO | 97/22596 | 6/1997 |
| WO | 97/32856 | 9/1997 |
| WO | 97/49688 | 12/1997 |
| WO | 98/02437 | 1/1998 |
| WO | 98/02438 | 1/1998 |
| WO | 98/03516 | 1/1998 |
| WO | 98/07697 | 2/1998 |
| WO | 98/23613 | 6/1998 |
| WO | 98/30566 | 7/1998 |
| WO | 98/33768 | 8/1998 |
| WO | 98/34915 | 8/1998 |
| WO | 98/34918 | 8/1998 |
| WO | 98/54093 | 12/1998 |
| WO | 99/10349 | 3/1999 |
| WO | 99/16755 | 4/1999 |
| WO | 99/52889 | 10/1999 |
| WO | 99/52910 | 10/1999 |
| WO | 99/61422 | 12/1999 |
| WO | 00/38665 | 7/2000 |
| WO | WO 01/94353 | 12/2001 |
| WO | WO 03/000194 | 1/2003 |

*Primary Examiner*—Rita Desai
(74) *Attorney, Agent, or Firm*—Reena R. Desai; Bryan C. Zielinski; Peter Richardson

(57) ABSTRACT

The invention relates to compounds represented by the formula I

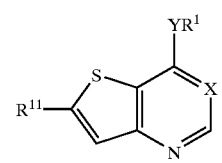

and to prodrugs thereof, pharmaceutically acceptable salts or solvates of said compounds or said prodrugs, wherein X, $R^1$ and $R^{11}$ are as defined herein. The invention also relates to pharmaceutical compositions containing the compounds of formula I and to methods of treating hyperproliferative disorders in a mammal by administering the compounds of formula I.

8 Claims, No Drawings

INDOLYL-UREA DERIVATIVES OF THIENOPYRIDINES USEFUL AS ANTIANGIOGENIC AGENTS, AND METHODS FOR THEIR USE

This application claims priority benefits under 35 U.S.C. § 119(e) of a U.S. Provisional Application No. 60/360,952, filed 1 Mar. 2002, in its entirety for all purposes.

FIELD OF THE INVENTION

This invention relates to novel thienopyridine and thienopyridine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

BACKGROUND OF THE INVENTION

Compounds that are useful in the treatment of hyperproliferative diseases are also disclosed in the following patents and applications: PCT international patent application publication number WO 00/38665 (published Jul. 6, 2001), PCT international patent application publication number WO 97/49688 (published Dec. 31, 1997), PCT international patent application publication number WO 98/23613 (published Jun. 4, 1998), U.S. patent application Ser. No. 60/299,879 (filed Jun. 21, 2001), U.S. patent application Ser. No. 09/502,129 (filed Feb. 10, 2000), U.S. patent application No. 60/209,686 (filed Jun. 6, 2000), U.S. patent application No. 60/214,373 (filed Jun. 28, 2000), U.S. patent application Ser. No. 08/953,078 (filed Oct. 17, 1997), U.S. Pat. No. 6,071,935 issued Jun. 6, 2000, PCT international patent application publication number WO 96/30347 (published Oct. 3, 1996), PCT international patent application publication number WO 96/40142 (published Dec. 19, 1996), PCT international patent application publication number WO 97/13771 (published Apr. 17, 1997), and PCT international patent application publication number WO 95/23141 (published Aug. 31, 1995). The foregoing patent and applications are incorporated herein by reference in their entirety.

It is known that a cell may become cancerous by virtue of the transformation of a portion of its DNA into an oncogene (i.e., a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype.

Receptor tyrosine kinases are large enzymes that span the cell membrane and possess an extracellular binding domain for growth factors such as epidermal growth factor, a transmembrane domain, and an intracellular portion that functions as a kinase to phosphorylate a specific tyrosine residue in proteins and hence to influence cell proliferation. The foregoing tyrosine kinases may be classified as growth factor receptor (e.g. EGFR, PDGFR, FGFR and erbB2) or non-receptor (e.g. c-src and bcr-abl) kinases. It is known that such kinases are often aberrantly expressed in common human cancers such as breast cancer, gastrointestinal cancer such as colon, rectal or stomach cancer, leukemia, and ovarian, bronchial or pancreatic cancer. Aberrant erbB2 activity has been implicated in breast, ovarian, non-small cell lung, pancreatic, gastric and colon cancers. It has also been shown that epidermal growth factor receptor (EGFR) is mutated or overexpressed in many human cancers such as brain, lung, squamous cell, bladder, gastric, breast, head and neck, oesophageal, gynecological and thyroid cancers. Thus, it is believed that inhibitors of receptor tyrosine kinases, such as the compounds of the present invention, are useful as selective inhibitors of the growth of mammalian cancer cells.

It has also been shown that EGFR inhibitors may be useful in the treatment of pancreatitis and kidney disease (such as proliferative glomerulonephritis and diabetes-induced renal disease), and may reduce successful blastocyte implantation and therefore may be useful as a contraceptive. See PCT international application publication number WO 95/19970 (published Jul. 27, 1995), hereby incorporated by reference in its entirety.

It is known that polypeptide growth factors such as vascular endothelial growth factor (VEGF) having a high affinity to the human kinase insert-domain-containing receptor (KDR) or the murine fetal liver kinase 1 (FLK-1) receptor have been associated with the proliferation of endothelial cells and more particularly vasculogenesis and angiogenesis. See PCT international application publication number WO 95/21613 (published Aug. 17, 1995), hereby incorporated by reference in its entirety. Agents, such as the compounds of the present invention, that are capable of binding to or modulating the KDR/FLK-1 receptor may be used to treat disorders related to vasculogenesis or angiogenesis such as diabetes, diabetic retinopathy, age related macular degeneration, hemangioma, glioma, melanoma, Kaposi's sarcoma and ovarian, breast, lung, pancreatic, prostate, colon and epidermoid cancer.

SUMMARY OF THE INVENTION

A compound represented by the formula I

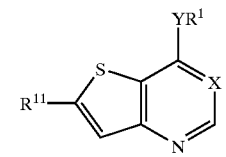

wherein
X is —CH— or —N—;
Y is —NH—, —O—, —S—, or —CH$_2$—;
R$^1$ is H, C$_1$–C$_6$ alkyl, C$_3$–C$_{10}$ cycloalkyl, —C(O)(C$_1$–C$_6$ alkyl), C$_6$–C$_{10}$ aryl or a 5 to 13 membered heterocyclic, wherein said C$_6$–C$_{10}$ aryl and 5 to 13 membered heterocyclic groups are unsubstituted or substituted with 1 to 5 R$^5$ substituents;
each R$^5$ is independently selected from halo, cyano, nitro, trifluoromethoxy, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, C$_1$–C$_6$ alkyl, C$_3$–C$_{10}$ cycloalkyl, C$_1$–C$_6$ alkylamino, —(CH$_2$)$_j$O(CH$_2$)$_q$NR$^6$R$^7$, —(CH$_2$)$_t$O(CH$_2$)$_9$OR$^9$, —(CH$_2$)$_t$OR$^9$, —S(O)$_j$(C$_1$–C$_6$ alkyl), —(CH$_2$)$_t$(C$_6$–C$_{10}$ aryl), —(CH$_2$)$_t$(5 to 10 membered heterocyclic), —C(O)(CH$_2$)$_t$(C$_6$–C$_{10}$ aryl), —(CH$_2$)$_t$O(CH$_2$)$_t$(C$_6$–C$_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O) R$^8$, (CH$_2$)$_j$NR$^7$(CH$_2$)$_q$O(CH$_2$)$_q$OR$^9$, —(CH$_2$)$_j$NR$^7$ (CH$_2$)$_q$S(O)$_j$(C$_1$–C$_6$ alkyl), —(CH$_2$)$_j$NR$^7$(CH$_2$)$_t$R$^6$, —$SO_2(CH_2)_t(C_6$–$C_{10}$ aryl), and —$SO_2(CH_2)_t$(5 to 10 membered heterocyclic), wherein j is an integer from 0 to 2, t is an integer from 0 to 6, q is an integer from 2 to 6, the —$(CH_2)_q$— and —$(CH_2)_t$— moieties of the said $R^5$ groups optionally include a carbon-carbon double or triple bond where t is an integer between 2 and 6, and the alkyl, aryl and heterocyclic moieties of the said $R^5$ groups are unsubstituted or substituted with one or more substituents independently selected from halo, cyano, nitro, trifluoromethyl, azido, —OH, —$C(O)R^8$, —$C(O)OR^8$, —$OC(O)R^8$, —$OC(O)OR^8$, —$NR^6C(O)R^7$, —$C(O)NR^6R^7$, —$(CH_2)_tNR^6R^7$, $C_1$–$C_6$ alkyl, $C_3$–$C_{10}$ cycloalkyl, —$(CH_2)_t(C_6$–$C_{10}$ aryl), —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6;

each $R^6$ and $R^7$ is independently selected from H, OH, $C_1$–$C_6$ alkyl, $C_3$–$C_{10}$ cycloalkyl, —$(CH_2)_t(C_6$–$C_{10}$ aryl), —$(CH_2)_t$(5 to 10 membered heterocyclic), —$(CH_2)_tO(CH_2)_qOR^9$, —$(CH_2)_tCN(CH_2)_tOR^9$, —$(CH_2)_tCN(CH_2)_tR^9$ and —$(CH_2)_tOR^9$, wherein t is an integer from 0 to 6 and q is an integer from 2 to 6, and the alkyl, aryl and heterocyclic moieties of the said $R^6$ and $R^7$ groups are unsubstituted or substituted with one or more substituents independently selected from hydroxy, halo, cyano, nitro, trifluoromethyl, azido, —$C(O)R^8$, —$C(O)OR^8$, —$CO(O)R^8$, —$OC(O)OR^8$, —$NR^9C(O)R^{10}$, —$C(O)NR^9R^{10}$, —$NR^9R^{10}$, $C_1$–$C_6$ alkyl, —$(CH_2)_t(C_6$–$C_{10}$ aryl), —$(CH_2)_t$(5 to 10 membered heterocyclic), —$(CH_2)_tO(CH_2)_qOR^9$, and —$(CH_2)_tOR^9$, wherein t is an integer from 0 to 6 and q is an integer from 2 to 6, where when $R^6$ and $R^7$ are both attached to the same nitrogen, then $R^6$ and $R^7$ are not both bonded to the nitrogen directly through an oxygen;

each $R^8$ is independently selected from H, $C_1$–$C_{10}$ alkyl, $C_3$–$C_{10}$ cycloalkyl, —$(CH_2)_t(C_6$–$C_{10}$ aryl), and —$(CH_2)_t$(5 to 10 membered heterocyclic), wherein t is an integer from 0 to 6;

each $R^9$ and $R^{10}$ is independently selected from H, —$OR^6$, $C_1$–$C_6$ alkyl, and $C_3$–$C_{10}$ cycloalkyl; and, $R^{11}$ is H, $C_1$–$C_6$ alkyl, $C_3$–$C_{10}$ cycloalkyl, —$C(O)NR^{12}R^{13}$, —$C(O)(C_6$–$C_{10}$ aryl), —$(CH_2)_t(C_6$–$C_{10}$ aryl), —$(CH_2)_t$(5 to 10 membered heterocyclic), —$(CH_2)_tNR^{12}R^{13}$, —$SO_2NR^{12}R^{13}$ and —$CO_2R^{12}$, wherein t is an integer from 0 to 6, wherein said $C_1$–$C_6$ alkyl, —$C(O)(C_6$–$C_{10}$ aryl), —$(CH_2)_t(C_6$–$C_{10}$ aryl), and —$(CH_2)_t$(5 to 10 membered heterocyclic) moieties of the said $R^{11}$ groups are unsubstituted or substituted by one or more $R^5$ groups;

each $R^{12}$ and $R^{13}$ is independently selected from H, $C_1$–$C_6$ alkyl, $C_3$–$C_{10}$ cycloalkyl, —$(CH_2)_t(C_3$–$C_{10}$ cycloalkyl), —$(CH_2)_t(C_6$–$C_{10}$ aryl), —$(CH_2)_t$(5 to 10 membered heterocyclic), —$(CH_2)_tO(CH_2)_qOR^9$, and —$(CH_2)_tOR^9$, q is an integer from 2 to 6, and the alkyl, aryl and heterocyclic moieties of the said $R^{12}$ and $R^{13}$ groups are unsubstituted or substituted with one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperazinyl, morpholinyl, thiomorpholinyl, isoquinolinyl, or dihydroisoquinoli-nyl rings are unsubstituted or substituted with one or more $R^5$ substituents, where $R^{12}$ and $R^{13}$ are not both bonded to the nitrogen directly through an oxygen;

or prodrugs thereof, or pharmaceutically acceptable salts or solvates of said compounds and said prodrugs.

In another embodiment of the compound of formula I $R^{11}$ is —$(CH_2)_t$(5 to 10 membered heterocyclic), —$C(O)NR^{12}R^{13}$, —$SO_2NR^{12}R^{13}$ and —$CO_2R^{12}$, wherein t is an integer from 0 to 6, wherein said $R^{11}$ group —$(CH_2)_t$(5 to 10 membered heterocyclic) is unsubstituted or substituted by one or more $R^5$ groups and wherein each $R^{12}$ and $R^{13}$ is independently selected from H, $C_1$–$C_6$ alkyl, $C_3$–$C_{10}$ cycloalkyl, —$(CH_2)_t(C_3$–$C_{10}$ cycloalkyl), —$(CH_2)_t(C_6$–$C_{10}$ aryl), —$(CH_2)_t$(5 to 10 membered heterocyclic), —$(CH_2)_tO(CH_2)_qOR^9$, —$(CH_2)_tOR^9$, q is an integer from 2 to 6, and the alkyl, aryl and heterocyclic moieties of said $R^{12}$ and $R^{13}$ groups are unsubstituted or substituted by one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperazinyl, morpholinyl, thiomorpholinyl, isoquinolinyl, or dihydroisoquinolinyl ring are unsubstituted or substituted by one or more $R^5$ substituents, where said $R^{12}$ and $R^{13}$ are not both bonded to the nitrogen directly through an oxygen.

In another embodiment of the compound of formula I $R^{11}$ is —$(CH_2)_t$(5 to 10 membered heterocyclic), and —$C(O)NR^{12}R^{13}$, wherein t is an integer from 0 to 6, wherein said $R^{11}$ group —$(CH_2)_t$(5 to 10 membered heterocyclic) is unsubstituted or substituted with one or more $R^5$ groups and wherein each $R^{12}$ and $R^{13}$ is independently selected from H, $C_1$–$C_6$ alkyl, $C_3$–$C_{10}$ cycloalkyl, —$(CH_2)_t(C_3$–$C_{10}$ cycloalkyl), —$(CH_2)_t(C_6$–$C_{10}$ aryl), —$(CH_2)_t$(5 to 10 membered heterocyclic), —$(CH_2)_tO(CH_2)_qOR^9$, —$(CH_2)_tOR^9$, q is an integer from 2 to 6, and the alkyl, aryl and heterocyclic moieties of said $R^{12}$ and $R^{13}$ groups are unsubstituted or substituted by one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperazinyl, morpholinyl, thiomorpholinyl, isoquinolinyl, or dihydroisoquinolinyl ring are unsubstituted or substituted with one or more $R^5$ substituents, where $R^{12}$ and $R^{13}$ are not both bonded to the nitrogen directly through an oxygen.

In still another embodiment of the compound of formula I $R^{11}$ is —$C(O)NR^{12}R^{13}$, wherein $R^{12}$ and $R^{13}$ are independently selected from H, $C_1$–$C_6$ alkyl, $C_3$–$C_{10}$ cycloalkyl, —$(CH_2)_t(C_3$–$C_{10}$ cycloalkyl), —$(CH_2)_t(C_6$–$C_{10}$ aryl), —$(CH_2)_t$(5 to 10 membered heterocyclic), —$(CH_2)_tO(CH_2)_qOR^9$, —$(CH_2)_tOR^9$, wherein t is an integer from 0 to 6, q is an integer from 2 to 6, and the alkyl, aryl and heterocyclic moieties of said $R^{12}$ and $R^{13}$ groups are unsubstituted or substituted with one or more substituents independently selected from $R^5$, or $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents, where $R^{12}$ and $R^{13}$ are not both bonded to the nitrogen directly through an oxygen.

In another embodiment of the compound of formula I $R^{11}$ is —C(O)$NR^{12}R^{13}$, wherein $R^{12}$ and $R^{13}$ are taken together with the nitrogen to which they are attached to form a $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring, wherein said $C_5$–$C_9$ azabicyclic, aziridinyl, azetidinyl, pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents.

In still another preferred embodiment of the compound of formula I $R^{11}$ is —C(O)$NR^{12}R^{13}$, wherein $R^{12}$ and $R^{13}$ are taken together with the nitrogen to which they are attached to form a pyrrolidinyl, piperidinyl, piperazinyl, morpholinyl, thiomorpholinyl, isoquinolinyl, or dihydroisoquinolinyl ring, wherein said pyrrolidinyl, piperidinyl, piperazinyl, morpholinyl, thiomorpholinyl, isoquinolinyl, or dihydroisoquinolinyl ring are unsubstituted or substituted with 1 to 5 $R^5$ substituents.

In still another preferred embodiment of the compound of formula I $R^{11}$ is —C(O)$NR^{12}R^{13}$, wherein $R^{12}$ and $R^{13}$ are taken together with the nitrogen to which they are attached to form a pyrrolidinyl, piperidinyl, piperazinyl, morpholinyl, or thiomorpholinyl ring, wherein said pyrrolidinyl, piperidinyl, piperazinyl, morpholinyl, or thiomorpholinyl rings are unsubstituted or substituted with 1 to 5 $R^5$ substituents.

In another preferred embodiment of the compound of formula I $R^{11}$ is —C(O)$NR^{12}R^{13}$, wherein $R^{12}$ and $R^{13}$ are taken together with the nitrogen to which they are attached to form a pyrrolidinyl or piperidinyl ring, wherein said pyrrolidinyl or piperidinyl ring are unsubstituted or substituted with 1 to 5 $R^5$ substituents.

In another preferred embodiment of the compound of formula I $R^{11}$ is —C(O)$NR^{12}R^{13}$, wherein $R^{12}$ and $R^{13}$ are taken together with the nitrogen to which they are attached to form a pyrrolidinyl ring, wherein said pyrrolidinyl is unsubstituted or substituted with 1 to 5 $R^5$ substituents.

In another preferred embodiment of the compound of formula I $R^{11}$ is —C(O)$NR^{12}R^{13}$, wherein $R^{12}$ and $R^{13}$ are taken together with the nitrogen to which they are attached to form a pyrrolidin-1-yl ring, wherein said pyrrolidin-1-yl is unsubstituted or substituted by 1 to 5 $R^5$ substituents.

In another preferred embodiment of the compound of formula I $R^{11}$ is —(CH$_2$)$_t$(5 to 10 membered heterocyclic) group, wherein t is an integer from 0 to 6, said —(CH$_2$)$_t$(5 to 10 membered heterocyclic) group is unsubstituted or substituted by 1 to 5 $R^5$ groups.

In another preferred embodiment of the compound of formula I $R^{11}$ is —(CH$_2$)$_t$(5–8 membered heterocyclic) group, wherein t is an integer from 0 to 6, said —(CH$_2$)$_t$(5–8 membered heterocyclic) group is unsubstituted or substituted by 1 to 5 $R^5$ groups.

In another preferred embodiment of the compound of formula I $R^{11}$ is —(CH$_2$)$_t$(5 or 6 membered heterocyclic) group, wherein t is an integer from 0 to 6, said —(CH$_2$)$_t$(5 or 6 membered heterocyclic) group is unsubstituted or substituted by 1 to 5 $R^5$ groups.

In another preferred embodiment of the compound of formula I $R^{11}$ is —(CH$_2$)$_t$(5 membered heterocyclic) group, wherein t is an integer from 0 to 6, said —(CH$_2$)$_t$(5 membered heterocyclic) group is unsubstituted or substituted by 1 to 5 $R^5$ groups.

In another preferred embodiment the compound of formula I $R^{11}$ is —(CH$_2$)$_t$thiazolyl, wherein t is an integer from 0 to 6, said —(CH$_2$)$_t$thiazolyl is unsubstituted or substituted by 1 to 5 $R^5$ groups.

In another preferred embodiment, the compound of formula I, $R^{11}$ is a thiazolyl, said thiazolyl is unsubstituted or substituted by 1 to 5 $R^5$ groups.

In another preferred embodiment, the compound of formula I, $R^{11}$ is an imidazolyl, said imidazolyl is unsubstituted or substituted by 1 to 5 $R^5$ groups.

Other preferred compounds include those of formula I wherein $R^1$ is phenyl unsubstituted or substituted with 1 to 5 $R^5$ substituents, or $R^1$ is a group of the formula

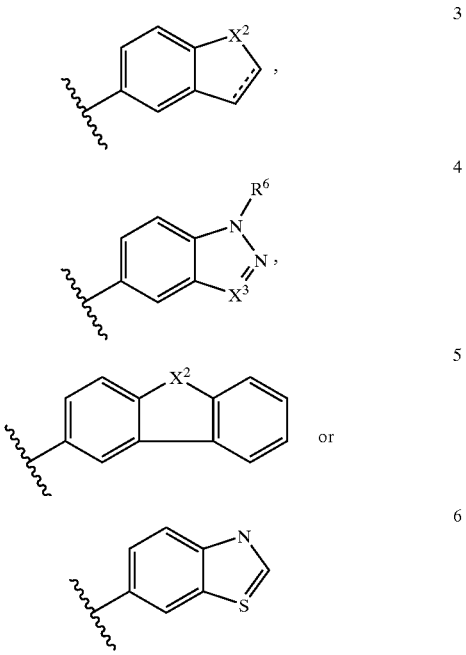

wherein $X^2$ is —S— or —N($R^6$)—, $X^3$ is N or CH, the dashed line in formula 3 represents an optional double bond, and the above $R^1$ groups of formulas 3 and 5 are unsubstituted or substituted with 1 to 5 $R^5$ substituents and the $R^1$ groups of formulas 4 and 6 are unsubstituted or substituted with 1 to 3 $R^5$ substituents. Specifically preferred compounds include those wherein $R^1$ is a group of formula 3 above wherein said group is unsubstituted or substituted by 1 to 5 $R^5$ substituents.

The present invention also relates to intermediate compounds of the formula II

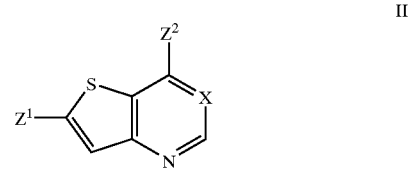

and to pharmaceutically acceptable salts thereof, wherein:

$Z^1$ is halo, —CO$_2$H, —CONH$_2$, —CSNH$_2$ and $Z^2$ is —O$R^1$; or $Z^1$ is $R^{11}$ and $Z^2$ is halo; or $Z^1$ and $Z^2$ are each independently halo; X is N or CH; and wherein $R^1$ and $R^{11}$ are as defined for said compounds of formula I. The above intermediates of formula III may be used to prepare the above compounds of formula I.

A compound represented by the formula III

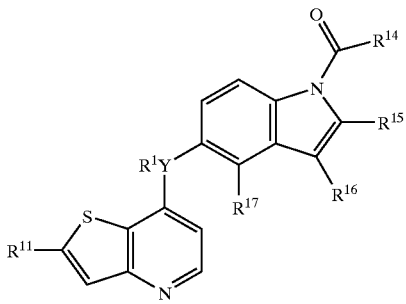

wherein:

Y is —NH—, —O—, —S—, —CH$_2$—;

R$^{14}$ is C$_1$–C$_6$ alkyl, C$_1$–C$_6$ alkylamino, C$_3$–C$_{10}$ cycloalkylamino, or methylureido;

R$^{15}$, R$^{16}$ and R$^{17}$ are independently H, halo, or C$_1$–C$_6$ alkyl group; and R$^{11}$ is a heteroaryl group unsubstituted or substituted by one or more halo, cyano, nitro, trifluoromethoxy, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, C$_1$–C$_6$ alkyl, C$_3$–C$_{10}$ cycloalkyl, —(CH$_2$)$_j$O(CH$_2$)$_q$NR$^6$R$^7$, —(CH$_2$)$_t$O(CH$_2$)$_q$OR$^9$, —(CH$_2$)$_t$OR$^9$, —S(O)$_j$(C$_1$–C$_6$ alkyl), —(CH$_2$)$_t$(C$_6$–C$_{10}$ aryl), —(CH$_2$)$_t$(5 to 10 membered heterocyclic), —C(O)(CH$_2$)$_t$(C$_6$–C$_{10}$ aryl), —(CH$_2$)$_t$O(CH$_2$)$_t$(C$_6$–C$_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, (CH$_2$)$_j$NR$^7$(CH$_2$)$_t$O(CH$_2$)$_q$OR$^9$, —(CH$_2$)$_j$NR$^7$(CH$_2$)$_q$S(O)$_j$(C$_1$–C$_6$ alkyl), —(CH$_2$)$_j$NR$^7$—(CH$_2$)$_t$R$^6$, —SO$_2$(CH$_2$)$_t$(C$_6$–C$_{10}$ aryl), and —SO$_2$(CH$_2$)$_t$(5 to 10 membered heterocyclic), wherein j is an integer from 0 to 2, t is an integer from 0 to 6, q is an integer from 2 to 6, the —(CH$_2$)$_q$— and —(CH$_2$)$_t$— moieties of the said R$^5$ groups optionally include a carbon-carbon double or triple bond where t is an integer between 2 and 6, and the alkyl, aryl and heterocyclic moieties of the said R$^5$ groups are unsubstituted or substituted with one or more substituents independently selected from halo, cyano, nitro, trifluoromethyl, azido, —OH, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2$)$_t$NR$^6$R$^7$, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6;

R$^6$ and R$^7$ is independently selected from H, OH, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, and the alkyl, aryl and heterocyclic moieties of the said R$^6$ and R$^7$ groups are unsubstituted or substituted with one or more substituents independently selected from hydroxy, halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, where when R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, C$_3$–C$_{10}$ cycloalkyl, —(CH$_2$)$_t$(C$_6$–C$_{10}$ aryl), and —(CH$_2$)$_t$(5 to 10 membered heterocyclic), wherein t is an integer from 0 to 6;

each R$^9$ and R$_{10}$ is independently selected from H, C$_1$–C$_6$ alkyl, and C$_3$–C$_{10}$ cycloalkyl; or prodrugs thereof, pharmaceutically acceptable salts or solvates of said compounds and said prodrugs.

Specific embodiments of the present invention include the following compounds:

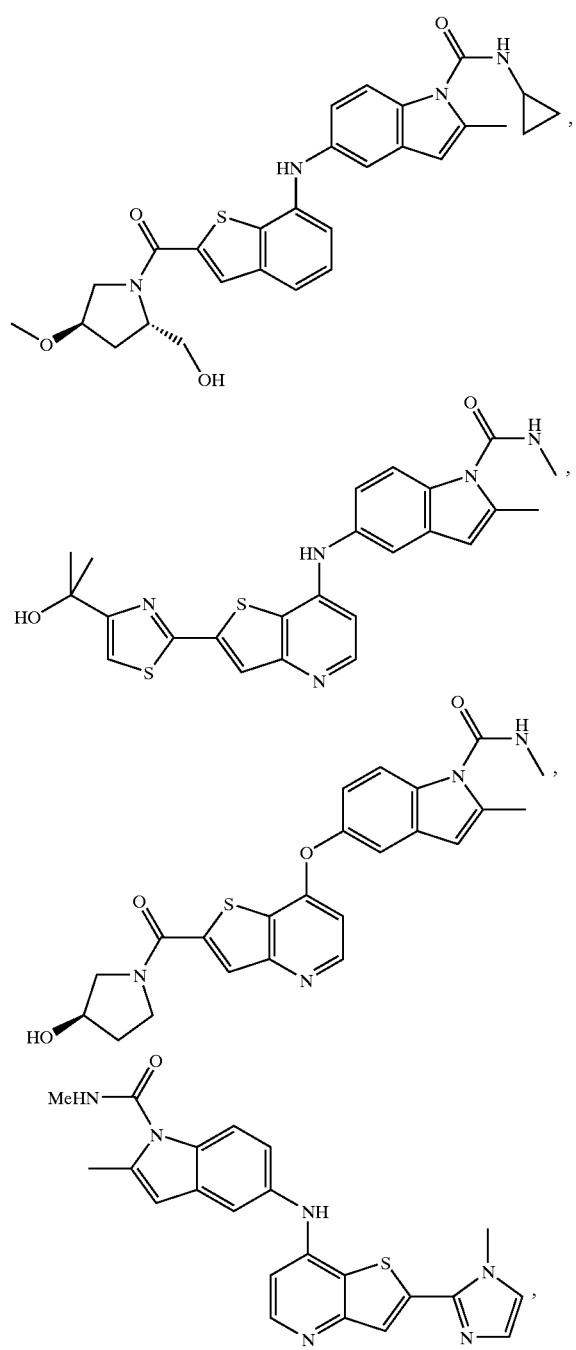

-continued

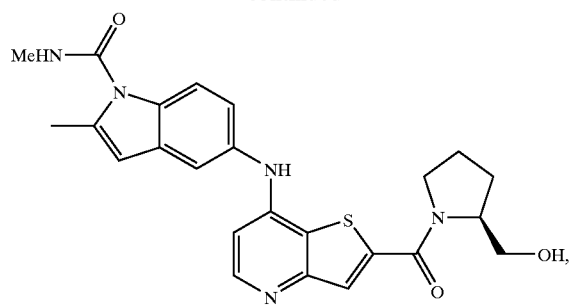

-continued

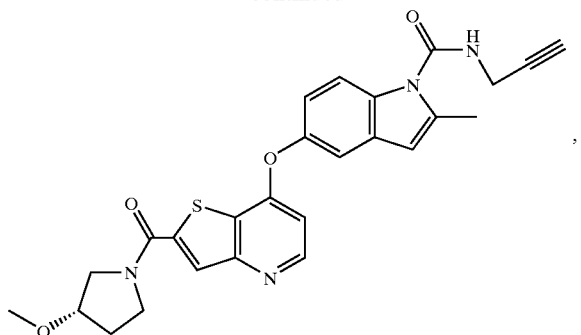

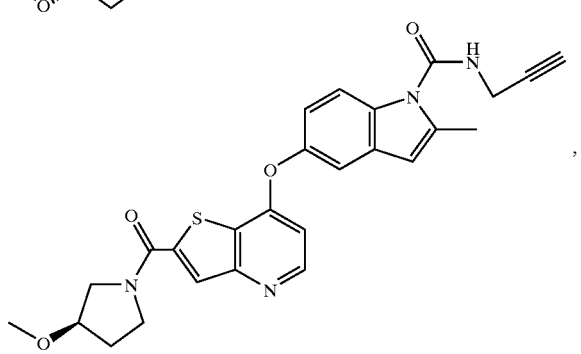

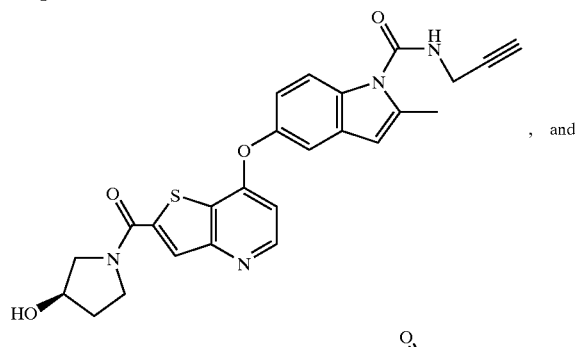

, and

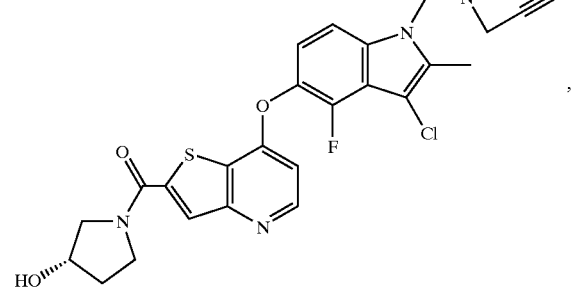

or prodrugs thereof, pharmaceutically acceptable salts or solvates of said compounds and said prodrugs.

This invention also relates to pharmaceutical compositions containing and methods for treating abnormal cell growth through administering prodrugs of compounds of the formula I. Compounds of formula I having free amino, amido, hydroxy or carboxylic groups can be converted into prodrugs.

The invention also relates to a pharmaceutical composition for the treatment of a hyperproliferative disorder in a mammal which comprises a therapeutically effective amount of a compound of formula I, or prodrugs thereof, pharmaceutically acceptable salts or solvates of said compounds and said prodrugs, and a pharmaceutically acceptable carrier. In one embodiment, said pharmaceutical composition is for the treatment of cancer such as brain, lung, ophthalmic, squamous cell, bladder, gastric, pancreatic, breast, head, neck, renal, kidney, ovarian, prostate, colorectal, oesophageal, gynecological or thyroid cancer. In another embodiment, said pharmaceutical composition is for the treatment of a non-cancerous hyperproliferative disorder such as benign hyperplasia of the skin (e.g., psoriasis) or prostate (e.g., benign prostatic hypertropy (BPH)).

The invention also relates to a pharmaceutical composition for the treatment of pancreatitis or kidney disease (including proliferative glomerulonephritis and diabetes-induced renal disease) in a mammal which comprises a therapeutically effective amount of a compound of formula I, or prodrugs thereof, pharmaceutically acceptable salts or solvates of said compounds and said prodrugs, and a pharmaceutically acceptable carrier.

The invention also relates to a pharmaceutical composition for the prevention of blastocyte implantation in a mammal which comprises a therapeutically effective amount of a compound of formula I, or prodrugs thereof, pharmaceutically acceptable salts or solvates of said compounds and said prodrugs, and a pharmaceutically acceptable carrier.

The invention also relates to a pharmaceutical composition for treating a disease related to vasculogenesis or angiogenesis in a mammal which comprises a therapeutically effective amount of a compound of formula I, or prodrugs thereof, pharmaceutically acceptable salts or solvates of said compounds and said prodrugs, and a pharmaceutically acceptable carrier. In one embodiment, said pharmaceutical composition is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also relates to a method of treating a hyperproliferative disorder in a mammal which comprises administering to said mammal a therapeutically effective amount of the compound of formula I, or prodrugs thereof, pharmaceutically acceptable salts or solvates of said compounds and said prodrugs. In one embodiment, said method relates to the treatment of cancer such as brain, ophthalmic, squamous cell, bladder, gastric, pancreatic, breast, head, neck, oesophageal, prostate, colorectal, lung, renal, kidney, ovarian, gynecological or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula I, or prodrugs thereof, pharmaceutically acceptable salts or solvates of said compounds and said prodrugs, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula I, or prodrugs thereof, pharmaceutically acceptable salts or solvates of said compounds and said prodrugs.

The invention also relates to a method of preventing blastocyte implantation in a mammal which comprises administering to said mammal a therapeutically effective amount of a compound of formula I, or prodrugs thereof, pharmaceutically acceptable salts or solvates of said compounds and said prodrugs.

The invention also relates to a method of treating diseases related to vasculogenesis or angiogenesis in a mammal which comprises administering to said mammal an effective amount of a compound of formula I, or prodrugs thereof, pharmaceutically acceptable salts or solvates of said compounds and said prodrugs. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with the compounds of formula I, and prodrugs thereof, pharmaceutically acceptable salts or solvates of said compounds and said prodrugs, according to the methods of this invention include, for example, patients that have been diagnosed as having psoriasis, BPH, lung cancer, eye cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphona, spinal axis tumors, brain stem gliomas or pituitary adenomas).

This invention also relates to a pharmaceutical composition for inhibiting abnormal cell growth in a mammal, including a human, comprising an amount of a compound of the formula I as defined above, or prodrug thereof, pharmaceutically acceptable salt or solvate of said compound and said prodrug, that is effective in inhibiting farnesyl protein transferase, and a pharmaceutically acceptable carrier.

This invention also relates to a pharmaceutical composition for inhibiting abnormal cell growth in a mammal which comprises an amount of a compound of formula I, or prodrug thereof, pharmaceutically acceptable salt or solvate of said compound and said prodrug, in combination with an amount of a chemotherapeutic, wherein the amounts of the compound, salt, solvate, or prodrug, and of the chemotherapeutic are together effective in inhibiting abnormal cell growth. Many chemotherapeutics are presently known in the art. In one embodiment, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, antihormones, e.g. anti-androgens.

This invention further relates to a method for inhibiting abnormal cell growth in a mammal which method comprises administering to the mammal an amount of a compound of formula I, or prodrug thereof, pharmaceutically acceptable salt or solvate of said compound and said prodrug, in combination with radiation therapy, wherein the amount of the compound, salt, solvate or prodrug is in combination with the radiation therapy effective in inhibiting abnormal cell growth in the mammal. Techniques for administering radiation therapy are known in the art, and these techniques can be used in the combination therapy described herein. The administration of the compound of the invention in this combination therapy can be determined as described herein.

It is believed that the compounds of formula I can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of formula I or prodrug thereof, pharmaceutically acceptable salt or solvate of said compound and said prodrug, which amount is effective in sensitizing abnormal cells to treatment with radiation. The amount of the compound, salt, solvate or prodrug in this method can be determined according to the means for ascertaining effective amounts of such compounds described herein.

This invention also relates to a method of and to a pharmaceutical composition for inhibiting abnormal cell growth in a mammal which comprises an amount of a compound of formula I, or prodrug thereof, pharmaceutically acceptable salt or solvate of said compound and said prodrug, or an isotopically-labelled derivative thereof, and an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX-II (cyclooxygenase II) inhibitors, can be used in conjunction with a compound of formula 1 and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Some specific examples of MMP inhibitors useful in the present invention are Prinomastat, RO 32-3555, RS 13-0830, and the compounds recited in the following list: 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxyamide; 3-endo-3-[4-(4-fluoro-phenoxy)-benzenesulfonylamino]-8-oxa-bicyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

A compound of formula I, can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc. of South San Francisco, Calif., USA).

EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein. EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.). These and other EGFR-inhibiting agents can be used in the present invention.

VEGF inhibitors, for example SU-5416 and SU-6668 (Sugen Inc. of South San Francisco, Calif., USA), can also be combined with the compound of the present invention. VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with the compound of the invention, for example those indicated in WO 98/02434 (published Jan. 22, 1998), WO 99/35146 (published Jul. 15, 1999), WO 99/35132 (published Jul. 15, 1999), WO 98/02437 (published Jan. 22,1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with the compounds of the present invention.

The compounds of the invention can also be used with other agents useful in treating abnormal cell growth or cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, and the like. Specific CTLA4 antibodies that can be used in the present invention include those described in U.S. Provisional Application 60/113,647 (filed Dec. 23, 1998) which is incorporated by reference in its entirety, however other CTLA4 antibodies can be used in the present invention.

The subject invention also includes isotopically-labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labelled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I, II, or III of this invention and prodrugs thereof can generally be prepared by carrying out the procedures disclosed in the Schemes and/or in the Examples below, by substituting a readily available isotopically labelled reagent for a non-isotopically labelled reagent.

The compounds of formula I and their pharmaceutically acceptable salts and solvates can each independently also furthermore be used in a palliative neo-adjuvant/adjuvant therapy in alleviating the symptoms associated with the diseases recited herein as well as the symptoms associated with abnormal cell growth. Such therapy can be a monotherapy or can be in a combination with chemotherapy and/or immunotherapy.

The terms "comprising" and "including" are used herein in their open, non-limiting sense.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

The term "halo", as used herein, unless otherwise indicated, means fluoro, chloro, bromo or iodo. Preferred halo groups are fluoro, chloro and bromo.

The term "alkyl", as used herein, unless otherwise indicated, means saturated monovalent hydrocarbon radicals having straight, cyclic or branched moieties. Said "alkyl"

group may include an optional carbon-carbon double or triple bond where said alkyl group comprises at least two carbon atoms. It is understood that for cyclic moieties at least three carbon atoms are required in said alkyl group.

The term "alkoxy", as used herein, unless otherwise indicated, means O-alkyl groups wherein "alkyl" is as defined above.

The term "heteroalkyl" as used herein refers to straight- and branched-chain alkyl groups having from one to twelve atoms containing one or more heteroatoms selected from S, O, and N.

The term "alkenyl" refers to straight- and branched-chain alkenyl groups having from two to twelve carbon atoms. Illustrative alkenyl groups include prop-2-enyl, but-2-enyl, but-3-enyl, 2-methylprop-2-enyl, hex-2-enyl, and the like.

The term "alkynyl" refers to straight- and branched-chain alkynyl groups having from two to twelve carbon atoms. Illustrative alkynyl groups include prop-2-ynyl, but-2-ynyl, but-3-ynyl, 2-methylbut-2-ynyl, hex-2-ynyl, and the like.

The term "cycloalkyl" refers to a monocyclic or polycyclic radical which may be saturated or unsaturated and contains carbocycles having from three to twelve carbon atoms, including bicyclic and tricyclic cycloalkyl structures.

A "heterocycloalkyl" group refers to a monocyclic or polycyclic radical which may be saturated or unsaturated and contains from three to twelve ring atoms, selected from carbon and heteroatoms, preferably 4 or 5 ring carbon atoms, and at least one heteroatom selected from nitrogen, oxygen and sulfur.

The term "aryl", as used herein, unless otherwise indicated, means an organic radical derived from an aromatic hydrocarbon by removal of one hydrogen, such as phenyl or naphthyl.

The terms "5 membered heterocyclic", "5 or 6 membered heterocyclic", "5 to 8 membered heterocyclic", "5 to 10 membered heterocyclic" or "5 to 13 membered heterocyclic", as used herein, unless otherwise indicated, includes aromatic and non-aromatic heterocyclic groups containing one to four heteroatoms each selected from O, S and N, wherein each heterocyclic group has from 5, 6, 5 to 8, 5 to 10 or 5 to 13 atoms in its ring system. The heterocyclic groups include benzo-fused ring systems and ring systems substituted with one or two oxo (═O) moieties such as pyrrolidin-2-one. An example of a 5 membered heterocyclic group is thiazolyl, an example of a 10 membered heterocyclic group is quinolinyl, and an example of a 13 membered heterocyclic group is a carbazole group. Examples of non-aromatic heterocyclic groups are pyrrolidinyl, piperidino, morpholino, thiomorpholino and piperazinyl. Examples of aromatic heterocyclic groups are pyridinyl, imidazolyl, pyrimidinyl, pyrazoyl, triazolyl, pyrazinyl, tetrazolyl, furyl, thienyl, isoxazolyl and thiazolyl. Heterocyclic groups having a fused benzene ring include benzimidazolyl, benzofuranyl, and benzo[1,3]dioxolyl. The term "alcohol" refers to the radical —R—OH where R is alkyl, alkenyl, alkynyl, Ar, heteroaryl, heterocycloalkyl, or cycloalkyl as defined above. Examples of alcohols include methanol, ethanol, propanol, phenol and the like.

The term "acyl" represents —C(O)R, —C(O)OR, —OC(O)R or —OC(O)OR where R is alkyl, alkenyl, alkynyl, Ar, heteroaryl, heterocycloalkyl, or cycloalkyl as defined as above.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl as defined above.

The term "alcohol" refers to the radical —R—OH where R is alkyl, alkenyl, alkynyl, Ar, heteroaryl, heterocycloalkyl, or cycloalkyl as defined above. Examples of alcohols include methanol, ethanol, propanol, phenol and the like.

The term "acyl" represents —C(O)R, —C(O)OR, —OC(O)R or —OC(O)OR where R is alkyl, alkenyl, alkynyl, Ar, heteroaryl, heterocycloalkyl, or cycloalkyl as defined as above.

The term "amide" refers to the radical —C(O)N(R')(R") where R' and R" are each independently selected from hydrogen, alkyl, alkenyl, alkynyl, —OH, alkoxy, cycloalkyl, heterocycloalkyl, heteroaryl, aryl as defined above; or R' and R" cyclize together with the nitrogen to form a heterocycloalkyl or heteroaryl as defined above.

The term "substituted" as used herein means that the group in question, e.g., alkyl group, etc., may bear one or more substituents.

The alkyl, cycloalkyl, aryl, heterocyclyl groups and the substituents containing these groups, as defined hereinabove, may be optionally substituted by at least one other substituent. The term "optionally substituted" is intended to expressly indicate that the specified group is unsubstituted or substituted by one or more substituents from the list above. Various groups may be unsubstituted or substituted (i.e., they are optionally substituted) as indicated.

If the substituents themselves are not compatible with the synthetic methods of this invention, the substituent may be protected with a suitable protecting group that is stable to the reaction conditions used in these methods. The protecting group may be removed at a suitable point in the reaction sequence of the method to provide a desired intermediate or target compound. Suitable protecting groups and the methods for protecting and de-protecting different substituents using such suitable protecting groups are well known to those skilled in the art; examples of which may be found in T. Greene and P. Wuts, Protecting Groups in Chemical Synthesis (3rd ed.), John Wiley & Sons, NY (1999), which is incorporated herein by reference in its entirety. In some instances, a substituent may be specifically selected to be reactive under the reaction conditions used in the methods of this invention. Under these circumstances, the reaction conditions convert the selected substituent into another substituent that is either useful in an intermediate compound in the methods of this invention or is a desired substituent in a target compound.

The compounds of the present invention may have asymmetric carbon atoms. Such diasteromeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomric mixture by reaction with an appropriate optically active compound (e.g., alcohol), separating the diastereomers and converting (e.g., hydrolyzing) the individual diastereomers to the corresponding pure enantiomers. All such isomers, including diastereomer mixtures and pure enantiomers are considered as part of the invention.

The compounds of present invention may in certain instances exist as tautomers. This invention relates to the use of all such tautomers and mixtures thereof.

The term "prodrug", as used herein, unless otherwise indicated, means compounds that are drug precursors, which following administration, release the drug in vivo via some chemical or physiological process (e.g., a prodrug on being brought to the physiological pH is converted to the desired drug form).

Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

It will be appreciated that any solvate (e.g. hydrate) form of compounds of formula I and prodrugs thereof can be used for the purpose of the present invention.

"A pharmaceutically acceptable salt" is intended to mean a salt that retains the biological effectiveness of the free acids and bases of the specified compound and that is not biologically or otherwise undesirable. A compound of the invention may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of the compounds of the present invention with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methanesulfonates, propanesulfonates, naphthalene-1-sulfonates, naphthalene-2-sulfonates, and mandelates.

If the inventive compound is a base, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, phosphoric acid and the like, or with an organic acid, such as acetic acid, phenylacetic acid, propionic acid, stearic acid, lactic acid, ascorbic acid, maleic acid, hydroxymaleic acid, isethionic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid, 2-acetoxybenzoic acid or cinnamic acid, a sulfonic acid, such as p-toluenesulfonic acid, methanesulfonic acid or ethanesulfonic acid, or the like.

If the inventive compound is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine and piperazine, and inorganic salts derived from sodium, calcium, potassium, magnesium, manganese, iron, copper, zinc, aluminum and lithium.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of protein kinases. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of one or more kinases, for example protein kinases such as tyrosine kinases, and includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

Agents that potently regulate, modulate, or inhibit cell proliferation are preferred. For certain mechanisms, inhibition of the protein kinase activity associated with CDK complexes, among others, and those which inhibit angiogenesis and/or inflammation are preferred. The present invention is further directed to methods of modulating or inhibiting protein kinase activity, for example in mammalian tissue, by administering an inventive agent. The activity of agents as anti-proliferatives is easily measured by known methods, for example by using whole cell cultures in an MTT assay. The activity of the inventive agents as modulators of protein kinase activity, such as the activity of kinases, may be measured by any of the methods available to those skilled in the art, including in vivo and/or in vitro assays. Examples of suitable assays for activity measurements include those described in International Publication No. WO 99/21845; Parast et al., *Biochemistry*, 37, 16788–16801 (1998); Connell-Crowley and Harpes, *Cell Cycle: Materials and Methods*, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I or Formula II and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methylmethacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary, but generally will be from about 25 mg to about 1 g. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid, such as 0.3M solution of succinic acid or citric acid. If a soluble salt form is not available, the agent may be dissolved in a suitable cosolvent or combinations of cosolvents. Examples of suitable cosolvents include, but are not limited to, alcohol, propylene glycol, polyethylene glycol 300, polysorbate 80, glycerin and the like in concentrations ranging from 0–60% of the total volume. In an exemplary embodiment, a compound of Formula I is dissolved in DMSO and diluted with water. The composition may also be in the form of a solution of a salt form of the active ingredient in an appropriate aqueous vehicle such as water or isotonic saline or dextrose solution.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage-determination tests in view of the experimental data for an agent. For oral administration, an exemplary daily dose generally employed is from about 0.001 to about 1000 mg/kg of body weight, with courses of treatment repeated at appropriate intervals. Administration of prodrugs is typically dosed at weight levels that are chemically equivalent to the weight levels of the fully active form.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations that can be used pharmaceutically.

Proper formulation is dependent upon the route of administration chosen. For injection, the agents of the invention may be formulated into aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores. Suitable excipients include: fillers such as sugars, including lactose, sucrose, mannitol, or sorbitol; and cellulose preparations, for example, maize starch, wheat starch, rice starch, potato starch, gelatin, gum, methyl cellulose, hydroxypropylmethyl-cellulose, sodium carboxymethylcellulose, or polyvinylpyrrolidone (PVP). If desired, disintegrating agents may be added, such as crosslinked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinyl pyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of agents.

Pharmaceutical preparations that can be used orally include push-fit capsules made of gelatin, as well as soft, sealed capsules made of gelatin and a plasticizer, such as glycerol or sorbitol. The push-fit capsules can contain the agents in admixture with fillers such as lactose, binders such as starches, and/or lubricants such as talc or magnesium stearate, and, optionally, stabilizers. In soft capsules, the agents may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions take the form of tablets or lozenges formulated in conventional manners.

For administration intranasally or by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator and the like may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the agents in water-soluble form. Additionally, suspensions of the agents may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

For administration to the eye, the agent is delivered in a pharmaceutically acceptable ophthalmic vehicle such that the compound is maintained in contact with the ocular surface for a sufficient time period to allow the compound to penetrate the corneal and internal regions of the eye, for example, the anterior chamber, posterior chamber, vitreous body, aqueous humor, vitreous humor, cornea, iris/ciliary, lens, choroid/retina and sciera. The pharmaceutically acceptable ophthalmic vehicle may be an ointment, vegetable oil, or an encapsulating material. A compound of the invention may also be injected directly into the vitreous and aqueous humor.

Alternatively, the agents may be in powder form for constitution with a suitable vehicle, e.g., sterile pyrogen-free water, before use. The compounds may also be formulated in rectal compositions such as suppositories or retention enemas, e.g, containing conventional suppository bases such as cocoa butter or other glycerides.

In addition to the formulations described above, the agents may also be formulated as a depot preparation. Such long-acting formulations may be administered by implantation (for example, subcutaneously or intramuscularly) or by intramuscular injection. Thus, for example, the compounds may be formulated with suitable polymeric or hydrophobic materials (for example, as an emulsion in an acceptable oil) or ion-exchange resins, or as sparingly soluble derivatives, for example, as a sparingly soluble salt.

An exemplary pharmaceutical carrier for hydrophobic compounds is a cosolvent system comprising benzyl alcohol, a nonpolar surfactant, a water-miscible organic polymer, and an aqueous phase. The cosolvent system may be a VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5 W) contains VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may be substituted for dextrose.

Alternatively, other delivery systems for hydrophobic pharmaceutical compounds may be employed. Liposomes and emulsions are known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semi-permeable matrices of solid hydrophobic polymers containing the therapeutic agent. Various sustained-release materials have been established and are known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid- or gel-phase carriers or excipients. Examples of such carriers or excipients include calcium carbonate, calcium phosphate, sugars, starches, cellulose derivatives, gelatin, and polymers such as polyethylene glycols.

Some of the compounds of the invention may be provided as salts with pharmaceutically compatible counter ions. Pharmaceutically compatible salts may be formed with many acids, including hydrochloric, sulfuric, acetic, lactic, tartaric, malic, succinic, etc. Salts tend to be more soluble in aqueous or other protonic solvents than are the corresponding free-base forms.

The agents of the invention may be useful in combination with known anti-cancer treatments such as: DNA interactive agents such as cisplatin or doxorubicin; topoisomerase II inhibitors such as etoposide; topoisomerase I inhibitors such as CPT-II or topotecan; tubulin interacting agents such as paclitaxel, docetaxel or the epothilones; hormonal agents such as tamoxifen; thymidilate synthase inhibitors such as 5-fluorouracil; and anti-metabolites such as methotrexate. They may be administered together or sequentially, and when administered sequentially, the agents may be administered either prior to or after administration of the known anticancer or cytotoxic agent.

The agents may be prepared using the reaction routes and synthesis schemes as described below, employing the general techniques known in the art using starting materials that are readily available. The preparation of preferred compounds of the present invention is described in detail in the following examples, but the artisan will recognize that the chemical reactions described may be readily adapted to prepare a number of other anti-proliferatives or protein kinase inhibitors of the invention. For example, the synthesis of non-exemplified compounds according to the invention may be successfully performed by modifications apparent to those skilled in the art, e.g., by appropriately protecting interfering groups, by changing to other suitable reagents known in the art, or by making routine modifications of reaction conditions. Alternatively, other reactions disclosed herein or generally known in the art will be recognized as having applicability for preparing other compounds of the invention.

DETAILED DESCRIPTION OF THE INVENTION

EXAMPLES

In the examples described below, unless otherwise indicated, all temperatures are set forth in degrees Celsius and all parts and percentages are by weight. Reagents were purchased from commercial suppliers such as Aldrich Chemical Company or Lancaster Synthesis Ltd. and were used without further purification unless otherwise indicated. Tetrahydrofuran (THF), N,N-dimethylformamide (DMF), dichloromethane, toluene, and dioxane were purchased from Aldrich in Sure seal bottles and used as received. All solvents were purified using standard methods readily known to those skilled in the art, unless otherwise indicated.

The reactions set forth below were done generally under a positive pressure of argon or nitrogen or with a drying tube, at ambient temperature (unless otherwise stated), in anhydrous solvents, and the reaction flasks were fitted with rubber septa for the introduction of substrates and reagents via syringe. Glassware was oven dried and/or heat dried. Analytical thin layer chromatography (TLC) was performed on glass-backed silica gel 60 F 254 plates Analtech (0.25 mm) and eluted with the appropriate solvent ratios (v/v), and are denoted where appropriate. The reactions were assayed by TLC and terminated as judged by the consumption of starting material.

Visualization of the TLC plates was done with a p-anisaldehyde spray reagent or phosphomolybdic acid reagent (Aldrich Chemical 20 wt % in ethanol) and activated with heat. Work-ups were typically done by doubling the reaction volume with the reaction solvent or extraction solvent and then washing with the indicated aqueous solutions using 25% by volume of the extraction volume unless otherwise indicated. Product solutions were dried over anhydrous $Na_2SO_4$ prior to filtration and evaporation of the solvents under reduced pressure on a rotary evaporator and noted as solvents removed in vacuo. Flash column chromatography (Still et al., *J. Org. Chem.*, 43, 2923 (1978)) was done using Baker grade flash silica gel (47–61 μm) and a silica gel: crude material ratio of about 20:1 to 50:1 unless otherwise stated. Hydrogenolysis was done at the pressure indicated in the examples or at ambient pressure.

$^1$H-NMR spectra were recorded on a Bruker instrument operating at 300 MHz and $^{13}$C-NMR spectra were recorded operating at 75 MHz. NMR spectra were obtained as $CDCl_3$ solutions (reported in ppm), using chloroform as the reference standard (7.25 ppm and 77.00 ppm) or $CD_3OD$ (3.4 and 4.8 ppm and 49.3 ppm), or internally tetramethylsilane (0.00 ppm) when appropriate. Other NMR solvents were used as needed. When peak multiplicities are reported, the following abbreviations are used: s (singlet), d (doublet), t (triplet), m (multiplet), br (broadened), dd (doublet of doublets), dt (doublet of triplets). Coupling constants, when given, are reported in Hertz (Hz).

Infrared (IR) spectra were recorded on a Perkin-Elmer FT-IR Spectrometer as neat oils, as KBr pellets, or as $CDCl_3$ solutions, and when given are reported in wave numbers ($cm^{-1}$). The mass spectra were obtained using LSIMS or electrospray. All melting points (mp) are uncorrected.

In one general synthetic process, compounds of Formula I are prepared according to the following reaction scheme:

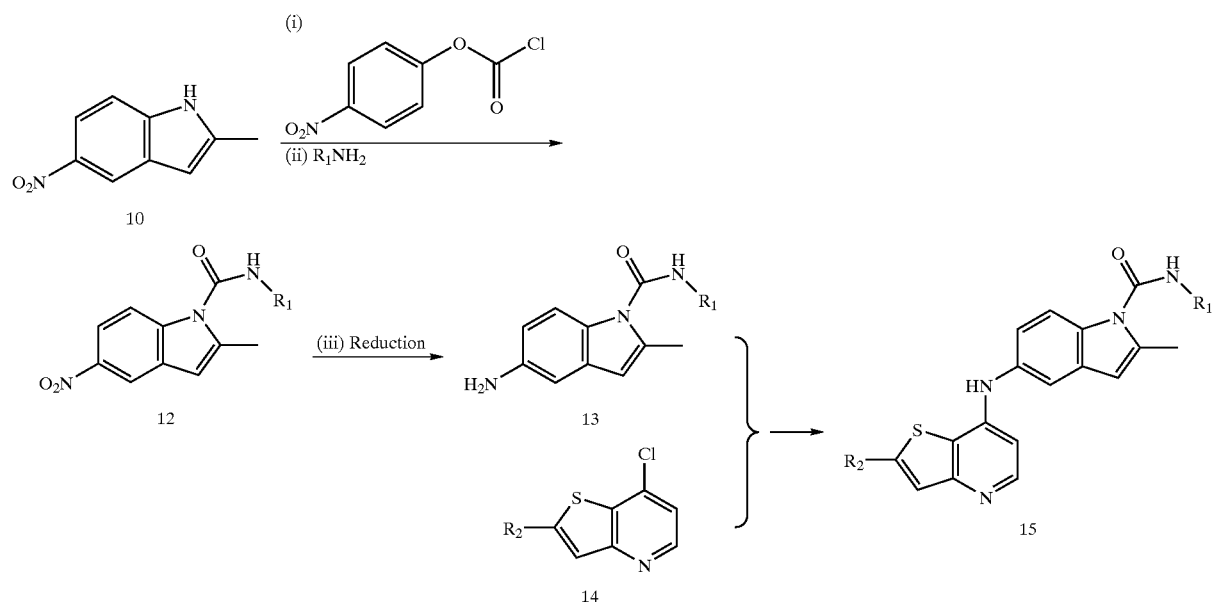

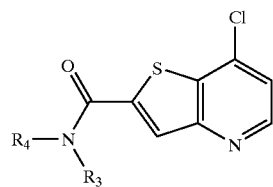

14a

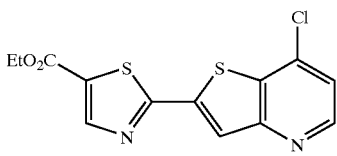

14b

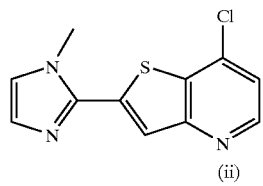

(ii)

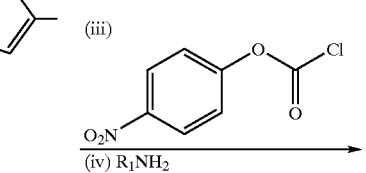

14c

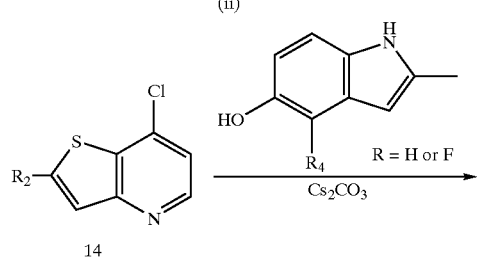

14

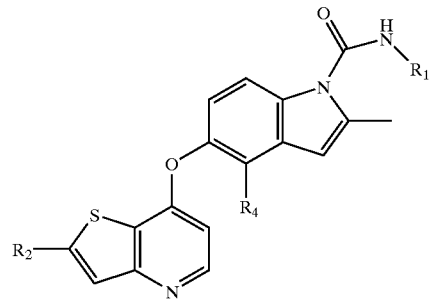

16

(iii)

(iv) R₁NH₂

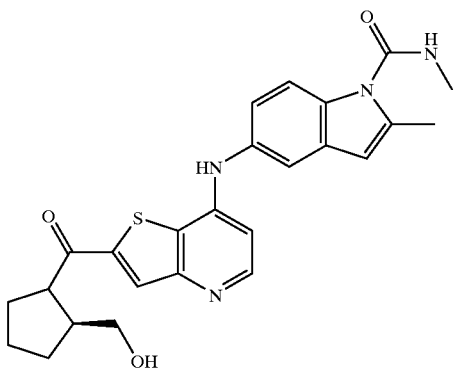

17

5-Nitroindole (compound 10) is treated with a base, e.g. NaH in THF or NaOH in organic/aqueous mixture and a reactive carbonate coupling reagent, e.g. p-nitrophenol chloroformate, phosgene, triphosgene. The resulting activated carbamate is treated with a suitable $R_1$ amine to give compounds of formula 12. Alternatively, the anion of 10 may be treated with a suitable $R_1$ isocyanate to give compounds of formula 12. Reduction of compounds of formula 12, preferably with Pd/C under $H_2$ or with $SnCl_2$ gives compounds of formula 13. Compounds of formula 13 and 14 are combined by heating them in solvent such as DMSO, isopropanol or ethanol/dichloroethane mixtures to produce compounds of formula 15. Alternatively, 5-hydroxy indoles, which are known in the literature, are combined with compounds of formula 14 by heating in DMSO with base, preferable $Cs_2CO_3$, to form compounds of formula 16. Compounds of formula 16 are treated with a base, e.g. NaH or NaOH in organic/aqueous mixture and a reactive carbonate coupling reagent, e.g. p-nitrophenol chloroformate, phosgene, triphosgene. The resulting activated carbamate is treated with a suitable $R_1$ amine to give compounds of formula 17. Alternatively, the anion of 16 may be treated with a suitable $R_1$ isocyanate to give compounds of formula 17. Alternatively to using compounds of formula 14a, compounds of formula 14 where $R_2$ is a carboxylic acid may be used in the coupling reaction that generates compounds of formula 15. Amide formation may then be the final step.

Example 1(a)

5-[2-(2R-Hydroxymethyl-pyrrolidine-1-carbonyl)-thieno[3,2-b]pyridin-7-ylamino]-2-methyl-indole-1-carboxylic acid methylamide To a solution of (7-chloro-thieno[3,2-b]pyridin-2-yl)-(2R-hydroxymethyl-pyrrolidin-1-yl)-methanone (59 mg 0.2 mmol), prepared in step (iv) below, and 5-amino-2-methylindole-1-carboxylic acid methylamide (45 mg, 0.22 mmol), prepared in step (iii) below, in 3 mL ethanol and 0.3 mL dichloroethane was added 4.0 M HCl in dioxane (0.05 mL, 0.2 mmol). The solution was heated to reflux under argon for 24 hours and was cooled to room temperature and concentrated in vacuo. The residue was purified by flash column chromatography eluting with 5% methanol in dichloromethane to render 50 mg desired product as yellow solid (54% yield). $^1$H NMR (300 MHz, CD$_3$OD) δ 8.20 (d, 1H, J=5.68 Hz), 7.75 (s, 1H), 7.65 (d, 1H, J=8.79 Hz), 7.38 (d, 1H, J=1.83 Hz), 7.13 (dd, 1H, J=8.79, 2.01 Hz), 6.74 (d, 1H, J=5.68 Hz), 6.33 (s, 1H), 4.32 (m, 1H), 3.71–3.90 (m, 4H), 3.00 (s, 3H), 2.53 (s, 3H), 1.90–2.12 (m, 4H). MS (ESI+) [M+H]/z Calc'd 464, found 464. Anal. (C$_{24}$H$_{25}$N$_5$O$_3$S.0.8H$_2$O) C, H, N.

The starting materials were prepared as follows:

2-methyl-5-nitro-1-(4-nitrophenoxycarbonyl)indole

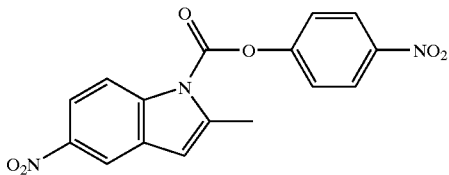

Method A:

To a stirred slurry of NaH (1.92 g of a 60% mineral oil dispersion, 48 mmole) in THF (120 ml) at −5°, under argon, was cautiously added 2-methyl-5-nitroindole (7.05 g, 40 mmole), in portions, as the solid. The reaction mixture was stirred at 0° for 40 minutes, then transferred, via cannula, to a solution of 4-nitrophenyl chloroformate (9.44 g, 47 mmole) in THF (60 ml). The resultant reaction mixture was stirred at ambient temperature for 15 hours prior to removal of the solvent by concentration, in vacuo. The residue obtained was suspended in EtOAc (200 ml), then filtered and washed with EtOAc and Et$_2$O to give 11.51 g (84%) of a pale yellow solid.

Method B:

To a stirred solution of 2-methyl-5-nitroindole (1.76 g, 10 mmole) in CH$_2$Cl$_2$ (90 ml) were added, sequentially, freshly crushed NaOH (1.20 g, 30 mmole), Bu$_4$NBr (32 mg, catalytic amount) and 4-nitrophenyl chloroformate (2.02 g, 10 mmole). After stirring at ambient temperature for 30 minutes, the reaction mixture was filtered and the filtrate was concentrated, in vacuo, to provide 2.89 g (85%) of a yellow solid. $^1$H NMR (DMSO-d6): δ 8.51 (1H, d, J=2.3 Hz), 8.41 (2H, d, J=9.1 Hz), 8.27 (1H, d, J=9.2 Hz), 8.17 (1H, dd, J=2.3, 9.2 Hz), 7.80 (2H, d, J=9.1 Hz), 6.85 (1H, s), 2.70 (3H, s). Anal. Calcd. for C$_{16}$H$_{11}$N$_3$O$_6$.1.9 NaCl: C, 42.48; H, 2.45; N, 9.29. Found: C, 42.46; H, 2.43; N, 9.32.

2-Methyl-5-nitro-indole-1-carboxylic acid methylamide

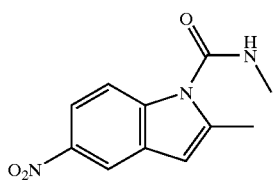

A 2.0 M solution of methylamine in THF (25 ml, 50 mmole) was added to a solution of 2-methyl-5-nitro-1-(4-nitrophenoxycarbonyl)indole 1a (2.11 g, 6.2 mmole) in THF (240 ml). The resultant reaction mixture was stirred at ambient temperature for 4 hours prior to removal of the solvent by concentration, in vacuo. The residue obtained was partitioned between EtOAc (200 ml) and H$_2$O (200 ml). The layers were separated and the aqueous phase was extracted with EtOAc (2×100 ml). The combined organic extracts were washed with sat'd NaHCO$_3$ (150 ml), dried over Na$_2$SO$_4$ and concentrated, in vacuo, to give a yellow solid which was suspended in Et$_2$O (35 ml), filtered and washed with Et$_2$O (2×20 ml) to give 1.17 g (81%) of a pale yellow solid. $^1$H NMR (DMSO-d6): δ 8.52 (1H, q, J=4.5 Hz), 8.46 (1H, d, J=2.3 Hz), 8.03 (1H, dd, J=2.3, 9.1 Hz), 7.71 (1H, d, J=9.1 Hz), 6.62 (1H, s), 2.89 (3H, d, J=4.5 Hz), 2.51 (3H, s). Anal. Calcd. for C$_{11}$H$_{13}$N$_3$O$_3$: C, 56.65; H, 4.75; N, 18.02. Found: C, 56.56; H, 4.78; N, 17.82.

5-Amino-2-methyl-indole-1-carboxylic acid methylamide

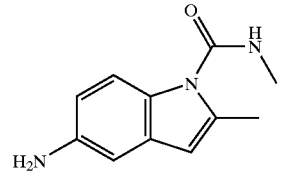

Method A:

To a stirred solution of 2-methyl-5-nitroindole-1-carboxylic acid methylamide 1b (1.30 g, 5.6 mmole) in EtOAc (50 ml) and THF (40 ml) was added 10% Pd on carbon (140 mg, ~10% wt. eq.). The resultant slurry was stirred under an H$_2$ atmosphere at ambient temperature for 90 minutes, then filtered through a pad of celite. The filtrate was subsequently concentrated, in vacuo, to give 1.2 g of an orange-brown resin which was purified by silica gel chromatography. Elution with CH$_2$Cl$_2$: CH$_3$OH (97:3) and evaporation of the appropriate fractions gave 0.99 g (88%) of a beige solid. $^1$H NMR (DMSO-d6): δ 7.82 (1H q, J=4.5 Hz), 7.27 (1H, d, J=8.7 Hz), 6.57 (1H, d, J=2.1 Hz), 6.46 (1H, dd, J=2.1, 8.7 Hz), 6.07 (1H, s), 4.64 (2H, br s), 2.81 (3H, d, J=4.5 Hz), 2.40 (3H, s). Anal. Calcd. for C$_{11}$H$_{13}$N$_3$O: C, 65.00; H, 6.45; N, 20.68. Found: C, 65.24; H, 6.34; N, 20.82.

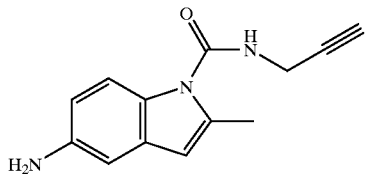

Method B (Used with Hydrogenation Sensitive Substrates)

A mixture of 5-nitro-2-methyl-indole-1-carboxylic acid prop-2-ynylamide (1.18 g, 4.23 mmol) and SnCl$_2$.2H$_2$O (3.34 g, 14.81 mmol) in EtOH (100 mL) was heated at 80° C. for 10 hours. The mixture was cooled to room temperature. Saturated aqueous NaHCO$_3$ was added slowly. The mixture was then filtered through Celite, washed with EtOAc. The filtrate was extracted with EtOAc for three times. The combined organic layer was dried over Na$_2$SO$_4$, concentrated to give the crude product. Elution with EtOAc and hexane (1:2) through a flash column and subsequent concentration provided the product as an orange solid (0.50 g, 52% yield). $^1$H NMR (300 MHz, CDCl$_3$) δ 7.47 (1H, d, J=8.7 Hz), 6.77 (1H, d, J=2.1 Hz), 6.62 (1H, d, J=8.7, 2.3 Hz), 6.16 (1H, s), 5.77 (1H, bs), 4.31–4.23 (2H, m), 3.68 (2H, bs), 3.55 (3H, s), 2.36–2.30 (1H, m). LCMS (ESI+) [M+H]/z Calc'd 228, found 228.

(7-Chloro-thieno[3,2-b]pyridin-2-yl)-(2R-hydroxymethyl-pyrrolidin-1-yl)-methanone

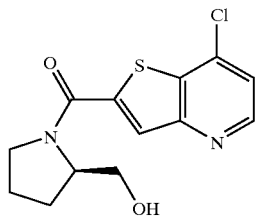

To a solution of pyrrolidin-2R-yl-methanol (1.12 g, 11 mmol) in 20 ml DMF was added 7-chloro-thieno[3,2-b]pyridine-2-carboxylic acid lithium salt (2.2 g, 10 mmol), followed by slow addition of HATU (4.2 g, 11 mmol) as solid. The mixture was stirred at room temperature for one hour and quenched with water. The mixture was then extracted with EtOAc. The combined organic layer was dried over $Na_2SO_4$, filtered, and concentrated to give crude product, which was further purified by flash column chromatography eluted with EtOAc: $CH_2Cl_2$: MeOH (1:1:0.1) to give desired product as yellow oil (1.4 g 50% yield). $^1$H NMR (300 MHz, DMSO-$d_6$) δ 8.73 (1H, d, J=5.12 Hz), 8.09 (1H, s), 7.69 (1H, d, J=5.13 Hz), 4.21 (1H, m), 3.86 (2H, m), 3.57 (2H, m), 1.90–2.10 (4H, m). MS (ESI+) [M+H]/z Calc'd 297, found 297.

Example 1(b)

5-[2-(2R-Methoxymethyl-pyrrolidine-1-carbonyl)-thieno[3,2-b]pyridin-7-ylamino]-2-methyl-indole-1-carboxylic acid methylamide

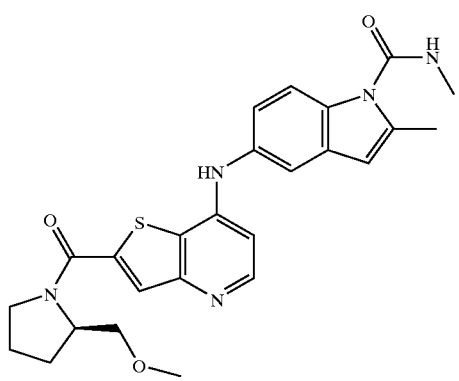

Example 1(b) was prepared in a similar manner as Example 1(a) except that R-2-(methoxymethyl)pyrrolidine was used instead of pyrrolidin-2R-yl-methanol in step (iv). $^1$H NMR (300 MHz, $CD_3OD$) δ 8.20 (1H, d, J=5.68 Hz), 7.73 (1H, s), 7.65 (1H, d, J=8.79 Hz), 7.38 (1H, d, J=1.47 Hz), 7.12 (1H, dd, J=8.79, 1.93 Hz), 6.74 (1H, d, J=5.67 Hz), 6.33 (1H, s), 4.40 (1H, m), 3.85 (2H, m), 3.60 (2H, m), 3.36 (3H, s), 3.00 (3H, s), 2.53 (3H, s), 1.90–2.12 (4H, m). MS (ESI+) [M+H]/z Calc'd 478, found 478. Anal. ($C_{25}H_{27}N_5O_3S \cdot 0.6H_2O$) C, H, N.

Example 1(c)

5-[2-(2R-Hydroxymethyl-pyrrolidine-1-carbonyl)-thieno[3,2-b]pyridin-7-ylamino]-2-methyl-indole-1-carboxylic acid cyclopropylamide

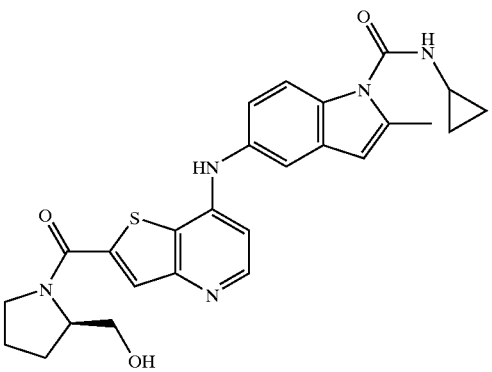

Example 1(c) was prepared in a similar manner as Example 1(a) except that cyclopropylamine was used instead of methylamine in step (ii). $^1$H NMR (300 MHz, $CD_3OD$) δ 8.20 (1H, d, J=3.48 Hz), 7.76 (1H, s), 7.59 (1H, d, J=8.42 Hz), 7.38 (1H, s), 7.12 (1H, d, J=8.79 Hz), 6.74 (1H, d, J=4.19 Hz), 6.33 (1H, s), 4.32 (1H, m), 3.81 (4H, m), 2.88 (1H, m), 2.52 (3H, s), 2.02 (4H, m), 0.86 (2H, m), 0.73 (2H, m). MS (ESI+) [M+H]/z Calc'd 490, found 490. Anal. ($C_{26}H_{27}N_5O_3S \cdot 0.5H_2O$) C, H, N.

Example 1(d)

5-[2-(2R-Methoxymethyl-pyrrolidine-1-carbonyl)-thieno[3,2-b]pyridin-7-ylamino]-2-methyl-indole-1-carboxylic acid cyclopropylamide

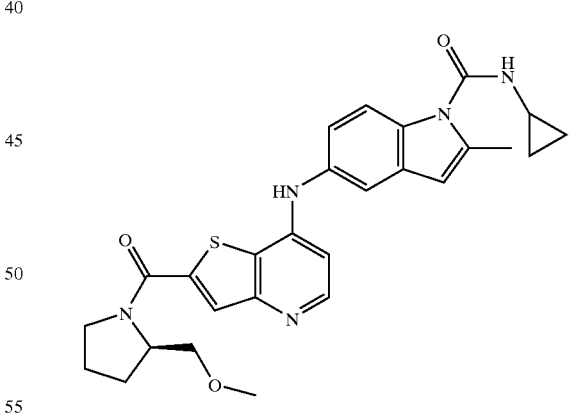

Example 1(d) was prepared in a similar manner as Example 1(b) except that cyclopropylamine was used instead of methylamine in step (ii). $^1$H NMR (300 MHz, $CD_3OD$) δ 8.19 (1H, d, J=5.5 Hz), 7.73 (1H, s), 7.58 (1H, d, J=8.79 Hz), 7.37 (1H, s), 7.12 (1H, d, J=8.79 Hz), 6.73 (1H, d, J=5.5 Hz), 6.32 (1H, s), 4.40 (1H, m), 3.85 (2H, m), 3.60 (2H, m), 3.36 (3H, s), 2.88 (1H, m), 2.51 (3H, s), 1.93–2.10 (4H, m), 0.86 (2H, m), 0.72 (2H, m). MS (ESI+) [M+H]/z Calc'd 504, found 504. Anal. ($C_{27}H_{29}N_5O_3S \cdot 0.3H_2O$) C, H, N.

Example 1(e)

5-[2-(2R-Hydroxymethyl-pyrrolidine-1-carbonyl)-thieno[3,2-b]pyridin-7-ylamino]-2-methyl-indole-1-carboxylic acid prop-2-ynylamide

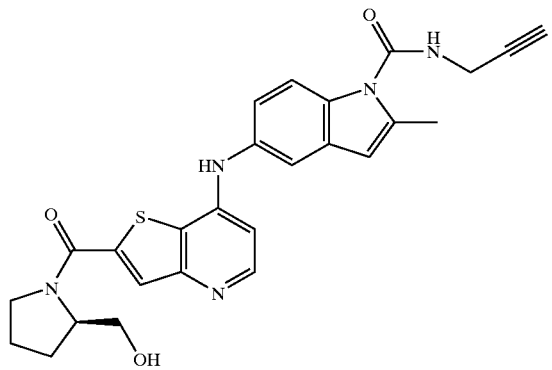

Example 1(e) was prepared in a similar manner as Example 1(a) except that propargylamine was used instead of methylamine in step (ii). $^1$H NMR (300 MHz, DMSO-$d_6$) δ 8.84 (1H, s), 8.76 (1H, t, J=5.46 Hz), 8.26 (1H, d, J=5.27 Hz), 7.80 (1H, s), 7.62 (1H, d, J=8.67 Hz), 7.37 (1H, d, J=1.88 Hz), 7.10 (1H, dd, J=8.67, 1.88 Hz), 6.71 (1H, d, J=5.46 Hz), 6.38 (1H, s), 4.18 (1H, m), 4.11 (2H, m), 3.81 (2H, m), 3.50 (2H, m), 3.25 (1H, t, J=2.26 Hz), 2.50 (3H, bs), 1.94 (4H, m). MS (ESI+) [M+H]/z Calc'd 488, found 488. Anal. ($C_{26}H_{25}N_5O_3S.0.15CH_2Cl_2$) C, H, N.

Example 1(f)

5-[2-(3S-Methoxy-pyrrolidine-1-carbonyl)-thieno[3,2-b]pyridin-7-ylamino]-2-methyl-indole-1-carboxylic acid cyclopropylamide

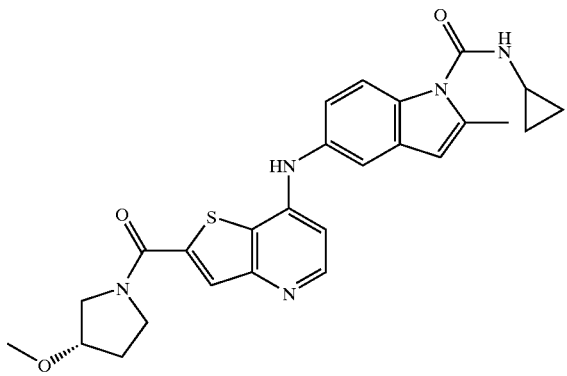

Example 1(f) was prepared in a similar manner as Example 1(c) except that 3S-methoxy-pyrrolidine was used instead of pyrrolidin-2R-yl-methanol in step (iv). $^1$H NMR (300 MHz, DMSO-$d_6$) δ 8.88 (1H, s), 8.55 (1H, s), 8.31 (1H, d, J=5.31 Hz), 7.88 (1H, s), 7.57 (1H, d, J=8.61 Hz), 7.39 (1H, s), 7.12 (1H, d, J=8.42 Hz), 6.74 (1H, d, J=5.31 Hz), 6.39 (1H, s), 3.84–4.10 (3H, m), 3.64 (2H, m), 3.31 (s, 1.5H), 3.28 (s, 1.5H), 2.88 (1H, m), 2.52 (3H, bs), 2.08 (2H, m), 0.80 (2H, m), 0.70 (2H, m). MS (ESI+) [M+H]/z Calc'd 490, found 490. Anal. ($C_{26}H_{27}N_5O_3S.0.2H_2O$) C, H, N.

Example 1(g)

5-[2-(3S-Methoxy-pyrrolidine-1-carbonyl)-thieno[3,2-b]pyridin-7-ylamino]-2-methyl-indole-1-carboxylic acid methylamide

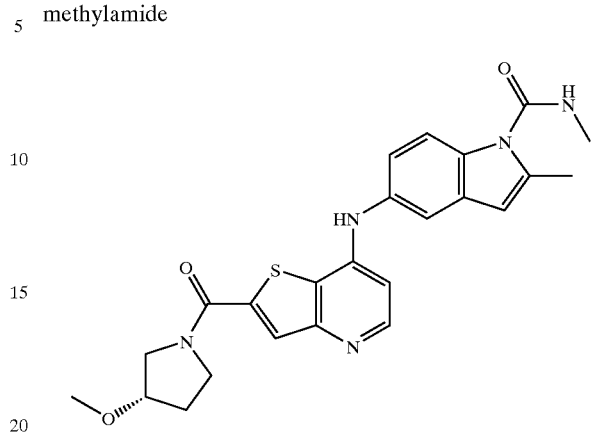

Example 1(g) was prepared in a similar manner as Example 1(a) except that 3S-methoxy-pyrolidine was used instead of pyrrolidin-2R-yl-methanol in step (iv). $^1$H NMR (300 MHz, DMSO-$d_6$) δ 8.86 (1H, s), 8.29 (1H, d, J=5.31 Hz), 8.22 (1H, d, J=4.39 Hz), 7.85 (1H, s), 7.62 (1H, d, J=8.79 Hz), 7.37 (1H, d, J=1.28 Hz), 7.10 (1H, dd, J=8.70, 1.74 Hz), 6.72 (1H, d, J=5.49 Hz), 6.37 (1H, s), 3.79–4.10 (3H, m), 3.59 (2H, m), 3.28 (s, 1.5H), 3.25 (s, 1.5H), 2.89 (3H, bs), 2.50 (3H, bs), 2.02 (2H, m). MS (ESI+) [M+H]/z Calc'd 464, found 464. Anal. ($C_{24}H_{25}N_5O_3S.1.0H_2O$) C, H, N.

Example 1(h)

5-[2-(3S-Methoxy-pyrrolidine-1-carbonyl)-thieno[3,2-b]pyridin-7-ylamino]-2-methyl-indole-1-carboxylic acid prop-2-ynylamide

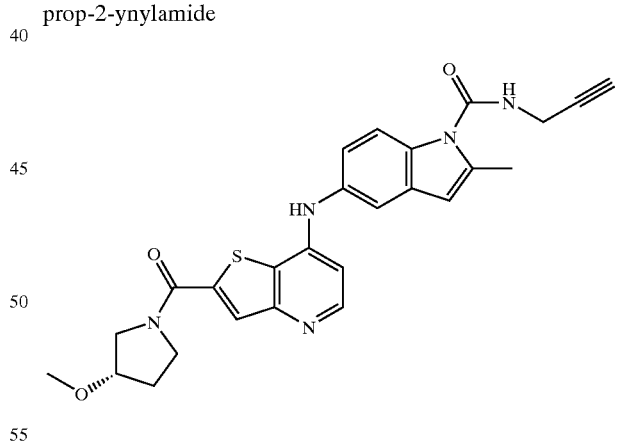

Example 1(h) was prepared in a similar manner as Example 1(e) except that 3S-methoxy-pyrrolidine was used instead of pyrrolidin-2R-yl-methanol in step (iv). $^1$H NMR (300 MHz, DMSO-$d_6$) δ 8.86 (1H, s), 8.77 (1H, t, J=5.40 Hz), 8.28 (1H, d, J=5.31 Hz), 7.85 (1H, s), 7.63 (1H, d, J=8.60 Hz), 7.37 (1H, s), 7.11 (1H, d, J=8.61 Hz), 6.73 (1H, d, J=5.49 Hz), 6.39 (1H, s), 4.11 (2H, d, J=2.56 Hz), 4.09 (1H, m), 3.98 (2H, m), 3.84 (2H, m), 3.60 (1H, bs), 3.27 (s, 1.5H), 3.24 (s, 1.5H), 2.50 (3H, bs), 2.05 (2H, m). MS (ESI+) [M+H]/z Calc'd 488, found 488. Anal. ($C_{24}H_{25}N_5O_3S$) C, H, N.

Example 1(i)

5-[2-(3S-Hydroxy-pyrrolidine-1-carbonyl)-thieno[3,2-b]pyridin-7-ylamino]-2-methyl-indole-1-carboxylic acid methylamide

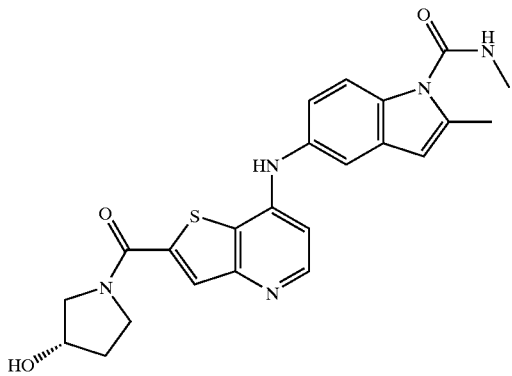

Example 1(i) was prepared in a similar manner as Example 1(a) except that 3S-hydroxyoxy-pyrrolidine was used instead of pyrrolidin-2R-yl-methanol in step (iv). $^1$H NMR (300 MHz, CD$_3$OD) δ8.24 (1H, d, J=5.7 Hz), 7.79 (1H, d, J=18.1 Hz), 7.69 (1H, d, J=8.7 Hz), 7.42 (1H, d, J=2.1 Hz), 7.16 (1H, dd, J=10.7, 2.1 Hz), 6.78 (1H, d, J=5.7 Hz), 6.37 (1H, s), 4.50 (1H, bs), 4.08–3.97 (2H, m), 3.84–3.76 (2H, m), 3.76–3.67 (1H, m), 3.04 (3H, s), 2.56 (3H, s), 2.18–1.98 (2H, m). LCMS (ESI+) [M+H]/z Calc'd 450, found 450. Anal. (C$_{23}$H$_{23}$N$_5$O$_3$S.0.8MeOH) C, H, N.

Example 1(j)

5-[2-(3S-Hydroxy-pyrrolidine-1-carbonyl)-thieno[3,2-b]pyridin-7-ylamino]-2-methyl-indole-1-carboxylic acid prop-2-ynylamide

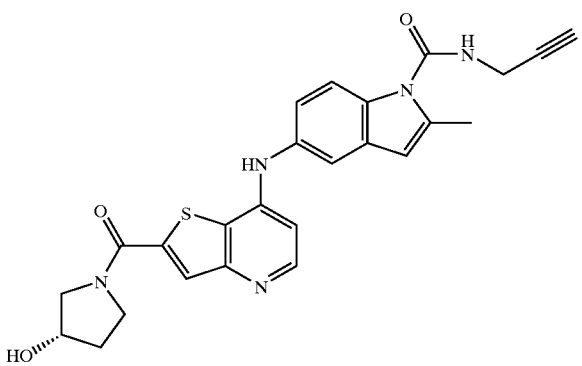

Example 1(j) was prepared in a similar manner as Example 1(e) except that 3S-hydroxy-pyrrolidine was used instead of pyrrolidin-2R-yl-methanol in step (iv). $^1$H NMR (300 MHz, CD$_3$OD) δ 8.25 (1H, d, J=5.7 Hz), 7.80 (1H, d, J=18.3 Hz), 7.73 (1H, d, J=8.8 Hz), 7.43 (1H, d, J=1.9 Hz), 7.18 (1H, d, J=8.8, 2.1 Hz), 6.80 (1H, d, J=5.8 Hz), 6.39 (1H, s), 4.53 (1H, bs), 4.24 (2H, d, J=2.4 Hz), 4.06–3.98 (2H, m), 3.85–3.76 (2H, m), 3.76–3.68 (1H, m), 2.77–2.72 (1H, m), 2.68 (3H, s), 2.19–2.02 (2H, m). LCMS (ESI+) [M+H]/z Calc'd 474, found 474. Anal. (C$_{25}$H$_{23}$N$_5$O$_3$S.1.0H$_2$O) C, H, N.

Example 1(k)

5-[2-(3S-Hydroxy-pyrrolidine-1-carbonyl)-thieno[3,2-b]pyridin-7-ylamino]-2-methyl-indole-1-carboxylic acid cyclopropylamide

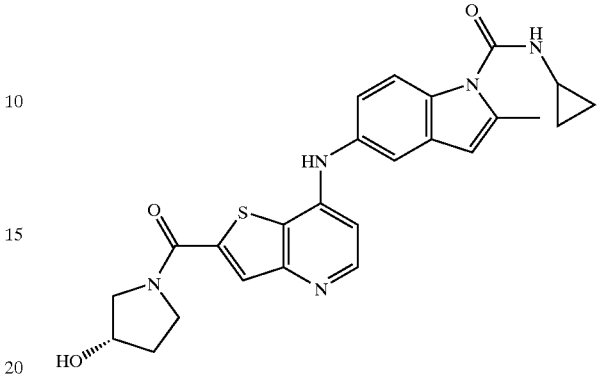

Example 1(k) was prepared in a similar manner as Example 1(c) except that 3S-hydroxy-pyrrolidine was used instead of pyrrolidin-2R-yl-methanol in step (iv). $^1$H NMR (300 MHz, CD$_3$OD) δ 8.02 (1H, d, J=5.6 Hz), 7.62 (1H, d, J=17.7 Hz), 7.39 (1H, d, J=8.8 Hz), 7.38 (1H, s), 7.20 (1H, s), 6.92 (1H, dd, J=8.7, 2.1 Hz), 6.57 (1H, d, J=5.5 Hz), 6.14 (1H, s), 4.30 (1H, bs), 3.90–3.70 (2H, m), 3.61–3.50 (2H, m), 3.50–3.45 (1H, m), 2.71–2.65 (1H, m), 2.32 (3H, s), 1.93–1.74 (2H, m), 0.68–0.60 (2H, m), 0.55–0.50 (2H, m). LCMS (ESI+) [M+H]/z Calc'd 476, found 476. Anal. (C$_{25}$H$_{25}$N$_5$O$_3$S.0.7CH$_2$Cl$_2$) C, H, N.

Example 1(l)

5-[2-(3R-Methoxy-pyrrolidine-1-carbonyl)-thieno[3,2-b]pyridin-7-ylamino]-2-methyl-indole-1-carboxylic acid methylamide

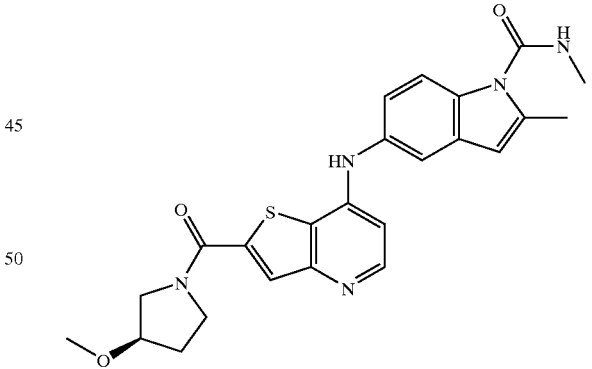

Example 1(l) was prepared in a similar manner as Example 1(a) except that 3R-methoxy-pyrrolidine was used instead of pyrrolidin-2R-yl-methanol in step (iv). $^1$H NMR (300 MHz, CDCl$_3$) δ 8.32 (1H, d, J=5.5 Hz), 7.76 (1H, d, J=17.7 Hz), 7.70 (1H, d, J=8.8 Hz), 7.40 (1H, s), 7.12 (1H, dd, J=8.8, 2.4 Hz), 6.70 (1H, d, J=5.5 Hz), 6.32 (1H, s), 6.17 (1H, d, J=3.4 Hz), 6.16 (1H, s), 4.07–4.01 (1H, m), 3.98–3.87 (2H, m), 3.87–3.68 (2H, m), 3.20 (3H, d, J=14.5 Hz), 3.17 (3H, d, J=3.4 Hz), 2.67 (3H, s), 2.35–2.04 (2H, m). LCMS (ESI+) [M+H]/z Calc'd 464, found 464. Anal. (C$_{24}$H$_{25}$N$_5$O$_3$S.1.5H$_2$O) C, H, N.

Example 1(m)

5-[2-(3R-Hydroxy-pyrrolidine-1-carbonyl)-thieno[3,2-b]pyridin-7-ylamino]-2-methyl-indole-1-carboxylic acid cyclopropylamide

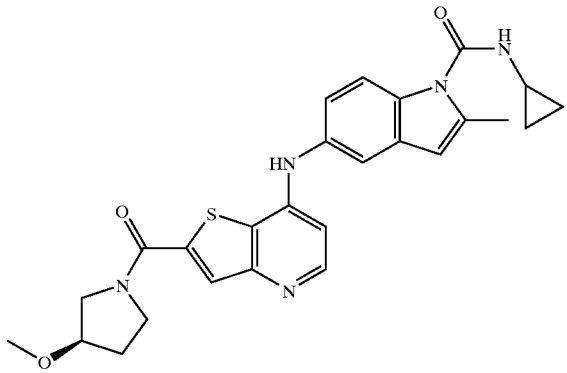

Example 1(m) was prepared in a similar manner as Example 1(c) except that 3R-methoxy-pyrrolidine was used instead of pyrrolidin-2R-yl-methanol in step (iv). $^1$H NMR (300 MHz, CD$_3$OD) δ 8.21 (1H, d, J=5.5 Hz), 7.75 (1H, d, J=5.5 Hz), 7.59 (1H, d, J=8.5 Hz), 7.39 (1H, s), 7.13 (1H, dd, J=8.8, 2.4 Hz), 6.77 (1H, d, J=5.5 Hz), 6.47 (1H, s), 4.17–4.11 (1H, m), 4.02–3.87 (2H, m), 3.86–3.63 (2H, m), 3.37 (3H, d, J=14.5 Hz), 2.95–2.85 (1H, m), 2.53 (3H, s), 2.30–2.02 (2H, m), 0.91–0.83 (2H, m), 0.77–0.70 (2H, m). LCMS (ESI+) [M+H]/z Calc'd 490, found 490. Anal. (C$_{26}$H$_{27}$N$_5$O$_3$S.2.0H$_2$O) C, H, N.

Example 1(n)

5-[2-(3R-Hydroxy-pyrrolidine-1-carbonyl)-thieno[3,2-b]pyridin-7-ylamino]-2-methyl-indole-1-carboxylic acid methylamide

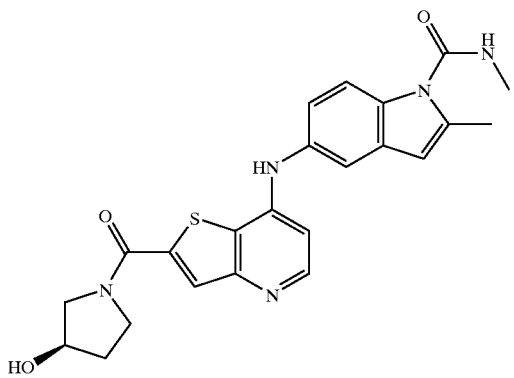

Example 1(n) was prepared in a similar manner as Example 1(a) except that 3R-hydroxy-pyrrolidine was used instead of pyrrolidin-2R-yl-methanol in step (iv). $^1$H NMR (300 MHz, CD$_3$OD) δ 8.25 (1H, d, J=5.5 Hz), 7.77 (1H, d, J=17.7 Hz), 7.67 (1H, d, J=8.5 Hz), 7.42 (1H, s), 7.17 (1H, dd, J=8.8, 2.4 Hz), 6.77 (1H, d, J=5.5 Hz), 6.36 (1H, s), 4.57 (1H, bs), 4.08–3.98 (2H, m), 3.82–3.72 (2H, m), 3.71–3.67 (1H, m), 3.02 (3H, s), 2.57 (3H, s), 2.18–1.98 (2H, m). LCMS (ESI+) [M+H]/z Calc'd 450, found 450. Anal. (C$_{23}$H$_{23}$N$_5$O$_3$S.1.2H$_2$O) C, H, N.

Example 1(o)

5-[2-(3R-Hydroxy-pyrrolidine-1-carbonyl)-thieno[3,2-b]pyridin-7-ylamino]-2-methyl-indole-1-carboxylic acid prop-2-ynylamide

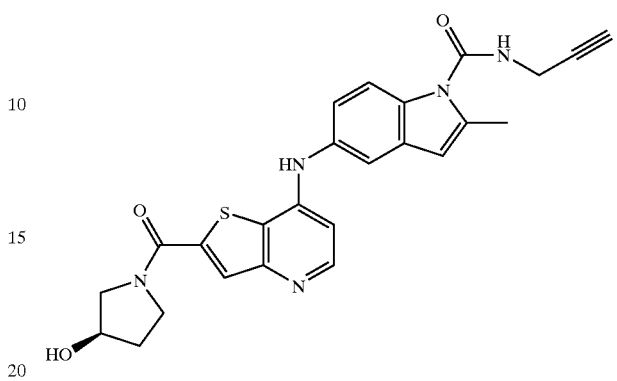

Example 1(o) was prepared in a similar manner as Example 1(e) except that 3R-hydroxy-pyrrolidine was used instead of pyrrolidin-2R-yl-methanol in step (iv). $^1$H NMR (300 MHz, CD$_3$OD) δ 8.25 (1H, d, J=5.5 Hz), 7.79 (1H, d, J=17.7 Hz), 7.67 (1H, d, J=8.5 Hz), 7.42 (1H, s), 7.19 (1H, dd, J=8.8, 2.4 Hz), 6.82 (1H, d, J=5.5 Hz), 6.39 (1H, s), 4.57 (1H, bs), 4.25 (2H, d, J=1.9 Hz), 4.11–4.00 (2H, m), 3.86–3.77 (2H, m), 3.77–3.68 (1H, m), 2.78–2.72 (1H, m), 2.59 (3H, s), 2.32–2.02 (2H, m). LCMS (ESI+) [M+H]/z Calc'd 474, found 474. Anal. (C$_{25}$H$_{23}$N$_5$O$_3$S.1.0MeOHe1.5H$_2$O) C, H, N.

Example 1(p)

5-[2-(3R-Methoxy-pyrrolidine-1-carbonyl)-thieno[3,2-b]pyridin-7-ylamino]-2-methyl-indole-1-carboxylic acid prop-2-ynylamide

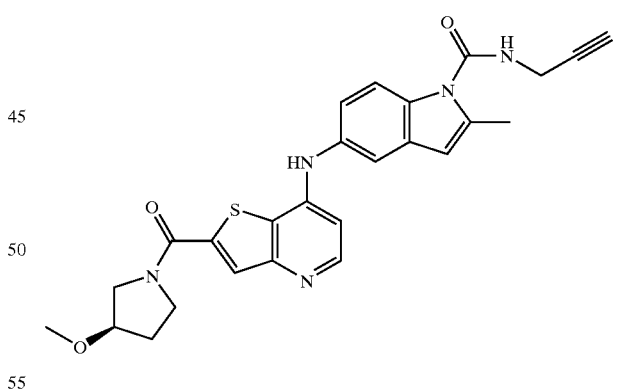

Example 1(p) was prepared in a similar manner as Example 1(e) except that 3R-methoxy-pyrrolidine was used instead of pyrrolidin-2R-yl-methanol in step (iv). $^1$H NMR (300 MHz, CD$_3$OD) δ 8.26 (1H, d, J=5.5 Hz), 7.81 (1H, d, J=5.5 Hz), 7.77 (1H, d, J=8.5 Hz), 7.43 (1H, s), 7.18 (1H, dd, J=8.8, 2.4 Hz), 6.79 (1H, d, J=5.5 Hz), 6.49 (1H, s), 4.24 (2H, d, J=1.9 Hz), 4.19–4.00 (2H, m), 4.05–3.88 (2H, m), 3.85–3.64 (1H, m), 3.38 (3H, d, J=14.5 Hz), 2.78–2.72 (1H, m), 2.59 (3H, s), 2.32–2.02 (2H, m). LCMS (ESI+) [M+H]/z Calc'd 488, found 488. Anal. (C$_{26}$H$_{25}$N$_5$O$_3$S.0.3H$_2$O) C, H, N.

Example 1(q)

5-[2-(3R-Hydroxy-pyrrolidine-1-carbonyl)-thieno[3,2-b]pyridin-7-ylamino]-2-methyl-indole-1-carboxylic acid cyclopropylamide

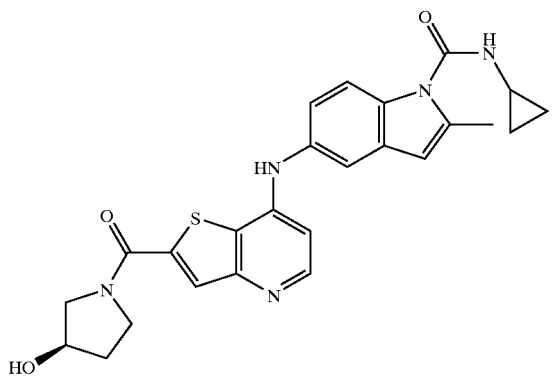

Example 1(q) was prepared in a similar manner as Example 1(c) except that 3R-hydroxy-pyrrolidine was used instead of pyrrolidin-2R-yl-methanol in step (iv). $^1$H NMR (300 MHz, DMSO-d6) δ 8.38 (1H, d, J=3.2 Hz), 8.13 (1H, d, J=5.3 Hz), 7.67 (1H, d, J=19.9 Hz), 7.39 (1H, d, J=8.7 Hz), 7.21 (1H, s), 6.94 (1H, d, J=8.3 Hz), 6.57 (1H, dd, J=8.7, 2.4 Hz), 6.21 (1H, s), 4.21 (1H, d, J=15.4 Hz), 3.86–3.74 (2H, m), 3.53–3.38 (2H, m), 3.35–3.28 (1H, m), 2.74–2.66 (1H, m), 2.32 (3H, s), 1.85–1.74 (2H, m), 0.66–0.57 (2H, m), 0.56–0.49 (2H, m). LCMS (ESI+) [M+H]/z Calc'd 476, found 476. Anal. ($C_{25}H_{25}N_5O_3S.0.7HCl$) C, H, N.

Example 1(r)

5-[2-(3S,4S-Dimethoxy-pyrrolidine-1-carbonyl)-thieno[3,2-b]pyridin-7-ylamino]-2-methyl-indole-1-carboxylic acid methylamide

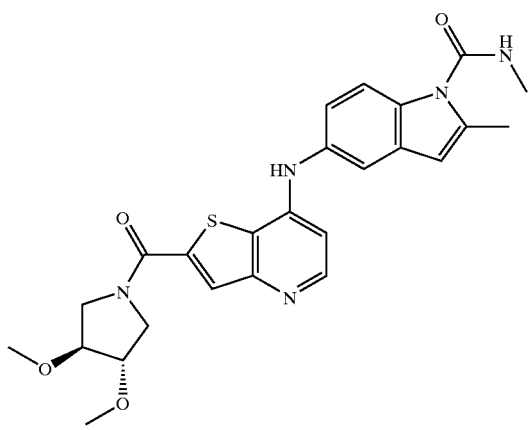

Example 1(r) was prepared in a similar manner as Example 1(a) except that 3S,4S-dimethoxy-pyrrolidine, prepared as described below, was used instead of pyrrolidin-2R-yl-methanol in step (iv). $^1$H NMR (300 MHz, CD$_3$OD) δ 8.11 (1H, d, J=5.65 Hz), 7.66 (1H, s), 7.56 (1H, d, J=8.66 Hz), 7.29 (1H, s), 7.03 (1H, dd, J=8.67, 2.07 Hz), 6.65 (1H, d, J=5.65 Hz), 6.24 (1H, s), 3.77–3.91 (2H, m), 3.62–3.65 (2H, m), 3.32 (3H, s), 3.27 (3H, s), 3.19–3.21 (2H, m), 2.90 (3H, s), 2.43 (3H, s). MS (ESI+) [M+H]/z Calc'd 494, found 494. Anal. ($C_{25}H_{27}N_5O_4S.1.0H_2O.0.3CHCl_3$) C, H, N.

The starting materials were prepared as follows:
(i) 3S,4S-Dihydroxy-pyrrolidine-1-carboxylic acid benzyl ester

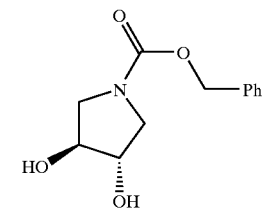

Pd on C (300 mg) was added to a solution of (3S,4S)-(+)-benzyl-3,4-pyrrolidindiol (2.5 g, 12.9 mmol, commercially available) in MeOH. The reaction mixture was stirred under H$_2$ balloon overnight, filtered thought Celite and concentrated under reduced pressure. The residue was dissolved in 1,4-dioxane (10 mL) and 6% Na$_2$CO$_3$ was added to adjust pH ~10. Benzyl chloroformate (3.69 mL, 25.87 mmol) was added to the reaction mixture (during addition of benzyl chloroformate, 6% Na$_2$CO$_3$ was added to adjust pH ~9). The reaction mixture was stirred at room temperature for 2 hours and concentrated under reduced pressure. The residue was taken into water (50 mL) and extracted with EtOAc (2×50 mL). The organic layers were dried over MgSO$_4$ and concentrated. The residue was purified by column chromatography (2% CH$_3$OH in CH$_2$Cl$_2$) to give colorless oil (1.51 g, 51%). $^1$H NMR (300 MHz, CDCl$_3$) δ 7.28–7.34 (5H, m), 5.10 (1H, s), 4.12 (2H, m), 3.65–3.70 (2H, m), 3.36–3.43 (2H, m), 2.83 (1H, bs), 2.65 (1H, bs).

(ii) 3S,4S-Dimethoxy-pyrrolidine-1-carboxylic acid benzyl ester

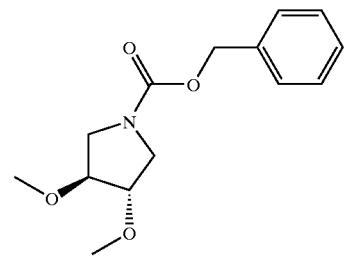

To a solution of NaH (0.347 g, 8.67 mmol) in THF at 0° C. was added 3S,4S-dihydroxy-pyrrolidine-1-carboxylic acid benzyl ester (0.823 g, 3.47 mmol). The reaction mixture was stirred at room temperature for 20 min and then iodomethane (1.08 mL, 17.35 mmol) was added. The reaction mixture was stirred at room temperature overnight, quenched with H$_2$O (30 mL), extracted with EtOAc (2×25 mL). The organic layers were dried over MgSO$_4$ and concentrated. The residue was purified by flash column chromatography (CH$_2$Cl$_2$ to 1% CH$_3$OH in CH$_2$Cl$_2$) to give colorless oil (0.639 g, 69%). $^1$H NMR (300 MHz, CDCl$_3$) δ 7.29–7.36 (5H, m), 5.12 (2H, s), 3.79 (2H, m), 3.50–3.55 (4H, m), 3.35 (s, 6H).

(iii) 3S,4S-Dimethoxy-pyrrolidine

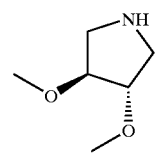

To a solution of 3S,4S-dimethoxy-pyrrolidine-1-carboxylic acid benzyl ester (0.639 g, 2.41 mmol) in EtOAc was added 10% Pd on C (0.135 mg). The reaction mixture was stirred under $H_2$ Balloon overnight, filtered thought Celite and concentrated under reduced pressure. The residue was used without further purification.

Example 1(s)

5-[2-(3S,4S-Dimethoxy-pyrrolidine-1-carbonyl)-thieno[3,2-b]pyridin-7-ylamino]-2-methyl-indole-1-carboxylic acid cyclopropylamide

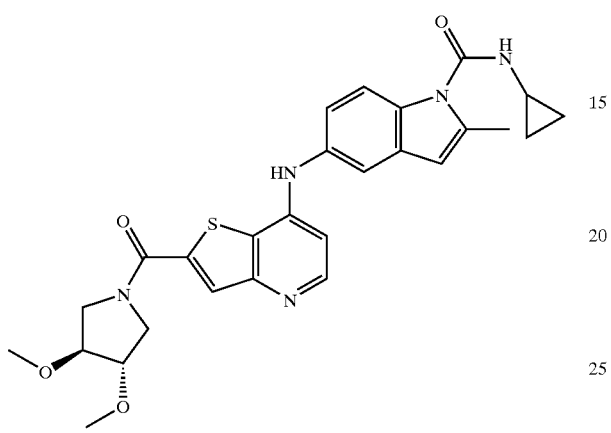

Example 1(s) was prepared in a similar manner as Example 1(r) except that cyclopropylamine was used in place of methylamine in step (ii). $^1$H NMR (300 MHz, $CD_3OD$) δ 8.12 (1H, d, J=5.65 Hz), 7.66 (1H, s), 7.59 (1H, d, J=8.87 Hz), 7.29 (1H, d, J=2.08 Hz), 7.03 (1H, dd, J=8.66, 2.07 Hz), 6.65 (1H, d, J=5.84 Hz), 6.23 (1H, s), 3.77–3.92 (4H, m), 3.33 (1H, s), 3.28 (3H, s), 3.19–3.20 (2H, m), 2.76–2.80 (1H, m), 2.41 (3H, s), 0.73–0.77 (2H, m), 0.62–0.65 (2H, m). MS (ESI+) [M+H]/z Calc'd 520, found 520. Anal. ($C_{27}H_{29}N_5O_4S.0.85H_2O$) C, H, N.

Example 1(t)

5-(2-[(S)-2-(methoxymethyl)pyrrolidine-1-carbonyl]thieno[3,2-b]pyridin-7-ylamino)-2-methylindole-1-carboxylic acid methylamide (2).

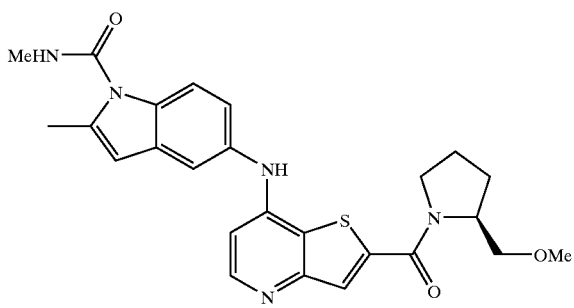

Example 1(t) was prepared in a similar manner as Example 1(a) except that S-2-methoxymethyl-pyrrolidine, was used instead of pyrrolidin-2R-yl-methanol in step (iv). $^1$H NMR (DMSO-$d_6$): δ 10.09 (1H, br s), 8.54 (1H, d, J=5.4 Hz), 8.27 (1H, q, J=4.5 Hz), 8.00 (1H, s), 7.68 (1H, d, J=9.0 Hz), 7.40 (1H, d, J=2.4 Hz), 7.07 (1H, dd, J=2.4, 9.0 Hz), 6.65 (1H, d, J=5.4 Hz), 6.40 (1H, s), 4.36–4.25 (1H, m), 3.93–3.76 (2H, m), 3.59–3.38 (2H, m), 3.27 (3H, s), 2.88 (3H, d, J=4.5 Hz), 2.48 (3H, s), 2.06–1.83 (4H, m). Anal. Calcd. for $C_{25}H_{27}N_5O_3S.0.5\ H_2O$: C, 61.71; H, 5.80; N, 14.39. Found: C, 61.92; H, 5.79; N, 14.33.

Example 1(u)

5-[2-(3S-Methoxy-pyrrolidine-1-carbonyl)-thieno[3,2-b]pyridin-7-ylamino]-2-methyl-2,3-dihydro-indole-1-carboxylic acid methylamide

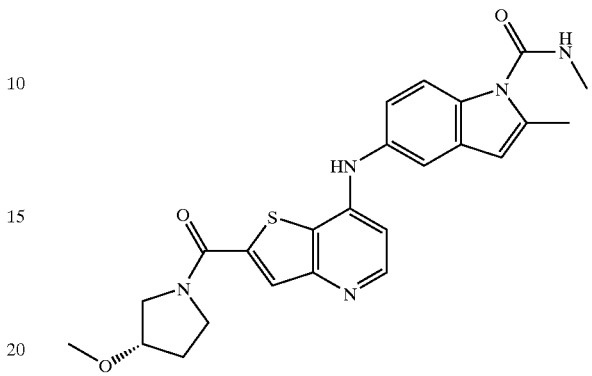

Example 1(u) was prepared in a similar manner as Example 1(g) except that 5-amino-2-methyl-2,3-dihydro-indole-1-carboxylic acid methylamide, prepared as described below, was used instead of 5-amino-2-methyl-indole-1-carboxylic acid methylamide in the final step. $^1$H NMR (300 MHz, $CD_3OD$) δ 8.21 (d, 1H, J=5.5 Hz), 7.81 (d, 1H, J=8.4 Hz), 7.75 (d, 1H, J=6.4 Hz), 7.12 (s, 1H), 7.07 (d, 1H, J=8.6 Hz), 6.73 (d, 1H, J=5.7 Hz), 4.46 (m, 1H), 4.10 (m, 1H), 3.86–3.99 (m, 2H), 3.64–3.79 (m, 2H), 3.41 (m, 1H), 3.36 (s, 3H), 2.82 (s, 3H), 2.67 (d, 1H, J=16 Hz), 2.02–2.25 (m, 2H), 1.25 (d, 3H, J=6.0 Hz). MS (ESI+) [M+H]/z Calc'd 466, found 466. Anal. ($C_{24}H_{27}N_5O_3S.0.4EtOAc.0.3H_2O$) C, H, N.

The starting material was prepared as follows:

(i) 5-Amino-2-methyl-2,3-dihydro-indole-1-carboxylic acid methylamide

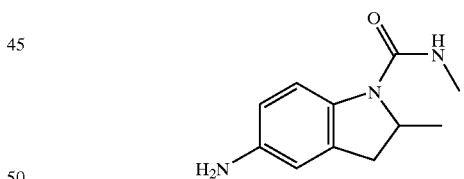

To a stirred solution of 2-methyl-5-nitro-indole-1-carboxylic acid methylamide (0.65 g, 2.78 mmol) in 20 mL EtOAc and 4 mL EtOH was added Pd on C (0.3 g, 10% w/w). The mixture was stirred under $H_2$ balloon at room temperature for one hour and filtered through a pad of silica gel. The filtrate was concentrated in vacuo. The residue was purified by flash column chromatography eluting with 1–3% MeOH in $CH_2Cl_2$ to give 140 mg 5-amino-2-methyl-indole-1-carboxylic acid methylamide (24% yield) together with 150 mg 5-amino-2-methyl-2,3-dihydro-indole-1-carboxylic acid methylamide (26% yield). $^1$H NMR (300 MHz, $CD_3OD$) δ 7.56 (d, 1H, J=6.2 Hz), 6.65 (s, 1H), 6.58 (d, 1H, J=6.1 Hz), 4.41 (m, 1H), 3.23–3.39 (m, 1H), 2.85 (s, 3H), 2.54 (d, 1H, J=15.5 Hz), 1.20 (d, 3H, J=6 Hz).

Example 1(v)
5-[2-(3S-Methoxy-pyrrolidine-1-carbonyl)-thieno[3,2-b]pyridin-7-ylamino]-2-methyl-2,3-dihydro-indole-1-carboxylic acid cyclopropylamide

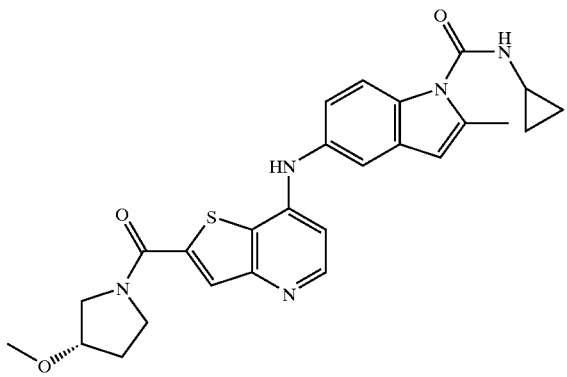

Example 1(v) was prepared in a similar manner as Example 1(u) except that cyclopropylamine was used instead of methylamine in step (ii). $^1$H NMR (300 MHz, CD$_3$OD) δ 8.20 (d, 1H, J=5.5 Hz), 7.84 (d, 1H, J=8.4 Hz), 7.73 (d, 1H, J=6.0 Hz), 7.10 (s, 1H), 7.07 (d, 1H, J=8.6 Hz), 6.74 (d, 1H, J=5.7 Hz), 4.46 (m, 1H), 4.10 (m, 1H), 3.88–3.98 (m, 2H), 3.62–3.78 (m, 2H), 3.39 (m, 1H), 3.35 (s, 3H), 2.58–2.69 (m, 2H), 2.04–2.26 (m, 2H), 1.23 (d, 3H, J=6.0 Hz), 0.74 (m, 2H), 0.57 (m, 2H). MS (ESI+) [M+H]/z Calc'd 492, found 492. Anal. (C$_{26}$H$_{29}$N$_5$O$_3$S.0.35EtOAc.0.4H$_2$O) C, H, N.

Example 2(a)
5-(2-[1-methyl-1H-imidazol-2-yl]thieno[3,2-b]pyridin-7-ylamino)-2-methylindole-1-carboxylic acid methylamide.

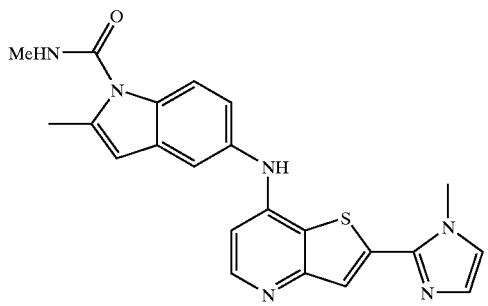

To a stirred slurry of 5-amino-2-methylindole-1-carboxylic acid methylamide (632 mg, 3.1 mmole), prepared in Example 1(a) step (iii), in 2-propanol (35 ml) was added 4.0 M HCl in 1,4-dioxane (0.75 ml, 3 mmole) followed by 7-chloro-2-(1-methyl-1H-imidazol-2-yl)thieno[3,2-b]pyridine (500 mg, 2 mmole), prepared as described in PCT application WO-99/24440, Example 149. The resultant solution was heated at reflux for 54 hours. After cooling to room temperature, the crude reaction mixture was poured into sat'd NaHCO$_3$ (150 ml), then diluted with water (50 ml). The precipitate that formed was collected by filtration, then washed with water (2×50 ml) and EtOAc (3×30 ml). The solid obtained was suspended in EtOAc (15 ml), filtered and washed with Et$_2$O (3×10 ml) to give 693 mg (83%) of a beige solid. $^1$H NMR (DMSO-d6): δ 8.76 (1H, s), 8.22 (1H, d, J=5.5 Hz), 8.20 (1H, q, J=5.4 Hz), 7.68 (1H, s), 7.60 (1H, d, J=8.7 Hz), 7.35 (1H, d, J=0.2 Hz), 7.34 (1H, d, J=1.9Hz), 7.08 (1H, dd, J=1.9, 8.7Hz), 6.98 (1H, d, J=0.2 Hz), 6.67 (1H, d, J=5.5Hz), 6.36 (1H, s), 3.94 (3H, s), 2.88 (3H, d, J=5.4 Hz), 2.48 (3H, s). Anal. Calcd. for C$_{22}$H$_{20}$N$_6$OS.1.0H$_2$O: C, 60.81; H, 5.10; N, 19.34; S, 7.38. Found: C, 60.53; H, 5.13; N, 19.07; S, 7.50.

Example 2(b)
5-(2-[(S)-2-(hydroxymethyl)pyrrolidine-1-carbonyl]thieno[3,2-b]pyridin-7-ylamino)-2-methylindole-1-carboxylic acid methylamide.

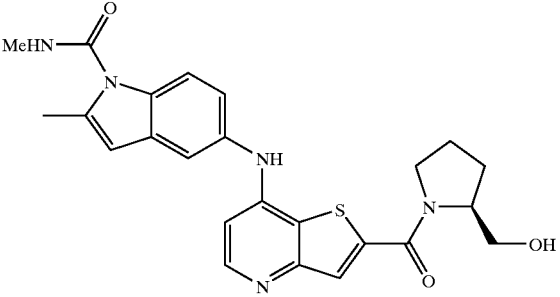

Example 2(b) was prepared in a similar manner as Example 2(a) except that 7-chloro-2-[(S)-2-([t-butyldimethylsilyloxy]methyl)-pyrrolidine-1-carbonyl]thieno[3,2-b]pyridine, prepared as described below, was used instead of 7-chloro-2-(1-methyl-1H-imidazol-2-yl)thieno[3,2-b]pyridine. $^1$H NMR (DMSO-d$_6$): δ 9.68 (1H, br s), 8.33 (1H, d, J=6.0 Hz), 8.26 (1H, q, J=4.5 Hz), 7.82 (1H, s), 7.65 (1H, d, J=8.7 Hz), 7.42 (1H, d, J=2.0 Hz), 7.12 (1H, dd, J=2.0, 8.7 Hz), 6.77 (1H, d, J=6.0 Hz), 6.39 (1H, s), 4.84 (1H, m), 4.23–4.04 (1H, m), 3.83–3.69 (2H, m), 3.59–3.38 (2H, m), 2.88 (3H, d, J=4.5 Hz), 2.48 (3H, s), 2.05–1.79 (4H, m). Anal. Calcd. for C$_{24}$H$_{25}$N$_5$O$_3$S.0.7H$_2$O:: C, 60.54; H, 5.59; N, 14.71. Found: C, 60.72; H, 5.74; N, 14.53.

The starting materials were prepared as follows:
(i) 7-chloro-2-[(S)-2-(hydroxymethyl)pyrrolidine-1-carbonyl]thieno[3,2-b]pyridine.

This material was prepared by the coupling of lithium 7-chlorothieno[3,2-b]pyridine-2-carboxylate and S-(+)-2-(hydroxymethyl)pyrrolidine in a manner as previously described for Example 1(a), step (iv) to give 4.95 g (55%) of an off-white solid. $^1$H NMR (DMSO-d6): δ 8.72 (1H, d, J=5.1 Hz), 8.08 (1H, s), 7.68 (1H, d, J=5.1 Hz), 4.27–4.13 (1H, m), 3.94–3.73 (2H, m), 3.67–3.44 (2H, m), 2.09–1.79 (4H, m). Anal. Calcd. for C$_{13}$H$_{13}$N$_2$O$_2$SCl: C, 52.61; H, 4.42; N, 9.44; S, 10.80; Cl, 11.95. Found: C, 52.61; H, 4.52; N, 9.62; S, 10.59; Cl, 11.96.

(ii) 7-chloro-2-[(S)-2-([t-butyldimethylsilyloxy]methyl)pyrrolidine-1-carbonyl]thieno[3,2-b]pyridine.

To a stirred solution of 7-chloro-2-[(S)-2-(hydroxymethyl)pyrrolidine-1-carbonyl]thieno[3,2-b]pyridine (4.50 g, 15 mmole) was added t-butyldimethylchlorosilane (3.18 g, 21 mmole) and triethylamine (3.4 ml, 2.47 g, 24 mmole). The resultant reaction mixture was stirred at ambient temperature for 16 hours. The crude reaction mixture was poured into water (150 ml) and extracted with CH$_2$Cl$_2$ (150 ml). The combined organic extracts were washed with brine (150 ml), dried over Na$_2$SO$_4$ and concentrated, in vacuo, to give 7.8 g of an orange syrup, which was purified by silica gel chromatography. Elution with Et$_2$O:hexane (67:33) and evaporation of the appropriate fractions gave 5.73 g (92%) of an off-white solid. $^1$H NMR (DMSO-d6): δ 8.72 (1H, d, J=5.0 Hz), 8.07 (1H, s), 7.68 (1H, d, J=5.0 Hz), 4.30–4.15 (1H, m), 3.94–3.67 (4H, m), 2.12–1.81 (4H, m), 0.85 (9H, s), 0.03 (3H, s), 0.00 (3H, s). Anal. Calcd. for C$_{19}$H$_{27}$N$_2$O$_2$SClSi: C, 55.52; H, 6.62; N, 6.82; S, 7.80; Cl, 8.63. Found: C, 55.49; H, 6.46; N, 6.92; S, 7.80; Cl, 8.88.

Example 2(c)

5-(2-[(S)-2-(methoxymethyl)pyrrolidine-1-carbonyl]thieno[3,2-b]pyridin-7-ylamino)-2-methylindole-1-carboxylic acid cyclopropylamide

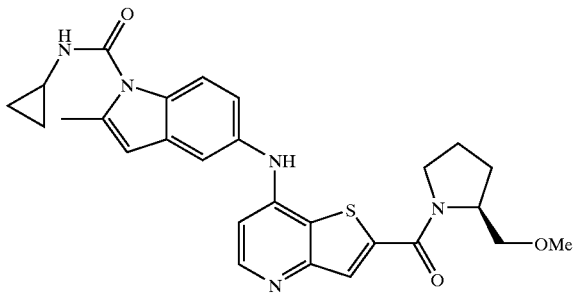

Example 2(c) was prepared in a similar manner as Example 2(b) except that S-2-(methoxymethyl)pyrrolidine was used instead of 7 S-(+)-2-(hydroxymethyl)pyrrolidine in step (i) and cyclopropyl amine was used instead of methylamine in the referenced procedure for Example 1(a), step (ii). $^1$H NMR (DMSO-$d_6$): δ 8.85 (1H, s), 8.50 (1H, d, J=3.3 Hz), 8.26 (1H, d, J=5.5 Hz), 7.80 (1H, s), 7.53 (1H, d, J=8.7 Hz), 7.34 (1H, d, J=1.9 Hz), 7.08 (1H, dd, J=1.9, 8.7 Hz), 6.70 (1H, d, J=5.5 Hz), 6.35 (1H, s), 4.37–4.21 (1H, m), 3.91–3.72 (2H, m), 3.59–3.47 (2H, m), 3.26 (3H, s), 2.88–2.79 (1H, m), 2.46 (3H, s), 2.06–1.81 (4H, m), 0.79–0.59 (4H, m). Anal. Calcd. for $C_{27}H_{29}N_5O_3S \cdot 0.8$ $CH_3OH \cdot 0.1$ $CH_2Cl_2$: C, 62.31; H, 6.07; N, 13.02; S, 5.96. Found: C, 62.38; H, 6.03; N, 12.84; S, 5.82.

Example 2(d)

5-(2-[1-methyl-1H-imidazol-2-yl]thieno[3,2-b]pyridin-7-ylamino)-2-methylindole-1-carboxylic acid cyclopropylamide

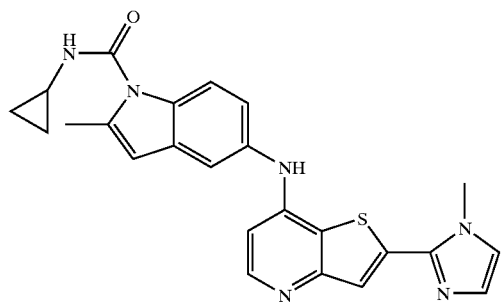

Example 2(d) was prepared in a similar manner as Example 2(a) except that cyclopropyl amine was used instead of methylamine in the referenced procedure for Example 1(a), step (ii). $^1$H NMR (DMSO-$d_6$): δ 8.78 (1H, s), 8.50 (1H, d, J=3.2 Hz), 8.22 (1H, d, J=5.5 Hz), 7.68 (1H, s), 7.53 (1H, d, J=8.7 Hz), 7.35 (1H, d, J=0.3 Hz), 7.34 (1H, d, J=1.9 Hz), 7.08 (1H, dd, J=1.9, 8.7 Hz), 6.98 (1H, d, J=0.3 Hz), 6.67 (1H, d, J=5.5 Hz), 6.35 (1H, s), 3.94 (3H, s), 2.88–2.79 (1H, m), 2.46 (3H, s), 0.79–0.62 (4H, m). Anal. Calcd. for $C_{24}H_{22}N_6OS \cdot 0.6$ $H_2O$: C, 63.58; H, 5.16; N, 18.54; S, 7.07. Found: C, 63.63; H, 5.19; N, 18.52; S, 7.02.

Example 2(e)

5-(2-[(S)-2-(hydroxymethyl)pyrrolidine-1-carbonyl]thieno[3,2-b]pyridin-7-ylamino)-2-methylindole-1-carboxylic acid cyclopropylamide

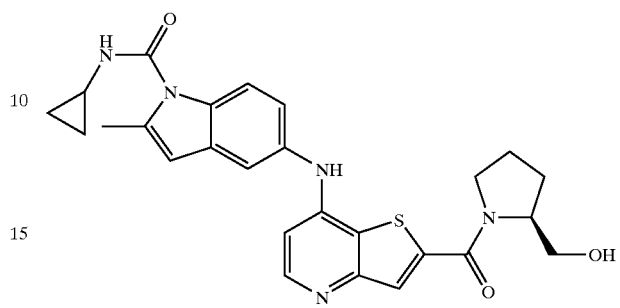

Example 2(e) was prepared in a similar manner as Example 2(b) except that cyclopropylamine was used instead of methylamine in the referenced procedure for Example 1(a), step (ii). $^1$H NMR (DMSO-$d_6$): δ 8.85 (1H, s), 8.51 (1H, d, J=2.8 Hz), 8.27 (1H, d, J=5.4 Hz), 7.80 (1H, s), 7.53 (1H, d, J=8.6 Hz), 7.35 (1H, d, J=1.5 Hz), 7.08 (1H, dd, J=1.5, 8.6 Hz), 6.71 (1H, d, J=5.4 Hz), 6.35 (1H, s), 5.11–4.76 (1H, m), 4.39–4.11 (1H, m), 3.91–3.72 (2H, m), 3.62–3.44 (2H, m), 2.88–2.78 (1H, m), 2.46 (3H, s), 2.08–1.79 (4H, m), 0.82–0.59 (4H, m). Anal. Calcd. for $C_{26}H_{27}N_5O_3S \cdot 0.75$ $CH_2Cl_2$: C, 58.07; H, 5.19; N, 12.66; S, 5.80. Found: C, 58.08; H, 5.27; N, 12.44; S, 5.74.

Example 2(f)

5-(2-[1-methyl-1H-imidazol-2-yl]thieno[3,2-b]pyridin-7-ylamino)-2-methylindole-1-carboxylic acid isopropylamide

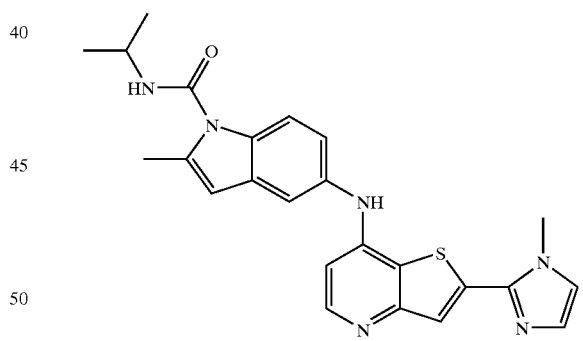

Example 2(f) was prepared in a similar manner to Example 2(a) except that 5-amino-2-methylindole-1-carboxylic acid cyclopropylamide, prepared as described below, was used instead of 5-amino-2-methylindole-1-carboxylic acid methylamide. $^1$H NMR (DMSO-$d_6$): δ 8.76 (1H, s), 8.22 (1H, d, J=5.5 Hz), 8.20 (1H, q, J=5.4 Hz), 7.81 (1H, d, J=8.5 Hz), 7.68 (1H, s), 7.36 (1H, d, J=0.2 Hz), 7.09 (1H, d, J=1.5 Hz), 7.01 (1H, dd, J=1.5, 8.5 Hz), 7.00 (1H, d, J=0.2 Hz), 6.67 (1H, d, J=5.5 Hz), 6.36, 6.34 (1H, s), 4.64–4.52 (1H, m), 3.95 (3H, s), 2.88 (3H, d, J=5.4 Hz), 2.64, 2.59 (3H, s) 1.14, 1.13 (6H, d, J=6.6 Hz). Anal. Calcd. for $C_{22}H_{20}N_6OS \cdot 0.8$ $H_2O \cdot 0.2$ $Et_2O$: C, 62.87; H, 5.87; N, 17.74. Found: C, 62.91; H, 6.07; N, 17.70.

The starting materials were prepared as follows:

(i) 2-methyl-5-nitroindole-1-carboxylic acid cyclopropylamide.

A solution of 2.5 M n-butyllithium in hexanes (1.5 ml, 3.75 mmole) was added, dropwise, to a solution of 2-methyl-5-nitroindole (525 mg, 3 mmole) in THF (10 ml) at −75°. This mixture was stirred for 20 minutes at −75° prior to addition of isopropyl isocyanate (3 ml, 2.60 g, 30 mmole). The cooling bath was removed and the reaction was stirred for a further 6 hours, then poured into water (20 ml) and extracted with ether (2×25 ml). The combined organic extracts were dried over $Na_2SO_4$ and concentrated, in vacuo. The residue obtained was triturated from hexane to give 690 mg (86%) of a yellow solid. $^1$H NMR (DMSO-$d_6$): δ 8.58 (1H, d, J=7.2 Hz), 8.46(1H, d, J=2.3 Hz), 8.03 (1H, dd, J=2.3, 9.1 Hz), 7.65 (1H, d, J=9.1 Hz), 6.61 (1H, s), 4.10–3.88 (1H, m), 2.41 (3H, s), 1.23 (6H, d, J=6.6 Hz).

(ii) 5-amino-2-methylindole-1-carboxylic acid cyclopropylamide.

This material was prepared by the reduction of 2-methyl-5-nitroindole-1-carboxylic acid in a manner as previously described for Example 1(a), step (iii), method A. $^1$H NMR (DMSO-$d_6$): δ 7.45 (1H, d, J=8.4 Hz), 6.48 (1H, d, J=1.2 Hz), 6.32 (1H, dd, J=1.2, 8.4 Hz), 6.00, 5.98 (1H, s), 4.71–4.49 (2H, m), 3.95–3.77 (1H, m), 2.44, 2.39 (3H, s), 1.11, 1.10(6H, d, J=6.7 Hz).

Example 2(g)

5-(2-[(S)-2-(hydroxymethyl)pyrrolidine-1-carbonyl]thieno[3,2-b]pyridin-7-ylamino)-2-methylindole-1-carboxylic acid isopropylamide

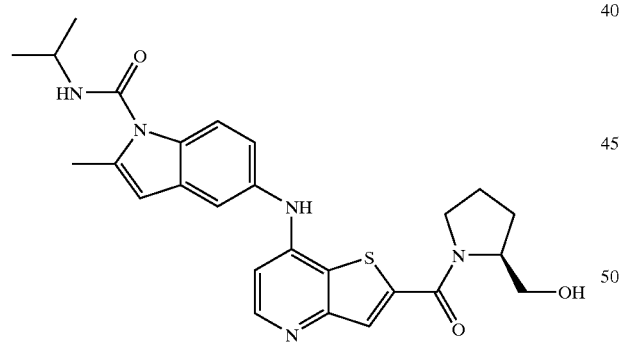

Example 2(g) was prepared in a similar manner as Example 2(b) except that 5-amino-2-methylindole-1-carboxylic acid cyclopropylamide was used instead of 5-amino-2-methylindole-1-carboxylic acid methylamide. $^1$H NMR (DMSO-$d_6$): δ 8.81 (1H, s), 8.23(1H, d, J=5.4 Hz), 7.72 (1H, s), 7.52 (1H, d, J=8.6 Hz), 7.32 (1H, d, J=1.5 Hz), 7.06 (1H, dd, J=1.5, 8.6 Hz), 6.71 (1H, d, J=5.4 Hz), 6.36, 6.34 (1H, s), 5.09–4.86 (1H, m), 4.63–4.53 (1H, m), 4.39–4.11 (1H, m), 3.93–3.74 (2H, m), 3.63–3.45 (2H, m), 2.46, 2.43 (3H, s), 2.06–1.76 (4H, m), 1.12, 1.10 (6H, d, J=6.6 Hz). Anal. Calcd. for $C_{26}H_{29}N_5O_3S.2.2\ H_2O$: C, 58.78; H, 6.34; N, 13.18. Found: C, 58.82; H, 6.09; N, 12.78.

Example 3(a)

5-{2-[4-(1-Hydroxy-1-methyl-ethyl)-thiazol-2-yl]-thieno[3,2-b]pyridin-7-ylamino}-2-methyl-indole-1-carboxylic acid methylamide

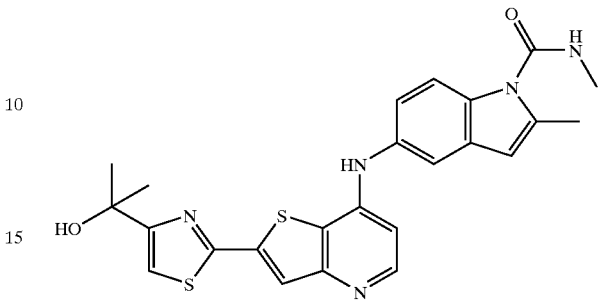

Example 3(a) was prepared in a similar manner to Example 1(a) except that the reaction was carried out in DMSO at 100° C. and that 2-[2-(7-Chloro-thieno[3,2-b]pyridin-2-yl)-thiazol-4-yl]-propan-2-ol, prepared in example 27 of section A of U.S. Ser. No. 60/209,686, filed Jun. 6, 2000, hereby incorporated by reference in its entirety for all purposes, was used instead of (7-chloro-thieno[3,2,b]pyridin-2-yl)-(2R-hydroxymethyl-pyrrolidin-1-yl)-methanone. Purification was through a flash column eluting with $EtOAc:CH_2Cl_2:MeOH$ (1:1:0.1) and subsequent concentration that provided the product as a yellow solid (0.48 g, 51% yield). HPLC: $R_t$ 3.77 min. (95% area). $^1$H NMR (CDCl$_3$, 400 MHz) δ: 9.14 (1H, s), 8.43 (1H, d, J=5.5 Hz), 8.37 (1H, d, J=4.3 Hz), 8.09 (1H, s), 7.79 (1H, d, J=8.5 Hz), 7.71 (1H, s), 7.56 (1H, s), 7.28 (1H, d, J=8.8 Hz), 6.90 (1H, d, J=5.5 Hz), 6.54 (1H, s), 5.47 (1H, s), 3.05 (3H, d, J=4.6 Hz), 2.71 (3H, s), 1.66 (6H, s). HRMS (ESI) $C_{24}H_{23}N_5O_2S_2$ (M+H$^+$) m/z: Calc. 478.1377, Found 478.1392. Anal. ($C_{24}H_{23}N_5O_2S_2.0.EtOAc$) Calc'd: C, 59.60; H, 5.41: N, 12.78. Found C, 59.57; H, 5.16; N, 12.90.

Example 3(b)

5-{2-[4-(1-Hydroxy-1-methyl-ethyl)-thiazol-2-yl]-thieno[3,2-b]pyridin-7-ylamino}-2-methyl-indole-1-carboxylic acid cyclopropylamide

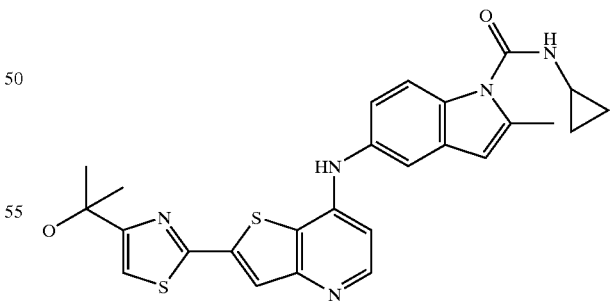

Example 3(b) was prepared in a similar manner to Example 3(a) except that cyclopropyl amine was used instead of methylamine (0.11 g, 40% yield). HPLC: $R_t$ 3.98 min. (100% area). HRMS (ESI) $C_{26}H_{25}\ N_5O_2S_2$ (M+H$^+$) m/z: Calc. 504.1533, Found 504.1541. Anal. ($C_{26}H_{25}N_5O_2S_2.0.5H_2O$) Calc'd: C, 60.90; H, 5.11: N, 13.66. Found C, 61.25; H, 5.14; N, 13.45.

Example 3(c)

2-[7-(2-Methyl-1-methylcarbamoyl-1H-indol-5-ylamino)-thieno[3,2-b]pyridin-2-yl]-thiazole-4-carboxylic acid ethyl ester

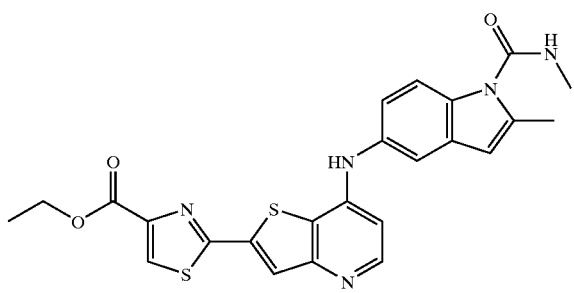

Example 3(c) was prepared in a similar manner to Example 3(a) except that 2-(7-Chloro-thieno[3,2-b]pyridin-2-yl)-thiazole-4-carboxylic acid ethyl ester, prepared in example 26 of section C of PC10795A, was used instead of (7-chloro-thieno[3,2-b]pyridin-2-yl)-(2R-hydroxymethyl-pyrrolidin-1-yl)-methanone (0.0.42 g, 30% yield). HPLC: $R_t$ 4.03 min. (100% area). HRMS (ESI) $C_{24}H_{23}N_5O_2S_2$ (M+H$^+$) m/z: Calc. 478.1377, Found 478.1392. Anal. ($C_{24}H_{21}N_5O_3S_2 \cdot 1H_2O$ & $0.2CH_2Cl_2$) Calc'd: C, 55.19; H, 4.48; N, 13.30. Found C, 55.14; H, 4.62; N, 12.99.

Example 3(d)

5-{2-[(2S,4R)-4-Hydroxy-2-(1-hydroxy-1-methyl-ethyl)-pyrrolidine-1-carbonyl]-thieno[3,2-b]pyridin-7-ylamino}-2-methyl-indole-1-carboxylic acid methylamide

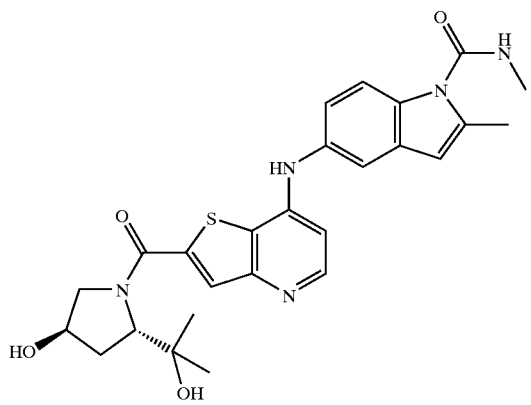

Example 3(d) was prepared in a similar manner to Example 3(a) except that (7-Chloro-thieno[3,2-b]pyridin-2-yl)-[(2S,4R)-4-hydroxy-2-(1-hydroxy-1-methyl-ethyl)-pyrrolidin-1-yl]-methanone, prepared as described below, was used instead of 2-[2-(7-Chloro-thieno[3,2-b]pyridin-2-yl)-thiazol-4-yl]-propan-2-ol (0.086 g, 33% yield) as white solid. HPLC: $R_t$ 3.13 min. (100% area). $^1$H NMR (DMSO-d$_6$, 300 MHz) δ: 8.94 (1H, s), 8.36 (1H, t, J=2.1 Hz), 8.30–8.26 (1H, m), 7.85 (1H, s), 7.67 (1H, d, J=8.5 Hz), 7.43 (1H, s), 7.15 (1H, dd, J=8.7, 1.8), 6.78 (1H, t, J=4.9 Hz), 6.43 (1H, s), 4.76 (1H, s), 3.90–3.78 (2H, m), 2.95 (3H, d, J=4.2 Hz), 2.20 (1H, bs), 1.88–1.72 (2H, m), 1.30 (1H, bs), 1.17 (3H, s), 1.12 (3H, s). HRMS (ESI) $C_{26}H_{29}N_5O_4S$ (M+H$^+$) m/z: Calc. 504.1994, Found 508.2018. Anal. ($C_{26}H_{29}N_5O_4S \cdot 0.2EtOAc$) Calc'd: C, 60.90; H, 5.11: N, 13.66. Found: C, 61.25; H, 5.14; N, 13.45.

The starting materials were prepared as follows:

(i) (2S,4R)-1-(7-Chloro-thieno[3,2-b]pyridine-2-carbonyl)-4-hydroxy-pyrrolidine-2-carboxylic acid methyl ester In 10 mL of DMF was added 3.0 g (16.7 mmol) of 7-Chloro-thieno[3,2-b]pyridine-2-carboxylic acid lithium salt, 3.20 g (14.66 mmol) of (2S,4R)-4-Hydroxy-pyrrolidine-2-carboxylic acid methyl ester hydrochloride, PyBop (9.12 g (17.5 mmol) and 5.59 mL (32.1 mmol) of DIEA and the mixture was stirred for 24 h. To the mixture was added 50 mL of EtOAc was washed with 50/50 aq. NaHCO$_3$ (2×50 mL). The organic layer was dried over Na$_2$SO$_4$ and concentrated to give an amber oil. Purification through 100 mL of silica eluting with EtOAc:CH$_2$Cl$_2$ (1:1) gave crude product. Diethyl ethyl was used to triturate (2×5 mL) the residue to afford 3.43 g (70%) of (2S,4R)-1-(7-Chloro-thieno[3,2-b]pyridine-2-carbonyl)-4-hydroxy-pyrrolidine-2-carboxylic acid methyl ester as off-white solid. HPLC: $R_t$ 3.36 min. (98.2% area). LCMS (ESI) (M+H$^+$) m/z: 341.0.

(ii) (7-Chloro-thieno[3,2-b]pyridin-2-yl)-[(2S,4R)-4-hydroxy-2-(1-hydroxy-1-methyl-ethyl)-pyrrolidin-1-yl]-methanone.

In 5 mL of anhydrous THF was added 0.60 g (1.761 mmol) of (2S,4R)-1-(7-Chloro-thieno[3,2-b]pyridine-2-carbonyl)-4-hydroxy-pyrrolidine-2-carboxylic acid methyl ester then cooled to −78 °C. under a Nitrogen atmosphere. To the mixture was then added 1.76 mL (5.28 mmol) of methyl bromo Grignard (3.0 M in THF) drop-wise over 10 min. and the solution was stirred at 0° C. for 3 h. The reaction was quenched with 1 mL of NaHCO$_3$ and 50 mL of EtOAc and was washed with 50/50 NaHCO$_3$ (2×50 mL). The organic layer was dried over Na$_2$SO$_4$ and concentrated. The residue was purified through silica (30 mL) eluting with EtOAc:CH$_2$Cl$_2$:MeOH (7:2:0.1). The uncontaminated fractions were combined and concentrated to give 0.24 g (40%) of (7-Chloro-thieno[3,2-b]pyridin-2-yl)-[(2S,4R)-4-hydroxy-2-(1-hydroxy-1-methyl-ethyl)-pyrrolidin-1-yl]-methanone as a white foam. HPLC: $R_t$ 3.14 min. (98.2% area). LCMS (ESI) (M+H$^+$) m/z: 341.1.

Example 3(e)

5-{2-[(2S,4R)-4-Hydroxy-2-(1-hydroxy-1-methyl-ethyl)-pyrrolidine-1-carbonyl]-benzo[b]thiophen-7-ylamino}-2-methyl-indole-1-carboxylic acid cyclopropylamide

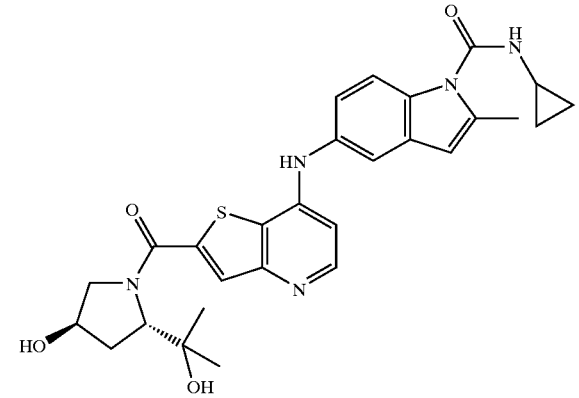

Example 3(e) was prepared in a similar manner to Example 3(d) except that cyclopropylamine was used istead of methylamine (0.042 g, 16% yield). HPLC: $R_t$ 3.35 min. (100% area). $^1$H NMR (DMSO-d$_6$, 300 MHz) δ: 8.74 (1H, s), 8.38 (1H, t, J=2.1 Hz), 8.13 (1H, d, J=5.1 Hz), 7.65 (1H, s), 7.40 (1H, d, J=8.8 Hz), 7.21 (1H, s), 6.94 (1H, d, J=8.4), 6.56 (1H, d, J=5.3 Hz), 6.21 (1H, s), 4.61 (1H, d, J=25.7 Hz), 4.27 (1H, t, J=7.9 Hz), 4.10 (1H, bs), 3.66–3.47 (2H, m), 2.85 (1H, d, J=3.3 Hz), 2.74–2.69 (1H, m), 2.32 (3H, s), 2.01–1.97 (1H, m), 1.63–1.58 (2H, m), 0.96 (3H, s), 0.91 (3H, s), 0.71–0.60 (2H, m), 0.52 (2H, bs). HRMS (ESI) $C_{28}H_{31}N_5O_4S$ (M+H$^+$) m/z: Calc. 534.2175, Found 534.2164. Anal. ($C_{28}H_{31}N_5O_4S \cdot 0.6CH_2Cl_2$) Calc'd: C, 57.86; H, 5.55: N, 11.98. Found: C, 57.71; H, 5.69; N, 11.74.

Example 3(f)

5-[2-((2S,4R)-2-Hydroxymethyl-4-methoxy-pyrrolidine-1-carbonyl)-benzo[b]thiophen-7-ylamino]-2-methyl-indole-1-carboxylic acid methylamide

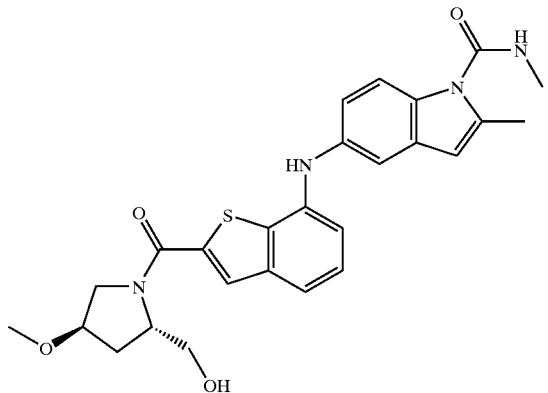

The compound 7-(2-Methyl-1-methylcarbamoyl-1H-indol-5-ylamino)-thieno[3,2-b]pyridine-2-carboxylic 0.125 g (0.33 mmol), prepared as described below in step (i), was dissolved in 1 mL of DMF. Added to this reaction mixture was (2S,4R)-4-Methoxy-pyrrolidin-2-yl)-methanol 0.051 g (0.40 mmol), prepared as described below in step (ii)–(iv), PyBop 0.22 g (0.43 mmol) and DIEA 0.13 mL (0.73 mmol) and the mixture was stirred for 12 h. The solution then was added to 50 mL of EtOAc and was washed with Sat. NaHCO$_3$ (2×50 mL). The organic layer was dried over NaSO$_4$ and concentrated. The residue was loaded onto 2-mm Chromatron plate and eluted with EtOAc:CH$_2$Cl$_2$:MeOH (1:1:0.1). The purified fractions were concentrated together to give 5-[2-((2S,4R)-2-Hydroxymethyl-4-methoxy-pyrrolidine-1-carbonyl)-benzo[b]thiophen-7-ylamino]-2-methyl-indole-1-carboxylic acid methylamide 0.10 g (63%) as yellow powder after precipitating from EtOAc:Hexane (1:1). HPLC: R$_t$ 3.29 min. (100% area). $^1$H NMR (CDCl$_3$, 400 MHz) δ: 8.92 (1H, s), 8.34 (1H, d, J=5.3 Hz), 8.27 (1H, d, J=4.3 Hz), 7.84 (1H, s), 7.69 (1H, d, J=8.6 Hz), 7.43 (1H, s), 7.16 (1H, d, J=7.3 Hz), 6.78 (1H, d, J=5.3 Hz), 6.43 (1H, s), 6.54 (1H, s), 4.88 (1H, t, J=5.3 Hz), 4.28 (1H, bs), 4.09 (1H, q, J=7.1 Hz), 3.97–3.94 (2H, m), 3.78–3.75 (1H, m), 3.58 (1H, bs), 3.23 (3H, s), 2.94 (3H, d, J=4.3 Hz), 2.16–2.10 (2H, m). HRMS (ESI) $C_{25}H_{27}N_5O_4S$ (M+H$^+$) m/z: Calc. 494.1863, Found 494.1876. Anal. ($C_{25}H_{27}N_5O_4S \cdot 0.2CH_2Cl_2$) Calc'd: C, 59.28; H, 5.41: N, 13.72. Found: C, 59.62; H, 5.46; N, 13.44.

The starting materials were prepared as described below:

(i) 7-(2-Methyl-1-methylcarbamoyl-1H-indol-5-ylamino)-thieno[3,2-b]pyridine-2-carboxylic acid

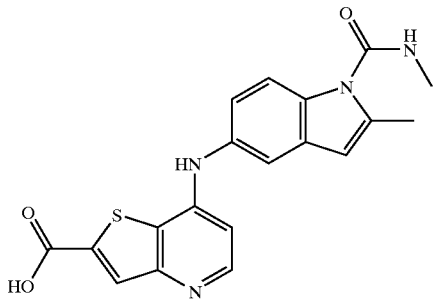

To 0.68 g (1.23 mmol) of 7-Chloro-thieno[3,2-b]pyridine-2-carboxylic acid, prepared as described in Groton patent, was added 0.25 g (1.23 mmol) of 5-Amino-2-methyl-indole-1-carboxylic acid methylamide, prepared as described in Example 1(a) steps (i) to (iii), dissolved in 3 mL of DMSO that was degassed with Ar and warmed to 75° C. The solution was stirred for 14 h, cooled to 25° C. and filtered. The precipitate was rinsed with EtOAc (2×5 mL) and put under high vacuum for 12 h to give 0.43 g (98%) of 7-(2-Methyl-1-methylcarbamoyl-1H-indol-5-ylamino)-thieno[3,2-b]pyridine-2-carboxylic acid as yellow solid. HPLC: R$_t$ 3.38 min. (97.2% area). $^1$H NMR (CDCl$_3$, 300 MHz) δ 9.18 (1H, bs), 8.37 (1H, d, J=5.6 Hz), 8.30 (1H, q, J=3.4 Hz), 7.94 (1H, s), 7.70 (1H, d, J=8.7 Hz), 7.46 (1H, s), 7.17 (1H, dd, J=8.8, 1.9 Hz), 6.79 (1H, d, J=5.6 Hz), 6.45 (1H, s), 2.96 (3H, s), 2.94 (3H, s). LCMS (APCI) (M+H$^+$) m/z: 381.1

(ii) (2S,4R)-4-Methoxy-pyrrolidine-1,2-dicarboxylic acid 1-benzyl ester 2-methyl ester

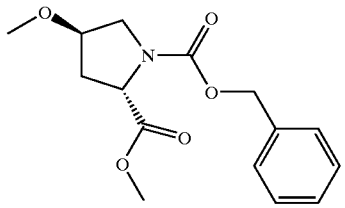

To 2.00 g (7.16 mmol) of (2S,4R)-4-Hydroxy-pyrrolidine-1,2-dicarboxylic acid 1-benzyl ester 2-methyl ester in 20 mL of acetone was added 5.64 g of silver oxide (24.3 mmol) and 1.56 mL of iodomethane (25.0 mmol) and the mixture was stirred at 57° C. for 28 h. The solution was cooled to 25° C., filtered through celite and concentrated. Purification was through 50 mL of silica by eluting with EtOAc:Hexane (8:1) and the purified fractions were concentrated to give a 2.0 g (96%) of (2S,4R)-4-Methoxy-pyrrolidine-1,2-dicarboxylic acid 1-benzyl ester 2-methyl ester as a clear oil. HPLC: R$_t$ 3.79 min. (100% area). ¹H NMR (CDCl$_3$, 400 MHz) δ: 7.31–7.23 (5H, m), 5.22–5.00 (2H, m), 4.44–4.40 (1H, m), 4.10–4.02 (1H, m), 3.76 (3H, s), 3.69–3.60 (1H, m), 3.54 (2H, s), 3.29 (3H, bs), 2.42–2.30 (1H, m). LCMS (ESI) (M+Na$^+$) m/z: 316.1.

(iii) (2S,4R)-2-Hydroxymethyl-4-methoxy-pyrrolidine-1-carboxylic acid benzyl ester

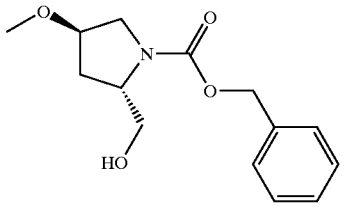

To 5 mL of anhydrous THF was added 1.50 g (5.62 mmol) of (2S,4R)-4-Methoxy-pyrrolidine-1,2-dicarboxylic acid 1-benzyl ester 2-methyl ester and the mix was cooled to 0° C. To reaction mixture was added 3.34 mL of LiBH$_4$ (2.0 M in THF) drop-wise over 5 min and was then stirred for 2 h. The mixture was quenched with 1 mL of Sat. NaHCO$_3$, diluted with 50 mL of EtOAc and washed with Sat. NaHCO$_3$ (2×50 mL). The organic layer was dried over NaSO$_4$ and concentrated to give an amber oil. Purification was accomplished through 50 mL of silica eluting with EtOAc/CH$_2$Cl$_2$ (7:3). The pure factions were combined, concentrated and subsequently put on the high vacuum for 24 h to give 1.3 g (92%) of (2S, 4R)-2-Hydroxymethyl-4-methoxy-pyrrolidine-1-carboxylic acid benzyl ester as clear oil. HPLC: R$_t$ 3.41 min. (100% area). ¹H NMR (CDCl$_3$, 300 MHz) δ; 7.51–7.38 (5H, m), 5.24–5.00 (2H, m), 4.45–4.40 (1H, m), 4.23–4.18 (1H, m), 3.95–3.73 (3H, m), 3.51–3.42 (1H, m), 3.31 (3H, s), 2.22–2.14 (1H, m). LCMS (APCI) (M+H$^+$) m/z: 266.2.

(iv) ((2S,4R)-4-Methoxy-pyrrolidin-2-yl)-methanol

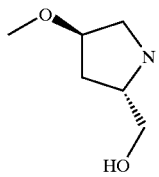

To 1.00 g (5.62 mmol) of (2S,4R)-2-Hydroxymethyl-4-methoxy-pyrrolidine-1-carboxylic acid benzyl ester in 3 mL of MeOH was added 0.1 g of 10% Pd(C) under 1 atmosphere of H$_2$ while stirring for 12 h. The mixture was filtered through 0.22 µM Teflon filter concentrated and put under high vacuum for 2 h to give 0.44 g (96%) of ((2S,4R)-4-Methoxy-pyrrolidin-2-yl)-methanol as clear oil. LCMS (APCI) (M+H$^+$) m/z: 266.2.

Example 3(g)
5-[2-((2S,4R)-2-Hydroxymethyl-4-methoxy-pyrrolidine-1-carbonyl)-benzo[b]thiophen-7-ylamino]-2-methyl-indole-1-carboxylic acid cyclopropylamide

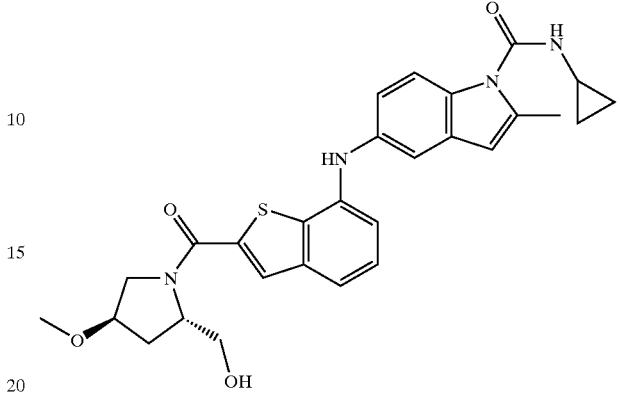

Example 3(g) was prepared in a similar manner to Example 3(f) except that cyclopropylamine was used instead of methylamine (0.181 g, 60% yield). HPLC: R$_t$ 3.42 min. (100% area). ¹H NMR (CDCl$_3$, 400 MHz) δ: 8.94 (1H, s), 8.58 (1H, d, J=3.0 Hz), 8.34 (1H, d, J=5.3 Hz), 7.84 (1H, s), 7.61 (1H, d, J=8.6 Hz), 7.43 (1H, d, J=1.8), 7.16(1H, dd, J=8.8, 2.0 Hz), 6.78 (1H, d, J=5.6 Hz), 6.43 (1H, s), 6.54 (1H, s), 4.86 (1H, t, J=5.5 Hz), 4.28 (1H, bs), 4.09 (1H, bs), 3.95–3.89 (2H, m), 3.78–3.75 (1H, m), 3.60–3.58 (1H, m), 3.23 (3H, s), 2.94–2.89 (1H, m), 2.56 (3H, m), 2.15 (2H, t, J=7.3 Hz), 0.84–0.82 (2H, m), 0.74–0.71 (2H, m). HRMS (ESI) C$_{27}$H$_{29}$N$_5$O$_4$S (M+H$^+$) m/z: Calc. 520.2019, Found 520.2020. Anal. (C$_{27}$H$_{29}$N$_5$O$_4$S.0.3EtOAc) Calc'd: C, 62.03; H, 5.80; N, 12.83; S, 5.87. Found: C, 61.80; H, 5.95; N, 13.01; S, 5.87.

Example 3(h)
5-[2-((2S,4R)-4-Hydroxy-2-methoxymethyl-pyrrolidine-1-carbonyl)-thieno[3,2-b]-pyridin-7-ylamino-2-methyl-indole-1-carboxylic acid cyclopropylamide

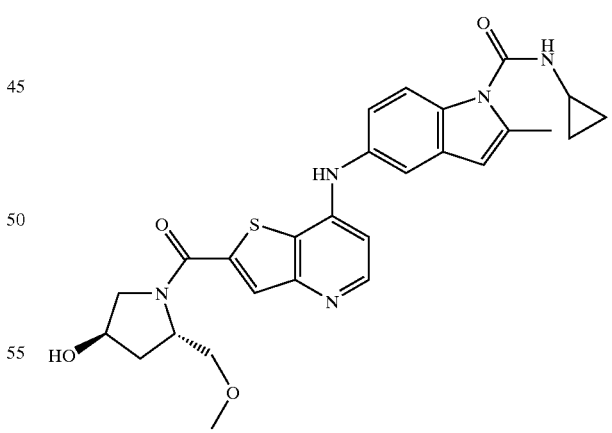

Example 3(h) was prepared in a similar manner to Example 3(f) except that (3R,5S)-5-Methoxymethyl-pyrrolidin-3-ol, prepared as described below, was used instead of (2S,4R)-4-Methoxy-pyrrolidin-2-yl)-methanol (0.181 g, 60% yield). HPLC: R$_t$ 3.39 min. (100% area). ¹H NMR (CDCl$_3$, 400 MHz) δ: 8.92 (1H, s), 8.58 (1H, d, J=3.0 Hz), 8.34 (1H, d, J=5.5 Hz), 7.80 (1H, s), 7.61 (1H, d, J=8.8 Hz), 7.41 (1H, s), 7.15 (1H, dd, J=8.8), 6.77 (1H, d, J=5.5

Hz), 6.42 (1H, s), 5.03 (1H, s), 4.43–4.38 (2H, m), 3.96 (1H, d, J=9.6), 3.78–3.74 (1H, m), 3.33 (3H, s), 2.93–2.89 (1H, m), 2.52 (3H, s), 2.07–1.96 (2H, m), 0.83 (2H, d, J=5.3), 0.73 (2H, d, J=2.5 Hz). HRMS (ESI) $C_{27}H_{29}N_5O_4S$ (M+H$^+$) m/z: Calc. 520.2019, Found 520.2014. Anal. ($C_{27}H_{29}N_5O_4S \cdot 0.3CH_2Cl_2$) Calc'd: C, 60.88; H, 5.52; N, 13.05. Found: C, 61.14; H, 5.55; N, 12.96.

The starting materials were prepared as follows:

(i) (2S,4R)-4-Trimethylsilanyloxy-pyrrolidine-1,2-dicarboxylic acid 1-benzyl ester 2-methyl ester

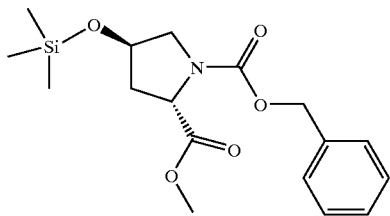

Dissolved (2S,4R)-4-Hydroxy-pyrrolidine-1,2-dicarboxylic acid 1-benzyl ester 2-methyl ester 1.5 g (5.37 mmol) in 10 mL of THF was treated with DIEA 1.31 mL (7.51 mmol) and 0.89 mL of TMS-Cl (6.98 mmol) added drop-wise while stirring. After 2 h of stirring, 50 mL of EtOAc was added and the mix was washed with Sat. NaHCO$_3$ (3×50 mL). The organic layer was then dried over Na$_2$SO$_4$, filter through silica and concentrated to afford 1.84 g (97%) of (2S,4R)-4-Trimethylsilanyloxy-pyrrolidine-1,2-dicarboxylic acid 1-benzyl ester 2-methyl ester as a clear oil. HPLC: R$_t$ 4.12 min. (100% area). $^1$H NMR (CDCl$_3$, 400 MHz) δ: 7.37–7.28 (5H, m), 5.22–5.01 (2H, m), 4.51–4.41 (2H, m), 3.76 (2H, s), 3.70–3.66 (1H, m), 3.51–3.39.(1H, m), 2.22–2.16 (1H, m), 2.04 (3H, s), 0.11 (9H, s).

(ii) (2S,4R)-2-Hydroxymethyl-4-trimethylsilanyloxy-pyrrolidine-1-carboxylic acid benzyl ester

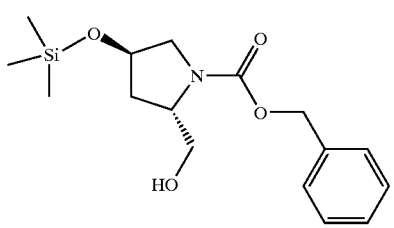

To (2S,4R)-4-Trimethylsilanyloxy-pyrrolidine-1,2-dicarboxylic acid 1-benzyl ester 2-methyl ester 1.50 g (4.22 mmol) in 5 mL of anhydrous THF under an atmosphere of Ar in an ice bath, was added 2.56 mL LiBH$_4$ (2.0 M in THF, 5.12 mmol) drop-wise. The solution was stirred for 3 h. The mixture was quenched with 1 mL of Sat. NaHCO$_3$ and EtOAc (50 mL). The organics were washed with Sat. NaHCO$_3$ (2×50 mL). The organic layer was dried over Na$_2$SO$_4$ and the solution was concentrated to afford 1.31 g (96%) of (2S,4R)-2-Hydroxymethyl-4-trimethylsilanyloxy-pyrrolidine-1-carboxylic acid benzyl ester as clear oil. HPLC: R$_t$ 2.87 min. (100% area). $^1$H NMR (CDCl$_3$, 400 MHz) δ 7.26–7.20 (5H, m), 5.05 (2H, s), 4.47 (1H, d, J=7.4 Hz), 4.20 (1H, bs), 4.08 (1H, q, J=7.3 Hz), 3.64 (1H, t, J=9.1 Hz), 3.51–3.47 (1H, m), 3.41–3.35 (2H, m), 1.89–1.84 (1H, m), 1.57–1.52 (1H, m), 0.11 (9H, s). LCMS (ESI) (M+H$^+$) m/z: 324.2.

(iii) (2S,4R)-2-Methoxymethyl-4-trimethylsilanyloxy-pyrrolidine-1-carboxylic acid benzyl ester

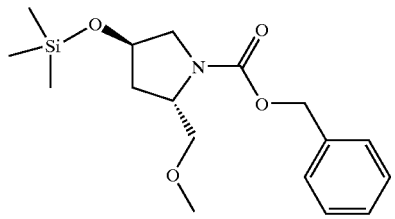

To (2S,4R)-2-Hydroxymethyl-4-trimethylsilanyloxy-pyrrolidine-1-carboxylic acid benzyl ester in 10 mL of acetone was added iodomethane 0.86 mL (13.5 mmol), silver oxide 3.04 g (13.2 mmol) and the solution was warmed to 57° C. for 8 h. The mixture was cooled to 25° C., filtered through celite and concentrated. The residue was taken up in 50 mL of EtOAc and was washed with Sat. NaHCO$_3$ (2×50 mL). The organic layer dried over Na$_2$SO$_4$ and concentrated. The residue was loaded onto 50 mL silica and eluted with Hexane:EtOAc (3:7). The purified fraction were concentrated to give 0.66 g (67%) of (2S,4R)-2-Methoxymethyl-4-trimethylsilanyloxy-pyrrolidine-1-carboxylic acid benzyl ester as clear oil. HPLC: R$_t$ 3.43 min. (98.2% area). $^1$H NMR (CDCl$_3$, 300 MHz) δ: 7.38–7.32 (5H, m), 4.70 (2H, s), 4.56–4.46 (2H, m), 4.18–4.13 (2H, m), 3.86 (1H, q, J=5.5 Hz), 3.07–3.02 (1H, m), 1.99–1.95 (1H, m), 1.61 (3H, bs), 1.57–1.52 (1H, m), 0.12 (9H, s). LCMS (ESI) (M+H$^+$) m/z: 338.2.

(iv) (3R,5S)-5-Methoxymethyl-pyrrolidin-3-ol

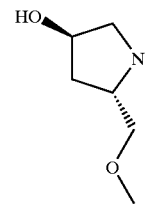

To (2S,4R)-2-Methoxymethyl-4-trimethylsilanyloxy-pyrrolidine-1-carboxylic acid benzyl ester 1.00 g (3.98 mmol) in 3 mL of methanol was added 10% Pd(C) 0.10 g and the mixture was stirred under 1 atmosphere of hydrogen for 24 h. The mixture was filtered through a 0.22 μM Teflon filter, concentrated and subsequently put on a high vacuum for 2 h to afford 0.43 g (86%) of (3R,5S)-5-Methoxymethyl-pyrrolidin-3-ol as clear oil. $^1$H NMR (CDCl$_3$, 400 MHz) δ: 5.30 (1H, s), 4.67 (1H, t, J=5.6 Hz), 4.56 (1H, t, J=7.6 Hz), 4.26–4.21 (1H, m), 4.19 (1H, dd, J=8.1, 3.3 Hz), 3.14 (1H, d, J=12.3 Hz), 2.08 (1H, dd, J=8.2, 3.2 Hz), 1.66–1.59 (3H, m). LCMS (ACPI) (M+H$^+$) m/z: 132.2.

Example 3(i)

5-[2-((2S,4R)-4-Hydroxy-2-hydroxymethyl-pyrrolidine-1-carbonyl)-benzo[b]thiophen-7-ylamino]-2-methyl-indole-1-carboxylic acid methylamide

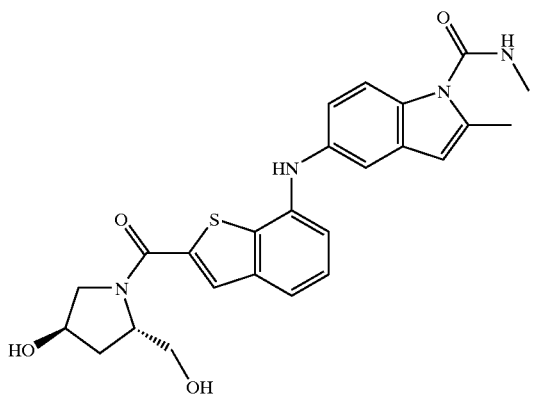

Example 3(f) was prepared in a similar manner to Example 3(d) except that (2S,4R)-4-hydroxy-2-hydroxymethyl-pyrrolidine, prepared as described below, was used instead of (2S,4R)-4-Methoxy-pyrrolidin-2-yl)-methanol (0.23 g, 59% yield). HPLC: $R_t$ 3.77. (95% area). $^1$H NMR (CDCl$_3$, 400 MHz) δ: 8.71 (1H, s), 8.10 (1H, d, J=4.8 Hz), 8.05 (1H, d, J=3.8 Hz), 7.55 (1H, s), 7.44 (1H, d, J=8.6 Hz), 7.19 (1H, s), 6.92 (1H, d, J=8.1), 6.54 (1H, d, J=5.3 Hz), 6.19 (1H, s), 4.75 (1H, s), 4.59 (1H, bs) 4.16–4.05 (2H, m), 3.69 (1H, d, J=7.9), 3.55–3.45 (2H, m), 3.36 (1H, bs), 3.23–3.19 (1H, m), 3.15 (3H, s), 2.70 (3H, d, J=3.8 Hz), 1.91–1.85 (1H, m), 1.73 (1H, t, J=6.2 Hz), 0.91 (1H, t, J=6.8 Hz). HRMS (ESI) C$_{24}$H$_{25}$N$_5$O$_4$S (M+H$^+$) m/z: Calc'd: 480.1706, Found: 480.1713. Anal. (C$_{24}$H$_{25}$N$_5$O$_4$S.1.1H$_2$O) Calc'd: C, 57.72; H, 5.49: N, 14.03. Found: C, 57.64; H, 5.27; N, 13.84.

The starting material was prepared as follows:

(i) (3R,5S)-5-Hydroxymethyl-pyrrolidin-3-ol

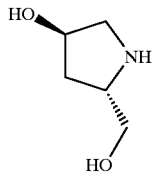

To (2S,4R)-2-Methoxymethyl-4-trimethylsilanyloxy-pyrrolidine-1-carboxylic acid benzyl ester (1.00 g, 3.98 mmol), prepared in Example 3(h) step (ii), in 3 mL of methanol was added 10% Pd(C) 0.10 g under 1 atmosphere of hydrogen. The mix was stirred for 24 h. The mixture was filtered through 0.22 μM Teflon filter concentrated and subsequently placed under a high vacuum for 4 h to afford 0.45 g (97%) of (3R,5S)-5-Hydroxymethyl-pyrrolidin-3-ol as clear oil. LCMS (ACPI) (M+H$^+$) m/z: 118.1.

Example 3(j)

5-{2-[4-(1-Hydroxy-1-methyl-ethyl)-thiazol-2-yl]-thieno[3,2-b]pyridin-7-yloxy}-2-methyl-3a,7a-dihydro-indole-1-carboxylic acid methylamide.

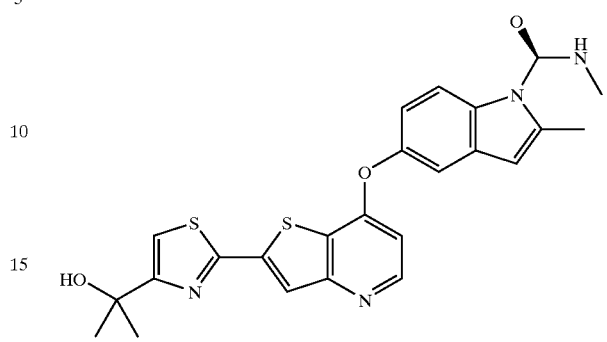

Example 3(j) was prepared by combining (0.10 g, 0.24 mmol) of 2-{2-[7-(2-Methyl-1H-indol-5-yloxy)-benzo[b]thiophen-2-yl]-thiazol-5-yl}-propan-2-ol dissolved in 3 ml CH$_2$Cl$_2$, NaOH (0.28 g, 0.72), TABBr (0.01 g, 0.024 mmol) and methylisocynate (0.04 g, 0.72 mmol) and stirring for 1 h. Partitioned the reaction mixture with 50/50 NaHCO$_3$ (2×50 mL) then concentrated. Purification was through a 2 mm C-tron silica plate eluting with EtOAc/CH$_2$Cl$_2$/MeOH (7:3:0.1) combined purified fraction afforded 5-{2-[4-(1-hydroxy-1-methyl-ethyl)-thiazol-2-yl]-thieno[3,2-b]pyridin-7-yloxy}-2-methyl-3a,7a-dihydro-indole-1-carboxylic acid methylamide (0.07 g, 62%) as white solid. HPLC: $R_t$ 4.10 min. (100% area). $^1$H NMR (CDCl$_3$, 400 MHz) δ 8.42 (1H, d, J=5.3 Hz), 7.86 (1H, s), 7.72 (1H, d, J=8.8 Hz), 7.29 (1H, s), 7.20 (1H, s), 7.02 (1H, d, J=6.3 Hz), 6.51 (1H, d, J=6.3 Hz), 6.32 (1H, s), 5.82 (1H, bs), 3.21 (3H, s), 2.60 (3H, s), 1.66 (6H, s). HRMS (ESI) C$_{24}$H$_{23}$N$_4$O$_3$S$_2$ (M+H$^+$) m/z: Calc. 479.1205, Found: 479.1207. Anal. (C$_{24}$H$_{23}$N$_4$O$_3$S$_2$.0.3CH$_2$Cl$_2$) Calc'd: C, 57.90; H, 4.52; N, 11.22. Found: C, 57. 53; H, 4.52; N, 11.22.

Example 3(k)

4-Fluoro-5-{2-[4-(1-hydroxy-1-methyl-ethyl)-thiazol-2-yl]-thieno[3,2-b]pyridin-7-yloxy}-2-methyl-indole-1-carboxylic acid methylamide.

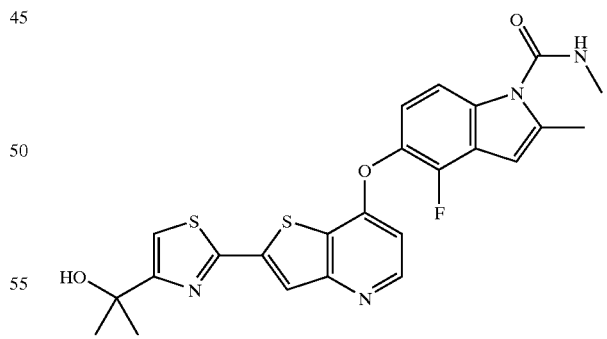

Example 3(k) was prepared in a similar manner to Example 3(j) except that 2-{2-[7-(4-Fluoro-2-methyl-1H-indol-5-yloxy)-benzo[b]thiophen-2-yl]-thiazol-5-yl}-propan-2-ol was used instead. After purification, 4-Fluoro-5-{2-[4-(1-hydroxy-1-methyl-ethyl)-thiazol-2-yl]-thieno[3,2-b]pyridin-7-yloxy}-2-methyl-indole-1-carboxylic acid methyl amide (0.098 g, 59% yield) was afforded as a white solid. HPLC: $R_t$ 4.27 min. (95% area).$^1$H NMR (CDCl$_3$, 400 MHz) δ: 8.46 (1H, d, J=5.6 Hz), 7.90 (1H, s), 7.50 (1H, d, J=8.9 Hz), 7.20(1H, s), 7.11 (1H, t, J=5.1 Hz), 6.48 (1H, bs), 5.66 (1H, bs), 3.14 (3H, s), 2.62 (3H, s), 1.67 (3H, s), 1.58 (3H, s). HRMS (ESI) $C_{24}H_{22}FN_4O_3S_2$ (M+H$^+$) m/z: Calc. 497.1116, Found: 497.1101. Anal. ($C_{24}H_{22}FN_4O_3S_2 \cdot 0.2$Hex) Calc'd: C, 58.90; H, 4.67; N, 10.90. Found: C, 58.88; H, 4.66; N, 10.73.

Example 3(l)
5-{2-[4-(1-Hydroxy-1-methyl-ethyl)-thiazol-2-yl]-thieno[3,2-b]pyridin-7-yloxy}-indole-1-carboxylic acid methylamide

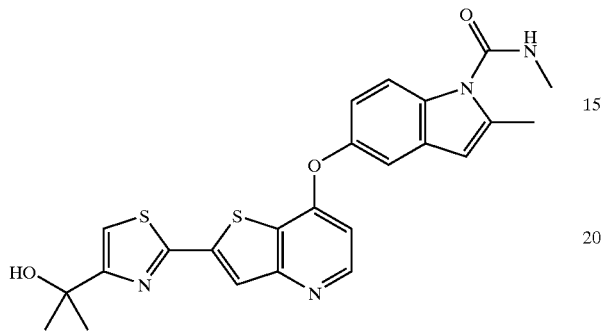

Example 3(l) was prepared in similar manner as 3(j) except that the starting material 2-{2-[7-(1H-Indol-5-yloxy)-benzo[b]thiophen-2-yl]-thiazol-5-yl}-propan-2-ol (0.100 g, 0.234 mmol) was used instead. After titration with Hex/CH$_2$Cl$_2$ (1: 1) to purify afforded the product 5-{2-[4-(1-Hydroxy-1-methyl-ethyl)-thiazol-2-yl]-thieno[3,2-b]pyridin-7-yloxy}-indole-1-carboxylic acid methylamide (0.56, 51.0%) as a white solid. HPLC: R$_t$ 4.07 min. (94% area). $^1$H NMR (CDCl$_3$, 400 MHz) δ: 8.47 (2H, t, J=5.4 Hz), 8.25 (1H, d, J=9.1 Hz), 7.89 (1H, bs), 7.49–7.41 (2H, m), 7.21–7.17 (1H, m), 6.66 (1H, d, J=16.7 Hz), 6.55 (1H, t, J=6.4 Hz), 5.62 (1H, bs), 3.10 (3H, d, J=4.6 Hz), 2.96 (3H, d, J=6.5 Hz), 2.75 (3H, s). HRMS (ESI) $C_{23}H_{21}N_4O_3S_2$ (M+H$^+$) m/z: Calc. 465.1047; Found: 465.1047. Anal. ($C_{23}H_{20}N_4O_3S_2 \cdot 0.6H_2O$) Calc'd: C, 58.11; H, 4.50; N, 11.79. Found: C, 58.47; H, 4.94; N, 10.12.08.

Example 3(m)
5-[2-(4-Hydroxymethyl-thiazol-2-yl)-thieno[3,2-b]pyridin-7-yloxy]-indole-1-carboxylic acid methylamide

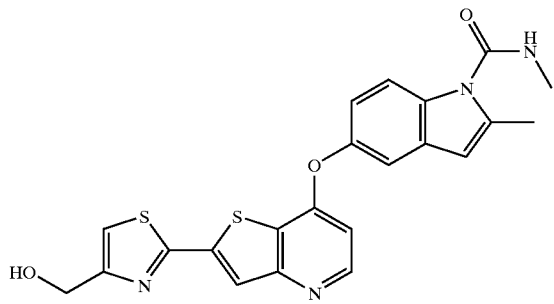

Example 3(m) was prepared in a similar manner to Example 3(j) except that the starting material [2-(7-Chloro-thieno[3,2-b]pyridin-2-yl)-thiazol-4-yl]-methanol, prepared in example 27 of section A of PC10795A, was used instead of [2-(7-Chloro-thieno[3,2-b]pyridin-2-yl)-thiazol-4-yl]-propan-2-ol. Elution with EtOAc:CH$_2$Cl$_2$:MeOH (1:1:0.1) through a flash column and subsequent concentration provided the product as a yellow solid (0.12 g, 56% yield). HPLC: R$_t$ 3.73 min. (100% area). $^1$H NMR (MeOD, 400 MHz) δ: 8.34 (1H, d, J=5.6 Hz), 7.84 (1H, s), 7.63 (1H, d, J=8.9 Hz), 7.45 (1H, s), 7.25 (1H, t, J=2.2 Hz), 6.97 (1H, dd, J=5.6, 2.5), 6.55 (1H, d, J=5.6 Hz), 6.26 (1H, s), 4.66 (2H, s), 2.62 (3H, s), 2.46 (3H, s). HRMS $C_{22}H_{19}N_4O_3S_2$ (ESI) (M+H$^+$) m/z: Calc. 451.0899, Found: 451.0921. Anal. ($C_{22}H_{19}N_4O_3S_2 \cdot 0.2$ CH$_2$Cl$_2$) Calc'd: C, 57.03; H, 3.97; N, 11.98. Found: C, 57.19; H, 3.95; N, 11.98.

Example 3(n)
7-(2-Methyl-1-methylcarbamoyl-1H-indol-5-yloxy)-thieno[3,2-b]pyridine-2-carboxylic acid (2-hydroxy-ethyl)-methyl-amide.

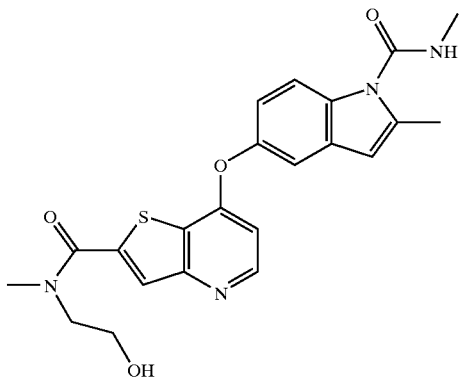

To a solution of DMF was added 7-(2-Methyl-1-methylcarbamoyl-1H-indol-5-yloxy)-thieno[3,2-b]pyridine-2-carboxylic acid (0.1 g, 0.26 mmol), as prepared in step (iv), 2-Methylamino-ethanol (0.025 mL, 0.35 mmol) as well as HATU (0.12 g, 0.32) and DIEA (0.051 mL, 0.32 mmol) then stirred for 3 h. To the solution was added 30 mL of EtOAc portioned between 50/50 NaHCO$_3$ (2×30 mL) and the organic layer dried over Na$_2$SO$_4$ then concentrated via rotor evaporator. The title compound was purified with flash chromatography eluting with EtOAc/CH$_2$Cl$_2$/MeOH (2:1:0.1) and the purified fraction concentrate to afford 7-(2-Methyl-1-methylcarbamoyl-1H-indol-5-yloxy)-thieno[3,2-b]pyridine-2-carboxylic acid (2-hydroxy-ethyl)-methyl-amide as an off-white solid (0.041 g, 36%). HPLC: R$_t$ 3.35 min. (96% area). $^1$H NMR (DMSO-d$_3$, 400 MHz) δ: 8.46 (1H, d, J=4.3 Hz), 8.22 (1H, bs), 7.90–7.81 (1H, m), 7.61 (1H, d, J=8.6 Hz), 7.34 (1H, s), 7.01 (1H, dd, J=8.6, 2.3 Hz), 6.57 (1H, d, J=5.5 Hz), 6.33 (1H, s), 3.56 (5H, m), 2.96 (2H, bs), 2.81 (3H, d, J=5.5 Hz), 2.43 (3H, s). LCMS (ACPI) M+H$^+$ m/z: 439.1. Anal. ($C_{22}H_{22}N_4O_4S \cdot 1.0$ H$_2$O$\cdot 0.3$ EtOAc) Calc'd: C, 57.60; H, 5.07; N, 11.63. Found: C, 57.87; H, 4.93; N, 11.25.

Step (i) 7-(2-Methyl-1H-indol-5-yloxy)-thieno[3,2-b]pyridine-2-carboxylic acid.

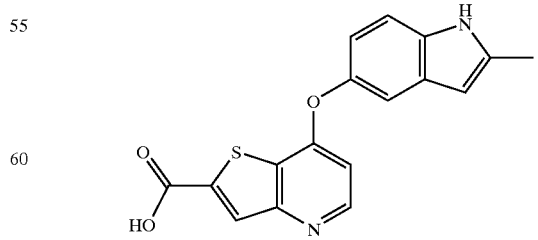

Method A: To a solution of 3 mL of DMSO was added 7-Chloro-thieno[3,2-b]pyridine-2-carboxylic acid (0.6 g, 2.63 mmol), 2-Methyl-3a,7a-dihydro-1H-indol-5-ol (0.42 g, 2.63 mmol), MeOH (0.5 mL) and Cs$_2$CO$_3$ (1.7 g, 5.35 mmol) then sealed and warmed to 165° C. for 3 h and cooled to 25° C. To the reaction solution was added 50 mL of EtOAc then portioned between 50/50 NaHCO$_3$ (50 mL). The aqueous layer was then acidified using concentrated HCl drop wise to afford 7-(2-Methyl-1H-indol-5-yloxy)-thieno[3,2-b]pyridine-2-carboxylic acid (0.65 g, 76%) as a white solid. HPLC: R$_t$ 3.62 min. (92% area). $^1$H NMR (DMSO-d$_3$, 400 MHz) δ: 11.07 (1H, s), 8.45 (1H, d, J=5.3 Hz), 7.98 (1H, s), 7.23 (1H, d, J=8.9 Hz), 7.19 (1H, d, J=7.5, 3.4 Hz), 6.78 (1H, dd, J=6.3, 2.3 Hz) 6.57 (1H, d, J=5.5 Hz), 6.03 (1H, s), 2.26 (3H, s). LCMS (ACPI) M+H$^+$ m/z: 325.
Step (ii) 7-(2-Methyl-1H-indol-5-yloxy)-thieno[3,2-b]pyridine-2-carboxylic acid methyl ester.

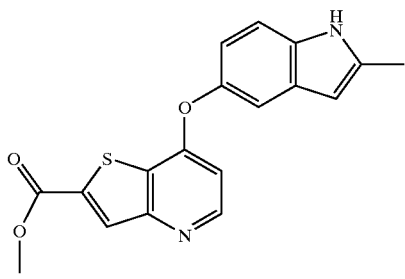

To a solution of DMF was added 7-(2-Methyl-1H-indol-5-yloxy)-thieno[3,2-b]pyridine-2-carboxylic acid (0.6 g, 1.85 mmol), DIEA (0.62 mL, 3.70 mmol), HATU (0.77 g, 2.03) and MeOH (0.5 mL). The solution was stirred for 3 h then 50 mL of EtOAc added and partitioned between 50/50 NaHCO$_3$ (2×50 mL). The organic layer was dried over Na$_2$SO$_4$ then concentrated. Purification was through silica (50 mL) eluting with EtOAc/Hex (2:1). The purified fraction combined and concentrated to give 7-(2-Methyl-1H-indol-5-yloxy)-thieno[3,2-b]pyridine-2-carboxylic acid methyl ester as white foam (0.6 g, 96%). HPLC: R$_t$ 4.01 min. (100% area). $^1$H NMR (CDCl$_3$-d$_3$, 400 MHz) δ: 8.42 (1H, d, J=5.6 Hz), 8.29 (1H, bs), 7.26–7.23 (2H, m), 6.85 (1H, dd, J=7.5, 1.6 Hz), 6.51 (1H, d, J=5.3 Hz), 6.17 (1H, s), 3.91 (3H, s), 2.40 (3H, s). LCMS (ACPI) M+H$^+$ m/z: 339.1.
Step (iii): 7-(2-Methyl-1-methylcarbamoyl-1H-indol-5-yloxy)-thieno[3,2-b] pyridine-2-carboxylic acid methyl ester.

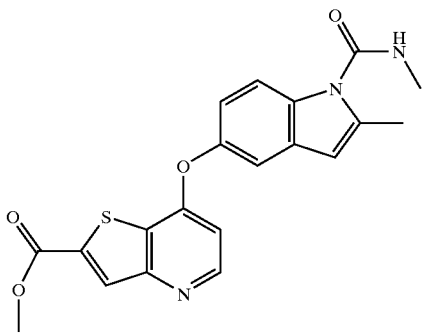

To a solution of methylene chloride (2 mL) was added 7-(2-Methyl-1H-indol-5-yloxy)-thieno[3,2-b]pyridine-2-carboxylic acid methyl ester (0.4 g, 1.82 mmol), DBU (0.5 mL, 3.5 mmol), 4-nitrophenyl chloroformate (0.72 g, 3.5 mmol) then stirred at 0° C. for 24 h. Next was added 2.4 mL of methyl amine (2.0 M in THF) via syringe and stirred an addition 1 h. To the reaction mixture was added 50 mL of EtOAc worked-up by portioning between 50/50 NaHCO$_3$ and concentrated. Purification was through silica (30 mL) eluting with EtOAc/CH$_2$Cl$_2$/MeOH (2:1:0.1) combined purified fraction to afford 7-(2-Methyl-1-methylcarbamoyl-1H-indol-5-yloxy)-thieno[3,2-b]pyridine-2-carboxylic acid methyl ester as yellow solid (0.35 g, 74%). HPLC: R$_t$ 3.96 min. (100% area). $^1$H NMR (CDCl$_3$-d$_3$, 400 MHz) δ: 8.40 (1H, d, J=5.6 Hz), 8.09 (1H, s), 7.64 (1H, d, J=8.8 Hz), 6.92 (1H, dd, J=7.4, 2.2 Hz), 6.84 (1H, d, J=9.1 Hz), 6.49 (1H, d, J=5.3 Hz), 6.23 (1H, s), 5.98 (1H, d, J=4.5 Hz), 3.89 (3H, s), 3.04 (3H, d, 4.5 Hz), 2.52 (3H, s). LCMS (ACPI) M+H$^+$ m/z: 396.2.
Step (iv): 7-(2-Methyl-1-methylcarbamoyl-1H-indol-5-yloxy)-thieno[3,2-b] pyridine-2-carboxylic acid.

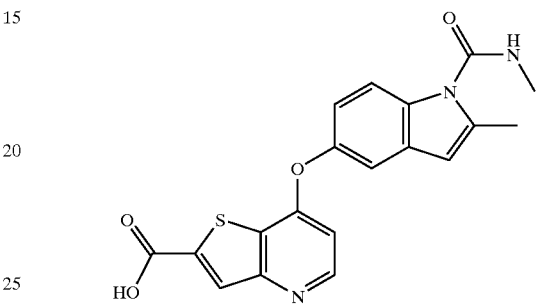

A solution of THF (5 mL), MeOH (1 mL) and H$_2$O (1 mL) was used to dissolve LiOH.H$_2$O (0.042 g, 1.0 mmol) and then added 7-(2-Methyl-1-methylcarbamoyl-1H-indol-5-yloxy)-thieno[3,2-b]pyridine-2-carboxylic acid methyl ester (0.35 g, 0.89 mmol) added. The solution was stirred at 25° C. for 2 h, quenched with several drops of 1N HCl then concentrated. The precipitate was rinsed with H$_2$O (2×5 mL) and Et$_2$O (2×5 mL), dried under high vacuum for 2 h and used as is to afford 7-(2-Methyl-1-methylcarbamoyl-1H-indol-5-yloxy)-thieno[3,2-b]pyridine-2-carboxylic acid (0.25 g, 73%) as yellow solid. HPLC: R$_t$ 3.43 min. (95% area). LCMS (ACPI) M+H$^+$ m/z: 382.1.

Example 3(o)
5-[2-(2-Hydroxymethyl-4-methoxy-pyrrolidine-1-carbonyl)-thieno[3,2-b]pyridin-7-yloxy]-2-methyl-indole-1-carboxylic acid methylamide.

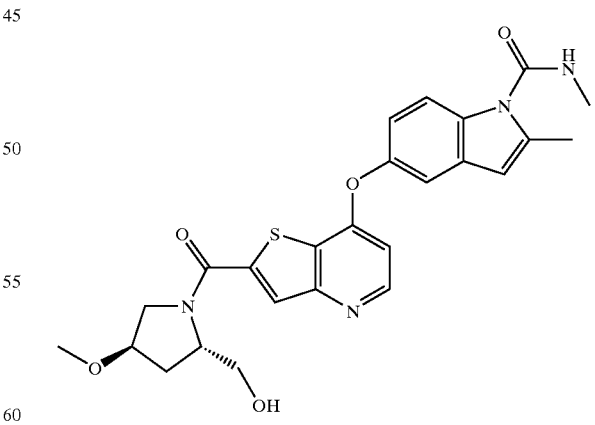

Example 3(o) was prepared by dissolving the starting material 5-{2-[2-(tert-Butyl-dimethyl-silanyloxymethyl)-4-methoxy-pyrrolidine-1-carbonyl]-thieno[3,2-b]pyridin-7-yloxy}-2-methyl-indole-1-carboxylic acid methylamide (0.55 g, 1.00 mmol), as prepared in step i below, in 1 mL of acetic acid in 0.5 mL of THF and 0.5 mL of TFA and stirring at 50° C. for 3 h. The reaction mixture was quenched with 5 mL of sat. NaHCO₃ and 50 mL of EtOAc the partitioned with 50/50 NaHCO₃ (2×50 mL) organic layer dried over NaSO₄ and concentrated. The residue purified with a 2 mm choromatotron rotor eluting with EtOAc/CH₂Cl₂/MeOH (2:1:0.2) then combining purified fractions. The product was then crashing out of EtOAc and diethyl ether producing 0.34 g (68.5%) of 5-[2-(2-Hydroxymethyl-4-methoxy-pyrrolidine-1-carbonyl)-thieno[3,2-b]pyridin-7-yloxy]-2-methyl-indole-1-carboxylic acid methylamide as white solid. HPLC: R$_t$ 5.06 min. (94% area). ¹H NMR (CDCl₃, 400 MHz) δ: 8.50 (1H, d, J=5.3 Hz), 7.81 (1H, s), 7.71 (1H, d, J=9.0), 7.30 (1H, s), 7.03 (1H, d, J=6.9 Hz), 6.60 (1H, d, J=5.3 Hz), 6.33 (1H, s), 5.69 (1H, bs), 4.57 (1H, q, J=6.8 Hz), 4.33 (1H, s), 4.08 (1H, d, J=11.6 Hz), 4.00 (1H, s), 3.86 (2H, t, J=11.6 Hz), 3.85–3.75 (1H, m), 3.28 (3H, d, J=4.3 Hz), 2.61 (3H, s), 2.34–2.29 (1H, m). HRMS (ESI) C₂₅H₂₇N₄O₅S₂ (M+H⁺) m/z: Calc. 495.1702, Found: 495.1704. Anal. (C₂₅H₂₆N₄O₅S₂.0.2 EtOAc) Calc'd: C, 60.50; H, 5.43; N, 10.94; Found: C, 60.73; H, 5.61; N, 10.10.86.

Example 3(p)

5-[2-(4,4-Difluoro-2-hydroxymethyl-pyrrolidine-1-carbonyl)-thieno[3,2-b]pyridin-7-yloxy]-2-methyl-indole-1-carboxylic acid methyl-amide.

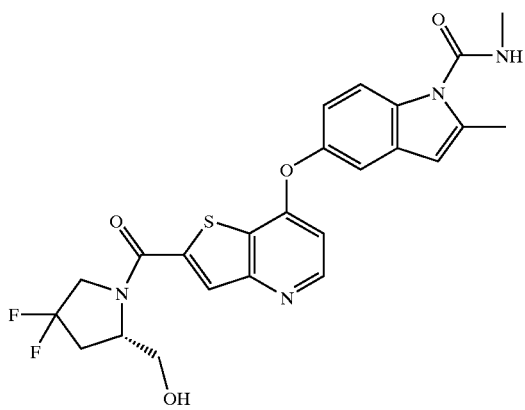

Example 3(p) was prepared in a similar manner to Example 3(n) except that 5-{2-[2-(tert-Butyl-dimethyl-silanyloxymethyl)-4,4-difluoro-pyrrolidine-1-carbonyl]-thieno[3,2-b]pyridin-7-yloxy}-2-methyl-indole-1-carboxylic acid methylamide was used instead of 5-{2-[2-(tert-Butyl-dimethyl-silanyloxymethyl)-4-methoxy-pyrrolidine-1-carbonyl]-thieno[3,2-b]pyridin-7-yloxy}-2-methyl-indole-1-carboxylic acid methylamide. The title compound was purified with flash chromatography eluting with EtOAc/CH₂Cl₂/IPA (3:1:0.2) and the purified fraction concentrate to afford an off-white solid (0.066 g, 74%) of 5-[2-(4,4-Difluoro-2-hydroxymethyl-pyrrolidine-1-carbonyl)-thieno[3,2-b]pyridin-7-yloxy]-2-methyl-indole-1-carboxylic acid methylamide. HPLC: R$_t$ 3.51 min. (100% area). ¹H NMR (CDCl-d₃, 400 MHz) δ: 8.49 (1H, d, J=5.6 Hz), 7.81 (1H, s), 7.63 (1H, d, J=8.8 Hz), 7.25 (1H, d, J=2.2 Hz), 6.65 (1H, dd, J=6.9, 2.2 Hz), 6.60 (1H, d, J=5.6 Hz), 6.30 (1H, s), 4.55 (1H, bs), 4.22–4.16 (2H, m), 3.90–3.75 (1H, m), 3.62–3.50 (1H, bs), 2.92 (3H, s), 2.60–2.51 (2H, m), 2.46 (3H, s). HRMS (ESI) C₂₅H₂₃N₄O₄S (M+H⁺) m/z: Calc. 501.1420, Found: 501.1425. Anal. (C₂₅H₂₃N₄S.3.2 H₂O) Calc'd: C, 51.64; H, 5.13; N, 10.04. Found: C, 51.42; H, 5.13; N, 10.04.

Example 3(q)

1-{5-[2-(4-Hydroxy-2-hydroxymethyl-pyrrolidine-1-carbonyl)-thieno[3,2-b]pyridin-7-yloxy]-2-methyl-indole-1-carbonyl}-3-methyl-urea.

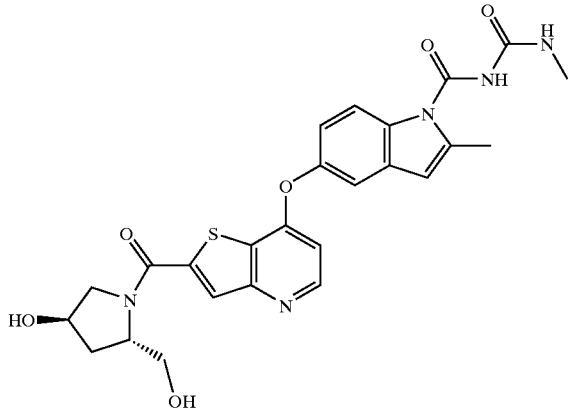

The starting material 1-{5-[2-(2-Hydroxymethyl-4-methoxy-pyrrolidine-1-carbonyl)-thieno[3,2-b]pyridin-7-yloxy]-2-methyl-indole-1-carbonyl}-3-methylurea (0.056 g, 0.11 mmol) was dissolved in 5 mL of anhydrous methylene chloride and cooled to 0° C. To reactrion mixture was the addition of BBr₃ (2.5 M in CH₂Cl₂, 0.16 mL, 0.40 mmol) drop-wise via airtight syringe under a nitrogen atmosphere. The reaction was quenched with 2 mL of Sat. NaHCO₃ and 20 mL of CH₂Cl₂ and partitioned between 50/50 NaHCO₃ (2×20 mL) and the organic layer dried over and concentrated. The residue was purified using a 2 mm chromatotron rotor eluting with EtOAc/CH₂Cl₂/MeOH (1:1:0.2) and the purified fraction concentrated. The purified residue was then added to 5 mL of 1:1 mixture of CH₂Cl₂/Hexane that afforded 0.025 g (48%) of 5-[2-(4-Hydroxy-2-hydroxymethyl-pyrrolidine-1-carbonyl)-thieno[3,2-b]pyridin-7-yloxy]-2-methyl-indole-1-carboxylic acid methylamide as a white solid. ¹H NMR (DMSO-d₆, 400 MHz) δ: 8.63 (1H, d, J=5.3 Hz), 8.06 (1H, d, J=4.6 Hz), 8.00 (1H, s), 7.60 (1H, d, J=9.1), 7.17 (1H, dd, J=8.9, 2.3 Hz), 6.74 (1H, s), 6.54 (1H, s), 5.02 (1H, s), 4.85 (1H, bs), 4.40–4.35 (2H, m), 3.98–3.90 (1H, m), 3.80–3.71 (2H, m), 3.60–3.53 (1H, m), 2.16–2.97 (2H, m). LCMS (ACPI) (M+H⁺) m/z: 524.1. Anal. (C₂₅H₂₅N₅O₆S.0.8 EtOAc.1.5 H₂O) Calc'd: C, 54.55; H, 5.58; N, 11.28. Found: C, 54.49; H, 5.27; N, 10.96.

Example 4(a)

5-(2-[(S)-2-(methoxymethyl)pyrrolidine-1-carbonyl]thieno[3,2-b]pyridin-7-yloxy)-2-methylindole-1-carboxylic acid methylamide

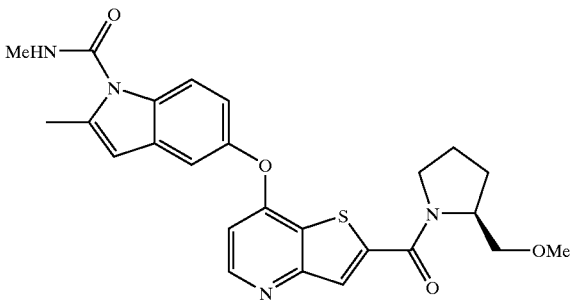

This material was prepared by the treatment of 2-methyl-5-(2-[(S)-2-(methoxymethyl)pyrrolidine-1-carbonyl]thieno[3,2-b]pyridin-7-yloxy)-1-(4-nitrophenoxy)indole (60 mg, 0.1 mmole) with methylamine in a manner as previously described for Example 1(a), step (ii) to give 40 mg (82%) of a yellow solid. $^1$H NMR (DMSO-d$_6$): δ 8.54 (1H, d, J=5.4 Hz), 8.27 (1H, q, J=4.5 Hz), 8.00 (1H, s), 7.68 (1H, d, J=9.0 Hz), 7.40 (1H, d, J=2.4 Hz), 7.07 (1H, dd, J=2.4, 9.0 Hz), 6.65 (1H, d, J=5.4 Hz), 6.40 (1H, s), 4.36–4.25 (1H, m), 3.93–3.76 (2H, m), 3.59–3.38 (2H, m), 3.27 (3H, s), 2.88 (3H, d, J=4.5 Hz), 2.48 (3H, s), 2.06–1.83 (4H, m). Anal. Calcd. for $C_{25}H_{26}N_4O_4S.0.25\ H_2O$:: C, 62.16; H, 5.53; N, 11.60. Found: C, 62.12; H, 5.49; N, 11.27.

The starting materials were prepared as follows:

(i) 7-chloro-2-[(S)-2-(methoxymethyl)pyrrolidine-1-carbonyl]thieno[3,2-b]pyridine The title compound was prepared in a similar manner to (7-Chloro-thieno[3,2-b]pyridin-2-yl)-(2R-hydroxymethyl-pyrrolidin-1-yl)-methanone, except that 2S-methoxymethyl-pyrrolidine was used instead of 2R-hydroxymethyl-pyrrolidine.

(ii) 2-methyl-5-(2-[(S)-2-(methoxymethyl)pyrrolidine-1-carbonyl]thieno[3,2-b]pyridin-7-yloxy)indole.

A solution of 7-chloro-2-[(S)-2-(methoxymethyl) pyrrolidine-1-carbonyl]thieno[3,2-b]pyridine (1.55 g, 5 mmol), and 5-hydroxy-2-methylindole (1.18 g, 8 mmole) in DMSO (40 ml) was purged with argon for minutes at ambient temperature prior to addition of freshly crushed Cs$_2$CO$_3$ (4.88 g, 15 mmol). The resultant reaction mixture was heated at 105° C. for 2 hours. After cooling to room temperature, the crude reaction mixture was poured into cold water (300 ml). The precipitate that formed was collected by filtration to give 2.4 g of a brown solid which was purified by silica gel chromatography. Elution with CH$_2$Cl$_2$: CH$_3$OH (96:4) and evaporation of the appropriate fractions gave 1.61 g (77%) of a yellow solid. $^1$H NMR (DMSO-d6): δ 11.14 (1H, s), 8.51 (1H, d, J=5.4 Hz), 7.98 (1H, s), 7.35 (1H, d, J=8.6 Hz), 7.29 (1H, d, J=2.3 Hz), 6.88 (1H, dd, J=2.3, 8.6 Hz), 6.62 (1H, d, J=5.4 Hz), 6.16 (1H, s), 4.36–4.25 (1H, m), 3.93–3.75 (2H, m), 3.59–3.49 (1H, m), 3.46–3.36 (1H, m), 3.27 (3H, s), 2.39 (3H, s), 2.06–1.83 (4H, m).

(iii) 2-methyl-5-(2-[(S)-2-(methoxymethyl)pyrrolidine-1-carbonyl]thieno[3,2-b]pyridin-7-yloxy)-1-(4-nitrophenoxy)indole.

This material was prepared by the acylation of 2-methyl-5-(2-[(S)-2-(methoxymethyl)pyrrolidine-1-carbonyl]thieno [3,2-b]pyridin-7-yloxy)indole (1.1 g, 2.6 mmole) with 4-nitrophenyl chloroformate (1.8 g, 8.9 mmole) as previously described for Example 1(a), step (i), Method B, to provide 742 mg (48%) of a yellow solid. $^1$H NMR (DMSO-d6): δ 8.57 (1H, d, J=5.4 Hz), 8.40 (2H, d, J=9.0 Hz), 8.18 (1H, d, J=8.9 Hz), 8.01 (1H, s), 7.80 (2H, d, J=9.0 Hz), 7.51 (1H, d, J=2.3 Hz), 7.23 (1H, dd, J=2.3, 8.6 Hz), 6.73 (1H, d, J=5.4 Hz), 6.66 (1H, s), 4.36–4.23 (1H, m), 3.93–3.75 (2H, m), 3.59–3.37 (2H, m), 3.27 (3H, s), 2.68 (3H, s), 2.05–1.81 (4H, m).

Example 4(b)

5-(2-[(S)-2-(methoxymethyl)pyrrolidine-1-carbonyl]thieno [3,2-b]pyridin-7-yloxy)-2-methylindole-1-carboxylic acid cyclopropylamide.

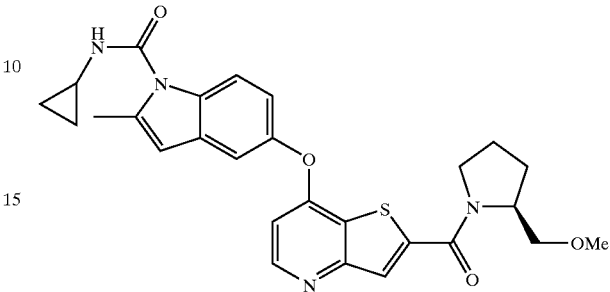

Example 4(b) was prepared in a similar manner as Example 4(a) except that cyclopropylamine was used instead of methylamine to give 355 mg (69%) of a yellow solid. $^1$H NMR (DMSO-d6): δ 8.56 (1H, d, J=3.4 Hz), 8.54 (1H, d, J=5.4 Hz), 8.00 (1H, s), 7.60 (1H, d, J=8.8 Hz), 7.39 (1H, d, J=2.3 Hz), 7.06 (1H, dd, J=2.3, 8.8 Hz), 6.64 (1H, d, J=5.4 Hz), 6.39 (1H, s), 4.36–4.25 (1H, m), 3.94–3.75 (2H, m), 3.59–3.38 (2H, m), 3.27 (3H, s), 2.91–2.78 (1H, m), 2.48 (3H, s), 2.06–1.83 (4H, m), 0.82–0.61 (4H, m). Anal. Calcd. for $C_{27}H_{28}N_4O_4S.0.5\ H_2O$: C, 63.14; H. 5.69; N, 10.91. Found: C, 63.14; H, 5.62; N, 10.65.

Example 4(c)

5-(2-[(S)-2-(methoxymethyl)pyrrolidine-1-carbonyl]thieno [3,2-b]pyridin-7-yloxy)-2-methylindole-1-carboxylic acid prop-2-ynylamide

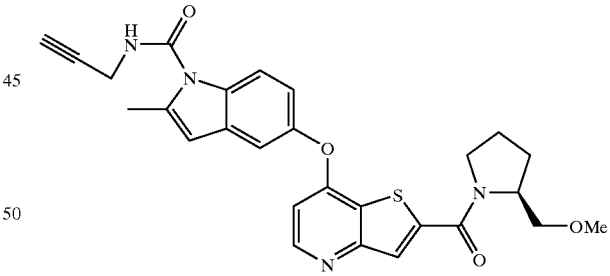

Example 4(c) was prepared in a similar manner as Example 4(a) except that propargylamine was used instead of methylamine to give 55 mg (71%) of a yellow solid. $^1$H NMR (DMSO-d6): δ 8.84 (1H, t, J=5.7 Hz), 8.53 (1H, d, J=5.4 Hz), 8.00 (1H, s), 7.69 (1H, d, J=8.8 Hz), 7.41 (1H, d, J=2.3 Hz), 7.10 (1H, dd, J=2.3, 8.8 Hz), 6.65 (1H, d, J=5.4 Hz), 6.42 (1H, s), 4.36–4.25 (1H, m), 4.11 (2H, dd, J=2.2, 5.7 Hz), 3.93–3.75 (2H, m), 3.59–3.38 (2H, m), 3.27 (3H, s), 2.48 (3H, s), 2.05–1.79 (5H, m). Anal. Calcd. for $C_{27}H_{26}N_4O_4S$: C, 64.52; H, 5.21; N, 11.15. Found: C, 64.21; H, 5.25; N, 11.00.

Example 4(d)

5-(2-[(S)-2-(methoxymethyl)pyrrolidine-1-carbonyl]thieno[3,2-b]pyridin-7-yloxy)-2-methylindole-1-carboxylic acid (4-hydroxybut-2-ynyl)amide.

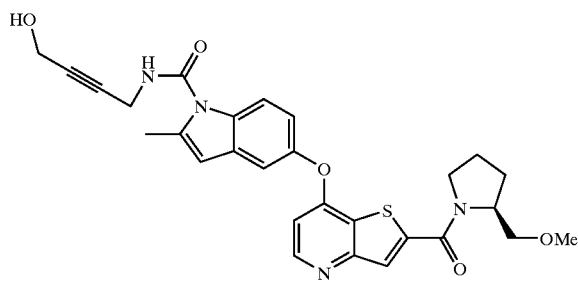

A solution of 5-(2-[(S)-2-(methoxymethyl)pyrrolidine-1-carbonyl]thieno[3,2-b]pyridin-7-yloxy)-2-methylindole-1-carboxylic acid [4-(t-butyldimethylsilyloxy)but-2-ynyl]amide (60 mg, 0.1 mmole), prepared as described below, in THF (5 ml) was treated with 2 M nBu$_4$NF in THF (0.2 ml). The reaction mixture was stirred at ambient temperature for 1 hour, then diluted with water (5 ml) and extracted with EtOAc (3×15 ml). The combined organic extracts were dried over Na$_2$SO$_4$ and concentrated, in vacuo, to give an amber resin, which was purified by silica gel chromatography. Elution with CH$_2$Cl$_2$: CH$_3$OH (95:5) and evaporation of the appropriate fractions gave 46 mg (94%) of a amber solid. $^1$H NMR (DMSO-d6): δ 8.83 (1H, t, J=5.7 Hz), 8.54 (1H, d, J=5.4 Hz), 8.00 (1H, s), 7.68 (1H, d, J=8.8 Hz), 7.40 (1H, d, J=2.2 Hz), 7.08 (1H, dd, J=2.2, 8.8 Hz), 6.64 (1H, d, J=5.4 Hz), 6.41 (1H, s), 4.38–4.24 (3H, m), 4.14 (2H, d, J=5.7 Hz), 3.93–3.76 (2H, m), 3.58–3.38 (2H, m), 3.27 (3H, s), 2.48 (3H, s), 2.04–1.82 (4H, m). Anal. Calcd. for C$_{28}$H$_{28}$N$_4$O$_5$S.0.5 toluene: C, 65.38; H, 5.57; N, 9.68. Found: C, 65.39; H, 5.60; N, 9.44.

The starting material was prepared as follows:

(i) 5-(2-[(S)-2-(methoxymethyl)pyrrolidine-1-carbonyl]thieno[3,2-b]pyridin-7-yloxy)-2-methylindole-1-carboxylic acid [4-(t-butyldimethylsilyloxy)but-2-ynyl]amide.

The title compound was prepared in a similar manner as Example 4(a) except that 4-(t-butyldimethylsilyloxy)but-2-ynylamine was used instead of methylamine to give 65 mg (66%) of a yellow solid. $^1$H NMR (DMSO-d6): δ 8.82 (1H, t, J=5.7 Hz), 8.54 (1H, d, J=5.4 Hz), 8.00 (1H, s), 7.69 (1H, d, J=8.8 Hz), 7.41 (1H, d, J=2.1 Hz), 7.07 (1H, dd, J=2.1, 8.8 Hz), 6.66 (1H, d, J=5.4 Hz), 6.42 (1H, s), 4.37–4.25 (3H, m), 4.16 (2H, d, J=5.7 Hz), 3.92–3.76 (2H, m), 3.56–3.37 (2H, m), 3.27 (3H, s), 2.48 (3H, s), 2.04–1.83 (4H, m), 0.85 (9H, s), 0.09 (6H, s).

Example 4(e)

5-[2-(2R-Methoxymethyl-pyrrolidine-1-carbonyl)-thieno[3,2-b]pyridin-7-yloxy]-2-methyl-indole-1-carboxylic acid methylamide

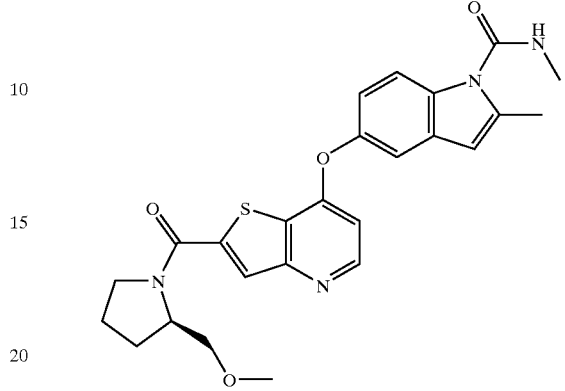

Example 4(e) was prepared in a similar manner as Example 4(a) except that 2R-methoxymethyl-pyrrolidine was used instead of 2S-methoxymethyl-pyrrolidine in step (i). $^1$H NMR (300 MHz, CD$_3$OD) δ 8.45 (1H, d, J=5.5 Hz), 7.87 (1H, s), 7.70 (1H, d, J=8.97 Hz), 7.31 (1H, d, J=2.38 Hz), 7.02 (1H, dd, J=8.79, 2.38 Hz), 6.65 (1H, d, J=5.67 Hz), 6.36 (1H, s), 4.42 (1H, m), 3.88 (2H, m), 3.61 (2H, m), 3.37 (3H, s), 3.01 (3H, s), 2.54 (3H, bs), 1.90–2.15 (4H, m). MS (ESI+) [M+H]/z Calc'd 479, found 479. Anal. (C$_{25}$H$_{26}$N$_4$O$_4$S) C, H, N.

Example 4(f)

5-[2-(3S-Methoxy-pyrrolidine-1-carbonyl)-thieno[3,2-b]pyridin-7-yloxy]-2-methyl-indole-1-carboxylic acid prop-2-ynylamide

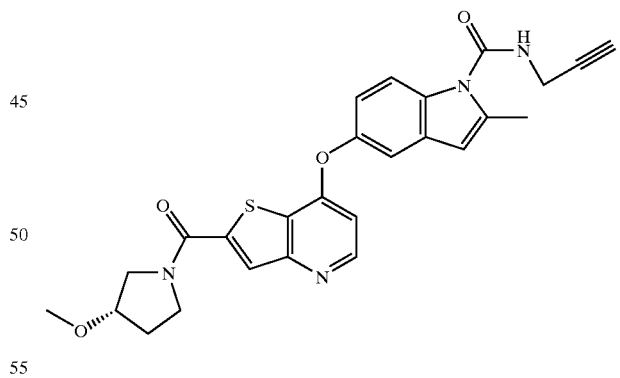

Example 4(f) was prepared in a similar manner as Example 4(c) except that 3S-methoxy-pyrrolidine was used instead of 2S-methoxymethyl-pyrrolidine in referenced step for Example 4(a), step (i). $^1$H NMR (300 MHz, CD$_3$OD) δ 8.46 (1H, d, J=5.27 Hz), 7.91 (1H, d, J=5.84 Hz), 7.76 (1H, d, J=8.85 Hz), 7.33 (1H, d, J=2.07 Hz), 7.04 (1H, dd, J=8.85, 2.26 Hz), 6.66 (1H, d, J=5.65 Hz), 6.36 (1H, s), 4.21 (2H, d, J=2.45 Hz), 4.12 (1H, m), 3.96 (2H, m), 3.75 (2H, m), 3.38 (s, 1.5H), 3.33 (s, 1.5H), 2.72 (1H, t, J=2.45 Hz), 2.55 (3H, s), 2.15 (2H, m). MS (ESI+) [M+H]/z Calc'd 489, found 489. Anal. (C$_{26}$H$_{24}$N$_4$O$_4$S) C, H, N.

Example 4(g)

5-[2-(3S-Methoxy-pyrrolidine-1-carbonyl)-thieno[3,2-b]pyridin-7-yloxy]-2-methyl-indole-1-carboxylic acid methylamide

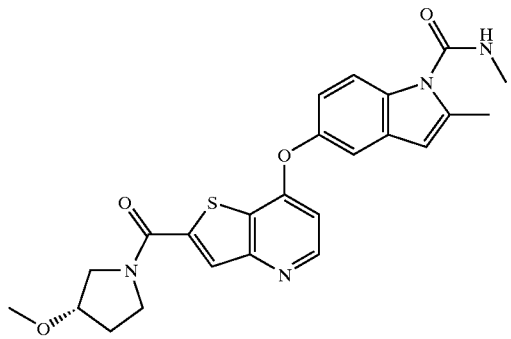

Example 4(g) was prepared in a similar manner as Example 4(a) except that 3S-methoxy-pyrrolidine was used instead of 2S-methoxymethyl-pyrrolidine in step (i). $^1$H NMR (300 MHz, CD$_3$OD) δ 8.46 (1H, d, J=5.46 Hz), 7.89 (1H, d, J=5.65 Hz), 7.69 (1H, d, J=8.85 Hz), 7.30 (1H, d, J=2.07 Hz), 7.02 (1H, dd, J=8.85, 2.07 Hz), 6.65 (1H, d, J=5.46 Hz), 6.37 (1H, s), 4.11 (1H, m), 3.96 (2H, m), 3.74 (2H, m), 3.38 (s, 1.5H), 3.33 (s, 1.5H), 3.01 (3H, s), 2.54 (3H, s), 2.16 (2H, m). MS (ESI+) [M+H]/z Calc'd 465, found 465. Anal. (C$_{24}$H$_{24}$N$_4$O$_4$S) C, H, N.

Example 4(h)

5-[2-(3S-Methoxy-pyrrolidine-1-carbonyl)-thieno[3,2-b]pyridin-7-yloxy]-2-methyl-indole-1-carboxylic acid cyclopropylamide

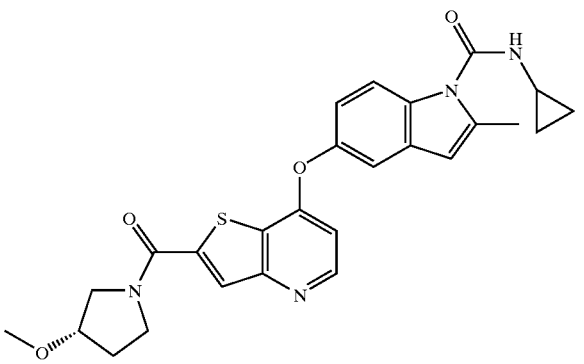

Example 4(h) was prepared in a similar manner as Example 4(g) except that cyclopropylamine was used instead of methylamine in the referenced step for Example 4(a). $^1$H NMR (300 MHz, CD$_3$OD) δ 8.47 (1H, d, J=4.90 Hz), 7.91 (1H, d, J=6.03 Hz), 7.66 (1H, d, J=8.85 Hz), 7.32 (1H, d, J=2.07 Hz), 7.03 (1H, dd, J=8.85, 2.45 Hz), 6.66 (1H, d, J=5.27 Hz), 6.37 (1H, s), 4.12 (1H, m), 3.95 (2H, m), 3.70 (2H, m), 3.38 (s, 1.5H), 3.33 (s, 1.5H), 2.89 (1H, m), 2.52 (3H, s), 2.15 (2H, m), 0.87 (2H, m), 0.72 (2H, m). MS (ESI+) [M+H]/z Calc'd 491, found 491. Anal. (C$_{26}$H$_{26}$N$_4$O$_4$S) C, H, N.

Example 4(i)

5-[2-(3S-Methoxy-pyrrolidine-1-carbonyl)-thieno[3,2-b]pyridin-7-yloxy]-2-methyl-indole-1-carboxylic acid (3-cyclopropyl-prop-2-ynyl)-amide

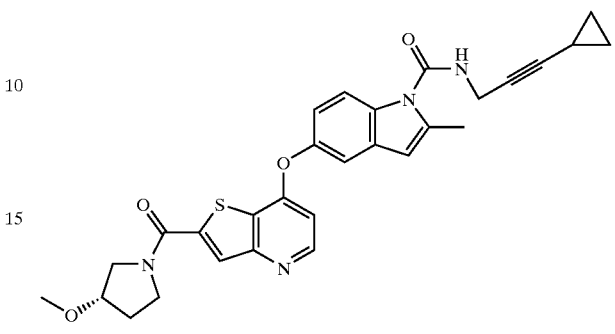

Example 4(i) was prepared in a similar manner as Example 4(g) except that 3-cyclopropyl-prop-2-ynylamine was used instead of methylamine in the referenced step for Example 4(a). $^1$H NMR (300 MHz, CD$_3$OD) δ 8.47 (1H, d, J=4.71 Hz), 7.91 (1H, d, J=5.27 Hz), 7.73 (1H, d, J=8.85 Hz), 7.31 (1H, d, J=1.88 Hz), 7.03 (1H, dd, J=8.85, 2.26 Hz), 6.66 (1H, d, J=4.71 Hz), 6.37 (1H, s), 4.15 (2H, d, J=1.70 Hz), 4.10 (1H, m), 3.95 (2H, m), 3.70 (2H, m), 3.38 (s, 1.5H), 3.33 (s, 1.5H), 2.54 (3H, s), 2.15 (2H, m), 1.28 (1H, m), 0.76 (2H, m), 0.64 (2H, m). MS (ESI+) [M+H]/z Calc'd 529, found 529. Anal. (C$_{29}$H$_{28}$N$_4$O$_4$S.0.85CH$_2$Cl$_2$) C, H, N.

Example 4(j)

5-[2-(3R-Methoxy-pyrrolidine-1-carbonyl)-thieno[3,2-b]pyridin-7-yloxy]-2-methyl-indole-1-carboxylic acid methylamide

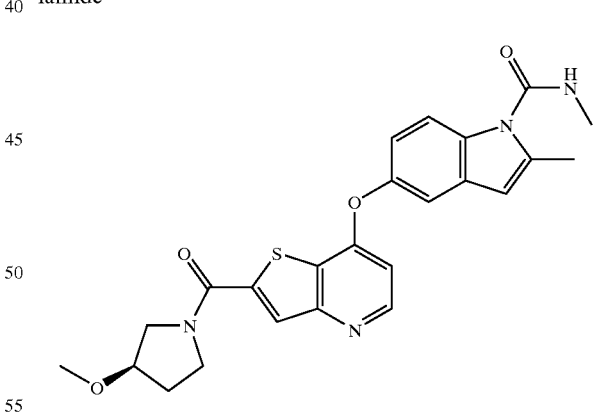

Example 4(j) was prepared in a similar manner as Example 4(a) except that 3R-methoxy-pyrrolidine was used instead of 2S-methoxymethyl-pyrrolidine in step (i). $^1$H NMR (300 MHz, CD$_3$OD) δ 8.51 (1H, d, J=5.5 Hz), 7.96 (1H, d, J=5.06 Hz), 7.77 (1H, d, J=8.8 Hz), 7.38 (1H, s), 7.08 (1H, dd, J=8.8, 2.4 Hz), 6.72 (1H, d, J=5.5 Hz), 6.41 (1H, s), 4.21–4.11 (1H, m), 4.11–3.95 (2H, m), 3.88–3.68 (2H, m), 3.39 (3H, d, J=14.5 Hz), 3.07 (3H, s), 2.59 (3H, s), 2.38–2.07 (2H, m). LCMS (ESI+) [M+H]/z Calc'd 465. Anal. (C$_{24}$H$_{24}$N$_4$O$_4$S.0.2H$_2$O) C, H, N.

Example 4(k)

5-[2-(3R-Methoxy-pyrrolidine-1-carbonyl)-thieno[3,2-b]pyridin-7-yloxy]-2-methyl-indole-1-carboxylic acid cyclopropylamide

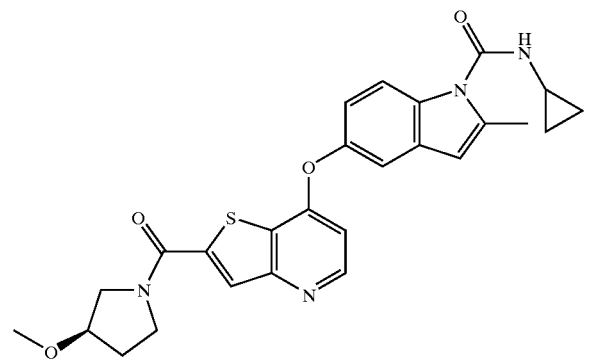

Example 4(k) was prepared in a similar manner as Example 4(j) except that cyclopropylamine was used instead of methylamine in the referenced step for Example 4(a). $^1$H NMR (300 MHz, CD$_3$OD) δ 8.50 (1H, d, J=5.5 Hz), 7.92 (1H, d, J=5.5 Hz), 7.68 (1H, d, J=8.8 Hz), 7.37 (1H, s), 7.08 (1H, dd, J=8.8, 2.4 Hz), 6.68 (1H, d, J=5.5 Hz), 6.40 (1H, s), 4.21–4.11 (1H, m), 4.08–3.90 (2H, m), 3.87–3.64 (2H, m), 3.39 (3H, d, J=14.5 Hz), 2.97–2.86 (1H, m), 2.49 (3H, s), 2.38–2.07 (2H, m), 0.97–0.87 (2H, m), 0.78–0.69 (2H, m). LCMS (ESI+) [M+H]/z Calc'd 491, found 491. Anal. (C$_{26}$H$_{26}$N$_4$O$_4$S.0.6EtOAc) C, H, N.

Example 4(l)

5-[2-(3R-Methoxy-pyrrolidine-1-carbonyl)-thieno[3,2-b]pyridin-7-yloxy]-2-methyl-indole-1-carboxylic acid prop-2-ynylamide

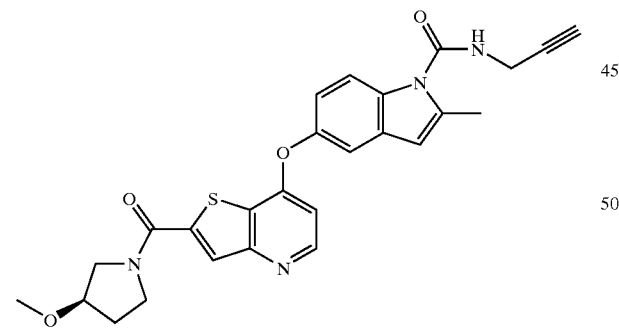

Example 4(l) was prepared in a similar manner as Example 4(j) except that propargylamine was used instead of methylamine in the referenced step for Example 4(a). $^1$H NMR (300 MHz, CD$_3$OD) δ 8.52 (1H, d, J=5.5 Hz), 7.97 (1H, d, J=5.1 Hz), 7.80 (1H, d, J=8.5 Hz), 7.38 (1H, s), 7.08 (1H, dd, J=8.8, 2.4 Hz), 6.72 (1H, d, J=5.5 Hz), 6.43 (1H, s), 4.28 (2H, d, J=1.9 Hz), 4.11–3.91 (3H, m), 3.88–3.68 (2H, m), 3.39 (3H, d, J=14.5 Hz), 2.78–2.72 (1H, m), 2.59 (3H, s), 2.38–2.08 (2H, m). LCMS (ESI+) [M+H]/z Calc'd 489, found 489. Anal. (C$_{26}$H$_{24}$N$_4$O$_4$S.0.5EtOAc) C, H, N.

Example 4(m)

5-[2-(3R-Methoxy-pyrrolidine-1-carbonyl)-thieno[3,2-b]pyridin-7-yloxy]-2-methyl-indole-1-carboxylic acid (3-cyclopropyl-prop-2-ynyl)-amide

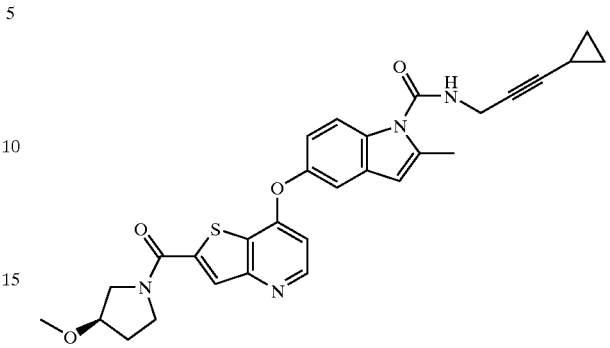

Example 4(m) was prepared in a similar manner as Example 4(j) except that 3-cyclopropyl-2-propynylamine was used instead of methylamine in the referenced step for Example 4(a). $^1$H NMR (300 MHz, CD$_3$OD) δ 8.36 (1H, d, J=5.5 Hz), 7.81 (1H, d, J=5.0 Hz), 7.64(1H, d, J=8.8 Hz), 7.24 (1H, s), 6.95 (1H, dd, J=8.8, 2.4 Hz), 6.68 (1H, d, J=5.5 Hz), 6.29 (1H, s), 4.05 (2H, d, J=1.9 Hz), 4.01–3.81 (3H, m), 3.73–3.57 (2H, m), 3.26 (3H, d, J=14.5 Hz), 2.45 (3H, s), 2.19–1.88 (2H, m), 1.27–1.10 (1H, m), 0.71–0.62 (2H, m), 0.56–0.51 (2H, m). LCMS (ESI+) [M+H]/z Calc'd 529, found 529. Anal. (C$_{29}$H$_{28}$N$_4$O$_4$S.0.6H$_2$O) C, H, N.

Example 4(n)

5-[2-(3R-Hydroxy-pyrrolidine-1-carbonyl)-thieno[3,2-b]pyridin-7-yloxy]-2-methyl-indole-1-carboxylic acid methylamide

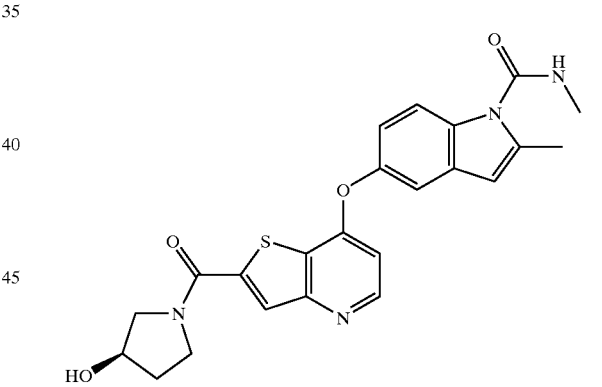

A solution of 5-[2-(3R-methoxy-pyrrolidine-1-carbonyl)-thieno[3,2-b]pyridin-7-yloxy]-2-methyl-indole-1-carboxylic acid methylamide (50 mg, 0.087 mmol), prepared in Example 4(j), in CH$_2$Cl$_2$ (3 mL) was cooled to 0° C., 0.1 mL of 1.0 M BBr$_3$ in CH$_2$Cl$_2$ was added. The mixture was stirred at 0° C. for 15 minutes, and was then warmed to room temperature. After being stirred at room temperature for 2 hours, methanol (0.5 mL) was added, and the mixture was basified with concentrated NH$_4$OH to pH ~8. The resulting solution was stirred at room temperature for 1 hour, and extracted with CH$_2$Cl$_2$. The combined organic layer was dried with Na$_2$SO$_4$, concentrated to give the crude product. Elution with EtOAc:CH$_2$Cl$_2$: MeOH (1:1:0.1) through a flash column and subsequent concentration provided the product as a white solid (24 mg, 78% yield). $^1$H NMR (300 MHz, CD$_3$OD) δ 8.55 (1H, d, J=5.5 Hz), 7.92 (1H, d, J=17.7 Hz), 7.76 (1H, d, J=8.8 Hz), 7.37 (1H, s), 7.08 (1H, dd, J=8.8, 2.4 Hz), 6.71 (1H, d, J=5.5 Hz), 6.40 (1H, s), 4.57 (1H, bs), 4.15–3.98 (2H, m), 3.87–3.78 (2H, m), 3.77–3.51 (1H, m), 3.05 (3H, s), 2.48 (3H, s), 2.22–2.00 (2H, m). LCMS (ESI+) [M+H]/z Calc'd 451, found 451. Anal. ($C_{23}H_{22}N_4O_4S.0.7EtOAc.1.0H_2O$) C, H, N.

Example 4(o)

5-[2-(3R-Hydroxy-pyrrolidine-1-carbonyl)-thieno[3,2-b]pyridin-7-yloxy]-2-methyl-indole-1-carboxylic acid prop-2-ynylamide

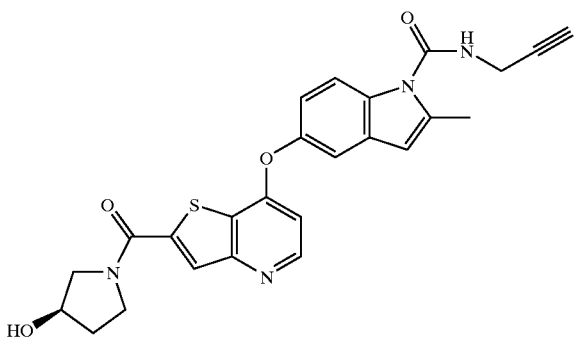

Example 4(o) was prepared in a similar manner as Example 4(n) except that the starting material was Example 4(l). $^1$H NMR (300 MHz, CD$_3$OD) δ 8.52 (1H, d, J=5.5 Hz), 7.95 (1H, d, J=17.7 Hz), 7.80 (1H, d, J=8.8 Hz), 7.38 (1H, s), 7.10 (1H, dd, J=8.8, 2.4 Hz), 6.72 (1H, d, J=5.5 Hz), 6.42 (1H, s), 4.57 (1H, bs), 4.27 (2H, d, J=1.9 Hz), 4.17–4.02 (2H, m), 3.87–3.78 (2H, m), 3.77–3.51 (1H, m), 2.78–2.72 (1H, m), 2.49 (3H, s), 2.23–2.01 (2H, m). LCMS (ESI+) [M+H]/z Calc'd 475, found 475. Anal. ($C_{25}H_{22}N_4O_4S.0.4CH_2Cl_2$) C, H, N.

Example 4(p)

5-[2-(3R-Hydroxy-pyrrolidine-1-carbonyl)-thieno[3,2-b]pyridin-7-yloxy]-2-methyl-indole-1-carboxylic acid cyclopropylamide

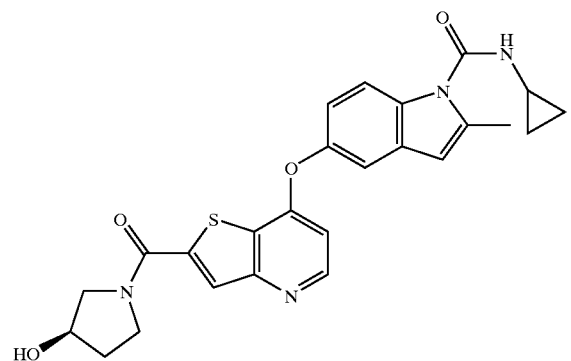

Example 4(p) was prepared in a similar manner as Example 4(n) except that Example 4(k) was used as starting material. $^1$H NMR (300 MHz, CD$_3$OD) δ 8.29 (1H, d, J=5.6 Hz), 7.73 (1H, d, J=17.7 Hz), 7.48 (1H, d, J=8.8 Hz), 7.11 (1H, s), 6.82 (1H, dd, J=8.7, 2.1 Hz), 6.46 (1H, d, J=5.5 Hz), 6.19 (1H, s), 4.29 (1H, bs), 3.91–3.74 (2H, m), 3.61–3.53 (2H, m), 3.53–3.48 (1H, m), 2.71–2.55 (1H, m), 2.36 (3H, s), 1.93–1.73 (2H, m), 0.68–0.60 (2H, m), 0.55–0.50 (2H, m). LCMS (ESI+) [M+H]/z Calc'd 477, found 477. Anal. ($C_{25}H_{24}N_4O_4S.1.0MeOH.1.5EtOAc$) C, H, N.

Example 4(q)

5-[2-(3S,4S-Dimethoxy-pyrrolidine-1-carbonyl)-thieno[3,2-b]pyridin-7-yloxy]-2-methyl-indole-1-carboxylic acid prop-2-ynylamide Example 4(q) was prepared in a similar manner as Example 4(l) except that 3S,4S-dimethoxy-pyrrolidine was used instead of 2S-methoxymethyl-pyrrolidine in step (i) of Example 4(a). $^1$H NMR (300 MHz, CD$_3$OD) δ 8.37 (1H, d, J=5.46 Hz), 7.81 (1H, s), 7.66 (1H, d, J=8.85 Hz), 7.23 (1H, s), 6.95 (1H, d, J=8.85 Hz), 6.56 (1H, d, J=5.47 Hz), 6.29 (1H, s), 4.11 (2H, s), 3.81–3.96 (4H, m), 3.66 (2H, m), 3.34 (3H, s), 3.29 (3H, s), 2.63 (1H, m), 2.46 (3H, m). MS (ESI+) [M+H]/z Calc'd 519, found 519. Anal. ($C_{27}H_{26}N_4O_5S.0.5H_2O$) C, H, N.

Example 4(r)

5-[2-(3,4-cis-Dimethoxy-pyrrolidine-1-carbonyl)-thieno[3,2-b]pyridin-7-yloxy]-2-methyl-indole-1-carboxylic acid methylamide Example 4(r) was prepared in a similar manner as Example 4(a) except that 3,4-cis-Dimethoxy-pyrrolidine, prepared as described below, was used instead of 2S-methoxymethyl-pyrrolidine. $^1$H NMR (300 MHz, CDCl$_3$) δ 8.48 (d, 1H, J=5.46 Hz), 7.85 (s, 1H), 7.72 (d, 1H, J=8.85 Hz), 7.28 (d, 1H, J=2.26 Hz), 7.03 (dd, 1H, J=8.85, 2.26 Hz), 6.58 (d, 1H, J=5.27 Hz), 6.30 (s, 1H), 5.77 (d, 1H, J=4.52 Hz), 3.72–4.10 (m, 6H), 3.50 (s, 3H), 3.47 (s, 3H), 3.13 (s, 1.5H), 3.12 (s, 1.5H), 2.61 (s, 3H). MS (ESI+) [M+H]/z Calc'd 495, found 495. Anal. ($C_{25}H_{26}N_4O_5S.0.15Hexane$) C, H, N.

The starting materials were prepared as follows:
(i) 3,4-cis-Dihydroxy-pyrrolidine-1-carboxylic acid benzyl ester

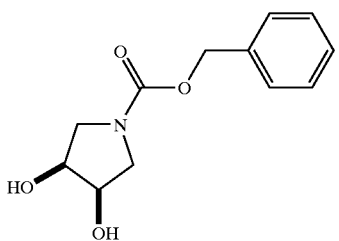

To a solution of benzyl 3-pyrroline-1-carboxylate (15 g, 90%, 66.4 mmol) in 100 mL THF and 25 mL water was added osmium tetroxide (10 mL, 2.5 wt. % solution in 2-methyl-2-propanol, 0.8 mmol) and 4-methylmorpholine N-oxide (8.56 g, 73 mmol) as solid. The mixture was stirred at room temperature overnight and concentrated in vacuo. The residue was re-dissolved in 300 mL ethyl acetate and washed with aqueous $Na_2SO_3$ (1.5 g in 100 mL water) solution and aqueous $NaHCO_3$ solution and brine. The combined aqueous layer was extracted once with ethyl acetate (100 mL). The combined organic layer was dried over $Na_2SO_4$, filtered, and concentrated in vacuo. The crude was further purified by flash column chromatography eluting with 4–5% MeOH in $CH_2Cl_2$ to give 15.26 g product as white solid (97% yield). $^1$H NMR (300 MHz, $CDCl_3$) δ 7.34 (m, 5H), 5.11 (bs, 2H), 4.26 (m, 2H), 3.66 (m, 2H), 3.41 (m, 2H), 1.56 (bs, 2H).
(ii) 3,4-cis-Dimethoxy-pyrrolidine-1-carboxylic acid benzyl ester

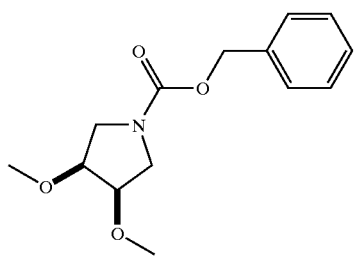

To a stirred solution of 3,4-cis-dihydroxy-pyrrolidine-1-carboxylic acid benzyl ester (15.2 g, 64.3 mmol) in 130 mL anhydrous THF was added iodomethane (36 g, 257 mmol) at 0° C.; sodium hydride (6.4 g, 60% in mineral oil, 160 mmol) was then added slowly as solid at 0° C. The mixture was allowed to warm to room temperature and stirred at room temperature for 3 hours. 30 mL 1N aqueous HCl was then added to the mixture which was concentrated in vacuo to remove THF. The residue was re-dissolved in 300 mL ethyl acetate and washed with water and brine. The organic layer was dried over $Na_2SO_4$, filtered, and concentrated in vacuo. The crude was further purified by flash column chromatography eluting with 5–25% EtOAc in $CH_2Cl_2$ to give 17 g product as yellow oil (99% yield). $^1$H NMR (300 MHz, $CDCl_3$) δ 7.35 (m, 5H), 5.12 (m, 2H), 3.87 (m, 2H), 3.55 (m, 2H), 3.42 (bs, 6H), 1.58 (s, 2H).
(iii) 3,4-cis-Dimethoxy-pyrrolidine

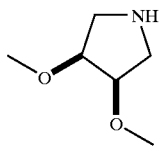

To a stirred solution of 3,4-cis-dimethoxy-pyrrolidine-1-carboxylic acid benzyl ester (16.95 g, 63.88 mmol) in 150 mL MeOH was added 1.3 g Pd on C (10% w/w). The mixture was stirred under $H_2$ balloon at room temperature for 3 hours and filtered through celite. The filtrate was concentrated in vacuo, re-dissolved in $CH_2Cl_2$ and dried over $Na_2SO_4$. The solution was concentrated to give 8.3 g product as yellow oil (99% yield). $^1$H NMR (300 MHz, $CDCl_3$) δ 3.80 (m, 2H), 3.47 (bs, 2H), 3.41 (s, 6H), 3.01 (bs, 2H).

Example 4(s)

5-[2-(3,4-cis-Dihydroxy-pyrrolidine-1-carbonyl)-thieno[3,2-b]pyridin-7-yloxy]-2-methyl-indole-1-carboxylic acid methylamide

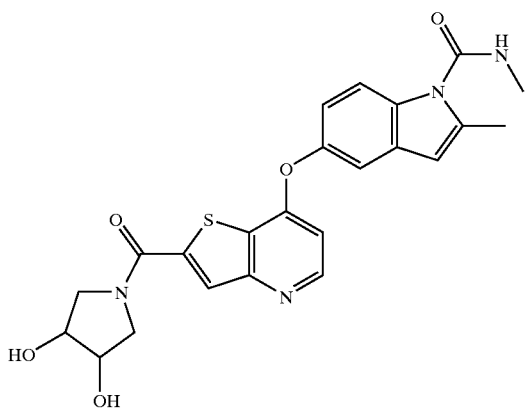

Example 4(s) was prepared in a similar manner as Example 4(n) except that Example 4(r) was used as starting material. $^1$H NMR (300 MHz, DMSO-d6) δ 8.54 (d, 1H, J=4.90 Hz), 7.96 (s, 1H), 7.64 (d, 1H, J=8.48 Hz), 7.38 (s, 1H), 7.01 (d, 1H, J=8.85 Hz), 6.59 (d, 1H, J=5.27 Hz), 6.35 (s, 1H), 3.95–4.20 (m, 4H), 3.58–3.70 (m, 2H), 2.87 (s, 3H), 2.50 (s, 3H). MS (ESI+) [M+H]/z Calc'd 467, found 467. Anal. ($C_{23}H_{22}N_4O_5S.0.07CH_2Cl_2$) C, H, N.

Example 4(t)

5-[2-(3,4-cis-Dimethoxy-pyrrolidine-1-carbonyl)-thieno[3,2-b]pyridin-7-yloxy]-2-methyl-indole-1-carboxylic acid cyclopropylamide

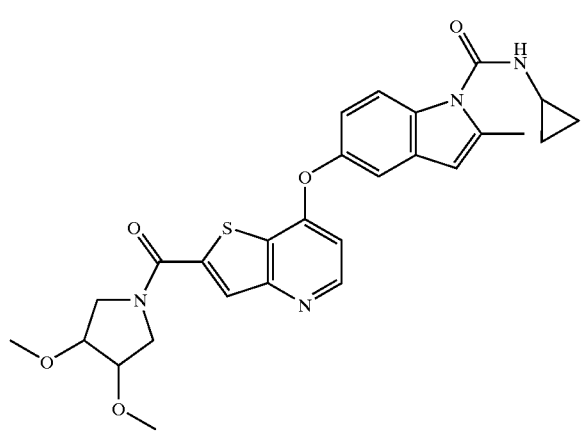

Example 4(t) was prepared in a similar manner as Example 4(r) except that cyclopropylamine was used instead of methylamine. $^1$H NMR (300 MHz, CDCl$_3$) δ 8.45 (d, 1H, J=5.46 Hz), 7.82 (s, 1H), 7.62 (d, 1H, J=8.85 Hz), 7.25 (bs, 1H), 6.98 (dd, 1H, J=8.85, 2.26 Hz), 6.55 (d, 1H, J=5.46 Hz), 6.29 (s, 1H), 6.05 (s, 1H), 3.65–4.08 (m, 6H), 3.48 (s, 3H), 3.45 (s, 3H), 2.91 (m, 1H), 2.57 (s, 3H), 0.93 (m, 2H), 0.75 (m, 2H). MS (ESI+) [M+H]/z Calc'd 521, found 521. Anal. (C$_{27}$H$_{28}$N$_4$O$_5$S.0.2Hexane) C, H, N.

Example 4(u)

5-[2-(3,4-cis-Dihydroxy-pyrrolidine-1-carbonyl)-thieno[3,2-b] pyridin-7-yloxy]-2-methyl-indole-1-carboxylic acid cyclopropylamide

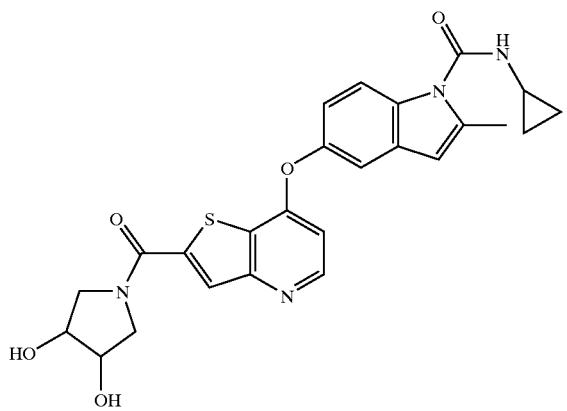

Example 4(u) was prepared in a similar manner as Example 4(n) except that Example 4(t) was used as starting material. $^1$H NMR (300 MHz, DMSO-d$_6$) δ 8.54 (d, 1H, J=5.46 Hz), 7.97 (s, 1H), 7.59 (d, 1H, J=8.85 Hz), 7.39 (d, 1H, J=2.26 Hz), 7.06 (dd, 1H, J=8.85, 2.26 Hz), 6.64 (d, 1H, J=5.27 Hz), 6.39 (s, 1H), 3.95–4.18 (m, 4H), 3.65 (m, 2H), 3.86 (m, 1H), 2.47 (s, 3H), 0.75 (m, 2H), 0.66 (m, 2H). MS (ESI+) [M+H]/z Calc'd 493, found 493. Anal. (C$_{25}$H$_{24}$N$_4$O$_5$S.0.2CH$_2$Cl$_2$) C, H, N.

Example 4(v)

5-[2-(3,4-cis-Dimethoxy-pyrrolidine-1-carbonyl)-thieno[3,2-b] pyridin-7-yloxy]-2-methyl-indole-1-carboxylic acid prop-2-ynylamide

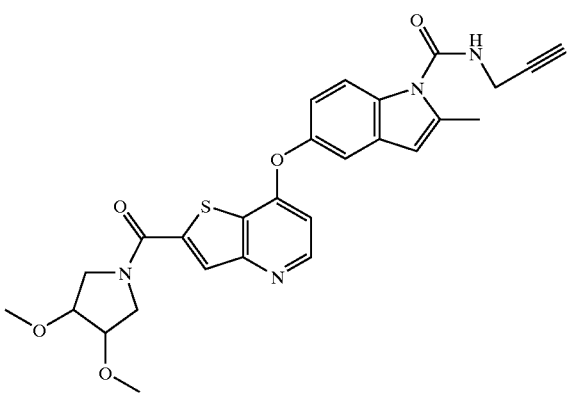

Example 4(v) was prepared in a similar manner as Example 4(r) except that propargylamine was used instead of methylamine. $^1$H NMR (300 MHz, CDCl$_3$) δ 8.44 (d, 1H, J=5.46 Hz), 7.82 (s, 1H), 7.76 (d, 1H, J=8.85 Hz), 7.26 (bs, 1H), 7.01 (dd, 1H, J=8.85, 2.26 Hz), 6.55 (d, 1H, J=5.46 Hz), 6.31 (s, 1H), 6.21 (bs, 1H), 4.30 (m, 2H), 3.70–4.10 (m, 6H), 3.48 (s, 3H), 3.45 (s, 3H), 2.59 (s, 3H), 2.35 (t, 1H, J=2.45 Hz). MS (ESI+) [M+H]/z Calc'd 519, found 519. Anal. (C$_{27}$H$_{26}$N$_4$O$_5$S.0.15Hexane) C, H, N.

Example 4(w)

5-[2-(3,4-cis-Dihydroxy-pyrrolidine-1-carbonyl)-thieno[3,2-b] pyridin-7-yloxy]-2-methyl-indole-1-carboxylic acid prop-2-ynylamide

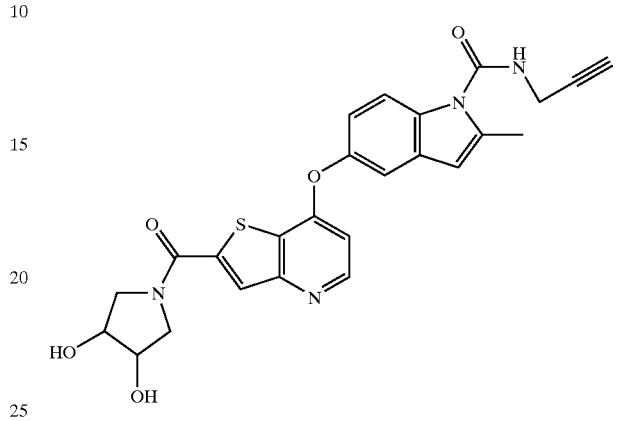

Example 4(w) was prepared in a similar manner as Example 4(n) except that Example 4(v) was used as starting material. $^1$H NMR (300 MHz, DMSO-d6) δ 8.54 (d, 1H, J=5.27 Hz), 7.97 (s, 1H), 7.70 (d, 1H, J=8.85 Hz), 7.42 (d, 1H, J=1.88 Hz), 7.09 (dd, 1H, J=8.67, 1.88 Hz), 6.67 (d, 1H, J=5.27 Hz), 6.40 (s, 1H), 4.11 (m, 4H), 4.00 (m, 2H), 3.65 (m, 2H), 2.50 (bs, 4H). MS (ESI+) [M+H]/z Calc'd 491, found 491. Anal. (C$_{25}$H$_{22}$N$_4$O$_5$S.0.7H$_2$O) C, H, N.

Example 4(x)

5-[2-(2R-Methoxymethyl-pyrrolidine-1-carbonyl)-thieno[3,2-b] pyridin-7-yloxy]-2-methyl-1H-indole-3-carboxylic acid methylamide

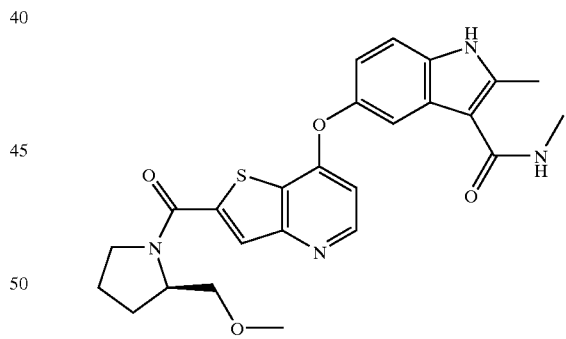

A solution of 40 mg 5-[2-(2R-methoxymethyl-pyrrolidine-1-carbonyl)-thieno[3,2-b]pyridin-7-yloxy]-2-methyl-indole-1-carboxylic acid methylamide, Example 4(e), in 20 mL 1:1 CH$_3$CN and H$_2$O with 1% TFA was kept at room temperature overnight. The mixture was concentrated in vacuo, re-dissolved in EtOAc, and washed with aqueous NaHCO$_3$ solution and brine. The organic layer was dried over Na$_2$SO$_4$, filtered and concentrated. The residue was purified by flash column chromatography eluting with 4–8% MeOH in CH$_2$Cl$_2$ to give 25 mg desired product (63% yield). $^1$H NMR (300 MHz, CD$_3$OD) δ 8.45 (d, 1H, J=5.5 Hz), 7.87 (s, 1H), 7.65 (d, 1H, J=2.2 Hz), 7.51 (bs, 1H), 7.43 (d, 1H, J=8.8 Hz), 7.00 (dd, 1H, J=8.6, 2.2 Hz), 6.67 (d, 1H, J=5.5 Hz), 4.43 (m, 1H), 3.89 (m, 2H), 3.62 (m, 2H), 3.37

(s, 3H), 2.90 (s, 3H), 2.65 (s, 3H), 1.94–2.18 (m, 4H). MS (ESI+) [M+H]/z Calc'd 479, found 479.

Example 4(y)

5-[2-(2R-Methoxymethyl-pyrrolidine-1-carbonyl)-thieno[3,2-b] pyridin-7-yloxy]-2-methyl-1H-indole-3-carboxylic acid cyclopropylamide

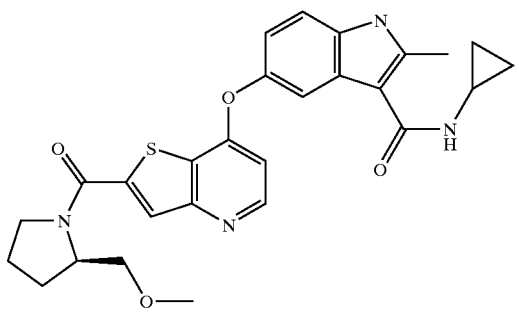

Example 4(y) was prepared in a similar manner as Example 4(x) except that cyclopropylamine was used instead of methylamine. $^1$H NMR (300 MHz, CD$_3$OD) δ 8.43 (d, 1H, J=5.5 Hz), 7.85 (s, 1H), 7.78 (bs, 1H), 7.58 (d, 1H, J=2.2 Hz), 7.40 (d, 1H, J=8.6 Hz), 6.98 (dd, 1H, J=8.6, 2.4 Hz), 6.65 (d, 1H, J=5.5 Hz), 4.42 (m, 1H), 3.88 (m, 2H), 3.60 (m, 2H), 3.36 (s, 3H), 2.79 (m, 1H), 2.62 (s, 3H), 1.90–2.18 (m, 4H), 0.76 (m, 2H), 0.61 (m, 2H). MS (ESI+) [M+H]/z Calc'd 505, found 505.

Example 5(a)

4-Fluoro-5-[2-(2S-methoxymethyl-pyrrolidine-1-carbonyl)-thieno[3,2-b]pyridin-7-yloxy]-2-methyl-indole-1-carboxylic acid methylamide

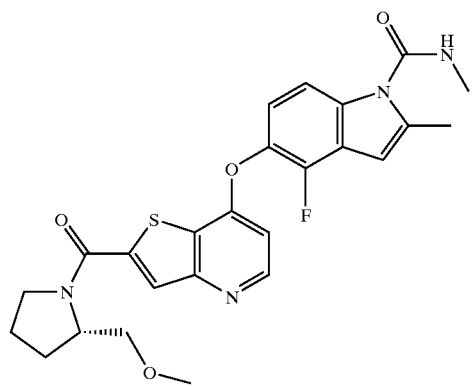

Example 5(a) was prepared in a similar manner as Example 4(a) except that 4-fluoro-2-methyl-5-(2-[(S)-2-(methoxymethyl)pyrrolidine-1-carbonyl]thieno[3,2-b]pyridin-7-yloxy)-1-(4-nitrophenoxy)indole, prepared as described below was used instead of 2-methyl-5-(2-[(S)-2-(methoxymethyl)pyrrolidine-1-carbonyl]thieno[3,2-b]pyridin-7-yloxy)-1-(4-nitrophenoxy)indole. $^1$H NMR (300 MHz, CD$_3$OD) δ 8.40 (1H, d, J=5.24 Hz), 7.81 (1H, s), 7.42 (1H, d, J=8.85 Hz), 7.04 (1H, m), 6.56 (1H, d, J=5.28 Hz), 6.38 (1H, s), 4.33 (1H, m), 3.80 (2H, m), 3.52 (2H, m), 3.27 (3H, s), 2.91 (3H, s), 2.45 (3H, s), 1.87–2.09 (4H, m). MS (ESI+) [M+H]/z Calc'd 497, found 497. Anal. (C$_{25}$H$_{25}$FN$_4$O$_4$S.1.0MeOH) C, H, N.

The starting materials were prepared as follows:

(i) [7-(4-Fluoro-2-methyl-1H-indol-5-yloxy)-thieno[3,2-b]pyridin-2-yl]-(2S-methoxymethyl-pyrrolidin-1-yl)-methanone

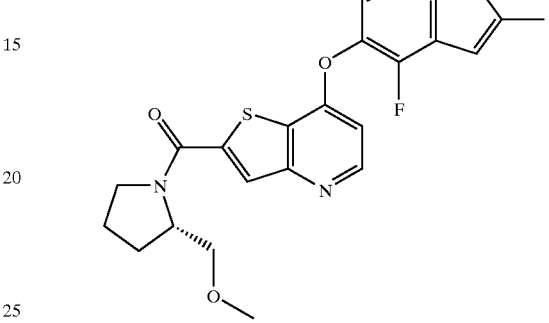

The title compound was prepared in a similar manner as Example 4(a), step (ii) except that 4-fluoro-5-hydroxy-2-methylindole was used instead of 5-hydroxy-2-methylindole. $^1$H NMR (300 MHz, CDCl$_3$) δ 8.47 (1H, d, J=5.47 Hz), 8.42 (1H, bs), 7.84 (1H, bs), 7.08 (1H, d, J=8.67 Hz), 6.92–6.97 (1H, m), 6.54 (1H, d, J=5.46 Hz), 6.34 (1H, bs), 4.49–4.52 (1H, m), 3.81–3.86 (2H, m), 3.57–3.65 (2H, m), 3.37 (3H, s), 2.46 (3H, s), 1.89–2.10 (4H, m). MS (ESI+) [M+H]/z Calc'd 440, found 440.

(ii) 4-fluoro-2-methyl-5-(2-[(S)-2-(methoxymethyl)pyrrolidine-1-carbonyl]thieno[3,2-b]pyridin-7-yloxy)-1-(4-nitrophenoxy)indole

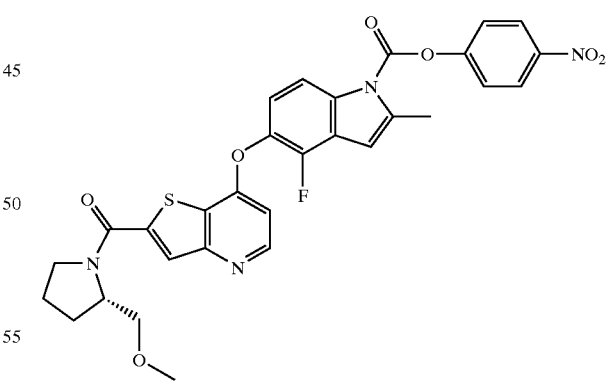

The title compound was prepared as described for Example 4(a), step (iii): $^1$H NMR (CHCl$_3$) δ 8.52 (d, 1H, J=5.47 Hz), 8.39 (d, 2H, J=9.23 Hz), 7.85 (s, 1H), 7.42 (d, 1H, J=8.85 Hz), 7.52 (d, 2H, J=9.23 Hz), 7.15–7.21 (m, 1H), 6.92 (d, 1H, J=9.24 Hz), 6.61 (s, 1H), 4.28–4.51 (m, 1H), 3.85 (m, 2H), 3.64 (m, 2H), 3.37 (s, 3H), 2.72 (s, 3H), 1.97–2.08 (m, 2H), 1.55–1.64 (m, 2H). Rf=0.65 (10% CH$_3$OH in 1:1 CH$_2$Cl$_2$/EtOAc).

Example 5(b)

4-Fluoro-5-[2-(2S-hydroxymethyl-pyrrolidine-1-carbonyl)-thieno[3,2-b]pyridin-7-yloxy]-2-methyl-indole-1-carboxylic acid cyclopropylamide

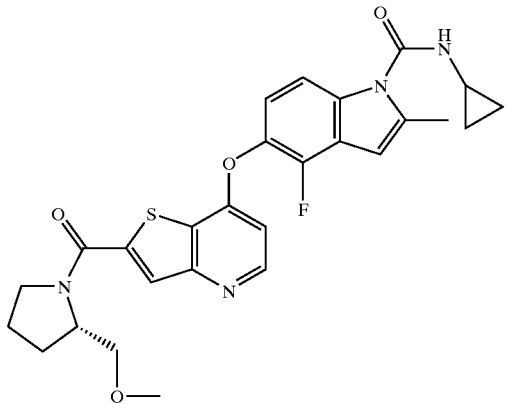

Example 5(b) was prepared in a similar manner as Example 5(a) except that cyclopropylamine was used instead of methylamine. $^1$H NMR (300 MHz, CD$_3$OD) δ 8.40 (1H, d, J=5.47 Hz), 7.82 (1H, bs), 7.37 (1H, d, J=8.85 Hz), 7.01–7.07 (1H, m), 6.56 (1H, d, J=5.46 Hz), 6.38 (1H, s), 4.34 (1H, bs), 3.80 (2H, m), 3.53 (2H, m), 3.33 (3H, m), 2.77–2.84 (1H, m), 2.44 (3H, s), 1.78–2.05 (4H, m), 0.75–0.79 (2H, m), 0.60–0.65 (2H, m). MS (ESI+) [M+H]/z Calc'd 523, found 523. Anal. (C$_{27}$H$_{27}$FN$_4$O$_4$S.0.25H$_2$O) C, H, N.

Example 5(c)

4-Fluoro-5-[2-(2S-methoxymethyl-pyrrolidine-1-carbonyl)-thieno[3,2-b]pyridin-7-yloxy]-2-methyl-indole-1-carboxylic acid prop-2-ynylamide

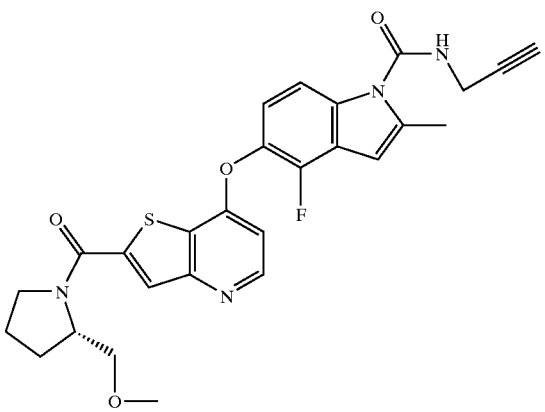

Example 5(c) was prepared in a similar manner as Example 5(a) except that propargylamine was used instead of methylamine. $^1$H NMR (300 MHz, CD$_3$OD) δ 8.53 (1H, d, J=5.65 Hz), 7.95 (1H, s), 7.60 (1H, d, J=8.85 Hz), 7.16–7.22 (1H, m), 6.71 (1H, d, J=5.46 Hz), 6.53 (1H, s), 4.43 (1H, bs), 4.12 (2H, m), 3.80 (2H, m), 3.53 (2H, m), 3.33 (3H, s), 2.63–2.65 (1H, m), 2.47 (3H, s), 1.85–2.04 (4H, m). MS (ESI+) [M+H]/z Calc'd 521, found 521. Anal. (C$_{27}$H$_{25}$FN$_4$O$_4$S) C, H, N.

Example 5(d)

4-Fluoro-5-[2-(2S-hydroxymethyl-pyrrolidine-1-carbonyl)-thieno[3,2-b]pyridin-7-yloxy]-2-methyl-indole-1-carboxylic acid cyclopropylamide

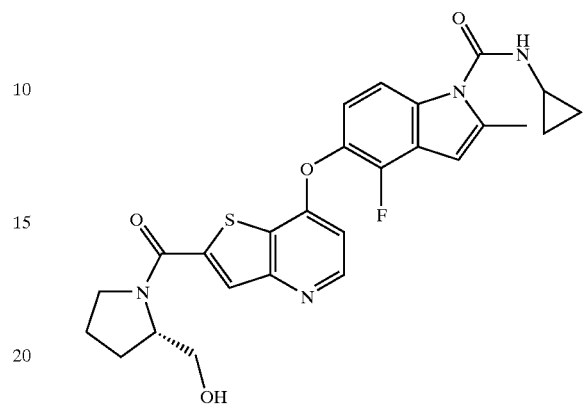

Example 5(d) was prepared in a similar manner as Example 4(n) except that Example 5(b) was used as starting material. $^1$H NMR (300 MHz, CD$_3$OD) δ 8.40 (1H, d, J=5.46 Hz), 7.83 (1H, s), 7.35 (1H, d, J=8.86 Hz), 7.01–7.07 (1H, m), 6.56 (1H, d, J=5.46 Hz), 6.38 (1H, s), 4.25 (1H, bs), 3.66–3.81 (2H, m), 3.19–3.21 (2H, m), 2.76–2.82 (1H, m), 2.43 (3H, s), 1.98–2.02 (4H, m), 0.75–0.79 (2H, m), 0.60–0.65 (2H, m). MS (ESI+) [M+H]/z Calc'd 509, found 509. Anal. (C$_{26}$H$_{25}$FN$_4$O$_4$S.0.75CH$_2$Cl$_2$) C, H, N.

Example 5(e)

4-Fluoro-5-[2-(2S-hydroxymethyl-pyrrolidine-1-carbonyl)-thieno[3,2-b]pyridin-7-yloxy]-2-methyl-indole-1-carboxylic acid prop-2-ynylamide

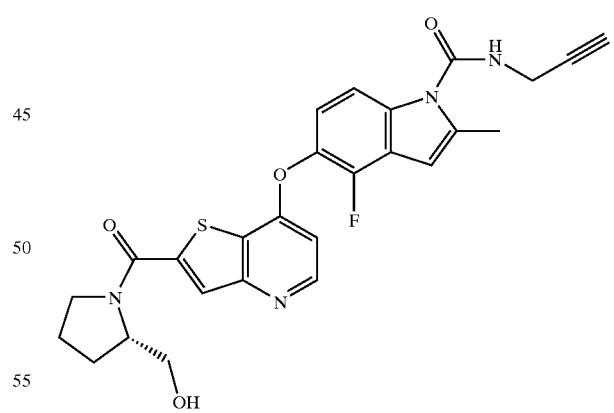

Example 5(e) was prepared in a similar manner as Example 4(n) except that Example 5(c) was used as starting material. $^1$H NMR (300 MHz, CD$_3$OD) δ 8.41 (1H, d, J=5.46 Hz), 7.83 (1H, s), 7.48 (1H, d, J=8.85 Hz), 7.04–7.07 (1H, m), 6.58 (1H, d, J=5.46.Hz), 6.40 (1H, s), 4.26–4.28 (1H, m), 4.12–4.13 (2H, m), 3.66–3.83 (2H, m), 3.19–3.22 (2H, m) 2.63–2.65 (1H, m), 2.47 (3H, s), 1.99–2.02 (4H, m). MS (ESI+) [M+H]/z Calc'd 507, found 507. Anal. (C$_{26}$H$_{23}$FN$_4$O$_4$S.0.5MeOH) C, H, N.

Example 5(f)

4-Fluoro-5-[2-(3S-methoxy-pyrrolidine-1-carbonyl)-thieno[3,2-b]pyridin-7-yloxy]-2-methyl-indole-1-carboxylic acid methylamide

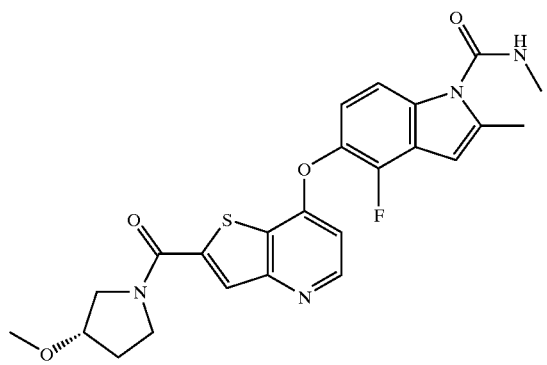

Example 5(f) was prepared in a similar manner as Example 5(a) except that 3S-methoxy-pyrrolidine was used instead of 2S-methoxymethyl-pyrrolidine in the referenced step (i) of Example 4(a). $^1$H NMR (300 MHz, CD$_3$OD) δ 8.41 (1H, d, J=5.1 Hz), 7.84 (1H, d, J=6.2 Hz), 7.43 (1H, d, J=8.8 Hz), 7.05 (1H, dd, J=8.8, 1.3 Hz), 6.58 (1H, d, J=5.5 Hz), 6.39 (1H, s), 4.07–3.80 (3H, m), 3.74–3.58 (2H, m), 3.27 (3H, d, J=14.3 Hz), 2.97 (3H, s), 2.46 (3H, s), 2.08–1.94 (2H, m). LCMS (ESI+) [M+H]/z Calc'd 483, found 483. Anal. (C$_{24}$H$_{23}$N$_4$O$_4$SF.0.5EtOAc) C, H, N.

Example 5(g)

4-Fluoro-5-[2-(3S-methoxy-pyrrolidine-1-carbonyl)-thieno[3,2-b]pyridin-7-yloxy]-2-methyl-indole-1-carboxylic acid prop-2-ynylamide

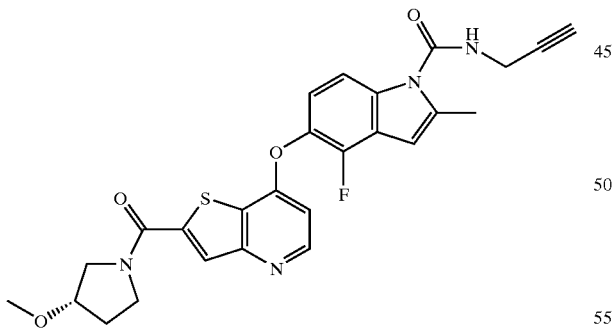

Example (g) was prepared in a similar manner as Example 5(f) except that propargylamine was used instead of methylamine. $^1$H NMR (300 MHz, CD$_3$OD) δ 8.40 (1H, d, J=5.5 Hz), 7.83 (1H, d, J=5.8 Hz), 7.47 (1H, d, J=8.8 Hz), 7.06 (1H, dd, J=8.7, 1.0 Hz), 6.58 (1H, d, J=5.5 Hz), 6.40 (1H, s), 4.12 (2H, d, J=2.4 Hz), 4.08–3.78 (3H, m), 3.75–3.55 (2H, m), 3.42 (3H, d, J=14.3 Hz), 2.66–2.60 (1H, m), 2.47 (3H, s), 2.21–1.94 (2H, m). LCMS (ESI+) [M+H]/z Calc'd 507, found 507. Anal. (C$_{26}$H$_{23}$N$_4$O$_4$SF) C, H, N.

Example 5(h)

4-Fluoro-5-[2-(3S-methoxy-pyrrolidine-1-carbonyl)-thieno[3,2-b]pyridin-7-yloxy]-2-methyl-indole-1-carboxylic acid cyclopropylamide

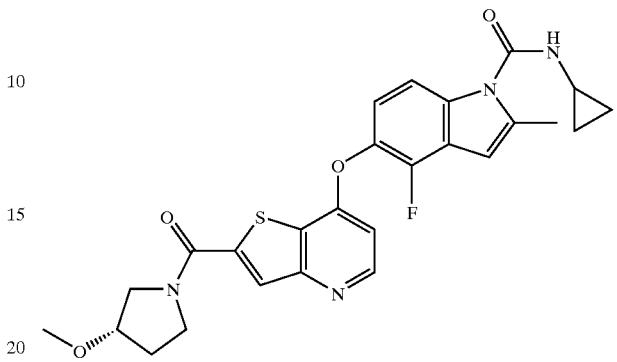

Example 5(h) was prepared in a similar manner as Example 5(f) except that cyclopropylamine was used instead of methylamine. $^1$H NMR (300 MHz, CD$_3$OD) δ 8.52 (1H, d, J=5.5 Hz), 7.94 (1H, d, J=6.2 Hz), 7.48 (1H, d, J=8.8 Hz), 7.15 (1H, dd, J=8.7, 0.8 Hz), 6.68 (1H, d, J=5.3 Hz), 6.49 (1H, s), 4.20–4.89 (3H, m), 3.85–3.69 (2H, m), 3.40 (3H, d, J=14.3 Hz), 2.93–2.84 (1H, m), 2.56 (3H, s), 2.33–2.06 (2H, m), 0.94–0.84 (2H, m), 0.78–0.70 (2H, m). LCMS (ESI+) [M+H]/z Calc'd 509, found 509. Anal. (C$_{26}$H$_{25}$N$_4$O$_4$SF) C, H, N.

Example 5(i)

4-Fluoro-5-[2-(3S-hydroxy-pyrrolidine-1-carbonyl)-thieno[3,2-b]pyridin-7-yloxy]-2-methyl-indole-1-carboxylic acid methylamide

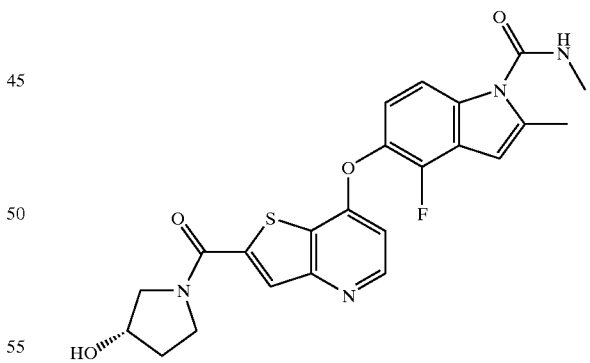

Example 5(i) was prepared in a similar manner as Example 4(n) except that 5(f) was used as starting material. $^1$H NMR (300 MHz, CD$_3$OD) δ 8.54 (1H, d, J=5.5 Hz), 7.97 (1H, d, J=17.5 Hz), 7.65 (1H, d, J=8.8 Hz), 7.18 (1H, dd, J=8.7, 1.1 Hz), 6.70 )1H, d, J=5.5 Hz), 6.52 (1H, s), 4.53 (1H, bs), 4.12–4.01 (2H, m), 3.87–3.77 (2H, m), 3.77–3.70 (1H, m), 3.04 (3H, s), 2.59 (3H, s), 2.24–1.99 (2H, m). LCMS (ESI+) [M+H]/z Calc'd 469, found 469. Anal. (C$_{23}$H$_{21}$N$_4$O$_4$SF.0.5CH$_2$Cl$_2$) C, H, N.

Example 5(j)

4-Fluoro-5-[2-(3S-hydroxy-pyrrolidine-1-carbonyl)-thieno[3,2-b]pyridin-7-yloxy]-2-methyl-indole-1-carboxylic acid cyclopropylamide

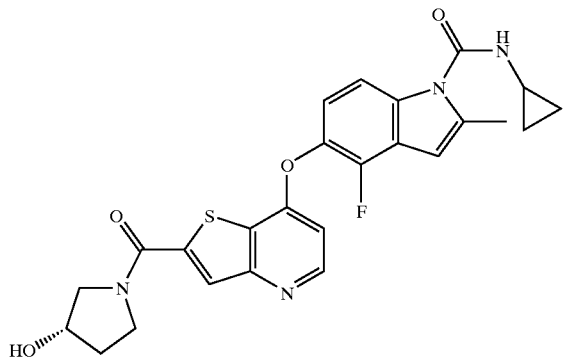

Example 5(j) was prepared in a similar manner as Example 4(n) except that 5(h) was used as starting material. $^1$H NMR (300 MHz, CD$_3$OD) δ 8.40 (1H, bs), 7.97 (1H, d, J=17.5 Hz), 7.35 (1H, d, J=8.8 Hz), 7.04 (1H, dd, J=8.8, 1.3 Hz), 6.56 (1H, d, J=5.5 Hz), 6.37 (1H, s), 4.41 (1H, bs), 4.00–3.89 (2H, m), 3.75–3.64 (2H, m), 3.62–3.56 (1H, m), 2.83–2.76 (1H, m), 2.43 (3H, s), 2.05–1.96 (2H, m), 0.83–0.74 (2H, m), 0.65–0.58 (2H, m). LCMS (ESI+) [M+H]/z Calc'd 495, found 495. Anal. (C$_{25}$H$_{23}$N$_4$O$_4$SF.0.6EtOAc) C, H, N.

Example 5(k)

4-Fluoro-5-[2-(3R-hydroxy-pyrrolidine-1-carbonyl)-thieno[3,2-b]pyridin-7-yloxy]-2-methyl-indole-1-carboxylic acid prop-2-ynylamide

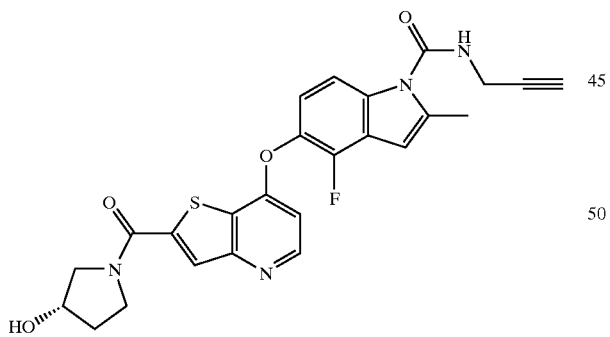

Example 5(k) was prepared in a similar manner as Example 4(n) except that Example 5(g) was used as starting material. $^1$H NMR (300 MHz, CD$_3$OD) δ 8.54 (d, 1H, J=5.7 Hz), 7.97 (d, 1H, J=17.5 Hz), 7.59 (d, 1H, J=9.0 Hz), 7.12 (dd, 1H, J=8.7, 0.9 Hz), 6.71 (d, 1H, J=5.5 Hz), 6.53 (s, 1H), 4.55 (bs, 1H), 4.26 (d, 2H, J=2.6 Hz), 4.16–4.01 (m, 2H), 3.88–3.77 (m, 2H), 3.77–3.70 (m, 1H), 2.78–2.73 (m, 1H), 2.60 (s, 3H), 2.22–2.12 (m, 2H). LCMS (ESI+) [M+H]/z Calc'd 493, found 493. Anal. (C$_{25}$H$_{21}$N$_4$O$_4$SF.MeOH) C, H, N.

Example 5(l)

4-Fluoro-5-[2-(3R-methoxy-pyrrolidine-1-carbonyl)-thieno[3,2-b]pyridin-7-yloxy]-2-methyl-indole-1-carboxylic acid methylamide

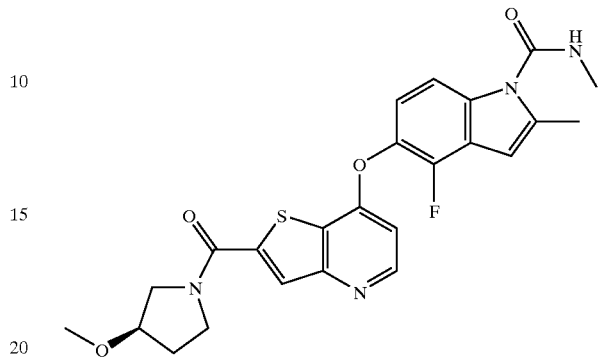

Example 5(l) was prepared in a similar manner as Example 5(a) except that 3R-methoxy-pyrrolidine was used instead of 2S-methoxymethyl-pyrrolidine in the referenced step (i) of Example 4(a). $^1$H NMR (300 MHz, CD$_3$OD) δ 8.36 (d, 1H, J=5.5 Hz), 7.81 (d, 1H, J=5.3 Hz), 7.41 (d, 1H, J=8.8 Hz), 7.02 (dd, 1H, J=8.7, 0.9 Hz), 6.55 (d, 1H, J=8.3 Hz), 6.36 (s, 1H), 4.08–3.75 (m, 3H), 3.73–3.51 (m, 2H), 3.26 (d, 3H, J=14.3 Hz), 2.91 (s, 3H), 2.44 (s, 3H), 2.21–1.93 (m, 2H). LCMS (ESI+) [M+H]/z Calc'd 483, found 483. Anal. (C$_{24}$H$_{23}$N$_4$O$_4$SF) C, H, N.

Example 5(m)

4-Fluoro-5-[2-(3R-hydroxy-pyrrolidine-1-carbonyl)-thieno[3,2-b]pyridin-7-yloxy]-2-methyl-indole-1-carboxylic acid methylamide

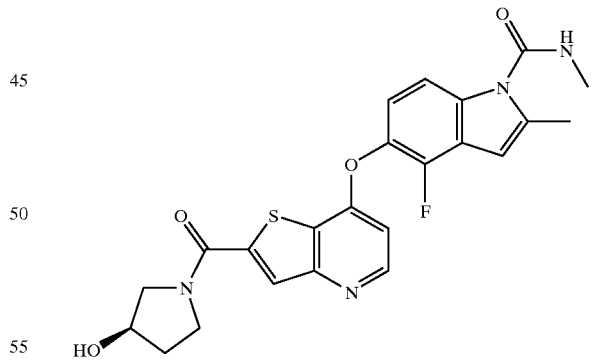

Example 5(m) was prepared in a similar manner as Example 4(n) except that Example 5(l) was used as starting material. $^1$H NMR (300 MHz, CD$_3$OD) δ 8.39 (d, 1H, J=5.5 Hz), 7.82 (d, 1H, J=17.3 Hz), 7.41 (d, 1H, J=8.9 Hz), 7.03 (dd, 1H, J=8.7, 0.7 Hz), 6.56 (d, 1H, J=5.5 Hz), 6.37 (s, 1H), 4.41 (bs, 1H), 4.01–3.88 (m, 2H), 3.75–3.63 (m, 2H), 3.63–3.54(m, 1H), 2.91 (s, 3H), 2.45 (s, 3H), 2.21–1.93 (m, 2H). LCMS (ESI+) [M+H]/z Calc'd 469, found 469. Anal. (C$_{23}$H$_{21}$N$_4$O$_4$SF.0.4CH$_2$Cl$_2$) C, H, N.

Example 5(n)

4-Fluoro-5-[(2-{[(2S)-2-(hydroxymethyl)pyrrolidin-1-yl]carbonyl}thieno[3,2-b]pyridin-7-yl)oxy]-N,2-dimethyl-1H-indole-1-carboxamide

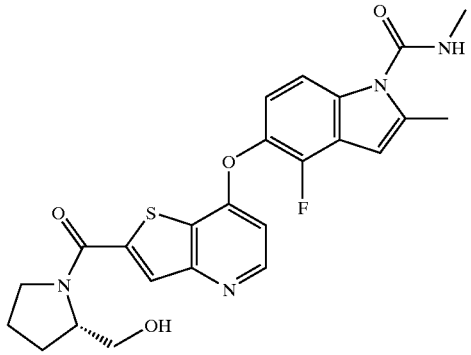

Example (5n) was prepared in a similar manner as Example (4n) except that Example 5(a) was used as starting material. $^1$H NMR (CD$_3$OD) δ 8.40 (1H, d, J=5.5 Hz), 7.83 (1H,s), 7.42 (1H, d, J=8.9 Hz), 7.04 (1H, s), 6.57 (1H, d, J=5.5 Hz), 6.39 (1H, s), 4.25(1H, s), 3.81–3.60 (4H, m), 2.91 (3H, s), 2.46 (3H, s), 2.04–1.98 (2H, m), 0.81–0.75 (2H, m). HRMS Calc'd for C$_{24}$H$_{23}$FN$_4$O$_4$S [MH$^+$] 483.1499; Found 483.1502.

Example 5(o)

4-Fluoro-5-[2-((R)-3-methoxy-pyrrolidine-1-carbonyl)-thieno[3,2-b]pyridin-7-yloxy]-2-methyl-indole-1-carboxylic acid prop-2-ynylamide

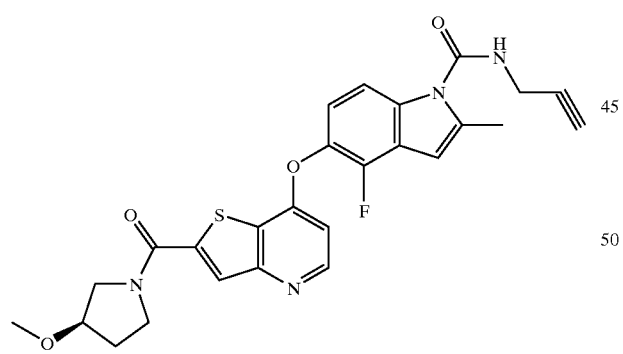

Example (5o) was prepared in a similar manner as Example (5l) except that propargylamine was used instead of methylamine. $^1$H NMR (300 MHz, CD$_3$OD) δ 8.52 (1H, d, J=5.7 Hz), 7.94 (1H, d, J=5.3 Hz), 7.58 (1H, d, J=8.9 Hz), 7.17 (1H, dd, J=1.1, 8.9 Hz), 6.69 (1H, d, J=5.7 Hz), 6.51 (1H, s), 4.26 (2H, d, J=2.5 Hz), 4.17–3.93 (3H, m), 3.88–3.70 (2H, m), 3.40 (3H, d, J=14.3 Hz), 2.76 (1H, s), 2.59 (3H, s), 2.35–2.08 (2H, m). LCMS (ESI+) [M+H]/z Calc'd 507, Found 507. Anal. (C$_{26}$H$_{23}$N$_4$O$_4$SF.0.4CH$_2$Cl$_2$) C, H, N.

Example 5(p)

4-Fluoro-5-[2-((R)-3-hydroxy-pyrrolidine-1-carbonyl)-thieno[3,2-b]pyridin-7-yloxy]-2-methyl-indole-1-carboxylic acid prop-2-ynylamide

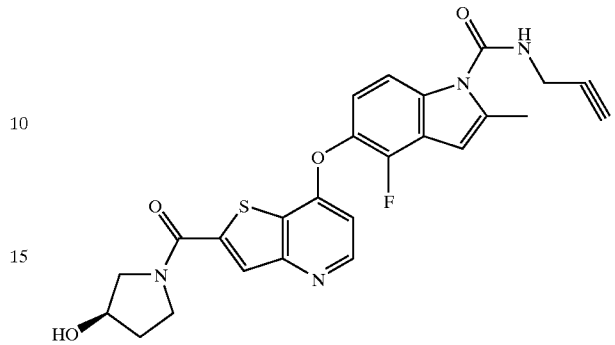

Example 5(p) was prepared in a similar manner as Example 4(n) except that Example 5(o) was used as starting material. $^1$H NMR (300 MHz, CD$_3$OD) δ 8.41 (1H, d, J=5.4 Hz), 7.83 (1H, d, J=17.3 Hz), 7.46 (1H, d, J=8.9 Hz), 7.08 (1H, d, J=7.5 Hz), 6.58 (1H, d, J=5.4 Hz), 6.40 (1H, s), 4.51–4.38 (br s, 1H), 4.12 (2H, d, J=2.5 Hz), 4.05–3.88 (2H, m), 3.79–3.57 (3H, m), 2.64 (1H, s), 2.47 (3H, s), 2.16–1.98 (2H, m). LCMS (ESI+) [M+H]/z Calc'd 493, found 493. Anal. (C$_{25}$H$_{21}$N$_4$O$_4$SF.0.2CH$_2$Cl$_2$) C, H, N.

Step i: 5-{-2-[2-(tert-Butyl-dimethyl-silanyloxymethyl)-4-methoxy-pyrrolidine-1-carbonyl]-thieno[3,2-b]pyridin-7-yloxy}-2-methyl-indole-1-carboxylic acid methylamide.

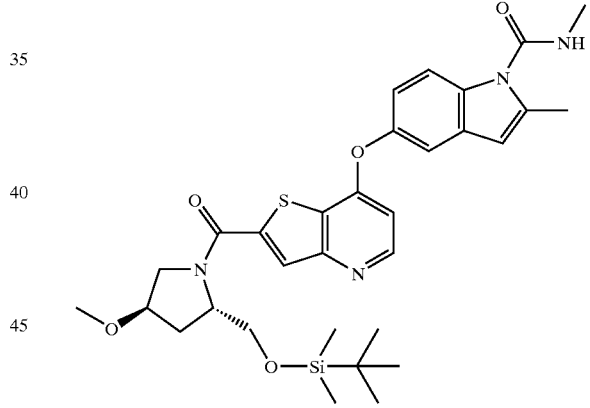

To a 2 mL of methylene chloride was added [2-(tert-Butyl-dimethyl-silanyloxymethyl)-4-methoxy-pyrrolidin-1-yl]-[7-(2-methyl-1H-indol-5-yloxy)-thieno[3,2-b]pyridin-2-yl]-methanone (0.15 g, 0.26 mmol), NaOH (0.032 g, 0.82 mmol), Tetrabutyl-ammonium bromide (0.01 g. 0.028 mmol) and methylisocynate (0.0.62 g, 1.08 mmol). After stirring for 3 h, the reaction mixture was partitioned between EtOAc (50 mL) and saturated NaHCO$_3$ (2×50 mL). The organic layer was dried over NaSO$_4$ and concentrated. The residue was purified using 2 mm chromatotron rotor eluting with EtOAc/CH$_2$Cl$_2$ (1:1) purified fraction concentrated to give 0.12 g (74%) of 5-{2-[2-(tert-Butyl-dimethyl-ilanyloxymethyl)-4-methoxy-pyrrolidine-1-carbonyl]-thieno [3,2-b]pyridin-7-yloxy}-2-methyl-indole-1-carboxylic acid methylamide as clear oil. HPLC: R$_t$ 5.02 min. (98% area). $^1$H NMR (CDCl$_3$, 400 MHz) δ: 8.48 (1H, d, J=5.5 Hz), 7.81 (1H, s), 7.36 (1H, bd, J=4.5), 7.75 (1H, s), 7.30–7.25 (2H, m), 7.04 (1H, d, J=7.4 Hz), 6.56 (1H, q, J=5.5 Hz), 6.39 (1H, s), 4.51 (1H, bs), 4.17–4.06 (3H, m), 3.83–3.77 (1H, m), 3.65 (1H, d, J=10.1 Hz), 3.24 (3H, S), 3.19 (3H, s), 2.96 (3H, d, J=4.4 Hz), 2.48 (3H, s), 2.31–2.24 (1H, m), 2.15–2.10 (1H, m), 0.97 (9H, s). ACPI LCMS (M+H⁺) m/z: 609.2.

Example 6(a)

3-Chloro-4-fluoro-5-[2-(3S-methoxy-pyrrolidine-1-carbonyl)-thieno[3,2-b]pyridin-7-yloxy]-2-methyl-indole-1-carboxylic acid prop-2-ynylamide

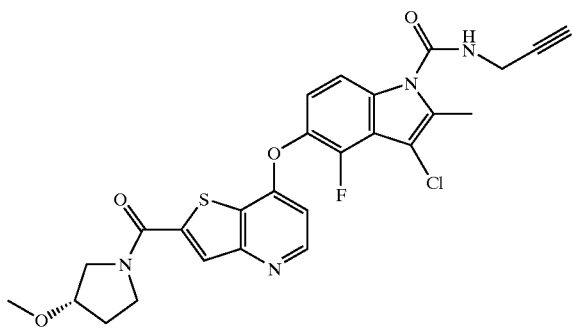

Example 6(a) was prepared in a similar manner as Example 4(a) except that propargylamine was used instead of methylamine and 3-Chloro-4-fluoro-5-[2-(3-methoxy-pyrrolidine-1-carbonyl)-thieno[3,2-b]pyridin-7-yloxy]-2-methyl-indole-1-carboxylic acid 4-nitro-phenyl ester, prepared as described below, was used intead of 2-methyl-5-(2-[(S)-2-(methoxymethyl)pyrrolidine-1-carbonyl]thieno[3,2-b]pyridin-7-yloxy)-1-(4-nitrophenoxy)indole. ¹H NMR (300 MHz, CD₃OD) δ 8.52 (1H, d, J=5.5 Hz), 7.93 (1H, d, J=5.1 Hz), 7.61 (1H, d, J=9.0 Hz), 7.24 (1H, dd, J=8.8, 1.3 Hz), 6.71 (1H, d, J=5.5 Hz), 4.24 (2H, d, J=2.4 Hz), 4.20–3.88 (3H, m), 3.85–3.66 (2H, m), 3.49 (3H, d, J=13.9 Hz), 2.79–2.74 (1H, m), 2.54 (3H, s), 2.38–2.08 (2H, m). LCMS (ESI+) [M+H]/z Calc'd 541, found 541. Anal. (C₂₆H₂₂N₄O₄SFCl.0.3CH₂Cl₂) C, H, N.

The starting materials were prepared as follows:
(i) [7-(4-Fluoro-2-methyl-1H-indol-5-yloxy)-thieno[3,2-b]pyridin-2-yl]-(3S-methoxy-pyrrolidin-1-yl)-methanone

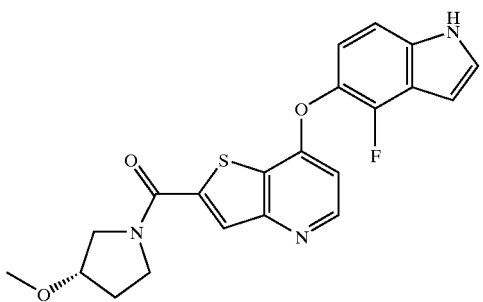

The title compound was prepared in a similar manner as Example 5(a) except that 3S-methoxy-pyrrolidine was used instead of 2S-methoxymethyl-pyrrolidine in the referenced step (i) of Example 4(a). ¹H NMR (300 MHz, CD₃OD) δ 8.39 (d, 1H, J=5.5 Hz), 8.02 (d, 1H, J=9.2 Hz), 7.82 (d, 1H, J=5.5 Hz), 7.09 (d, 1H, J=8.7 Hz), 6.93 (dd, 1H, J=8.7, 1.5 Hz), 6.77 (d, 1H, J=9.2 Hz), 6.46 (s, 1H), 4.05–3.78 (m, 2H), 3.73–3.55 (m, 2H), 3.29 (d, 3H, J=14.1 Hz), 2.29 (s, 3H), 2.20–1.95 (m, 2H). LCMS (ESI+) [M+H]/z Calc'd 426, found 426.

(ii) 3-Chloro-4-fluoro-5-[2-(3-methoxy-pyrrolidine-1-carbonyl)-thieno[3,2-b]pyridin-7-yloxy]-2-methyl-indole-1-carboxylic acid 4-nitro-phenyl ester

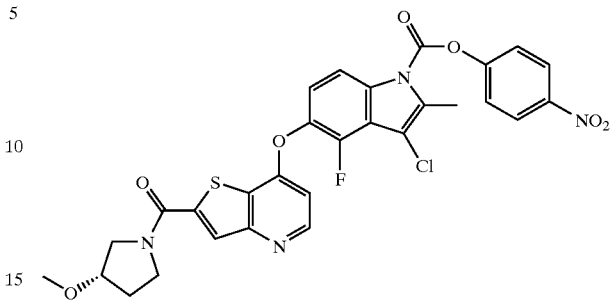

To a stirred solution of [7-(4-Fluoro-2-methyl-1h-indol-5-yloxy)-thieno[3,2-b]pyridin-2-yl]-(3-methoxy-pyrrolidin-1-yl)-methanone (399 mg, 0.94 mmole) in CH₂Cl₂ (30 ml) and DMSO (0.2 ml) were added, sequentially, freshly crushed NaOH (700 mg, 17.50 mmole), Bu₄NBr (25 mg, catalytic amount) and 4-nitrophenyl chloroformate (1.18 g, 5.84 mmole). After stirring at ambient temperature for overnight, the reaction mixture was filtered and the filtrate was concentrated, in vacuo, to give crude product, which was further purified by flash column chromatography eluted with EtOAc : CH₂Cl₂:MeOH (1:1:0.02) to provide 110 mg (19%) of a yellow solid. ¹H NMR (300 MHz, CDCl₃): δ 8.55 (1H, d, J=5.5 Hz), 8.40 (2H, d, J=8.7 Hz), 8.04 (1H, d, J=9.1 Hz), 7.86 (1H, d, J=10.7 Hz), 7.53 (2H, d, J=9.04 Hz), 7.26 (1H, dd, J=9.2, 1.9 Hz), 6.62 (1H, d, J=5.5 Hz), 4.02–3.89 (3H, m), 3.88–3.71 (2H, m), 3.37 (3H, d, J=15.1 Hz), 2.73 (3H, s), 2.29–2.08 (2H, m).

Example 6(b)

3-Chloro-4-fluoro-5-[2-(3S-methoxy-pyrrolidine-1-carbonyl)-thieno[3,2-b]pyridin-7-yloxy]-2-methyl-indole-1-carboxylic acid methylamide

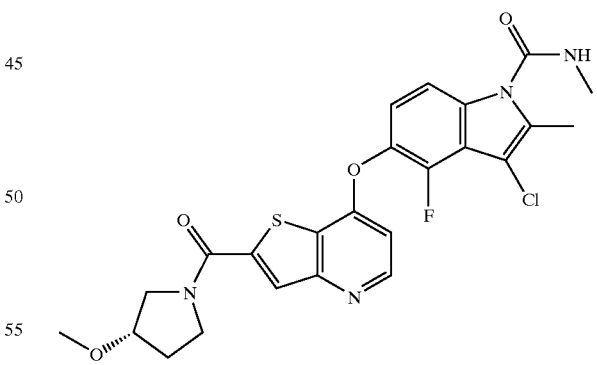

Example 6(b) was prepared in a similar manner as Example 6(a) except that methylamine was used instead of propargylamine. ¹H NMR (300 MHz, CD₃OD) δ 8.56 (1H, d, J=5.5 Hz), 7.98 (1H, d, J=5.2 Hz), 7.53 (1H, d, J=8.8 Hz), 7.13 (1H, dd, J=8.3, 0.2 Hz), 6.61 (1H, d, J=5.5 Hz), 4.09–3.82 (3H, m), 3.76–3.54 (2H, m), 3.29 (3H, d, J=14.3 Hz), 2.92 (3H, s), 2.44 (3H, s), 2.30–2.04 (2H, m). LCMS (ESI+) [M+H]/z Calc'd 517, found 517. Anal. (C₂₄H₂₂N₄O₄SFCl.0.5CH₂Cl₂) C, H, N.

Example 6(c)

3-Chloro-4-fluoro-5-[2-(3S-methoxy-pyrrolidine-1-carbonyl)-thieno[3,2-b]pyridin-7-yloxy]-2-methyl-indole-1-carboxylic acid cyclopropyl-amide

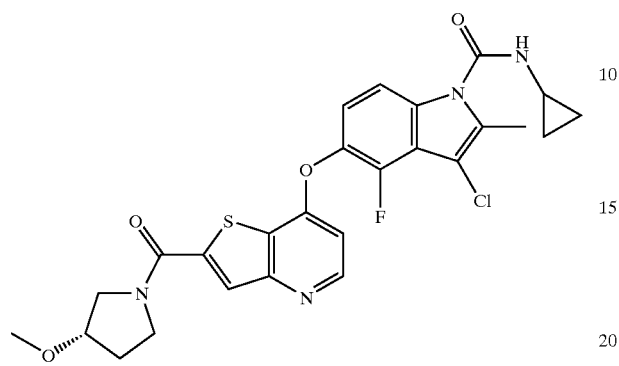

Example 6(c) was prepared in a similar manner as Example 6(a) except that cyclopropylamine was used instead of propargylamine. $^1$H NMR (300 MHz, CD$_3$OD) δ 8.56 (1H, d, J=5.5 Hz), 7.98 (1H, d, J=6.2 Hz), 7.53 (1H, d, J=8.8 Hz), 7.26 (1H, dd, J=8.7, 0.1 Hz), 6.73 (1H, d, J=6.0 Hz), 4.19–4.01 (3H, m), 3.82–3.68 (2H, m), 3.40 (3H, d, J=14.2 Hz), 2.95–2.86 (1H, m), 2.53 (3H, s), 2.30–2.04 (2H, m), 0.93–0.87 (2H, m), 0.79–0.70 (2H, m). LCMS (ESI+) [M+H]/z Calc'd 543, found 543. Anal. (C$_{26}$H$_{24}$N$_4$O$_4$SFCl.0.3CH$_2$Cl$_2$) C, H, N.

Example 6(d)

3-Chloro-4-fluoro-5-[2-(3S-hydroxy-pyrrolidine-1-carbonyl)-thieno[3,2-b]pyridin-7-yloxy]-2-methyl-indole-1-carboxylic acid prop-2-ynylamide

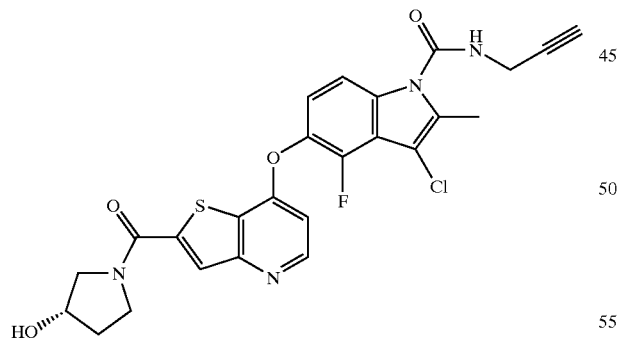

Example 6(d) was prepared in a similar manner as Example 4(n) except that Example 6(a) was used as starting material. $^1$H NMR (300 MHz, CD$_3$OD) δ 8.56 (1H, d, J=5.5 Hz), 7.79 (1H, d, J=5.1 Hz), 7.63 (1H, d, J=8.8 Hz), 7.27 (1H, dd, J=8.8, 1.3 Hz), 6.74 (1H, d, J=5.5 Hz), 6.40 (1H, s), 4.25 (2H, d, J=2.6 Hz), 4.12–3.76 (3H, m), 3.86–3.74 (2H, m), 2.78–2.74 (1H, m), 2.56 (3H, s), 2.23–2.00 (2H, m). LCMS (ESI+) [M+H]/z Calc'd 527, found 527. Anal. (C$_{25}$H$_{20}$N$_4$O$_4$SFCl.1.0H$_2$O) C, H, N.

Example 6(e)

3-Chloro-4-fluoro-5-[2-(3S-hydroxy-pyrrolidine-1-carbonyl)-thieno[3,2-b]pyridin-7-yloxy]-2-methyl-indole-1-carboxylic acid methylamide

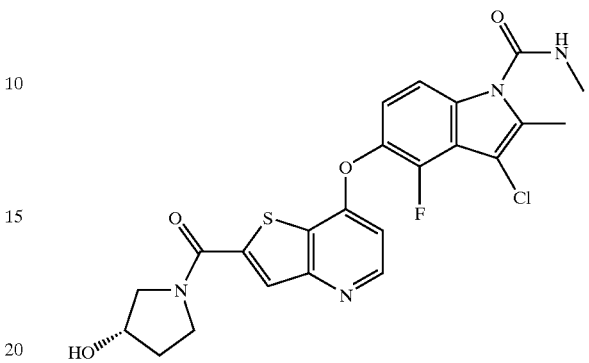

Example 6(e) was prepared in a similar manner as Example 4(n) except that Example 6(b) was used as starting material. $^1$H NMR (300 MHz, CD$_3$OD) δ 8.41 (1H, d, J=5.6 Hz), 7.84 (H, d, J=17.1 Hz), 7.47 (H, d, J=9.0 Hz), 7.13 (1H, dd, J=8.7, 1.1 Hz), 6.60 (1H, d, J=5.5 Hz), 4.41 (1H, bs), 4.01–3.90 (2H, m), 3.73–3.63 (2H, m), 3.63–3.55 (1H, m), 2.91 (3H, s), 2.42 (3H, s), 2.09–1.92 (2H, m). LCMS (ESI+) [M+H]/z Calc'd 503, found 503. Anal. (C$_{23}$H$_{20}$N$_4$O$_4$SFCl.0.2CH$_2$Cl$_2$) C, H, N.

Example 6(f)

3-Chloro-4-fluoro-5-[2-(3S-hydroxy-pyrrolidine-1-carbonyl)-thieno[3,2-b]pyridin-7-yloxy]-2-methyl-indole-1-carboxylic acid cyclopropyl-amide

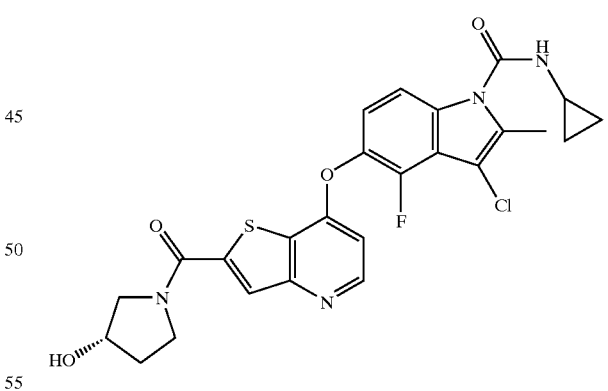

Example 6(f) was prepared in a similar manner as Example 4(n) except that Example 6(c) was used as starting material. $^1$H NMR (300 MHz, CD$_3$OD) δ 8.43 (1H, d, J=5.6 Hz), 7.84 (1H, d, J=17.1 Hz), 7.40 (1H, d, J=9.0 Hz), 7.13 (1H, dd, J=8.7, 1.1 Hz), 6.60 (1H, d, J=5.5 Hz), 4.42 (1H, bs), 4.09–3.89 (2H, m), 3.74–3.65 (2H, m), 3.65–3.58 (1H, m), 2.83–2.77 (1H, m), 2.40 (3H, s), 2.10–1.89 (2H, m), 0.81–0.72 (2H, m), 0.66–0.61 (2H, m). LCMS (ESI+) [M+H]/z Calc'd 529, found 529. Anal. (C$_{25}$H$_{22}$N$_4$O$_4$SFCl.0.5CH$_2$Cl$_2$) C, H, N.

Example 6(g)

3-Chloro-4-fluoro-5-[2-(3R-methoxy-pyrrolidine-1-carbonyl)-thieno[3,2-b]pyridin-7-yloxy]-2-methyl-indole-1-carboxylic acid methylamide

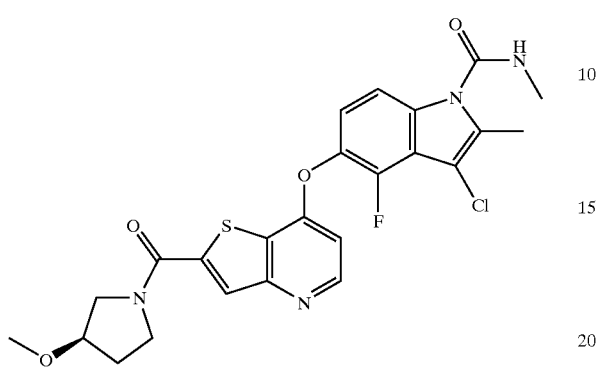

Example 6(g) was prepared in a similar manner as Example 6(b) except that 3R-methoxy-pyrrolidine instead of 3S-methoxy-pyrrolidine. $^1$H NMR (300 MHz, CD$_3$OD) δ8.41 (d, 1H, J=5.5 Hz), 7.83 (d, 1H, J=5.5 Hz), 7.45 (d, 1H, J=9.0 Hz), 7.02 (dd, 1H, J=8.7, 1.1 Hz), 6.59 (d, 1H, J=5.5 Hz), 4.09–3.78 (m, 3H), 3.75–3.54 (m, 2H), 3.26 (d, 3H, J=13.9 Hz), 2.92 (s, 3H), 2.42 (s, 3H), 2.23–1.93 (m, 2H). LCMS (ESI+) [M+H]/z Calc'd 517, found 517. Anal. (C$_{24}$H$_{22}$N$_4$O$_4$SFCl.0.4MeOH) C, H, N.

Example 6(h)

3-Chloro-4-fluoro-5-[2-((R)-3-methoxy-pyrrolidine-1-carbonyl)-thieno[3,2-b]pyridin-7-yloxy]-2-methyl-indole-1-carboxylic acid prop-2-ynylamide

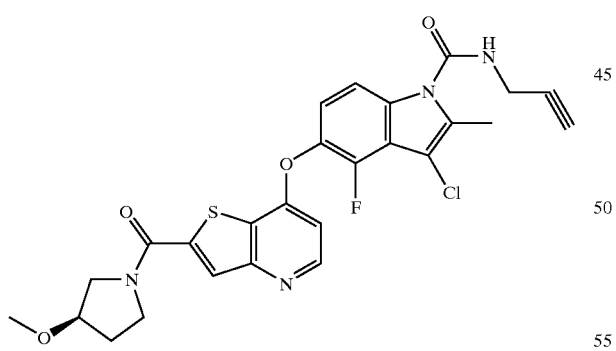

Example 6(h) was prepared in a similar manner as Example 6(g) except that propargylamine was used instead of methylamine. $^1$H NMR (300 MHz, CD$_3$OD) δ 8.65 (1H, d, J=5.5 Hz), 7.97 (1H, d, J=5.7 Hz), 7.63 (1H, d, J=8.9 Hz), 7.26 (1H, dd, J=1.1, 8.9 Hz), 6.74 (1H, d, J=5.5 Hz), 4.25 (2H, d, J=2.5 Hz), 4.17–3.91 (3H, m), 3.86–3.70 (2H, m), 3.40 (3H, d, J=14.1 Hz), 2.74 (1H, s), 2.56 (3H, s), 2.34–2.06 (2H, m). LCMS (ESI+) [M+H]/z Calc'd 541, Found 541. Anal. (C$_{26}$H$_{22}$N$_4$O$_4$SFCl.0.5CH$_2$Cl$_2$) C, H, N.

Example 7(a)

5-[(2-{[(4R)-3-Fluoro-4-methoxypyrrolidin-1-yl]carbonyl}thieno[3,2-b]pyridin-7-yl)amino]-N,2-dimethyl-1H-indole-1-carboxamide

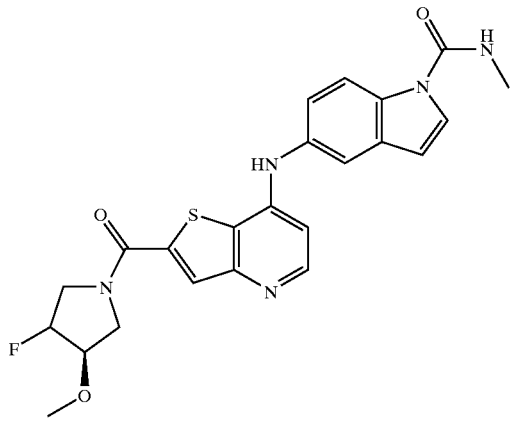

Example 7(a) was prepared in a similar manner as Example 2(a) except that 7-Chloro-2-{[(4R)-3-fluoro-4-methoxypyrrolidin-1-yl]carbonyl}thieno [3,2-b]pyridine, prepared as described below, was used instead of 7-chloro-2-(1-methyl-1H-imidazol-2-yl)thieno[3,2-b]pyridine. $^1$H NMR (CD$_3$OD) δ 8.13 (1H, d, J=5.7 Hz), 7.69 (1H, d, J=6.8 Hz), 7.57 (1H, d, J=8.6 Hz), 7.30 (1H, d, J=1.9 Hz), 7.04 (1H, dd, J=1.9, 8.6 Hz), 6.66 (1H, d, J=5.7 Hz), 6.52 (1H, s), 5.24–5.03 (1H, m), 4.06–3.95 (4H, m), 3.77–3.73 (1H, m), 3.33 (3H, d, J=15.3 Hz), 2.91 (3H, s), 2.44 (3H, s). Anal. Calc'd for C$_{24}$H$_{24}$FN$_5$O$_3$S.0.45CH$_3$OH: C, 59.21; H, 5.24; N, 14.12; found: C, 59.76; H, 5.27; N, 13.76. ESIMS (MH$^+$): 482.15.

Step (i) Benzyl (3R,4R)-3-hydroxy-4-methoxypyrrolidine-1-carboxylate

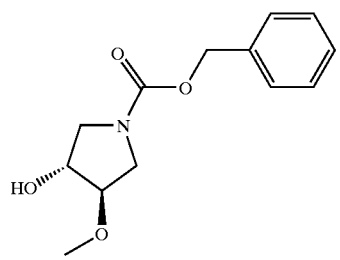

To a solution of benzyl (3R,4R)-3,4-dihydroxypyrrolidine-1-carboxylate (3.81 g, 16.1 mmol) in 60 mL THF was added NaH (0.803 g, 20.07 mmol). The reaction mixture was stirred at room temperature for 15 min, CH$_3$I (2.0 mL, 32.2 mmol) was added and stirred at room temperature overnight. The reaction mixture was quenched with H$_2$O (80 mL) and extracted with EtOAc (2×100 mL). The organic layer was dried and concentrated. The residue was purified by flash column chromatography (1~2% CH$_3$OH in CH$_2$Cl$_2$) to give a white solid (1.12 g, 28%). $^1$H NMR (CDCl$_3$) δ 7.36–7.29 (5H, m), 5.12 (2H, s), 4.28–4.27 (1H, m), 3.72–3.37 (5H, m), 3.35 (3H, s), 1.95–1.89 (1H, m). ESIMS (MH$^+$): 252.05.

Step (ii) Benzyl (4R)-3-fluoro-4-methoxypyrrolidine-1-carboxylate

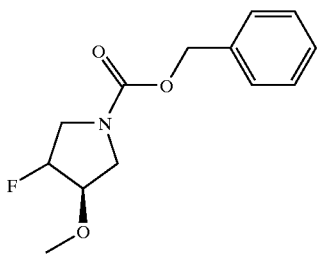

To a solution of benzyl (3R,4R)-3-hydroxy-4-methoxypyrrolidine-1-carboxylate (0.818 g, 3.26 mmol) in 20 mL $CH_2Cl_2$ at −20° C. was added DAST (0.946 mL, 7.16 mmol). The reaction mixture was stirred at −20 ° C. and then room temperature overnight. The reaction mixture was quenched with 30 mL half saturated $NaHCO_3$, stirred at room temperature for 15 min and extracted with EtOAc (2×30 mL). The organic layer was dried and concentrated. The residue was purified by flash column chromatography (25% EtOAc in Hexane) to give pale yellow solid (0.551 g, 67%). $^1$H NMR ($CDCl_3$) δ 7.36–7.29 (5H, m), 5.13 (2H, s), 5.09, 4.92 (1H, m), 3.95–3.91 (1H, m), 3.74–3.35 (4H, m), 3.37 (3H, s).

Step (iii) 7-Chloro-2-{[(4R)-3-fluoro-4-methoxypyrrolidin-1-yl]carbonyl}thieno [3,2-b]pyridine

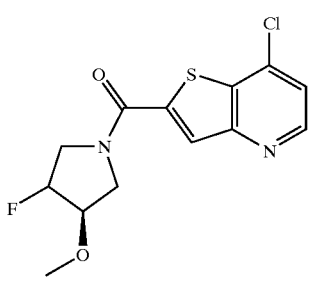

This material was prepared by the coupling of lithium 7-chlorothieno[3,2-b]pyridine-2-carboxylate and (4R)-3-fluoro-4-methoxypyrrolidine in a manner as previously described for Example 1(a), step (iv). $^1$H NMR ($CD_3OD$) δ 8.57 (1H, d, J=5.1 Hz), 7.94 (1H, d, J=7.2 Hz), 7.48 (1H, d, J=5.1 Hz), 5.27–5.05 (1H, m), 4.18–3.93 (4H, m), 3.78–3.75 (1H, m), 3.35 (3H, d, J=14.1 Hz). ESIMS ($MH^+$): 315.05

Example 7(b)
5-[(2-{[(4R)-3-Fluoro-4-hydroxypyrrolidin-1-yl]carbonyl}thieno[3,2-b]pyridin-7-yl)amino]-N,2-dimethyl-1H-indole-1-carboxamide

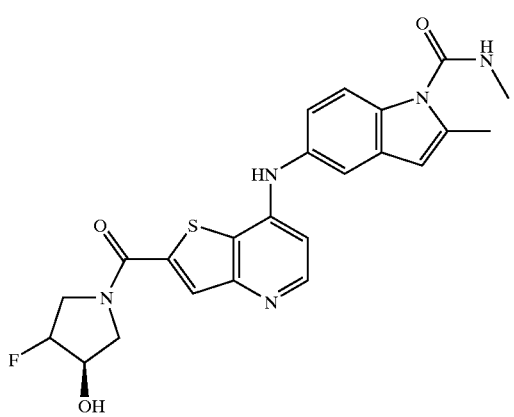

Example 7(b) was prepared in a similar manner as Example 4(n) except that 7(a) was used as starting material. $^1$H NMR ($CD_3OD$) δ 8.13 (1H, d, J=5.7 Hz), 7.70 (1H, s), 7.56 (1H, d, J=8.7 Hz), 7.30 (1H, d, J=2.0 Hz), 7.04 (1H, dd, J=2.0, 8.7 Hz), 6.66 (1H, d, J=5.7 Hz), 6.25 (1H, s), 5.06–4.81 (1H, m), 4.37–4.17 (1H, m), 4.11–3.63 (4H, m), 3.24 (3H, s), 2.91 (3H, s), 2.44 (3H, s). Anal. Calc'd for $C_{23}H_{22}FN_5O_3S$·0.4$CH_3OH$·0.25$CH_2Cl_2$: C, 56.63; H, 4.84; N, 13.96; Found: C, 56.98; H, 4.85; N, 13.70. ESIMS ($MH^+$): 468.20.

Example 7(c)

5-[2-(Azetidine-1-carbonyl)-thieno[3,2-b]pyridin-7-ylamino]-2-methyl-indole-1-carboxylic acid methylamide

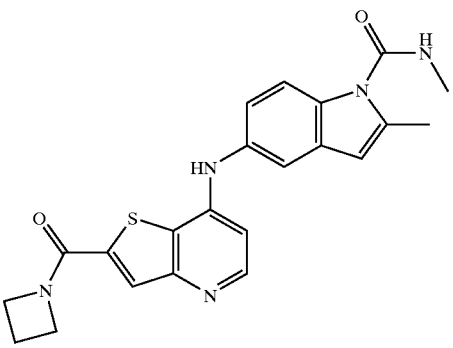

Example 7(c) was prepared in a similar manner as Example 2(a) except that 7-Chloro-2-([azetidin-1-yl]carbonyl)thieno[3,2-b]pyridine, prepared as described below, was used instead of 7-chloro-2-(1-methyl-1H-imidazol-2-yl)thieno[3,2-b]pyridine. $^1$H NMR (300 MHz, DMSO) δ 8.87 (1H, s), 8.30 (1H, d, J=5.4 Hz), 8.22 (1H, d, J=4.2 Hz), 7.68 (1H, s), 7.62 (1H, d, J=8.7 Hz), 7.36 (1H, s), 7.09 (1H, d, J=8.9 Hz), 6.72 (1H, d, J=5.4 Hz), 6.36 (1H, s), 4.61–4.56 (2H, m), 4.13–4.05 (2H, m), 3.33 (3H, s), 2.87 (3H, s), 2.39–2.29 (2H, m). LCMS (ESI+) [M+H]/z Calc'd 420, Found 420. Anal. ($C_{22}H_{21}N_5O_2S$·0.2$CH_2Cl_2$) C, H, N.

Step (i) 7-Chloro-2-([azetidin-1-yl]carbonyl)thieno[3,2-b] pyridine

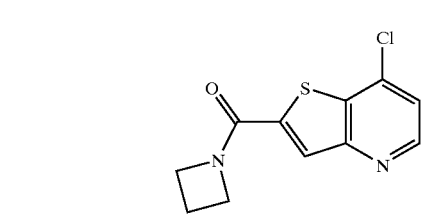

This material was prepared by the coupling of lithium 7-chlorothieno[3,2-b]pyridine-2-carboxylate and azetidine in a manner as previously described for Example 1 (a), step (iv). $^1$H NMR (300 MHz, $CD_3OD$) δ 8.63 (1H, d, J=5.6 Hz), 7.85 (1H, s), 7.54 (1H, d, J=5.6 Hz), 4.74–4.62 (2H, m), 4.32–4.23 (2H, m), 2.58–2.49 (2H, m). LCMS (ESI+) [M+H]/z Calc'd 253, Found 253.

Example 7(d)
5-[2-(2R-Methoxymethyl-pyrrolidine-1-carbonyl)-thieno[3,2-b]pyridin-7-ylamino]-2-methyl-indole-1-carboxylic acid prop-2-ynylamide

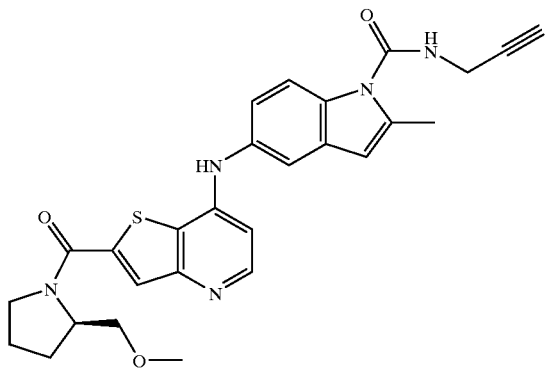

Example 7(d) was prepared in a similar manner as Example 1(b) except that propargylamine was used instead of methylamine. ¹H NMR (300 MHz, CD₃OD) δ 8.21 (1H, d, J=5.6 Hz), 7.74 (1H, s), 7.70 (1H, d, J=8.8 Hz), 7.39 (1H, d, J=2.0 Hz), 7.14 (1H, dd, J=2.0, 8.8 Hz), 6.76 (1H, d, J=5.6 Hz), 6.35 (1H, s), 4.41 (1H, m), 4.21 (2H, d, J=2.5 Hz), 3.86 (2H, m), 3.60 (2H, m), 3.36 (3H, s), 2.72 (1H, t, J=2.5 Hz), 2.54 (3H, s), 2.15–1.90 (4H, m). LCMS (ESI+) [M+H]/z Calc'd 502, Found 502.

Example 8(a)
5-[(2-{[(3R)-3-(Dimethylamino)pyrrolidin-1-yl]carbonyl}thieno[3,2-b]pyridin-7-yl)oxy]-N,N',2-trimethyl-1H-indole-1,3-dicarboxamide

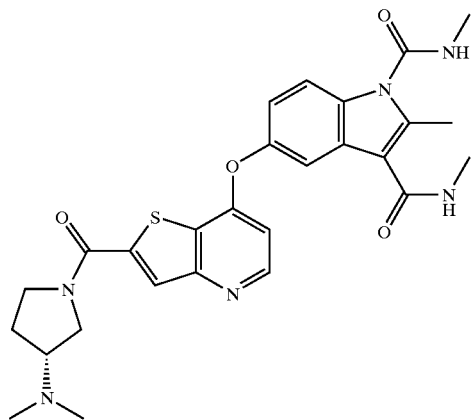

To a solution of 2,2,6,6-tetramethylpiperidine (0.30 mmol, 0.051 mL) in THF cooled at 0° C. was added 1.6 M n-BuLi in hexane (0.30 mmol, 0.191 mL). The mixture was cooled to −78° C. and 5-[(2-{[(3R)-3-(dimethylamino)pyrrolidin-1-yl]carbonyl}thieno[3,2-b]pyridin-7-yl)oxy]-2-methyl-1H-indole-1,3-dicarboxamide (0.30 mmol, 0.126 g) in 2 mL THF was added dropwise. The reaction mixture was stirred at −78° C. for 5 min and methyl isocyanate (0.31 mmol, 0.018 g) was added. The reaction was stirred at −78° C. for 15 min and then warmed to room temperature overnight. The reaction mixture was concentrated and partition between CH₂Cl₂ and brine. The organic layer was dried over MgSO₄ and concentrated. The residue was purified by flash column chromatography (3–5% CH₃OH in CH₂Cl₂) to give pale yellow solid (0.064 g, 40%). ¹H NMR (CD₃OD) δ 8.39 (1H, d, J=5.4 Hz), 7.82 (1H, d, J=8.7 Hz), 7.37 (1H, d, J=8.9 Hz), 7.28 (1H, d, J=2.3 Hz), 6.99 (1H, dd, J=2.3, 8.9 Hz), 6.59 (1H, d, J=5.4 Hz), 4.09–3.96 (1H, m), 3.88–3.33 (3H, m), 3.14 (3H, s), 2.89–2.78 (1H, m), 2.70 (3H, s), 2.41 (3H, s), 2.25 (3H, s), 2.22 (3H, s), 2.21–2.19 (1H, m), 1.97–1.73 (1H, m). Anal. Calc'd for C₂₇H₃₀N₆O₄S.0.3 CH₂Cl₂: C, 58.54; H, 5.51; N, 15.00; Found: C, 58.48; H, 5.59; N, 14.88. ESIMS (MH⁺): 535.25.

Step (i): 7-Chloro-2-[3(R)-(dimethylamino)pyrrolidine-1-carbonyl]thieno[3,2-b]pyridine

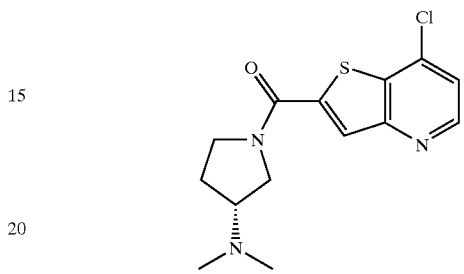

HATU (4.99 g, 26.25 mmol) and Et₃N (7.23 mL, 52.50 mmol) was added to a solution of (3R)-N,N-dimethylpyrrolidin-3-amine (1.0 g, 17.5 mmol) and 7-chlorothieno[3,2-b]pyridine-2-carboxylic acid lithium salt (3.85 g, 17.5 mmol) in 30 mL DMF at 0° C. The reaction mixture was stirred at 0° C. for 15 min and solvent was concentrated. The residue was partition between H₂O and 10% CH₃OH in EtOAC. The organic layer was dried over MgSO₄ and concentrated. The residue was purified by flash column chromatography (5–7% CH₃OH in CH₂Cl₂) to give a white solid (1.74 g, 32%). ¹H NMR (CD₃OD) δ 8.57 (1H, d, J=5.2 Hz), 7.90 (1H, d, J=7.9 Hz), 7.48 (1H, d, J=5.2 Hz), 4.11–3.97 (1H, m), 3.90–3.36 (3H, m), 2.99–2.90 (1H, m), 2.30 (3H, s), 2.26 (3H, s), 1.97–1.72 (2H, m). ESIMS (MH⁺): 310.10.

Step (ii): 5-(2-[3(R)-(dimethylamino)pyrrolidine-1-carbonyl]thieno[3,2-b]pyridin7-yloxy)-2-methyl-1H-indole

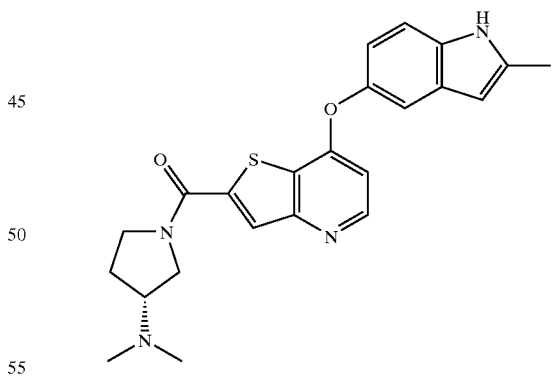

The title compound was prepared in a similar manner as Example 4(a), step (ii) except that 7-chloro-2-([3(R)-(dimethylamino)pyrrolidin-1-yl]carbonyl)thieno[3,2-b]pyridine was used instead of 7-chloro-2-[(S)-2-(methoxymethyl)pyrrolidine-1-carbonyl]thieno[3,2-b]pyridine. ¹H NMR (CD₃OD) δ 8.34 (1H, d, J=5.46 Hz), 7.79 (1H, d, J=7.5 Hz), 7.24 (1H, d, J=8.6 Hz), 7.15 (1H, d, J=2.2 Hz), 6.76 (1H, d, J=2.2, 8.66 Hz), 6.55–6.52(1H, m), 6.06 (1H, s), 4.07–3.94 (1H, m), 3.87–3.32 (3H, m), 2.89–2.79 (1H, m), 2.33 (3H, s), 2.25 (3H, s), 2.22 (3H, s), 2.21–2.12 (1H, m), 1.93–1.72 (1H, m). ESIMS (MH⁺): 421.20.

Example 8(b)

5-[(2-{[(3S,4S)-3,4-Dimethoxypyrrolidin-1-yl]carbonyl}thieno[3,2-b]pyridin-7-yl)oxy]-2-dimethyl-1H-indole-1-carboxylic acid methylamide

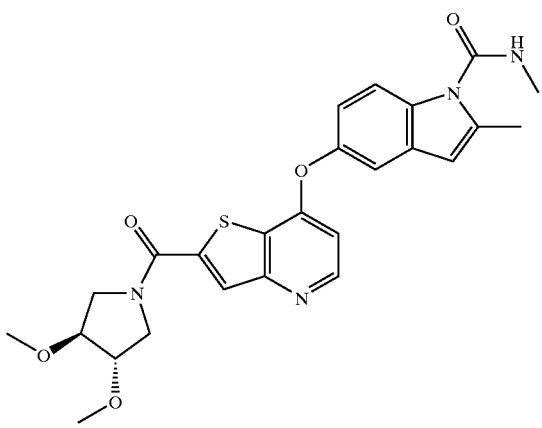

Example 8(b) was prepared in a similar manner as Example 4(q) except that methylamine was used instead of propargylamine. $^1$H NMR (CD$_3$OD) δ 8.38 (1H, d, J=5.5 Hz), 7.82 (1H, s,), 7.63 (1H, d, J=8.9 Hz), 7.23 (1H, d, J=2.3 Hz), 6.94 (1H, dd, J=2.3, 8.9 Hz), 6.57 (1H, d, J=5.5 Hz), 6.28 (1H, s), 3.96–3.81 (4H, m), 3.66–3.65 (2H, m), 3.34 (3H, s), 3.29 (3H, s), 2.91 (3H, s), 2.45 (3H, s). Anal. Calc'd for C$_{25}$H$_{26}$N$_4$O$_5$S.0.4 CH$_3$OH: C, 60.12; H, 5.48; N, 11.04; Found: C, 60.46; H, 5.77; N, 10.90.

Step (i): 2-{[(3S,4S)-3,4-Dimethoxypyrrolidin-1-yl]carbonyl}-7-[(2-methyl-1H-indol-5-yl)oxy]thieno[3,2-b]pyridine

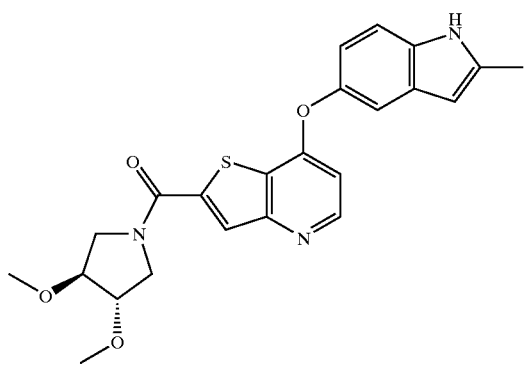

The title compound was prepared in a similar manner as Example 4(a), step (ii) except that 7-chloro-2-([3(S),4(S)-dimethoxypyrrolidin-1-yl]carbonyl)thieno[3,2-b]pyridine was used instead of 7-chloro-2-[(S)-2-(methoxymethyl)pyrrolidine-1-carbonyl]thieno[3,2-b]pyridine. $^1$H NMR (CD$_3$OD) δ 8.35 (1H, d, J=5.5 Hz), 7.81 (1H, s,), 7.25 (1H, d, J=8.5 Hz), 7.16 (1H, d, J=2.3 Hz), 6.77 (1H, dd, J=2.3, 8.5 Hz), 6.54 (1H, d, J=5.5 Hz), 6.07 (1H, s), 4.00–3.81 (4H, m), 3.72–3.65 (2H, m), 3.34 (3H, s), 3.29 (3H, s), 2.34 (3H, s). ESIMS (MH$^+$): 438.20.

Example 8(c)

5-[(2-{[(3S,4S)-3-Hydroxy-4-methoxypyrrolidin-1-yl]carbonyl}thieno[3,2-b]pyridin-7-yl)amino]-N,2-dimethyl-1H-indole-1-carboxamide

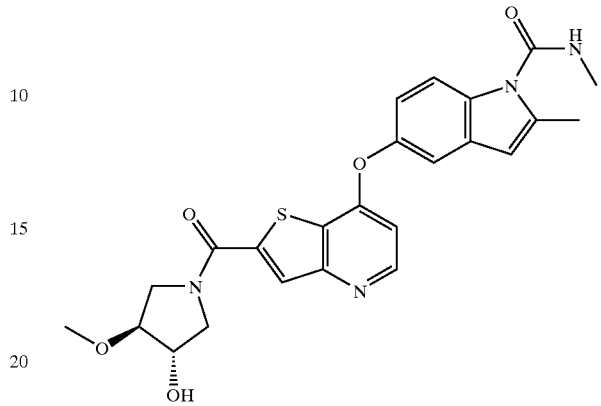

Example 8(c) was prepared in a similar manner as Example 8(b) except that 3(S)-hydroxy-4(S)-methoxypyrrolidine was used in place of 3(S),4(S)-dimethoxypyrrolidine. $^1$H NMR (CD$_3$OD) δ 8.38 (1H, br. s), 7.83 (1H, d, J=9.42 Hz), 7.63 (1H, d, J=8.9 Hz), 7.23 (1H, d, J=2.3 Hz), 6.94 (1H, dd, J=2.3, 8.9 Hz), 6.58 (1H, d, J=5.5 Hz), 6.28 (1H, s), 4.29–4.22 (1H, m), 4.06–3.96 (1H, m), 3.83–3.54 (4H, m), 3.30 (3H, d, J=14.0), 2.91 (3H, s), 2.45 (3H, s). HRMS Calc'd for C$_{24}$H$_{24}$N$_4$O$_5$S [MH$^+$]: 481.1537; Found 481.1546.

Example 8(d)

5-[(2-{[(3S,4S)-3,4-Dihydroxypyrrolidin-1-yl]carbonyl}thieno[3,2-b]pyridin-7-yl)amino]-N,2-dimethyl-1H-indole-1-carboxamide

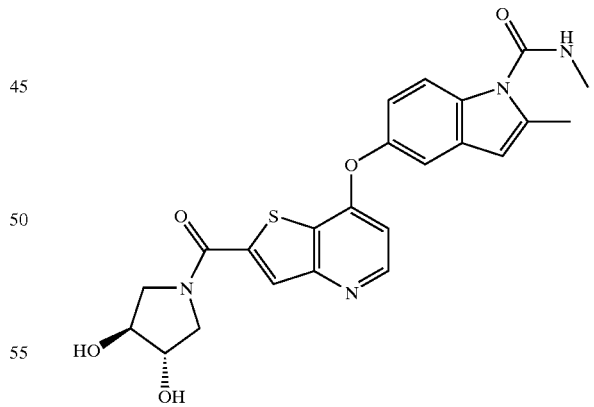

Example 8(d) was prepared in a similar manner as Example 4(n) except that 8(b) was used as starting material. $^1$H NMR (DMSO-d$_6$) δ 8.54 (1H, d, J=5.4 Hz),8.28 (1 H, m),8.03 (1H, s), 7.68 (1H, d, J=8.9 Hz), 7.41 (1H, d, J=2.3 Hz), 7.07 (1H, dd, J=2.3, 8.9 Hz), 6.65 (1H, d, J=5.4 Hz), 6.40 (1H, s), 5.27 (2H, m), 4.11–3.99 (4H, m), 3.71–3.65 (2H, m), 3.32 (3H, s), 2.87 (3H, s). HRMS Calc'd for C$_{23}$H$_{22}$N$_4$O$_5$S [MH$^+$]: 467.1390; Found: 467.1389.

Example 8(e)

5-[(2-{[(3S,4S)-3,4-dimethoxypyrrolidin-1-yl]carbonyl}thieno[3,2-b]pyridin-7-yl)oxy]-2-methyl-N-propyl-1H-indole-1-carboxamide

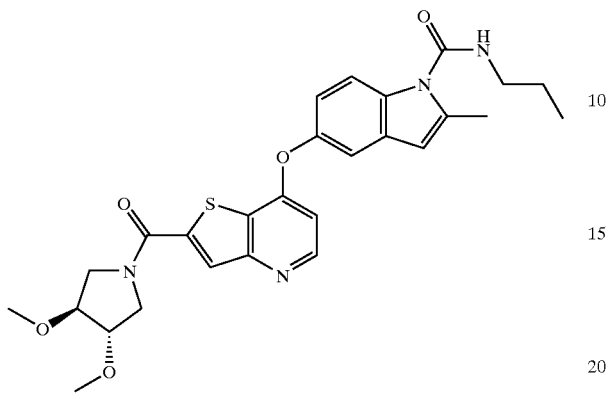

Example 8(e) was prepared in a similar manner as Example 8(b) except that propylamine was used instead of methylamine. $^1$H NMR (CD$_3$OD) δ 8.38 (1H, d, J=5.5 Hz), 7.82 (1H, s), 7.61 (1H, d, J=8.9 Hz), 7.24 (1H, d, J=2.3 Hz), 6.95 (1H, dd, J=2.3, 8.9 Hz), 6.57 (1H, d, J=5.5 Hz), 6.29 (1H, s), 4.00–3.81 (4H, m), 3.73–3.65 (2H, m), 3.34 (3H, s), 3.29 (3H, s), 3.30–3.24 (2H, m), 2.45 (3H, s), 1.69–1.57 (2H, m), 0.95 (3H, t, J=7.4 Hz). Anal. Calc'd for C$_{27}$H$_{30}$N$_4$O$_5$S·0.4H$_2$O: C, 61.21; H, 5.86; N, 10.58; Found: C, 60.85; H, 6.03; N, 10.90. ESIMS (MH$^+$): 523.20.

Example 8(f)

5-[(2-{[(3S,4S)-3,4-Dihydroxypyrrolidin-1-yl]carbonyl}thieno[3,2-b]pyridin-7-yl)oxy]-2-methyl-N-propyl-1H-indole-1-carboxamide

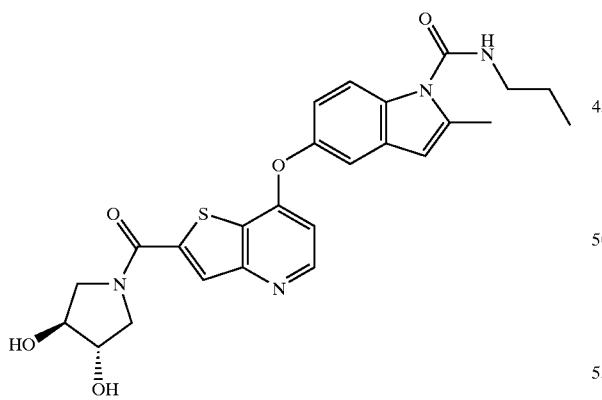

Example 8(f) was prepared in a similar manner as Example 8(d) except that propylamine was used instead of methylamine. $^1$H NMR (DMSO-d$_6$) δ 8.54 (1H, d, J=5.5 Hz), 8.44–8.41 (1H, m), 8.03 (1H, s), 7.65 (1H, d, J=8.9 Hz), 7.41 (1H, d, J=2.3 Hz), 7.08 (1H, dd, J=2.3, 8.9 Hz), 6.65 (1H, d, J=5.5 Hz), 6.40 (1H, s), 5.29–5.25 (2H, m), 4.11–3.99 (4H, m), 3.71–3.65 (2H, m), 3.42–3.24 (5H, m), 1.69–1.57 (2H, m), 0.95 (3H, t, J=7.4 Hz). HRMS Calc'd for C$_{25}$H$_{26}$N$_4$O$_5$S [MH$^+$]: 495.1702; Found: 495.1702.

Example 8(g)

5-[(2-{[(3R)-3-(Dimethylamino)pyrrolidin-1-yl]carbonyl}thieno[3,2-b]pyridin-7-yl)oxy]-N,2-dimethyl-1H-indole-1-carboxamide

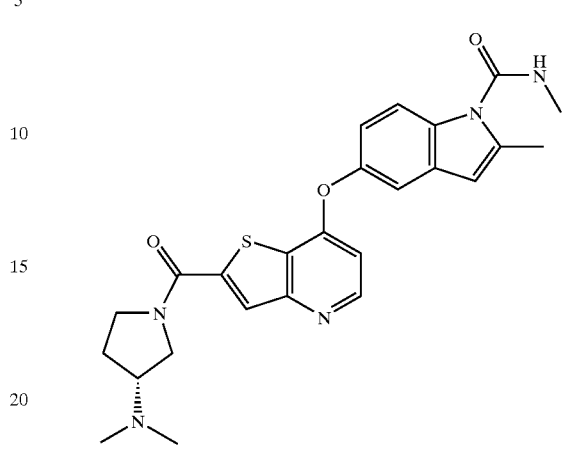

Example 8(g) was prepared in a similar manner as Example 8(b) except that 3(R)-(dimethylamino)pyrrolidine was used in place of 3(S),4(S)-dimethoxypyrrolidine. $^1$H NMR (CD$_3$OD) δ 8.38 (1H, d, J=5.5 Hz), 7.81 (1H, d, J=7.5 Hz), 7.63 (1H, d, J=8.9 Hz), 7.23 (1H, d, J=2.2 Hz), 6.94 (1H, dd, J=2.2, 8.9 Hz), 6.58 (1H, d, J=5.5 Hz), 6.28 (1H, s), 4.08–3.74 (3H, m), 3.61–3.35 (2H, m), 2.91 (3H, s), 2.45 (3H, s), 2.25 (3H, s), 1.93–1.74 (2H, m). HRMS Calc'd for C$_{25}$H$_{27}$N$_5$O$_3$S [MH$^+$]: 478.1934; Found: 478.1913.

Example 8(h)

5-[(2-{[(3R)-3-(Dimethylamino)pyrrolidin-1-yl]carbonyl}thieno[3,2-b]pyridin-7-yl)oxy]-2-methyl-N-propyl-1H-indole-1-carboxamide

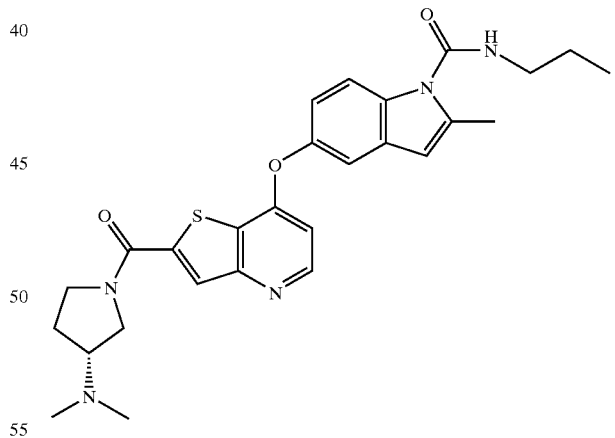

Example 8(h) was prepared in a similar manner as Example 8(d) except that propylamine was used instead of methylamine. $^1$H NMR (CD$_3$OD) δ 8.37 (1H, d, J=5.5 Hz), 7.80 (1H, d, J=8.1 Hz), 7.60 (1H, d, J=8.9 Hz), 7.23 (1H, d, J=2.3 Hz), 6.94 (1H, dd, J=2.3, 8.9 Hz), 6.56 (1H, d, J=5.5 Hz), 6.27 (1H, s), 4.07–3.95 (1H, m), 3.86–3.73 (1H, m), 3.60–3.49 (1H, m), 3.39–3.14 (m, 3H), 2.87–2.80 (1H, m), 2.45 (3H, s), 2.24 (3H, s), 2.21 (3H, s), 1.93–1.75 (1H, m), 1.62 (2H, q, J=7.2 Hz), 1.34–1.25 (1H, m), 0.95 (3H, t, J=7.2 Hz), HRMS Calc'd for C$_{27}$H$_{31}$N$_5$O$_3$S [MH$^+$]: 506.2216; Found: 506.2226.

Example 8(i)

5-[(2-{[(3R)-3-(Dimethylamino)pyrrolidin-1-yl]carbonyl}thieno[3,2-b]pyridin-7-yl)oxy]-N-(3-hydroxypropyl)-2-methyl-1H-indole-1-carboxamide

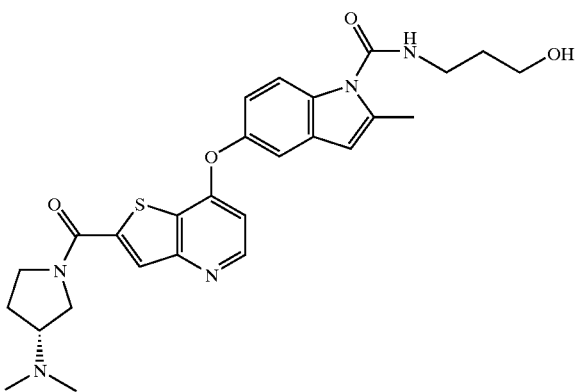

Example 8(i) was prepared in a similar manner as Example 8(d) except that 3-aminopropan-1-ol was used instead of methylamine. $^1$H NMR (CD$_3$OD) δ 8.37 (1H, d, J=5.5 Hz), 7.81 (1H, d, J=8.9 Hz), 7.64 (1H, d, J=8.9 Hz), 7.24 (1H, d, J=2.5 Hz), 6.94 (1H, dd, J=2.5, 8.9 Hz), 6.57 (1H, d, J=5.5 Hz), 6.29 (1H, s), 4.08–3.95 (1H, m), 3.87–3.74 (2H, m), 3.64–3.51 (3H, m), 3.47–3.36 (3H, m), 2.88–2.81 (1H, m), 2.46 (3H, s), 2.25 (3H, s), 2.22 (3H, s), 1.90–1.78 (3H, m). Anal Calc'd for C$_{27}$H$_{21}$N$_5$O$_4$S.1.2H$_2$O: C, 59.69; H, 6.20; N, 12.89; Found: C, 60.13; H, 6.17; N, 12.38.

Example 8(j)

5-[(2-{[(4S)-3-Fluoro-4-methoxypyrrolidin-1-yl]carbonyl}thieno[3,2-b]pyridin-7-yl)oxy]-N,2-dimethyl-1H-indole-1-carboxamide

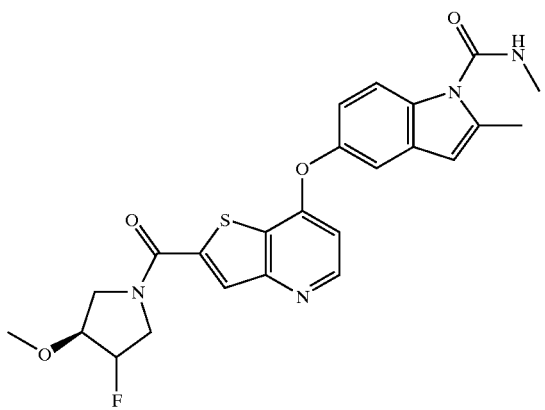

Example 8(j) was prepared in a similar manner as Example 8(b) except that 3-fluoro-4(S)-methoxypyrrolidine was used in place of 3(S),4(S)-dimethoxypyrrolidine. $^1$H NMR (CD$_3$OD) δ 8.38 (1H, d, J=5.5 Hz), 7.84 (1H, d, J=6.8 Hz), 7.62 (1H, d, J=8.9 Hz), 7.24 (1H, d, J=2.3 Hz), 6.94 (1H, dd, J=2.3, 8.96 Hz), 6.58 (1H, d, J=5.5 Hz), 6.28 (1H, s), 5.26–5.21 (m, 0.5H), 5.09–5.04 (m, 0.5H), 4.15–3.68 (5H, m), 3.32 (3H, d, J=14.5 Hz), 2.91 (3H, m), 2.45 (3H, s). Anal. Calc'd for C$_{24}$H$_{23}$FN$_4$O$_4$S: C, 59.74; H, 4.80; N, 11.61; Found: C, 59.89; H, 5.03; N, 11.34. ESIMS (MH$^+$): 483.05.

Example 8(k)

5-[(2-{[(4S)-3-Fluoro-4-methoxypyrrolidin-1-yl]carbonyl}thieno[3,2b]pyridin-7-yl)oxy]-N-(2-hydroxyethyl)-2-methyl-1H-indole-1-carboxamide

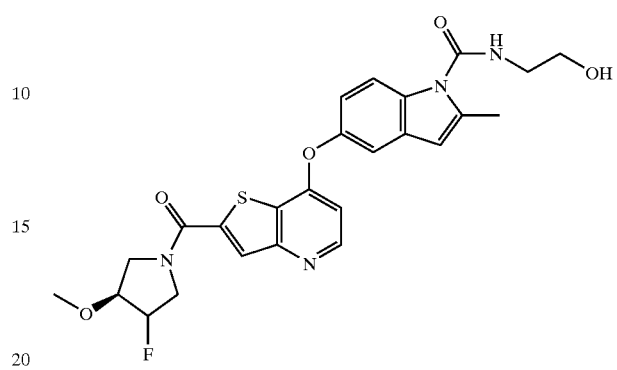

Example 8(k) was prepared in a similar manner as Example 8(j) except that ethanolamine was used instead of methylamine. $^1$H NMR (CD$_3$OD) δ 8.38 (1H, d, J=5.5 Hz), 7.68 (1H, d, J=8.9 Hz), 7.62 (1H, d, J=8.9 Hz), 7.24 (1H, d, J=2.5 Hz), 6.96 (1H, dd, J=2.5, 8.9 Hz), 6.56 (1H, d, J=5.5 Hz), 6.28 (1H, s), 5.26–5.21 (m, 0.5H), 5.09–5.04 (m, 0.5H), 4.08–3.23 (5H, m), 3.69–3.66 (2H, m), 3.43–3.35 (2H, m), 3.32 (3H, d, J×14.7 Hz), 2.45 (3H, s). Anal. Calc'd for C$_{25}$H$_{25}$FN$_4$O$_5$S: C, 58.58; H, 4.92; N, 10.93; Found: C, 58.50; H, 5.05; N, 10.61. ESIMS (MH$^+$): 513.10.

Example 8(l)

5-[(2-{[(3R)-3-(Dimethylamino)pyrrolidin-1-yl]carbonyl}thieno[3,2-b]pyridin-7-yl)oxy]-N-(2-hydroxyethyl)-2-methyl-1H-indole-1-carboxamide

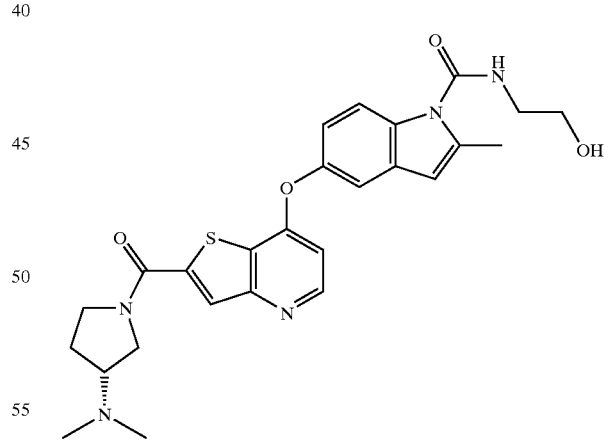

Example 8(l) was prepared in a similar manner as Example 8(d) except that ethanolamine was used instead of methylamine. $^1$H NMR (CD$_3$OD) δ 8.37 (1H, d, J=5.4 Hz), 7.81 (1H, d, J=7.9 Hz), 7.72 (1H, d, J=8.9 Hz), 7.23 (1H, d, J=2.3 Hz), 6.94 (1H, dd, J=2.3, 8.9 Hz), 6.57 (1H, d, J=5.4 Hz), 6.28 (1H, s), 4.06–3.96 (1H, m), 3.87–3.77 (2H, m), 3.70 (2H, t, J=5.7 Hz), 3.57–3.37 (4H, m), 2.91–2.79 (1H, m), 1.94–1.76 (1H, m). HRMS Calc'd for C$_{26}$H$_{29}$N$_5$O$_4$S [MH$^+$]: 508.2026; Found: 508.2019.

Example 8(m)

5-[2-(Azetidine-1-carbonyl)-thieno[3,2-b]pyridin-7-yloxy]-2-methyl-indole-1-carboxylic acid methylamide

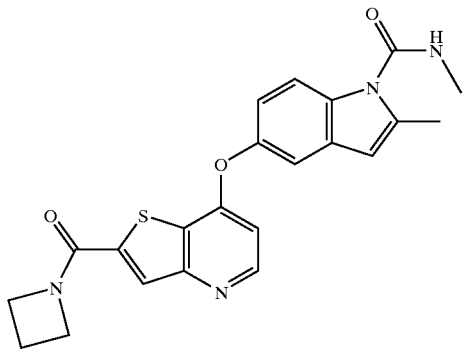

Example 8(m) was prepared in a similar manner as Example 8(b) except that azetidine was used in place of 3(S),4(S)-dimethoxypyrrolidine. $^1$H NMR (300 MHz, DMSO) δ 8.56 (1H, d, J=4.3 Hz), 8.30 (1H, d, J=8.3 Hz), 7.90 (1H, s), 7.70 (1H, d, J=8.9 Hz), 7.43 (1H, s), 7.09 (1H, d, J=10.4 Hz), 6.66 (1H, d, J=5.3 Hz ), 6.42 (1H, s), 4.68–4.61 (2H, m), 4.15–4.10 (2H, m), 3.35 (3H, s), 2.90 (3H, s) 2.42–2.30 (2H, m). LCMS (ESI+) [M+H]/z Calc'd 421, Found 421. Anal. ($C_{22}H_{20}N_4O_3S$) C, H, N.

Example 8(n)

5-[2-(Azetidine-1-carbonyl)-thieno[3,2-b]pyridin-7-yloxy]-2-methyl-indole-1-carboxylic acid (3-hydroxy-propyl)-amide

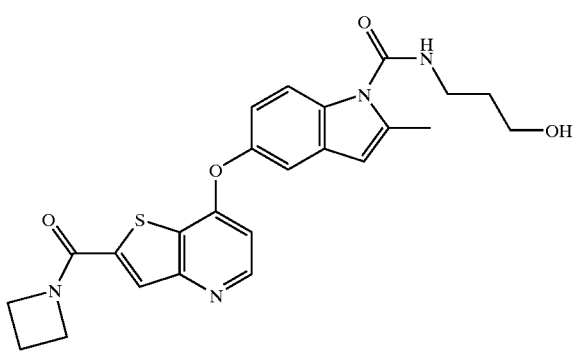

Example 8(n) was prepared in a similar manner as Example 8(m) except that 3-aminopropan-1-ol was used instead of methylamine. $^1$H NMR (300 MHz, CD$_3$OD) δ 8.49 (1H, d, J=5.5 Hz), 7.81 (1H, s), 7.76 (1H, d, J=8.9 Hz), 7.35 (1H, s), 7.06 (1H, d, J=11.7 Hz), 6.70 (1H, d, J=5.5 Hz), 6.40 (1H, s), 4.73–4.68 (2H, m), 4.33–4.22 (2H, m), 3.79–3.73 (2H, m), 3.62–3.55 (2H, m), 2.58 (3H, s) 2.55–2.45 (2H, m), 1.97–1.90 (2H, m). LCMS (ESI+) [M+H]/z Calc'd 465, Found 465. Anal. ($C_{24}H_{24}N_4O_4S\cdot0.01CH_2Cl_2$) C, H, N.

Example 8(o)

5-[2-(3-Hydroxy-azetidine-1-carbonyl)-thieno[3,2-b]pyridin-7-yloxy]-2-methyl-indole-1-carboxylic acid methylamide

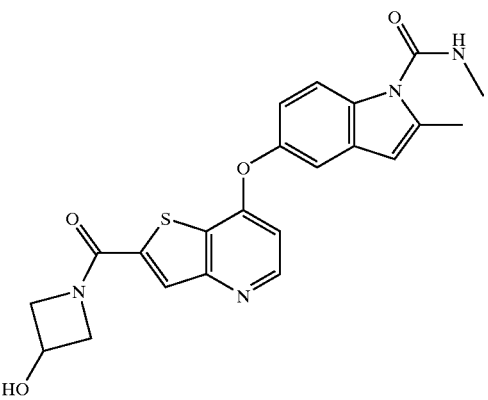

Example 8(o) was prepared in a similar manner as Example 8(b) except that 3-hydroxyazetidine was used in place of 3(S),4(S)-dimethoxypyrrolidine. $^1$H NMR (300 MHz, DMSO) δ 8.86 (1H, s), 8.27 (1H, d, J=5.5 Hz), 7.69 (1H, d, J=4.5 Hz), 7.60 (1H, d, J=8.7 Hz), 7.35 (1H, s), 7.08 (1H, d, J=10.4 Hz), 6.70 (1H, d, J=5.5 Hz), 6.36 (1H, s), 5.84 (1H, d, J=6.2 Hz), 4.79–4.73 (1H, m), 4.61–4.52 (1H, m), 4.33–4.28(2H, m), 3.83–3.79 (1H, m), 2.87 (3H, d, J=3.4 Hz). LCMS (ESI+) [M+H]/z Calc'd 436, Found 436. Anal. ($C_{22}H_{21}N_5O_3S\cdot0.8CH_2Cl_2$) C, H, N.

Step (i) 7-Chloro-2-[3-hydroxyazetidin-1-yl)carbonyl]thieno[3,2-b]pyridine

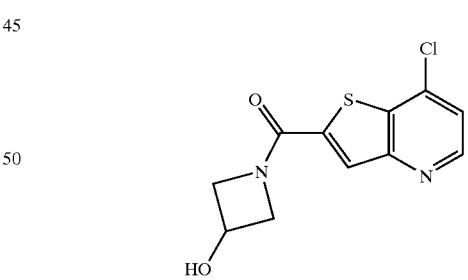

This material was prepared by the coupling of lithium 7-chlorothieno[3,2-b]pyridine-2-carboxylate and 3-hydroxyazetidine in a manner as previously described for Example 1(a), step (iv). $^1$H NMR (300 MHz, DMSO) δ 8.76 (1H, d, J=5.1 Hz), 8.01 (1H, s), 7.72 (1H, d, J=5.1 Hz), 5.92 (1H, d, J=6.4 Hz), 4.83–4.76 (1H, m), 4.64–4.56 (1H, m), 4.37–4.29 (2H, m), 3.86–3.72 (1H, m). LCMS (ESI+) [M+H]/z Calc'd 269, Found 269.

Example 8(p)

5-[2-(2R-Methoxymethyl-pyrrolidine-1-carbonyl)-thieno[3,2-b]pyridin-7-yloxy]-2-methyl-indole-1-carboxylic acid prop-2-ynylamide

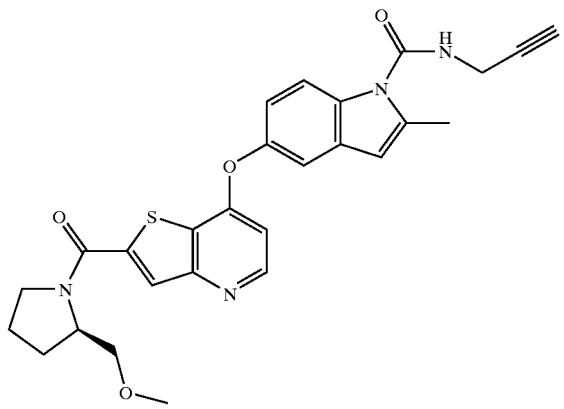

Example 8(p) was prepared in a similar manner as Example 4(e) except that propargylamine was used instead of methylamine. $^1$H NMR (300 MHz, CDCl$_3$) δ 8.41 (1H, d, J=5.5 Hz), 7.81 (1H, s), 7.76 (1H, d, J=8.9 Hz), 7.24 (1H, d, J=2.4 Hz), 7.00 (1H, dd, J=2.4, 8.9 Hz), 6.53 (1H, d, J=5.5 Hz), 6.33 (1H, d, J=5.5 Hz), 6.30 (1H, s), 4.46 (1H, m), 4.30 (2H, m), 3.83 (2H, m), 3.62 (2H, m), 3.36 (3H, s), 2.59 (3H, s), 2.35 (1H, m), 2.20–1.85 (4H, m). LCMS (ESI+) [M+H]/z Calc'd 503, Found 503.

Example 8(q)

5-[2-(2R-Hydroxymethyl-pyrrolidine-1-carbonyl)-thieno[3,2-b]pyridin-7-yloxy]-2-methyl-indole-1-carboxylic acid prop-2-ynylamide

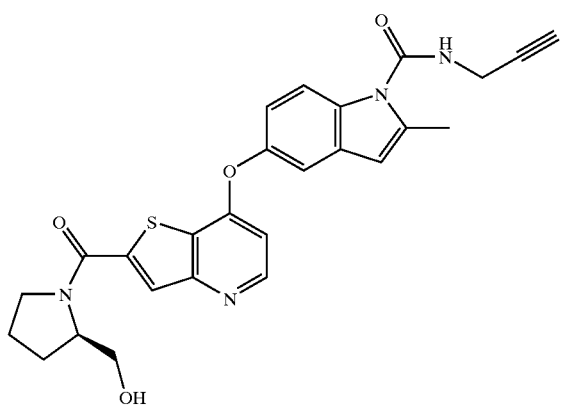

Example 8(q) was prepared in a similar manner as Example 4(n) except that 8(p) was used as starting material. $^1$H NMR (300 MHz, CD$_3$OD) δ 8.47 (1H, d, J=5.67 Hz), 7.90 (1H, s), 7.77 (1H, d, J=8.8 Hz), 7.33 (1H, d, J=2.2 Hz), 7.05 (1H, dd, J=2.2, 8.8 Hz), 6.67 (1H, d, J=5.6 Hz), 6.39 (1H, s), 4.35 (1H, m), 4.21 (2H, d, J=2.5 Hz), 3.95–3.70 (4H, m), 2.72 (1H, t, J=2.5 Hz), 2.56 (3H, s), 2.20–1.90 (4H, m). LCMS (ESI+) [M+H]/z Calc'd 489, Found 489.

Example 9(a)

5-[2-(3S-Methoxy-pyrrolidine-1-carbonyl)-thieno[3,2-b]pyridin-7-yloxy]-2-methyl-indole-1-carboxylic acid (4-hydroxy-butyl)-amide

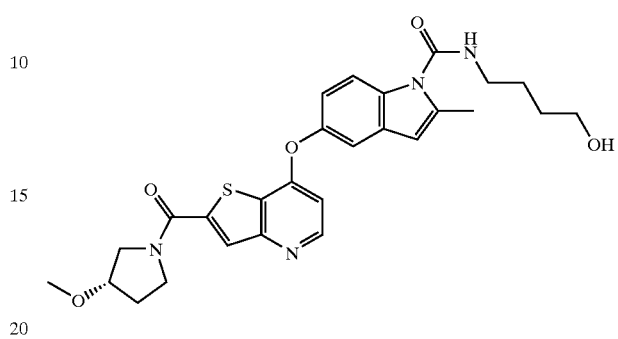

Example 9(a) was prepared in a similar manner as Example 4(g) except that 4-aminobutan-1-ol was used instead of methylamine. $^1$H NMR (300 MHz, CD$_3$OD) δ 8.46 (1H, d, J=5.4 Hz), 7.89 (1H, d, J=5.6 Hz), 7.71 (1H, d, J=8.8 Hz), 7.32 (1H, d, J=2.1 Hz), 7.03 (1H, dd, J=2.2, 8.8 Hz), 6.65 (1H, d, J=5.5 Hz), 6.37 (1H, s), 4.13–3.70 (5H, m), 3.63 (2H, t, J=6.2 Hz), 3.46 (2H, t, J=6.8 Hz), 3.38, 3.33 (3H, s), 2.55 (3H, s), 2.25–2.05 (2H, m), 1.80–1.63 (4H, m). LCMS (ESI+) [M+H]/z Calc'd 523, Found 523. Anal. (C$_{27}$H$_{30}$N$_4$O$_5$S.0.2H$_2$O.0.2Hexanes) C, H, N.

Example 9(b)

5-[2-(3S-Methoxy-pyrrolidine-1-carbonyl)-thieno[3,2-b]pyridin-7-yloxy]-2-methyl-indole-1-carboxylic acid (3-hydroxy-propyl)-amide

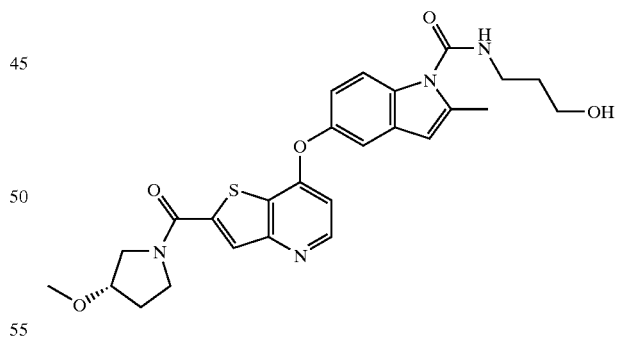

Example 9(b) was prepared in a similar manner as Example 4(g) 3-aminopropan-1-ol was used instead of methylamine. $^1$H NMR (300 MHz, CD$_3$OD) δ 8.48 (1H, d, J=5.4 Hz), 7.91 (1H, d, J=6.4 Hz), 7.74 (1H, d, J=8.8 Hz), 7.34 (1H, d, J=2.3 Hz), 7.05 (1H, dd, J=2.4, 8.8 Hz), 6.67 (1H, d, J=5.4 Hz), 6.39 (1H, s), 4.15–3.70 (5H, m), 3.72 (2H, t, J=6.2 Hz), 3.54 (2H, t, J=6.9 Hz), 3.38, 3.34 (3H, s), 2.56 (3H, s), 2.15 (2H, m), 1.92 (2H, m). LCMS (ESI+) [M+H]/z Calc'd 509, Found 509. Anal. (C$_{26}$H$_{28}$N$_4$O$_5$S.0.5H$_2$O.0.3Hexanes) C, H, N.

Example 9(c)

5-[2-(3S-Methoxy-pyrrolidine-1-carbonyl)-thieno[3,2-b]pyridin-7-yloxy]-2-methyl-indole-1-carboxylic acid (2-hydroxy-ethyl)-amide

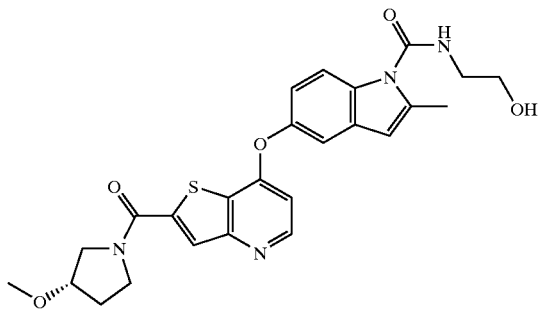

Example 9(c) was prepared in a similar manner as Example 4(g) except that ethanolamine was used instead of methylamine. $^1$H NMR (300 MHz, CD$_3$OD) δ 8.47 (1H, d, J=5.4 Hz), 7.91 (1H, d, J=6.1 Hz), 7.82 (1H, d, J=8.9 Hz), 7.32 (1H, d, J=2.2 Hz), 7.03 (1H, dd, J=2.2, 8.9 Hz), 6.66 (1H, d, J=5.5 Hz), 6.38 (1H, s), 4.16–3.70 (5H, m), 3.79 (2H, t, J=5.7 Hz), 3,56 (2H, t, J=5.7 Hz), 3.38, 3.33 (3H, s), 2.56 (3H, s), 2.30–2.02 (2H, m). LCMS (ESI+) [M+H]/z Calc'd 495, Found 495. Anal. (C$_{25}$H$_{26}$N$_4$O$_5$S.0.25H$_2$O.0.25Hexanes) C, H, N.

Example 9(d)

5-[2-(3S-Methoxy-pyrrolidine-1-carbonyl)-thieno[3,2-b]pyridin-7-yloxy]-2-methyl-indole-1-carboxylic acid propylamide

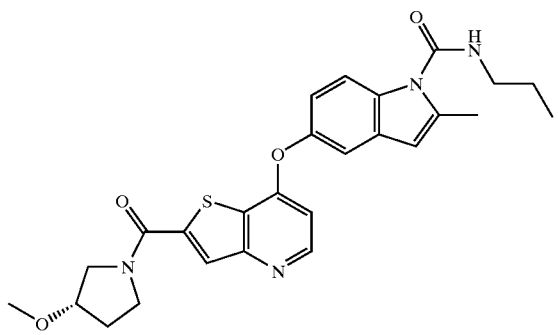

Example 9(d) was prepared in a similar manner as Example 4(g) except that propylamine was used instead of methylamine. $^1$H NMR (300 MHz, CDCl$_3$) δ 8.46 (1H, br s), 7.84 (1H, d, J=9.7 Hz), 7.70 (1H, d, J=8.9 Hz), 7.27 (1H, d, J=2.3 Hz), 7.00 (1H, dd, J=2.3, 8.9 Hz), 6.57 (1H, d, J=4.7 Hz), 6.30 (1H, s), 5.82 (1H, br s), 4.10–3.70 (5H, m), 3.48 (2H, q, J=6.7 Hz), 3.37, 3.32 (3H, s), 2.58 (3H, s), 2.25–1.90 (2H, m), 1.75 (2H, m), 1.05 (3H, t, J=7.4 Hz). LCMS (ESI+) [M+H]/z Calc'd 493, Found 493.

Example 9(e)

5-[2-(3S-Methoxy-pyrrolidine-1-carbonyl)-thieno[3,2-b]pyridin-7-yloxy]-2-methyl-indole-1-carboxylic acid ethylamide

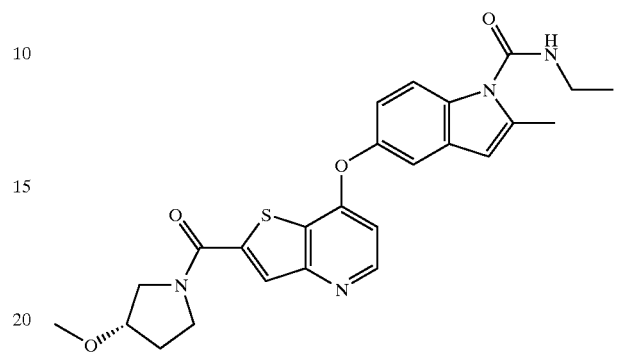

Example 9(e) was prepared in a similar manner as Example 4(g) except that ethylamine was used instead of methylamine. $^1$H NMR (300 MHz, CDCl$_3$) δ 8.46 (1H, br s), 7.82 (1H, d, J=10.6 Hz), 7.69 (1H, d, J=8.8 Hz), 7.26 (1H, d, J=2.2 Hz), 6.99 (1H, dd, J=2.2, 8.8 Hz), 6.56 (1H, d, J=4.2 Hz), 6.29 (1H, s), 5.89 (1H, br s), 4.15–3.70 (5H, m), 3.55 (2H, m), 3.37, 3.32 (3H, s), 2.58 (3H, s), 2.25–1.90 (2H, m), 1.34 (3H, t, J=7.2 Hz). LCMS (ESI+) [M+H]/z Calc'd 479, Found 479.

Example 9(f)

5-[2-(3S-Methoxy-pyrrolidine-1-carbonyl)-thieno[3,2-b]pyridin-7-yloxy]-2-methyl-indole-1-carboxylic acid cyanomethyl-amide

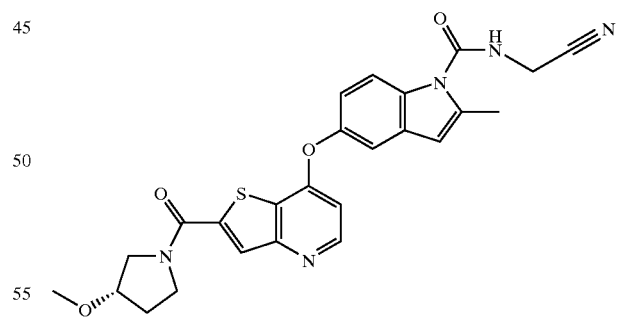

Example 9(f) was prepared in a similar manner as Example 4(g) except that aminoacetonitrile was used instead of methylamine. $^1$H NMR (300 MHz, DMSO-d$_6$) δ 8.99 (1H, s), 8.55 (1H, d, J=3.5 Hz), 8.04 (1H, s), 7.72 (1H, d, J=8.8 Hz), 7.44 (1H, s), 7.14 (1H, d, J=8.8 Hz), 6.66 (1H, d, J=4.2 Hz), 6.47 (1H, s), 4.42 (s, 2H), 4.10–3.70 (5H, m), 3.30 (3H, s), 2.52 (3H, s), 2.01 (2H, m). LCMS (ESI+) [M+H]/z Calc'd 490, Found 490.

Example 9(g)

5-[2-(3S-Hydroxy-pyrrolidine-1-carbonyl)-thieno[3,2-b]pyridin-7-yloxy]-2-methyl-indole-1-carboxylic acid methylamide

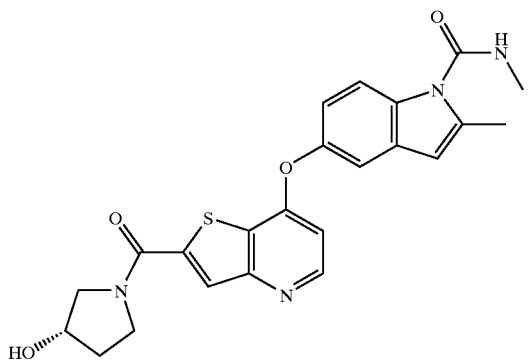

Example 9(g) was prepared in a similar manner as Example 4(n) except that 4(g) was used as starting material. $^1$H NMR (300 MHz, CD$_3$OD) δ 8.47 (1H, d, J=5.7 Hz), 7.91 (1H, d, J=17.5 Hz), 7.72 (1H, d, J=8.8 Hz), 7.33 (1H, d, J=2.1 Hz), 7.04 (1H, dd, J=2.1, 8.8 Hz), 6.66 (1H, d, J=5.5 Hz), 6.38 (1H, s), 4.53 (1H, m), 4.10–3.70 (4H, m), 3.01 (3H, s), 2.54 (3H, s), 2.11 (2H, m). LCMS (ESI+) [M+H]/z Calc'd 451, Found 451.

Example 9(h)

5-[2-(3S-Hydroxy-pyrrolidine-1-carbonyl)-thieno[3,2-b]pyridin-7-yloxy]-2-methyl-indole-1-carboxylic acid ethylamide

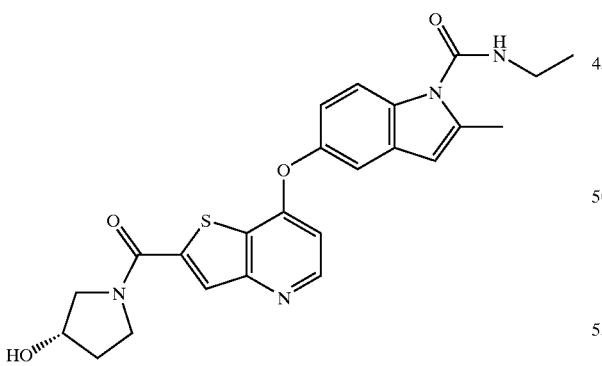

Example 9(h) was prepared in a similar manner as Example 4(n) except that 9(e) was used as starting material. $^1$H NMR (300 MHz, CD$_3$OD) δ 8.47 (1H, d, J=5.5 Hz), 7.91 (1H, d, J=17.3 Hz), 7.71 (1H, d, J=8.8 Hz), 7.33 (1H, d, J=2.1 Hz), 7.04 (1H, dd, J=2.1, 8.8 Hz), 6.66 (1H, d, J=5.5 Hz), 6.37 (1H, s), 4.50 (1H, m), 4.10–3.68 (4H, m), 3.47 (2H, q, J=7.2 Hz), 2.54 (3H, s), 2.11 (2H, m), 1.31 (3H, t, J=7.2 Hz). LCMS (ESI+) [M+H]/z Calc'd 465, Found 465.

Example 9(i)

5-[2-(3S-Hydroxy-pyrrolidine-1-carbonyl)-thieno[3,2-b]pyridin-7-yloxy]-2-methyl-indole-1-carboxylic acid propylamide

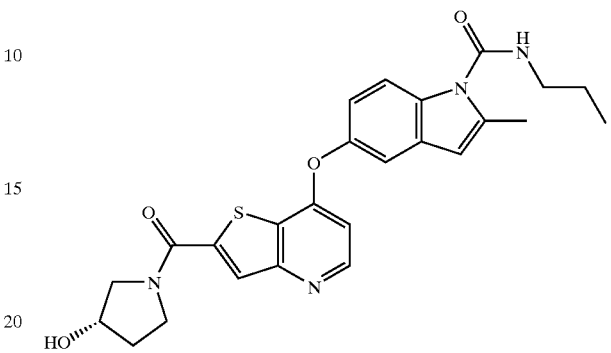

Example 9(i) was prepared in a similar manner as Example 4(n) except that 9(d) was used as starting material. $^1$H NMR (300 MHz, CD$_3$OD) δ 8.48 (1H, d, J=5.5 Hz), 7.92 (1H, d, J=17.5 Hz), 7.71 (1H, d, J=8.9 Hz), 7.34 (1H, d, J=2.3 Hz), 7.05 (1H, dd, J=2.3, 8.9 Hz), 6.68 (1H, d, J=5.5 Hz), 6.39 (1H, s), 4.53 (1H, m), 4.10–3.70 (4H, m), 3.40 (2H, t, J=7.2 Hz), 2.55 (3H, s), 2.11 (2H, m), 1.72 (2H, m), 1.05 (3H, t, J=7.4 Hz). LCMS (ESI+) [M+H]/z Calc'd 479, Found 479.

Example 9(j)

5-[2-(3S-Hydroxy-pyrrolidine-1-carbonyl)-thieno[3,2-b]pyridin-7-yloxy]-2-methyl-indole-1-carboxylic acid prop-2-ynylamide

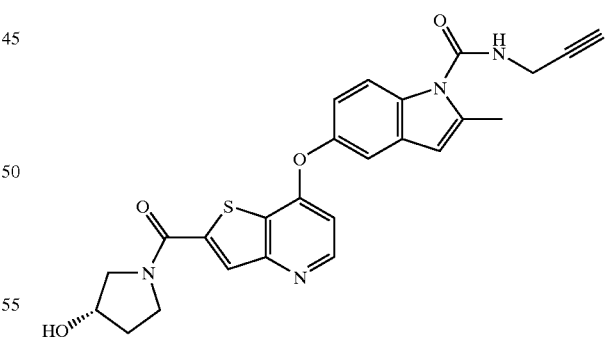

Example 9(j) was prepared in a similar manner as Example 4(n) except that 4(f) was used as starting material. $^1$H NMR (300 MHz, CD$_3$OD) δ 8.48 (1H, d, J=5.5 Hz), 7.92 (1H, d, J=17.5 Hz), 7.77 (1H, d, J=8.9 Hz), 7.34 (1H, d, J=2.3 Hz), 7.06 (1H, dd, J=2.3, 8.9 Hz), 6.68 (1H, d, J=5.5 Hz), 6.40 (1H, s), 4.53 (1H, m), 4.22 (2H, d, J=2.4 Hz), 4.10–3.60 (4H, m), 2.72 (1H, t, J=2.4 Hz), 2.56 (3H, s), 2.11 (2H, m). LCMS (ESI+) [M+H]/z Calc'd 475, Found 475.

Example 9(k)

5-[2-(3S-Hydroxy-pyrrolidine-1-carbonyl)-thieno[3,2-b]pyridin-7-yloxy]-2-methyl-indole-1-carboxylic acid (2-hydroxy-ethyl)-amide

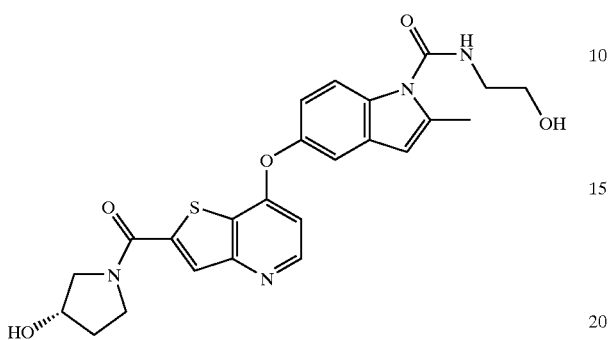

Example 9(k) was prepared in a similar manner as Example 4(n) except that 9(c) was used as starting material. $^1$H NMR (300 MHz, CD$_3$OD) δ 8.48 (1H, d, J=5.7 Hz), 7.92 (1H, d, J=17.5 Hz), 7.82 (1H, d, J=8.7 Hz), 7.33 (1H, d, J=2.1 Hz), 7.04 (1H, dd, J=2.1, 8.7 Hz), 6.68 (1H, d, J=5.4 Hz), 6.39 (1H, s), 4.52 (1H, m), 4.02 (2H, m), 3.85–3.60 (4H, m), 3.56 (2H, t, J=5.6 Hz), 2.57 (3H, s), 2.11 (2H, m). LCMS (ESI+) [M+H]/z Calc'd 481, Found 481.

Example 9(l)

5-[2-(3S-Hydroxy-pyrrolidine-1-carbonyl)-thieno[3,2-b]pyridin-7-yloxy]-2-methyl-indole-1-carboxylic acid (3-hydroxy-propyl)-amide

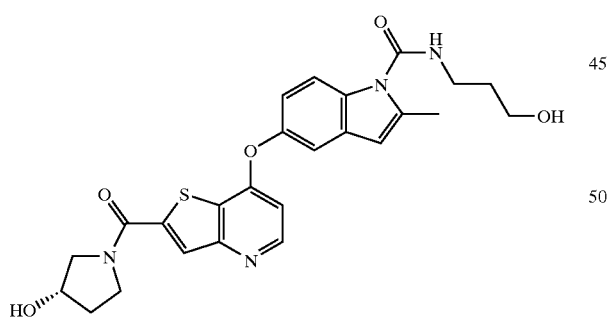

Example 9(l) was prepared in a similar manner as Example 4(n) except that 9(b) was used as starting material. $^1$H NMR (300 MHz, CD$_3$OD) δ 8.46 (1H, d, J=5.5 Hz), 7.91 (1H, d, J=17.3 Hz), 7.73 (1H, d, J=8.8 Hz), 7.32 (1H, d, J=2.0 Hz), 7.04 (1H, dd, J=2.0, 8.8 Hz), 6.66 (1H, d, J=5.5 Hz), 6.37 (1H, s), 4.53 (1H, m), 4.10–4.00 (2H, m), 3.90–3.65 (4H, m), 3.54 (2H, t, J=6.8 Hz), 2.55 (3H, s), 2.11 (2H, m), 1.91 (2H, m). LCMS (ESI+) [M+H]/z Calc'd 495, Found 495.

Example 10(a)

2-{[(3S)-3-Methoxypyrrolidin-1-yl]carbonyl}-7-[(2-methyl-1-propionyl-1H-indol-5-yl)oxy]thieno[3,2-b]pyridine

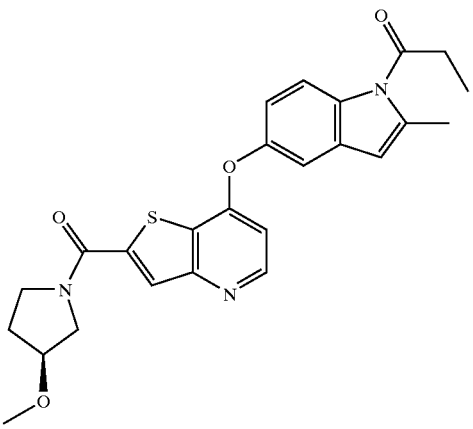

NaH (0.016 g, 0.4 mmol) was added to a solution of 2-{[(3S)-3-methoxypyrrolidin-1-yl]carbonyl}-7-[(2-methyl-1H-indol-5-yl)oxy]thieno[3,2-b]pyridine (0.108 g, 0.26 mmol) in 2 mL THF. The reaction mixture was stirred at room temperature for 10 min and propanoic anhydride (0.052 mL, 0.4 mmol) was added. The reaction mixture was stirred at room temperature for 2 h and more NaH (0.016 g, 0.4 mmol) and propanoic anhydride (0.052 mL, 0.4 mmol) were added. After 3 h, the reaction was quenched with H$_2$O (10 mL) and extracted with CH$_2$Cl$_2$ (2×10 mL). The organic layer was dried and concentrated. The residue was purified by flash column chromatography (0–2% CH$_3$OH in CH$_2$Cl$_2$) to give a white solid (0.115 g, 95%). $^1$H NMR (CD$_3$OD) δ 8.39 (1H, d, J=5.5 Hz), 8.14 (1H, d, J=9.0 Hz), 7.81 (1H, d, J=5.4 Hz), 7.23 (1H, d, J=2.3 Hz), 7.00 (1H, dd, J=2.3, 9.0 Hz), 6.59 (1H, d, J=5.5 Hz), 6.37 (1H, s), 4.04–4.00 (1H, m), 3.95–3.80 (2H, m), 3.73–3.57 (2H, m), 3.27 (1H, d, J=14.3 Hz), 3.00 (2H, q, J=7.2 Hz), 2.58 (3H, s), 2.20–1.92 (2H, m), 1.21 (3H, t, J=7.2 Hz). Anal. Calc'd for C$_{24}$H$_{23}$N$_3$O$_4$S: C, 64.78; H, 5.44; N, 9.06; Found: C, 64.54; H, 5.67; N, 8.92; ESIMS (MH$^+$): 464.15.

Example 10(b)

(3S)-1-({7-[(2-Methyl-1-propionyl-1H-indol-5-yl)oxy]thieno[3,2-b]pyridin-2-yl}carbonyl)pyrrolidin-3-ol

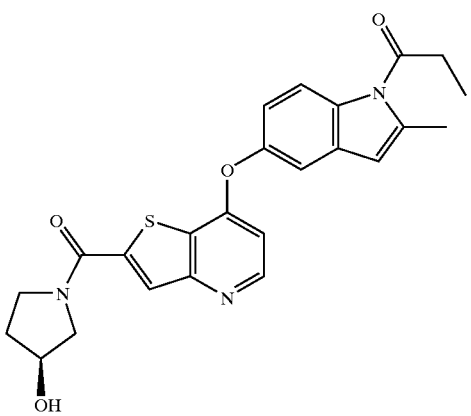

Example 10(b) was prepared in a similar manner as Example 4(n) except that 10(a) was used as starting material.

¹H NMR (DMSO-d₆) δ 8.55 (1H, d, J=5.3 Hz), 8.24 (1H, d, J=9.0 Hz), 8.01 (1H, d, J=19.6 Hz), 7.43 (1H, d, J=2.3 Hz), 7.15 (1H, dd, J=2.3, 9.0 Hz), 6.70 (1H, d, J=5.3 Hz), 6.53 (1H, s), 4.36 (1H, d, J=14.7 Hz), 4.01–3.93 (1H, m), 3.67–3.56 (2H, m), 3.35 (2H, m,), 3.10 (2H, q, J=7.2 Hz), 2.65 (3H, s), 2.04–1.80 (2H, m), 1.19 (3H, t, J=7.2 Hz). HRMS Calc'd for $C_{24}H_{23}N_3O_4S$ [MH⁺]: 450.1495; Found: 450.1488.

Example 11(a)

S: 4-(2-Methyl-1-methylcarbamoyl-1H-indol-5-ylamino)-thieno[3,2-b]pyrimidine-6-carboxylic acid ethyl ester

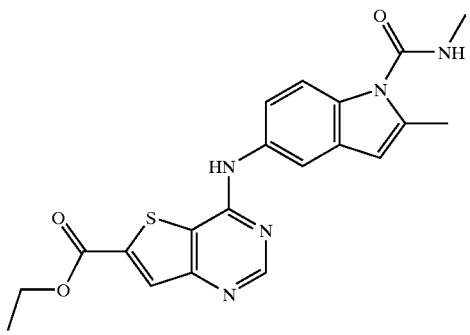

A solution of 4-chloro-thieno[3,2-b]pyrimidine-6-carboxylic acid ethyl ester (0.15 g, 0.62 mmol) and 5-amino-2-methyl-indole-1-carboxylic acid methylamide (0.13 g, 065 mmol) in acetonitrile (3 mL) was heated at 100° C. in the microwave for 1 h. After cooling to room temperature, the reaction mixture was poured into water 5 (mL). The precipitate that formed was collected by filtration, then triturated from EtOAc (10 mL) and hexane (5 mL) to afford 4-(2-Methyl-1-methylcarbamoyl-1H-indol-5-ylamino)-thieno[3,2-b]pyrimidine-6-carboxylic acid ethyl ester (0.17 g, 71%) as yellow solid. HPLC: R_t 3.59 min. (96% area). ¹H NMR (DMSO-d₆, 400 MHz) δ: 10.33 (1H, s), 8.72 (1H, s), 8.27 (1H, q, J=3.5 Hz), 8.67 (1H, q, J=8.6 Hz), 7.42 (1H, d, J=8.0 Hz), 6.46 (1H, s), 4.42 (2H, q, J=8.0), 3.63 (3H, s), 2.94 (3H, d, J=4.3 Hz), 1.38 (3H, t, J=5.0 Hz). LCMS (ACPI) (M+H⁺) m/z: 410.0. Anal. ($C_{20}H_{19}N_5O_3S \cdot 0.35$ $CH_2Cl_2$): Calc'd: C, 55.65; H, 4.52; N, 15.95. Found: C, 55.64; H, 4.59; N, 116.07.

Step (i): 4-Chloro-thieno[3,2-d]pyrimidine-6-carboxylic acid ethyl ester

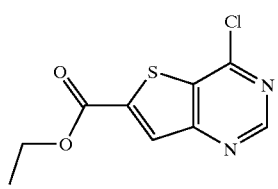

To a solution of 4-chloro-thieno[3,2-b]pyrimidine (1.0 g, 5.86 mmol) in THF (20 mL) was added LDA (6.74 mL, 1.0 M) at −78° C. After stirring for 0.5 h, a solution of ethyl chloroformate (1.7 mL 17.6 mmol) in of THF (10 mL) was added to the reaction mixture. After stirring for an additional 0.5 h, the reaction was quenched with 1 mL of CH₃COOH/MeOH (1:1), then diluted with EtOAc (50 mL). The organic layer was washed with 50/50 NaHCO₃, dried over NaHSO₃ and concentrated. Purification was with silica (50 mL) eluting with Hex/EtOAc, combining purified fraction to afford 4-Chloro-thieno[3,2-b]pyrimidine-6-carboxylic acid ethyl ester (0.64 g, 45%) as white solid. HPLC: R_t 4.19 min. (100% area). ¹H NMR (DMSO-d₆, 400 MHz) δ: 9.06 (1H, s), 8.21 (1H, s), 4.49 (2H, q, J=7.0 Hz), 1.46 (3H, t, J=7.3 Hz). LCMS (ACPI) (M+H⁺) m/z: 243.0.

Example 11(b)

5-[6-(2-Methoxymethyl-pyrrolidine-1-carbonyl)-thieno[3,2-b]pyrimidin-4-ylamino]-2-methyl-indole-1-carboxylic acid methylamide.

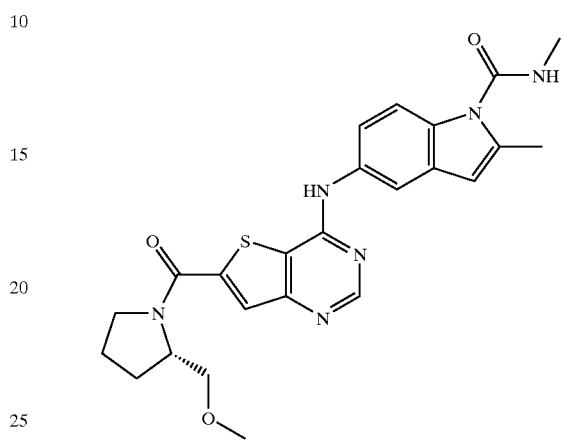

A solution of 4-(2-methyl-1-methylcarbamoyl-1H-indol-5-ylamino)-thieno[3,2-b]pyrimidine-6-carboxylic acid (0.093 g, 0.24 mmol), DIEA (0.10 mL, 0.57 mmol) and HATU (0.12 g, 0.31 mmol) in DMF (2 mL) was stirred for 3 h. The reaction mixture was partitioned between saturated NaHCO₃ (50 mL) and EtOAc (50 mL). The layers were separated and the organic phase was washed with saturated NaHCO₃ (50 mL), dried over NaSO₄ and concentrated, in vacuo. The residue obtained was purified by silica gel chromatography (50 mL), eluting with EtOAc/Hex. (2:1), combining purified fractions which were concentrated, then triturated with MTBE (2×2 mL) to afford 5-[6-(2-methoxymethyl-pyrrolidine-1-carbonyl)-thieno[3,2-b]pyrimidin-4-ylamino]-2-methyl-indole-1-carboxylic acid methylamide (0.074 g, 63%). HPLC: R_t 3.50 min. (100% area). ¹H NMR (DMSO-d₆, 400 MHz) δ: 9.77 (1H, s), 8.55 (1H, s), 8.20 (1H, d, J=4.3 Hz), 7.80 (2H, s), 7.59 (1H, d, 8.6 Hz), 7.34 (1H, 8.8 Hz), 6.38 (1H, s), 4.28 (1H, bs), 3.82–3.75 (2H, m), 3.70–3.60 (2H, m), 3.38 (1H, bs), 3.27 (3H, s), 2.87 (3H, d, J=4.3 Hz), 2.48 (3H, s), 2.01–1.80 (4H, m), HRMS (ESI) $C_{24}H_{27}N_6O_3S$ (M+H⁺) m/z: Calc. 479.1865, Found: 479.1881. Anal. ($C_{24}H_{26}N_6O_3S \cdot 0.4\ H_2O$): Calc'd: C, 59.34; H, 5.56; N, 17.30. Found: C, 59.24; H, 5.46; N, 17.04.

Step (i): 4-(2-Methyl-1-methylcarbamoyl-1H-indol-5-ylamino)-thieno[3,2-b]pyrimidine-6-carboxylic acid:

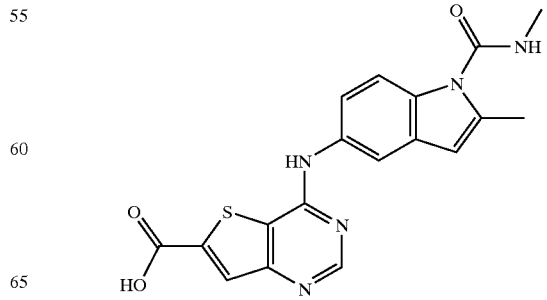

4-(2-Methyl-1-methylcarbamoyl-1H-indol-5-ylamino)-thieno[3,2-b]pyrimidine-6-carboxylic acid ethyl ester (0.10 g, 0.24 mmol) was added to a solution of LiOH (0.011 g, 0.28 mmol) in 7 mL of THF/MeOH/H$_2$O (0.7:0.0.2:0.1), then stirred for 2 h. The mixture was then neutralized by addition of 1N HCl. The precipitate that formed was collected by filtration, then rinsed with H$_2$O (10 mL) and Et$_2$O (10 mL) and dried under vacuum to afford 4-(2-Methyl-1-methylcarbamoyl-1H-indol-5-ylamino)-thieno[3,2-b]pyrimidine-6-carboxylic acid (0.086 g, 92%) as yellow solid. HPLC: R$_t$ 3.02 min. (100% area). $^1$H NMR (DMSO-d$_6$, 400 MHz) δ: 10.0 (1H, s), 8.70 (1H, s), 8.34 (1H, d, J=4.0 Hz), 8.03 (1H, s), 7.93 (1H, s), 7.74 (1H, d, J=9.1 Hz), 7.49 (1H, s), 6.53 (1H, s), 3.02 (3H, d, J=5.1 Hz), 2.62 (3H, s). LCMS (ACPI) (M+H$^+$) m/z: 382.0.

Example 12(a)
4-(2-Methyl-1-methylcarbamoyl-1H-indol-5-ylamino)-thieno[2,3-b]pyrimidine-6-carboxylic acid ethyl ester

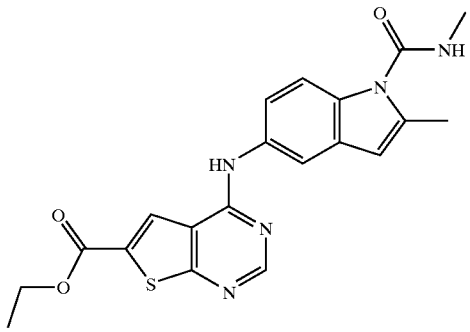

Example 12(a) was made in similar manner to 11(a) except that 4-chloro-thieno[2,3-b]pyrimidine-6-carboxylic acid ethyl ester was used instead of 4-chloro-thieno[3,2-b]pyrimidine-6-carboxylic acid ethyl ester. HPLC: R$_t$ 4.08 min. (97% area). $^1$H NMR (DMSO-d$_6$, 400 MHz) δ: 10.11 (1H, s), 8.83 (1H, s), 8.64 (1H, s), 8.27 (1H, d, J=4.5 Hz), 8.10 (1H, s), 7.71 (1H, d, J=8.1 Hz), 7.56 (1H, d, J=7.3 Hz), 6.50 (1H, s), 4.49 (2H, q, J=7.1 Hz), 3.41 (3H, s), 2.98 (3H, d, J=4.3 Hz), 1.46 (3H, t, J=7.1 Hz). HRMS (ESI) C$_{20}$H$_{20}$N$_5$O$_4$S (M+H$^+$) m/z: Calc. 410.1287, Found: 410.1308. Anal. (C$_{20}$H$_{19}$N$_5$O$_4$S.0.5H$_2$O): Calc'd: C, 57.40; H, 4.82; N, 16.74. Found: C, 57.60; H, 4.74; N, 16.50.

Example 12(b)
5-[6-(2-Methoxymethyl-pyrrolidine-1-carbonyl)-thieno[2,3-b]pyrimidin-4-ylamino]-2-methyl-indole-1-carboxylic acid methylamide

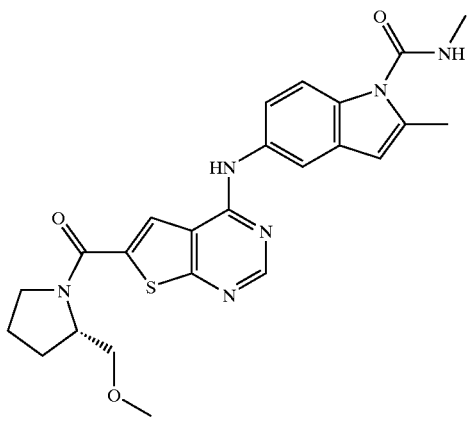

Example 12(b) was made in similar manner to 11(b) except that 4-(2-Methyl-1-methylcarbamoyl-1H-indol-5-ylamino)-thieno[2,3-b]pyrimidine-6-carboxylic acid was used instead of 4-(2-methyl-1-methylcarbamoyl-1H-indol-5-ylamino)-thieno[3,2-b]pyrimidine-6-carboxylic acid. HPLC: R$_t$ 4.08 min. (97% area). $^1$H NMR (DMSO-d$_6$, 400 MHz) δ: 8.71 (1H, s), 8.34 (1H, d, J=4.3 Hz), 8.07 (1H, s), 7.71 (1H, d, J=8.3 Hz), 7.47 (1H, s), 7.15 (1H, dd, J=9.1, 2.5 Hz), 6.46 (1H, s), 4.39 (1H, bs), 3.98–3.80 (1H, m), 3.72–3.59 (1H, s), 3.45–3.30 (2H, m), 3.37 (3H, s), 2.96 (1H, d, J=4.6 Hz), 2.60 (3H, s), 2.05–1.94 (4H, m). HRMS (ESI) C$_{24}$H$_{26}$N$_5$O$_4$S (M+H$^+$) m/z: Calc. 480.1706, Found: 480.1696. Anal. (C$_{24}$H$_{25}$N$_5$O$_4$S.0.1 EtOAc): Calc'd: C, 60.01; H, 5.33; N, 14.34. Found: C, 60.15; H, 5.43; N, 14.06.

Example 12(c)
4-(2-Methyl-1-methylcarbamoyl-1H-indol-5-yloxy)-thieno[2,3-b]pyrimidine-6-carboxylic acid ethyl ester

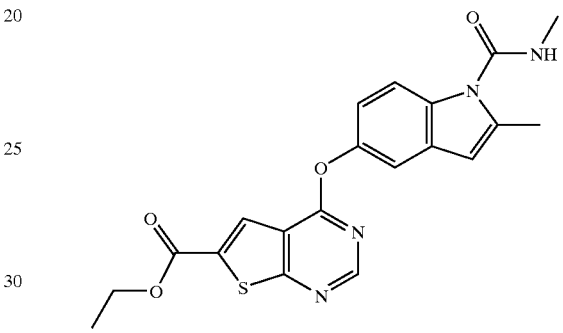

Example 12(c) was made in similar manner to Example 12(a) except that 5-hydroxyindole-1-carboxylic acid methylamide and DBU (1 equivalent) was used instead of 5-aminoindole-1-carboxylic acid methylamide. HPLC: R$_t$ 4.59 min. (100% area). $^1$H NMR (DMSO-d$_6$, 400 MHz) δ: 8.77 (1H, s), 8.34 (2H, s), 7.72 (1H, d, J=8.8 Hz), 7.48 (1H, d, J=2.3 Hz), 7.16 (1H, d, J=6.6 Hz), 6.47 (1H, s), 4.47 (2H, q, J=7.1), 3.38 (3H, s), 2.96 (3H, d, J=5.6 Hz), 1.43 (3H, t, J=7.1 Hz). HRMS (ESI) C$_{20}$H$_{19}$N$_4$O$_4$S (M+H$^+$) m/z: Calc. 411.1127, Found: 411.1118. Anal. (C$_{20}$H$_{19}$N$_4$O$_4$S.0.6 CH$_2$Cl$_2$): Calc'd: C, 53.62; H, 4.19; N, 12.14. Found: C, 53.35; H, 4.04; N, 12.14.

The exemplary compounds described above may be tested for their activity using the tests described below.

BIOLOGICAL TESTING; ENZYME ASSAYS

The stimulation of cell proliferation by growth factors such as VEFG, FGF, and others is dependent upon their induction of autophosphorylation of each of their respective receptor's tyrosine kinases. Therefore, the ability of a protein kinase inhibitor to block cellular proliferation induced by these growth factors is directly correlated with its ability to block receptor autophosphorylation. To measure the protein kinase inhibition activity of the compounds, the following constructs were devised.

VEGF-R2 Construct for Assay

This construct determines the ability of a test compound to inhibit tyrosine kinase activity. A construct (VEGF-R2Δ50) of the cytosolic domain of human vascular endothelial growth factor receptor 2 (VEGF-R2) lacking the 50 central residues of the 68 residues of the kinase insert domain was expressed in a baculovirus/insect cell system. Of the 1356 residues of full-length VEGF-R2, VEGF- R2Δ50 contains residues 806–939 and 990–1171, and also one point mutation (E990V) within the kinase insert domain relative to wild-type VEGF-R2. Autophosphorylation of the purified construct was performed by incubation of the enzyme at a concentration of 4 μM in the presence of 3 mM ATP and 40 mM $MgCl_2$ in 100 mM HEPES, pH 7.5, containing 5% glycerol and 5 mM DTT, at 4° C. for 2 h. After autophosphorylation, this construct has been shown to possess catalytic activity essentially equivalent to the wild-type autophosphorylated kinase domain construct. See Parast et al., *Biochemistry*, 37, 16788–16801 (1998).

FGF-R1 Construct for Assay

The intracellular kinase domain of human FGF-R1 was expressed using the baculovirus vector expression system starting from the endogenous methionine residue 456 to glutamate 766, according to the residue numbering system of Mohammadi et al., *Mol. Cell. Biol.*, 16, 977–989 (1996). In addition, the construct also has the following 3 amino acid substitutions: L457V, C488A, and C584S.

VEGF-R2 Assay

Coupled Spectrophotometric (FLVK-P) Assay

The production of ADP from ATP that accompanies phosphoryl transfer was coupled to oxidation of NADH using phosphoenolpyruvate (PEP) and a system having pyruvate kinase (PK) and lactic dehydrogenase (LDH). The oxidation of NADH was monitored by following the decrease of absorbance at 340 nm ($C_{340}$=6.22 $cm^{-1}$ $mM^{-1}$) using a Beckman DU 650 spectrophotometer. Assay conditions for phosphorylated VEGF-R2Δ50 (indicated as FLVK-P in the tables below) were the following: 1 mM PEP; 250 μM NADH; 50 units of LDH/mL; 20 units of PK/mL; 5 mM DTT; 5.1 mM poly($E_4Y_1$); 1 mM ATP; and 25 mM $MgCl_2$ in 200 mM HEPES, pH 7.5. Assay conditions for unphosphorylated VEGF-R2Δ50 (indicated as FLVK in the tables) were the following: 1 mM PEP; 250 μM NADH; 50 units of LDH/mL; 20 units of PK/mL; 5 mM DTT; 20 mM poly($E_4Y_1$); 3 mM ATP; and 60 mM $MgCl_2$ and 2 mM $MnCl_2$ in 200 mM HEPES, pH 7.5. Assays were initiated with 5 to 40 nM of enzyme. $K_i$ values were determined by measuring enzyme activity in the presence of varying concentrations of test compounds. The percent inhibition at 50 nm (% inhibition@ 50 nm) was determined by linear least-squares regression analysis of absorbance as a function of time. The binding inhibitions were fitted to equation as described by Morrison. The data were analyzed using Enzyme Kinetic and Kaleidagraph software.

FGF-R Assay

The spectrophotometric assay was carried out as described above for VEGF-R2, except for the following changes in concentration: FGF-R=50 nM, ATP=2 mM, and poly(E4Y1)=15 mM.

HUVEC+VEGF Proliferation Assay

This assay determines the ability of a test compound to inhibit the growth factor-stimulated proliferation of human umbilical vein endothelial cells ("HUVEC"). HUVEC cells (passage 3–4, Clonetics, Corp.) were thawed into EGM2 culture medium (Clonetics Corp) in T75 flasks. Fresh EGM2 medium was added to the flasks 24 hours later. Four or five days later, cells were exposed to another culture medium (F12K medium supplemented with 10% fetal bovine serum (FBS), 60 μg/mL endothelial cell growth supplement (ECGS), and 0.1 mg/mL heparin). Exponentially-growing HUVEC cells were used in experiments thereafter. Ten to twelve thousand HUVEC cells were plated in 96-well dishes in 100 μl of rich, culture medium (described above). The cells were allowed to attach for 24 hours in this medium. The medium was then removed by aspiration and 105 μl of starvation media (F12K+1% FBS) was added to each well. After 24 hours, 15 μl of test agent dissolved in 1% DMSO in starvation medium or this vehicle alone was added into each treatment well; the final DMSO concentration was 0.1%. One hour later, 30 μl of VEGF (30 ng/mL) in starvation media was added to all wells except those containing untreated controls; the final VEGF concentration was 6 ng/mL. Cellular proliferation was quantified 72 hours later by MTT dye reduction, at which time cells were exposed for 4 hours MTT (Promega Corp.). Dye reduction was stopped by addition of a stop solution (Promega Corp.) and absorbance at 595 nm was determined on a 96-well spectrophotometer plate reader.

Mouse PK Assay

The pharmacokinetics (e.g., absorption and elimination) of drugs in mice were analyzed using the following experiment. Test compounds were formulated as a suspension in a 30:70 (PEG 400: acidified $H_2O$) vehicle. This solution was administered orally (p.o.) and intraperitoneally (i.p.) at 50 mg/kg to two distinct groups (n=4) of B6 female mice. Blood samples were collected via an orbital bleed at time points: 0 hour (pre-dose), 0.5 hr, 1.0 hr, 2.0 hr, and 4.0 hr post dose. Plasma was obtained from each sample by centrifugation at 2500 rpm for 5 min. Test compound was extracted from the plasma by an organic protein precipitation method. For each time bleed, 50 μL of plasma was combined with 1.0 mL of acetonitrile, vortexed for 2 min. and then spun at 4000 rpm for 15 min. to precipitate the protein and extract out the test compound. Next, the acetonitrile supernatant (the extract containing test compound) was poured into new test tubes and evaporated on a hot plate (25° C.) under a steam of $N_2$ gas. To each tube containing the dried test compound extract, 125 μL of mobile phase (60:40, 0.025 M $NH_4H_2PO_4$+2.5 mL/L TEA:acetonitrile) was added. The test compound was resuspended in the mobile phase by vortexing and more protein was removed by centrifugation at 4000 rpm for 5 min. Each sample was poured into an HPLC vial for test compound analysis on an Hewlett Packard 1100 series HPLC with UV detection. From each sample, 95 μL was injected onto a Phenomenex-Prodigy reverse phase C-18, 150×3.2 mm column and eluted with a 45–50% acetonitrile gradient run over 10 min. Test-compound plasma concentrations (μg/mL) were determined by a comparison to standard curve (peak area vs. conc. μg/mL) using known concentrations of test compound extracted from plasma samples in the manner described above. Along with the standards and unknowns, three groups (n=4) of quality controls (0.25 μg/mL, 1.5 μg/mL, and 7.5 μg/mL) were run to insure the consistency of the analysis. The standard curve had an $R_2$>0.99 and the quality controls were all within 10% of their expected values. The quantitated test samples were plotted for visual display using Kaleidagraph software and their pharmacokinetic parameters were determined using WIN NONLIN software.

Human Liver Microsome (HLM) Assay

Compound metabolism in human liver microsomes was measured by LC-MS analytical assay procedures as follows. First, human liver microsomes (HLM) were thawed and diluted to 5 mg/mL with cold 100 mM potassium phosphate ($KPO_4$) buffer. Appropriate amounts of $KPO_4$ buffer, NADPH-regenerating solution (containing B-NADP, glucose-6-phosphate, glucose-6-phosphate dehydrogenase, and $MgCl_2$), and HLM were preincubated in 13×100 mm glass tubes at 37° C. for 10 min. (3 tubes per test compound—triplicate). Test compound (5 μM final) was added to each tube to initiate reaction and was mixed by gentle vortexing, followed by incubation at 37° C. At t=0, and 2 h, a 250-uL sample was removed from each incubation tube to separate 12×75 mm glass tubes containing 1 mL ice-cold acetonitrile with 0.05 μM reserpine. Samples were centrifuged at 4000 rpm for 20 min. to precipitate proteins and salt (Beckman Allegra 6KR, S/N ALK98DO6, #634). Supernatant was transferred to new 12×75 mm glass tubes and evaporated by Speed-Vac centrifugal vacuum evaporator. Samples were reconstituted in 200 μL 0.1% formic acid/acetonitrile (90/10) and vortexed vigorously to dissolve. The samples were then transferred to separate polypropylene microcentrifuge tubes and centrifuged at 14000×g for 10 min. (Fisher Micro 14, S/N M0017580). For each replicate (#1–3) at each timepoint (0 and 2 h), an aliquot sample of each test compound was combined into a single HPLC vial insert (6 total samples) for LC-MS analysis, which is described below.

The combined compound samples were injected into the LC-MS system, composed of a Hewlett-Packard HP1100 diode array HPLC and a Micromass Quattro II triple quadruple mass spectrometer operating in positive electrospray SIR mode (programmed to scan specifically for the molecular ion of each test compound). Each test compound peak was integrated at each timepoint. For each compound, peak area at each timepoint (n=3) was averaged, and this mean peak area at 2 h was divided by the average peak area at time 0 hour to obtain the percent test compound remaining at 2 h.

KDR (VEGFR2) Phosphorylation in PAE-KDR Cells Assay

This assay determines the ability of a test compound to inhibit the autophosphorylation of KDR in porcine aorta endothelial (PAE)-KDR cells. PAE cells that overexpress human KDR were used in this assay. The cells were cultured in Ham's F12 media supplemented with 10% fetal bovine serum (FBS) and 400 ug/mL G418. Thirty thousands cells were seeded into each well of a 96-well plate in 75 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37° C. for 1 hour and the cells were then stimulated with 500 ng/ml VEGF (commercially available from R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (commercially available from Pierce) which was pre-coated with Rabbit anti Human Anti-flk-1 C-20 antibody (commercially available from Santa Cruz). The plates were incubated at room temperature for 2 hours and washed seven times with 1% Tween 20 in PBS. HRP-PY20 (commercially available from Santa Cruz) was diluted and added to the plate for a 30-minute incubation. Plates were then washed again and TMB peroxidase substrate (commercially available from Kirkegaard & Perry) was added for a 10-minute incubation. One hundred μL of 0.09 N $H_2SO_4$ was added to each well of the 96-well plates to stop the reaction. Phosphorylation status was assessed by spectrophotometer reading at 450 nm. $IC_{50}$ values were calculated by curve fitting using a four-parameter analysis.

PAE-PDGFβ Phosphorylation in PAE-PDGFRB Cells Assay

This assay determines the ability of a test compound to inhibit the autophosphorylation of PDGFRβ in porcine aorta endothelial (PAE)-PDGFRβ cells. PAE cells that overexpress human PDGFRβ were used in this assay. The cells were cultured in Ham's F12 media supplemented with 10% fetal bovine serum (FBS) and 400 ug/ml G418. Twenty thousands cells were seeded in each well of a 96-well plate in 50 μL of growth media and allowed to attach for 6 hours at 37° C. Cells were then exposed to the starvation media (Ham's F12 media supplemented with 0.1% FBS) for 16 hours. After the starvation period was over, 10 μL of test agent in 5% DMSO in starvation media were added to the test wells and 10 μL of the vehicle (5% DMSO in starvation media) were added into the control wells. The final DMSO concentration in each well was 0.5%. Plates were incubated at 37° C. for 1 hour and the cells were then stimulated with 1 μg/mL PDGF-BB (R & D System) in the presence of 2 mM $Na_3VO_4$ for 8 minutes. The cells were washed once with 1 mm $Na_3VO_4$ in HBSS and lysed by adding 50 μL per well of lysis buffer. One hundred μL of dilution buffer were then added to each well and the diluted cell lysate was transferred to a 96-well goat ant-rabbit coated plate (Pierce), which was pre-coated with Rabbit anti Human PDGFRβ antibody (Santa Cruz). The plates were incubated at room temperature for 2 hours and washed seven times with 1% Tween 20 in PBS. HRP-PY20 (Santa Cruz) was diluted and added to the plate for a 30-minute incubation. Plates were then washed again and TMB peroxidase substrate (Kirkegaard & Perry) was added for a 10-minute incubation. One hundred μL of 0.09 N $H_2SO_4$ was added into each well of the 96-well plate to stop the reaction. Phosphorylation status was assessed by spectrophotometer reading at 450 nm. $IC_{50}$ values were calculated by curve fitting using a four-parameter analysis.

The results of the testing of the compounds using various assays are summarized in Tables 1 and 2 below, where a notation of "% @" indicates the percent inhibition at the stated concentration.

TABLE 1

| Example Number | FLVK (% @ 50 nM) | FLVK Ki (nM) | HUVEC + VEGF IC50 (nM) | PAE KDR autophos IC50 (nM) | PAE PDGFR autophos IC50 (nM) | bFGF HUVEC IC50 (nM) | Mouse PK AUC, po ng-h/mL | Mouse Cmax, po ng-h/mL |
|---|---|---|---|---|---|---|---|---|
| 5m | 98 | 0.586 | NT | NT | NT | NT | NT | NT |
| 4w | 99 | 0.172 | NT | NT | NT | NT | NT | NT |
| 4v | 99 | 0.416 | NT | NT | NT | NT | NT | NT |
| 4u | 98 | 0.2 | NT | NT | NT | NT | NT | NT |
| 4t | 98 | 0.594 | NT | NT | NT | NT | NT | NT |
| 4s | 98 | 0.085 | NT | NT | NT | NT | NT | NT |
| 6g | 97 | 1.23 | NT | NT | NT | NT | NT | NT |
| 5l | 99 | 0.189 | NT | NT | NT | NT | NT | NT |

TABLE 1-continued

| Example Number | FLVK (% @ 50 (nM) | FLVK Ki (nM) | HUVEC + VEGF IC50 (nM) | PAE KDR autophos IC50 (nM) | PAE PDGFR autophos IC50 (nM) | bFGF HUVEC IC50 (nM) | Mouse PK AUC, po ng-h/mL | Mouse Cmax, po ng-h/mL |
|---|---|---|---|---|---|---|---|---|
| 4r | 96 | 0.701 | NT | NT | NT | NT | NT | NT |
| 5k | 99 | 0.148 | NT | NT | NT | NT | NT | NT |
| 6f | 98 | 0.154 | NT | NT | NT | NT | NT | NT |
| 6e | 99 | 0.279 | NT | NT | NT | NT | NT | NT |
| 5j | 100 | 0.388 | NT | NT | NT | NT | NT | NT |
| 5i | 97 | 0.525 | 0.11 | NT | NT | NT | NT | NT |
| 3h | 95 | 1.194 | 1.94 | NT | NT | 225 | NT | NT |
| 4q | 98 | 0.475 | 0.27 | 0.26 | NT | NT | NT | NT |
| 5h | 98 | 0.52 | 0.28 | 0.29 | 9.9 | NT | NT | NT |
| 6c | 97 | 0.688 | 0.99 | 1.27 | 32 | NT | NT | NT |
| 3g | 95 | 1.117 | 0.44 | 2.6 | >1000 | 656 | 46 | 19 |
| 3f | 57 | 10.52 | 3.99 | 1.85 | >1000 | 2053 | 44 | 24 |
| 6b | 99 | 0.647 | 1.46 | 0.952 | 21.2 | NT | NT | NT |
| 6d | 99 | 0.32 | 0.068; 0.22 | 0.123, 0.31 | 29.1 | NT | 1628 | 302 |
| 5g | 99 | 0.45 | 0.15; 0.12 | NT | 11.2 | NT | 1170 | 321 |
| 5f | 100 | 0.095 | 0.116; 0.10 | 0.178 | 9.9 | NT | NT | NT |
| 5e | 100 | 0.431 | 0.042; 0.56 | 0.256; 0.52; 0.237 | 14.1 | NT | 1961 | 1101 |
| 5d | 96 | 0.324 | 0.35 | 0.53; 0.44; 0.275 | 21.5 | NT | NT | NT |
| 6a | 98 | 0.428 | 0.427 | NT | 28.6 | NT | NT | NT |
| 5c | 99 | 0.605 | 0.115 | NT | 7.7 | NT | 36246 | 19734 |
| 5b | 98 | 0.504 | 0.054; 0.42 | 0.5 | 13.1 | 13.6 | NT | NT |
| 3i | 74 | 4.17 | 5.5 | NT | NT | NT | NT | NT |
| 5a | 99 | 0.16 | 0.14 | NT | 3.8 | NT | NT | NT |
| 3e | 87 | 2.1 | 4.9 | NT | NT | NT | NT | NT |
| 4p | 98 | 0.25 | 0.128 | 0.22 | 4.0 | NT | 4628 | 2711 |
| 1k | 97 | 0.63 | 0.24; 0.08 | 2.1; 5.4; 4.74 | >1000 | 26.6 | 18 | 8 |
| 1j | 96 | 0.72 | 0.149 | NT | NT | NT | NT | NT |
| 1i | 93 | 0.69 | 1.03 | NT | ~1000 | 44.2 | NT | NT |
| 4m | 99 | 0.271 | 0.37 | NT | 3.8 | NT | NT | NT |
| 1e | 97 | 0.51 | 0.18 | 0.73; 0.41 | 11.3 | NT | NT | NT |
| 1h | 94 | 1.23 | 0.114; 0.42 | NT | 57.7 | NT | NT | NT |
| 3d | 60 | 1.11 | 61.6 | 2.7; 6.9 | >1000 | NT | NT | NT |
| 1q | 99 | 0.17 | 0.481 | NT | >1000 | NT | 6 | 5 |
| 4i | 97 | 1.56 | 0.569 | NT | 5.5 | NT | NT | NT |
| 4h | 91 | 1.6 | 0.65 | 0.116; 0.34; 0.21 | 19 | NT | 2604 | 657 |
| 4g | 97 | 0.23 | 0.139 | 0.58; 0.98 | 10.5 | NT | 3625 | 2277 |
| 1s | 98 | 1.1 | 0.308 | 0.42; 0.7 | 165; 98 | NT | NT | NT |
| 1r | 93 | 0.64 | 0.301 | NT | 155; 120 | NT | NT | NT |
| 4n | 99 | 0.62 | 0.042 | 0.35; 0.16; 0.167 | 5.8 | NT | 1850 | 1107 |
| 4o | 97 | 0.63 | 0.071; 0.09 | 0.012; 0.009 | 9 | 7.9 | 28509 | 5074 |
| 4f | 95 | 0.85 | 0.057; 0.03 | 0.149 | 14;14 | 9.1; 43 | 15629 | 8840 |
| 4l | 96 | 0.19 | 0.176 | 0.09 | 15 | NT | 321227 | 11304 |
| 4k | 96 | 0.1 | NT | 0.569 | 10 | 5.8 | NT | NT |
| 4j | 96 | 0.121 | 0.088 | 0.86; 0.35; 0.34 | 10; 13 | 2.5; 4.7 | 5075 | 3434 |
| 3b | 95 | 0.21 | 0.181; 0.04 | 0.32; 0.444 | 142; 125 | 7; 27.8 | 18776 | 11092 |
| 3c | 81 | 0.79 | 2.33 | 0.1; 0.041 | 631 | 184; 262 | 0 | 0 |
| 3a | 91 | 0.45 | 0.245; 0.41 | 0.72; 0.33; 0.35 | 84; 99 | 24.9; 52 | 10268 | 3954 |
| 1p | 93 | 0.2 | 0.303; 0.145 | NT | 56 | 119 | 2531 | 1228 |
| 1o | 96 | 0.37 | 0.34 | 1.6 | 533 | 49.6; 52 | 219 | 100 |
| 2e | 95 | 0.16 | 0.5; 0.403 | 1.32; 1.38 | >1000 | 27.8; 31.6 | 43 | 28 |
| 1u | NT | NT | >10 | NT | >100 | 4844 | NT | NT |
| 1g | NT | NT | 1; 0.56; 0.56 | NT | 95; 152 | 58.9; 21; 22 | NT | NT |

TABLE 1-continued

| Example Number | FLVK (% @ 50 (nM) | FLVK Ki (nM) | HUVEC + VEGF IC50 (nM) | PAE KDR autophos IC50 (nM) | PAE PDGFR autophos IC50 (nM) | bFGF HUVEC IC50 (nM) | Mouse PK AUC, po ng-h/mL | Mouse Cmax, po ng-h/mL |
|---|---|---|---|---|---|---|---|---|
| 1v | 10 | NT | >10 | NT | NT | >1000 | 1084 | 725 |
| 1n | 94 | NT | 0.64; 0.46 | 4.01; 2.77 | >1000; 2596 | 30.2; 19.4 | 12 | 8 |
| 1m | 98 | NT | 0.37 | NT | 57 | 5.4 | 1725 | 902 |
| 1l | 94 | NT | 0.3 | NT | 49; 45; 95 | 6.1; 6.1 | 719 | 504 |
| 1f | 97 | 0.21 | 0.68 | NT | 175 | NT | 1837 | 1205 |
| 4y | 10 | 24 | NT | NT | NT | NT | 383 | 265 |
| 4x | 1 | 100 | NT | NT | NT | NT | NT | NT |
| 4e | 96 | 0.14 | 0.6 | NT | 16.7 | 14 | 5541 | 3786 |
| 4d | 91 | 0.41 | 0.8; 4.4; 4.3; 2.86 | 0.55; 0.37; 0.26 | 71; 64; 76 | 246; 121; 267 | 4064 | 1963 |
| 4c | 96 | 0.1 | 0.6; 0.05; 0.34; 0.32 | 0.28; 0.24; 0.36 | 16; 18; 15 | 492; 211; 269 | 8313 | 2763 |
| 4b | 97 | 0.13 | 0.4; 0.9; 1.0; 0.48 | 0.21; 0.21; 0.25 | 22; 24; 23 | 11.7 | 3638 | 2112 |
| 2d | 98 | 0.32 | 0.15 | NT | 11; 25 | 34 | 457 | 411 |
| 2c | 97 | 0.56 | 0.44; 0.47 | 0.67; 0.42; 0.42 | 84; 105; 87 | 41; 27; 33; 24; 40 | 6703 | 3705 |
| 1d | 97 | 1.1 | 0.2; 0.54; 0.56; 0.56; 0.63 | 0.45; 0.51 | 42; 45; 74 | 24; 23.4 | 5072 | 2824 |
| 1c | 98 | 0.67 | 0.7 | NT | >100; 179 | 158 | 616 | 317 |
| 4a | 96 | 1.1 | 0.2 | NT | 16.5 | 33; 34 | 703 | 575 |
| 1b | 88 | 0.96 | 0.69 | 0.28; 0.25 | 73; 86 | 80 | 78 | 24 |
| 1a | 90 | 0.69 | 0.91 | 1.06 | 239 | 59 | 1016 | 526 |
| 1t | 87 | 1.13 | 2.2; 0.12; 0.6; 0.88; 0.57 | 0.67; 0.35; 0.41 | 116; >100; 97 | 126; 123; 51 | 5862 | 4652 |
| 2b | 85 | 1.03 | 0.68; 0.46; 0.84; <1.4; 0.05; 0.77 | 1.42; 1.43; 1.27 | 856; >100; 616; 556; 657; 682 | 100; 27; 65 | 2795 | 1895 |
| 2a | 84 | 2.1 | 0.3; 0.1; 0.1; 0.2; 0.23; 0.29 | 0.36; 0.28; 0.32 | 57; 96; 61; 41 | 331; 24; 368; 26 | 1168 | 1011 |
| 2g | 82 | 29.6 | >33.3 | NT | NT | NT | 542 | 252 |
| 2f | 2 | | >10; >100 | NT | NT | NT | 10600 | 7700 |
| 3j | 95 | 0.326 | 0.1 | 0.27 | 32 | NT | NT | NT |
| 3k | 100 | 0.071 | 0.01; 0.194 | 0.3 | 18.4 | NT | NT | NT |
| 3l | 97 | 0.462 | 0.16 | NT | 8.1; 6.3 | 101 | NT | NT |
| 3m | 83 | 0.2 | NT | NT | 2.48 | NT | NT | NT |
| 3n | 88 | 0.505 | 0.267 | NT | 76.3 | 87 | NT | NT |
| 3o | 93 | 1.35 | 0.24; 0.48 | 0.43; 0.52 | 599 126 | 246; | 2881 | 2821 |
| 3p | 81 | 0.98 | 0.33 | NT | 212 | 227 | NT | NT |
| 3q | NT | NT | NT | NT | NT | NT | NT | NT |
| 5n | 100 | 0.12 | 0.076; 0.182 | 0.28; 0.5; 0.53 | 18.2 | 93 | 2556 | 1824 |
| 5o | 99 | 0.09 | NT | NT | 3.65 | NT | NT | NT |
| 5p | 100 | 0.083 | NT | 0.35 | 4.6 | NT | NT | NT |
| 6h | 98 | 0.142 | NT | NT | NT | NT | NT | NT |
| 7a | 93 | 0.796 | NT | NT | NT | NT | NT | NT |
| 7b | 95 | 0.406 | NT | NT | >1000 | NT | NT | NT |
| 7c | 97 | 1.911 | NT | NT | NT | NT | NT | NT |
| 7d | 96 | 0.504 | 0.074; 0.28 | 0.26 | 62 | NT | NT | NT |
| 8a | 68 | 4.55 | NT | NT | >1000 | NT | NT | NT |
| 8b | 97 | 0.202 | NT | 0.24 | NT | NT | NT | NT |

TABLE 1-continued

| Example Number | FLVK (% @ 50 (nM) | FLVK Ki (nM) | HUVEC + VEGF IC50 (nM) | PAE KDR autophos IC50 (nM) | PAE PDGFR autophos IC50 (nM) | bFGF HUVEC IC50 (nM) | Mouse PK AUC, po ng-h/mL | Mouse Cmax, po ng-h/mL |
|---|---|---|---|---|---|---|---|---|
| 8c | 98 | 0.123 | NT | NT | NT | NT | NT | NT |
| 8d | 99 | 0.109 | NT | NT | NT | NT | NT | NT |
| 8e | 98 | 0.115 | NT | NT | NT | NT | NT | NT |
| 8f | 99 | 0.35 | NT | NT | NT | NT | NT | NT |
| 8g | 99 | 0.643 | 0.15 | NT | 15.4 | 9 | NT | NT |
| 8h | 99 | 0.301 | 0.16; 0.2 | NT | 19 | 15, 33, 67 | 2393 | 920 |
| 8i | 99 | 0.477 | 0.17; 0.25 | NT | 26, 34 | 73, >100, 166 | NT | NT |
| 8j | 99 | 0.142 | NT | NT | NT | NT | NT | NT |
| 8k | 95 | 0.868 | 0.32 | NT | 18 | NT | NT | NT |
| 8l | 88 | 0.88 | 1.5 | NT | 18.8 | 63 | NT | NT |
| 8m | 99 | 0.004 | 0.084 | NT | 4.5 | NT | NT | NT |
| 8n | 97 | 0.089 | 0.03; 0.12; 0.195 | NT | 10.2 | 58 | NT | NT |
| 8o | 74 | 4.471 | 1.25 | NT | NT | 61 | NT | NT |
| 8p | 98 | 0.143 | 0.137 | NT | 13 | 197 | NT | NT |
| 8q | 97 | 0.286 | 0.19 | 0.45; 0.19 | 29, 13 | 95 | 31323 | 10374 |
| 9a | 89 | 0.521 | NT | NT | NT | NT | NT | NT |
| 9b | 97 | 0.488 | 0.33 | 0.67 | 60 | NT | NT | NT |
| 9c | 81 | 3.24 | NT | 1.44; 1.1 | 56 | NT | NT | NT |
| 9d | 99 | 0.228 | NT | 1.47 | 25 | 143 | NT | NT |
| 9e | 99 | 0.105 | NT | 0.24 | 26 | NT | NT | NT |
| 9f | 84 | 0.667 | 0.68 | NT | 13 | NT | NT | NT |
| 9g | 98 | 0.243 | 0.34; 0.48; 0.8 | 0.29; 0.86; 0.34 | 27, 33 | 45, 40 | 9529 | 4537 |
| 9h | 99 | 0.258 | 0.9 | NT | 31 | NT | NT | NT |
| 9i | 98 | 0.245 | 0.37 | 0.33 | 36 | 5 | 9477 | 2321 |
| 9j | 97 | 0.162 | 0.29 | NT | 18, 20 | 81 | NT | NT |
| 9k | 90 | 0.932 | 0.49 | 1.0 | 274 | NT | 1104 | 371 |
| 9l | 97 | 0.327 | 0.27 | 0.76; 0.51 | 216 | 37.6 | 138 | 56 |
| 10a | 64 | 4.696 | 0.79 | 1.2 | NT | 21 | NT | NT |
| 10b | 90 | 2.723 | NT | NT | NT | NT | NT | NT |
| 11a | 20 | 37.8 | NT | NT | NT | NT | NT | NT |
| 11b | 18 | 28.8 | NT | NT | NT | NT | NT | NT |
| 12a | 0 | 240 | NT | NT | NT | NT | NT | NT |
| 12b | 5 | 141 | NT | NT | >1000 | NT | NT | NT |
| 12c | 14 | 34.3 | NT | NT | NT | NT | NT | NT |

TABLE 2

| Example Number | Mouse Cmin, po (ng/mL) | % remain (HLM-UDPG A, 0.5 h) | % remain (HLM-NADP H, 0.5 h) |
|---|---|---|---|
| 5m | NT | NT | NT |
| 4w | NT | NT | NT |
| 4v | NT | NT | NT |
| 4u | NT | NT | NT |
| 4t | NT | NT | NT |
| 4s | NT | NT | NT |
| 6g | NT | NT | NT |
| 5l | NT | NT | NT |
| 4r | NT | NT | NT |
| 5k | 16470 | 5209 | 940 |
| 6f | NT | NT | NT |
| 6e | NT | NT | NT |
| 5j | NT | NT | NT |
| 5i | NT | NT | NT |
| 3h | NT | NT | NT |
| 4q | NT | NT | NT |
| 5h | NT | NT | NT |
| 6c | NT | NT | NT |
| 3g | 2 | NT | NT |
| 3f | 2 | NT | NT |
| 6b | NT | NT | NT |
| 6d | 125 | NT | NT |
| 5g | 65 | NT | NT |
| 5f | NT | NT | NT |
| 5e | 19 | NT | NT |
| 4p | 68 | NT | NT |
| 1k | 0 | NT | NT |
| 1j | NT | NT | NT |
| 1i | NT | NT | NT |
| 4m | NT | NT | NT |
| 1e | NT | NT | NT |
| 1h | NT | NT | NT |
| 3d | NT | NT | NT |
| 1q | 0 | NT | NT |
| 4i | NT | NT | NT |
| 4h | 161 | NT | NT |
| 4g | 20 | NT | NT |
| 1s | NT | NT | NT |

TABLE 2-continued

| Example Number | Mouse Cmin, po (ng/mL) | % remain (HLM-UDPGA, 0.5 h) | % remain (HLM-NADPH, 0.5 h) |
|---|---|---|---|
| 1r | NT | NT | NT |
| 4n | 45 | NT | NT |
| 4o | 825 | NT | NT |
| 4f | 112 | NT | NT |
| 4l | 9020 | NT | NT |
| 4k | NT | NT | NT |
| 4j | 32 | NT | NT |
| 3b | 252 | NT | NT |
| 3c | 0 | NT | NT |
| 3a | 408 | NT | NT |
| 1p | 34 | NT | NT |
| 1o | 6 | NT | NT |
| 2e | 0 | NT | NT |
| 1u | NT | NT | NT |
| 1g | NT | NT | NT |
| 1v | 7 | NT | NT |
| 1n | 0 | NT | NT |
| 1m | 27 | NT | NT |
| 1l | 5 | NT | NT |
| 1f | 4 | NT | NT |
| 4y | 11 | NT | NT |
| 4x | NT | NT | NT |
| 4e | 23 | NT | NT |
| 4d | 54 | NT | NT |
| 4c | 313 | NT | 76.1 |
| 4b | 108 | NT | 70.9 |
| 2d | 0 | NT | NT |
| 2c | 35 | NT | 76.2 |
| 1d | 32 | NT | 85 |
| 1c | 7 | NT | NT |
| 4a | 3 | NT | NT |
| 1b | 5 | NT | NT |
| 1a | 3 | NT | NT |
| 1t | 4 | NT | 76.3 |
| 2b | 10 | 104.8 | 92.1 |
| 2a | 19 | 101.8 | 91.1 |
| 2g | 6 | 113.4 | 106 |
| 2f | 163 | 119.4 | 70.9 |
| 3j | NT | NT | NT |
| 3k | NT | NT | NT |
| 3l | NT | NT | NT |
| 3m | NT | NT | NT |
| 3n | NT | NT | NT |
| 3o | 20 | NT | NT |
| 3p | NT | NT | NT |
| 3q | NT | NT | NT |
| 5n | 47 | NT | NT |
| 5o | NT | NT | NT |
| 5p | NT | NT | NT |
| 6h | NT | NT | NT |
| 7a | NT | NT | NT |
| 7b | NT | NT | NT |
| 7c | NT | NT | NT |
| 7d | NT | NT | NT |
| 8a | NT | NT | NT |
| 8b | NT | NT | NT |
| 8c | NT | NT | NT |
| 8d | NT | NT | NT |
| 8e | NT | NT | NT |
| 8f | NT | NT | NT |
| 8g | NT | NT | NT |
| 8h | 204 | NT | NT |
| 8i | NT | NT | NT |
| 8j | NT | NT | NT |
| 8k | NT | NT | NT |
| 8l | NT | NT | NT |
| 8m | NT | NT | NT |
| 8n | NT | NT | NT |
| 8o | NT | NT | NT |
| 8p | NT | NT | NT |
| 8q | 1297 | NT | NT |
| 9a | NT | NT | NT |
| 9b | NT | NT | NT |
| 9c | NT | NT | NT |
| 9d | NT | NT | NT |
| 9e | NT | NT | NT |
| 9f | NT | NT | NT |
| 9g | NT | NT | NT |
| 9h | NT | NT | NT |
| 9i | 461 | NT | NT |
| 9j | NT | NT | NT |
| 9k | 43 | NT | NT |
| 9l | 4 | NT | NT |
| 10a | NT | NT | NT |
| 10b | NT | NT | NT |
| 11a | NT | NT | NT |
| 11b | NT | NT | NT |
| 12a | NT | NT | NT |
| 12b | NT | NT | NT |
| 12c | NT | NT | NT |

The exemplary compounds described above may be formulated into pharmaceutical compositions according to the following general examples.

Example 1

Parenteral Composition

To prepare a parenteral pharmaceutical composition suitable for administration by injection, 100 mg of a water-soluble salt of a compound of Formula I is dissolved in DMSO and then mixed with 10 mL of 0.9% sterile saline. The mixture is incorporated into a dosage unit form suitable for administration by injection.

Example 2

Oral Composition

To prepare a pharmaceutical composition for oral delivery, 100 mg of a compound of Formula I is mixed with 750 mg of lactose. The mixture is incorporated into an oral dosage unit for, such as a hard gelatin capsule, which is suitable for oral administration.

It is to be understood that the foregoing description is exemplary and explanatory in nature, and is intended to illustrate the invention and its preferred embodiments. Through routine experimentation, the artisan will recognize apparent modifications and variations that may be made without departing from the spirit of the invention. Thus, the invention is intended to be defined not by the above description, but by the following claims and their equivalents.

We claim:

1. A compound represented by the formula I

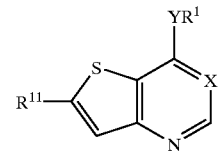

wherein
X is —CH—;
Y is —NH—, —O—, or —S—,

R$^1$ is indole substituted at the N position by —C(O)NR$^6$R$^7$ or —C(O)NHCH$_2$—C≡CH, and is optionally further substituted with 1 to 5 R$^5$ substituents;

each R$^5$ is independently selected from halo, cyano, nitro, trifluoromethoxy, trifluoromethyl, azido, —C(O)R$^8$, —C(O)OR$^8$, —OC(O)R$^8$, —OC(O)OR$^8$, —NR$^6$C(O)R$^7$, —C(O)NR$^6$R$^7$, —NR$^6$R$^7$, —OR$^9$, —SO$_2$NR$^6$R$^7$, C$_1$–C$_6$ alkyl, C$_1$–C$_6$ alkylamino, C$_3$–C$_{10}$ cycloalkyl, —(CH$_2$)$_j$O(CH$_2$)$_q$NR$^6$R$^7$, —(CH$_2$)$_t$O(CH$_2$)$_q$OR$^9$, —(CH$_2$)$_t$OR$^9$,—S(O)$_j$(C$_1$–C$_6$ alkyl), —(CH$_2$)$_t$(C$_6$–C$_{10}$ aryl), —(CH$_2$)$_t$(5 to 10 membered heterocyclic), —C(O)(CH$_2$)$_t$(C$_6$–C$_{10}$ aryl), —(CH$_2$)$_t$O(CH$_2$)$_j$(C$_8$–C$_{10}$ aryl), —(CH$_2$)$_t$O(CH$_2$)$_q$(5 to 10 membered heterocyclic), —C(O)(CH$_2$)$_t$(5 to 10 membered heterocyclic), —(CH$_2$)$_j$NR$^7$(CH$_2$)$_q$NR$^6$R$^7$, —(CH$_2$)$_j$NR$^7$CH$_2$C(O)NR$^6$R$^7$, —(CH$_2$)$_j$NR$^7$(CH$_2$)$_q$NR$^9$C(O)R$^8$, —(CH$_2$)$_j$NR$^7$(CH$_2$)$_t$O(CH$_2$)$_q$OR$^9$, —(CH$_2$)$_j$NR$^7$(CH$_2$)$_q$S(O)$_j$(C$_1$–C$_6$alkyl), —(CH$_2$)$_j$NR$^7$(CH$_2$)$_t$R$^6$, —SO$_2$(CH$_2$)$_t$(C$_6$–C$_{10}$ aryl), and —SO$_2$(CH$_2$)$_t$(5 to 10 membered heterocyclic), wherein j is an integer from 0 to 2, t is an integer from 0 to 6, q is an integer from 2 to 6, the —(CH$_2$)$_q$— and —(CH$_2$)$_t$— moieties of the said R$^5$ groups optionally include a carbon-carbon double or triple bond where t is an integer between 2 and 6, and the alkyl, aryl and heterocyclic moieties of the said R$^5$ groups are unsubstituted or substituted with one or more substituents independently selected from halo, cyano, nitro, trifluoromethyl, azido, —OH, —C(O)R$^8$, —C(O)OR$^8$, —OC(O)R$^8$, —OC(O)OR$^8$, —NR$^6$C(O)R$^7$, —C(O)NR$^6$R$^7$, —(CH$_2$)$_t$NR$^6$R$^7$, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6;

each R$^6$ and R$^7$ is independently selected from H, OH, C$_1$–C$_6$ alkyl, C$_3$–C$_{10}$ cycloalkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, —(CH$_2$)$_t$CN(CH$_2$)$_q$OR$^9$, —(CH$_2$)$_t$CN(CH$_2$)$_q$R$^9$ and —(CH$_2$)$_t$OR$^9$, wherein t is an integer from 0 to 6 and q is an integer from 2 to 6, and the alkyl, aryl and heterocyclic moieties of the said R$^6$ and R$^7$ groups are unsubstituted or substituted with one or more substituents independently selected from hydroxy, halo, cyano, nitro, trifluoromethyl, azido, —C(O)R$^8$, —C(O)OR$^8$, —CO(O)R$^8$, —OC(O)OR$^8$, —NR$^9$C(O)R$^{10}$, —C(O)NR$^9$R$^{10}$, —NR$^9$R$^{10}$, C$_1$–C$_6$ alkyl, —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, wherein t is an integer from 0 to 6 and q is an integer from 2 to 6, where when R$^6$ and R$^7$ are both attached to the same nitrogen, then R$^6$ and R$^7$ are not both bonded to the nitrogen directly through an oxygen;

each R$^8$ is independently selected from H, C$_1$–C$_{10}$ alkyl, C$_3$–C$_{10}$ cycloalkyl, —(CH$_2$)$_t$(C$_6$–C$_{10}$ aryl), and —(CH$_2$)$_t$(5 to 10 membered heterocyclic), wherein t is an integer from 0 to 6;

each R$^9$ and R$^{10}$ is independently selected from H, —OR$^6$, C$_1$–C$_6$ alkyl, and C$_3$–C$_{10}$ cycloalkyl; and, R$^{11}$ is —C(O)NR$^{12}$R$^{13}$, (CH$_2$)$_t$(5 to 10 membered heterocyclic), —(CH$_2$)$_t$NR$^{12}$R$^{13}$, or —SO$_2$NR$^{12}$R$^{13}$ wherein the heterocyclic is thiazolyl, imidazolyl, or pyrrolidinyl, and is optionally substituted by one or more R$^5$ groups;

each R$^{12}$ and R$^{13}$ is independently selected from H, C$_1$–C$_6$ alkyl, C$_3$–C$_{10}$ cycloalkyl, —(CH$_2$)$_t$(C$_3$–C$_{10}$ cycloalkyl), —(CH$_2$)$_t$(C$_6$–C$_{10}$ aryl), —(CH$_2$)$_t$(5 to 10 membered heterocyclic), —(CH$_2$)$_t$O(CH$_2$)$_q$OR$^9$, and —(CH$_2$)$_t$OR$^9$, q is an integer from 2 to 6, and the alkyl, aryl and heterocyclic moieties of the said R$^{12}$ and R$^{13}$ groups are unsubstituted or substituted with one or more substituents independently selected from R$^5$, or R$^{12}$ and R$^{13}$ are taken together with the nitrogen to which they are attached to form a pyrrolidinyl, ring, wherein said pyrrolidinyl, rings are unsubstituted or substituted with one or more R$^5$ substituents and wherein t is an integer from 0 to 6 or pharmaceutically acceptable salts or solvates of said compounds.

2. A compound of claim 1, wherein R$^{11}$ is C(O)NR$^{12}$R$^{13}$, wherein R$^{12}$ and R$^{13}$ are taken together with the nitrogen to which they are attached to form a pyrrolidinyl, ring, wherein said pyrrolidinyl ring is unsubstituted or substituted by 1 to 5 R$^5$ substituents.

3. A compound of claim 1 wherein R$^{11}$ is —(CH$_2$)$_t$(5 to 10 membered heterocyclic), wherein t is an integer from 0 to 6, wherein said —(CH$_2$)$_t$(5 to 10 membered heterecyclic) wherein the heterocyclic group is selected from thiazolyl, imidazolyl or pyrrolidinyl. group is unsubstituted or substituted with one or more R$^5$ groups.

4. A compound of claim 1, wherein R$^{11}$ is a thiazolyl unsubstituted or substituted with one or more R$^5$ groups.

5. A compound of claim 1, wherein R$^{11}$ is an imidazolyl unsubstituted or substituted with one or more R$^5$ substituents.

6. A compound of claim 1 wherein said compound is selected from the group consisting of:

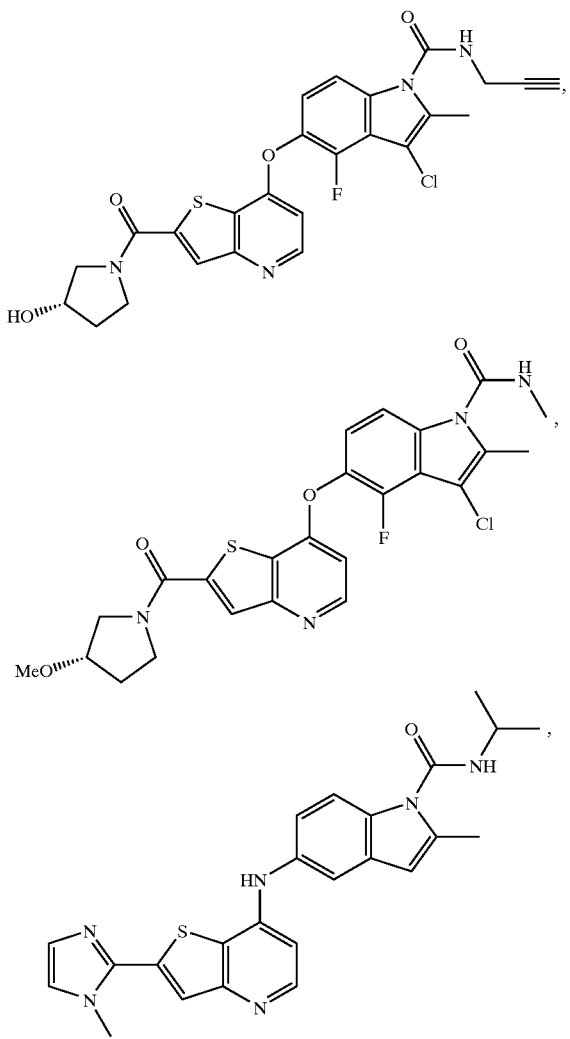

133
-continued
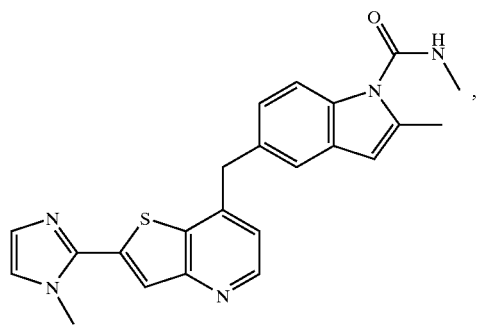
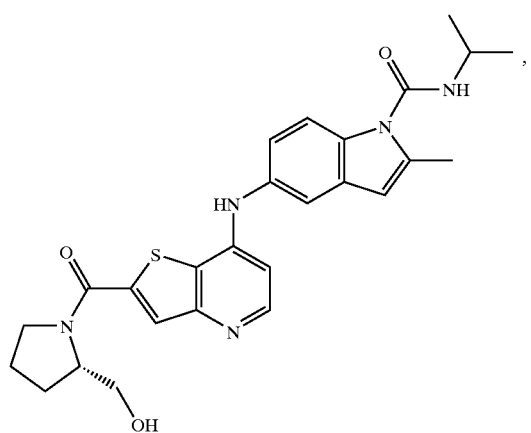
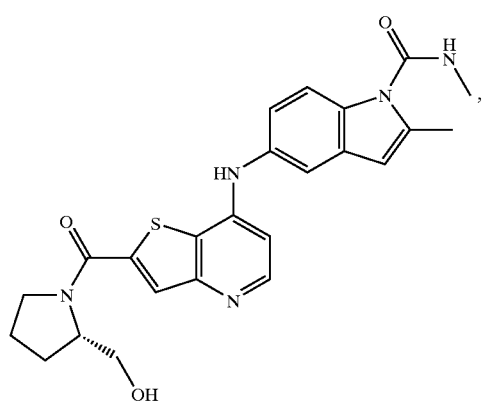
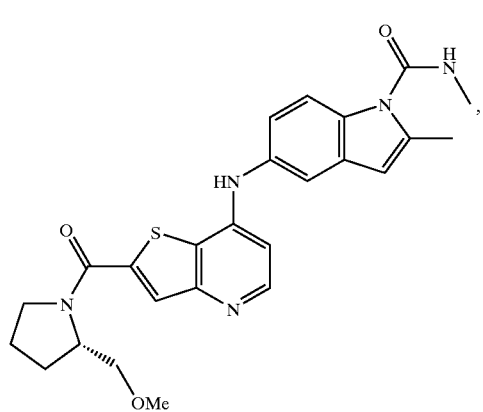
134
-continued
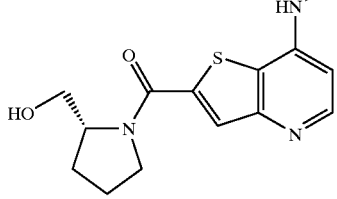
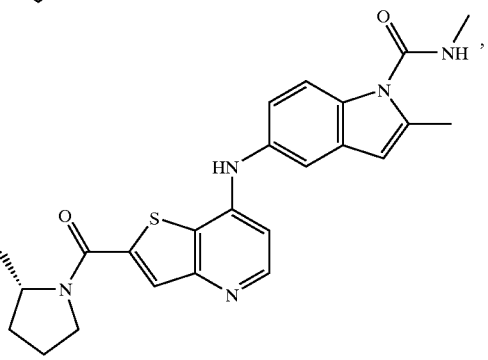
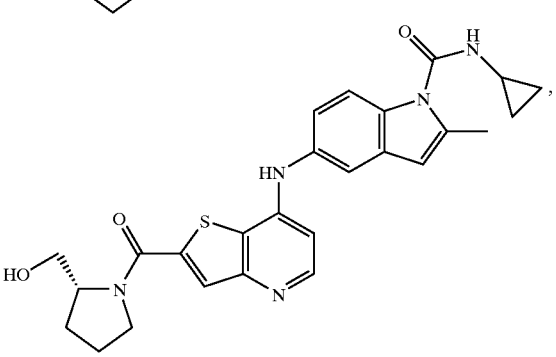
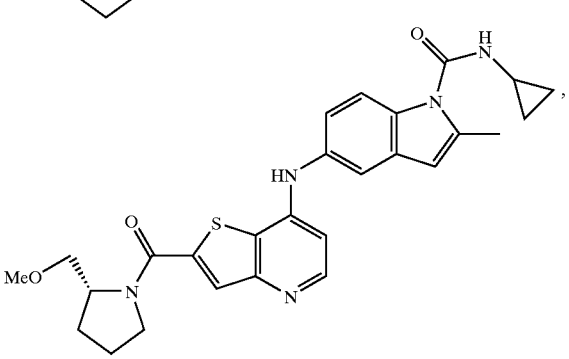
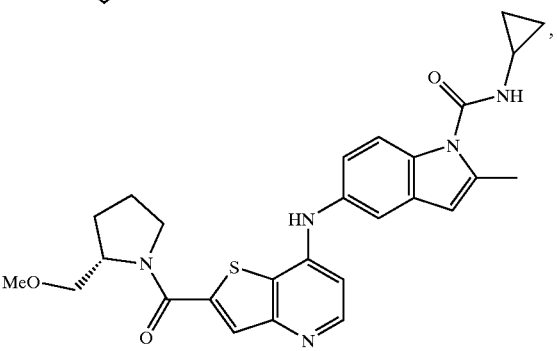

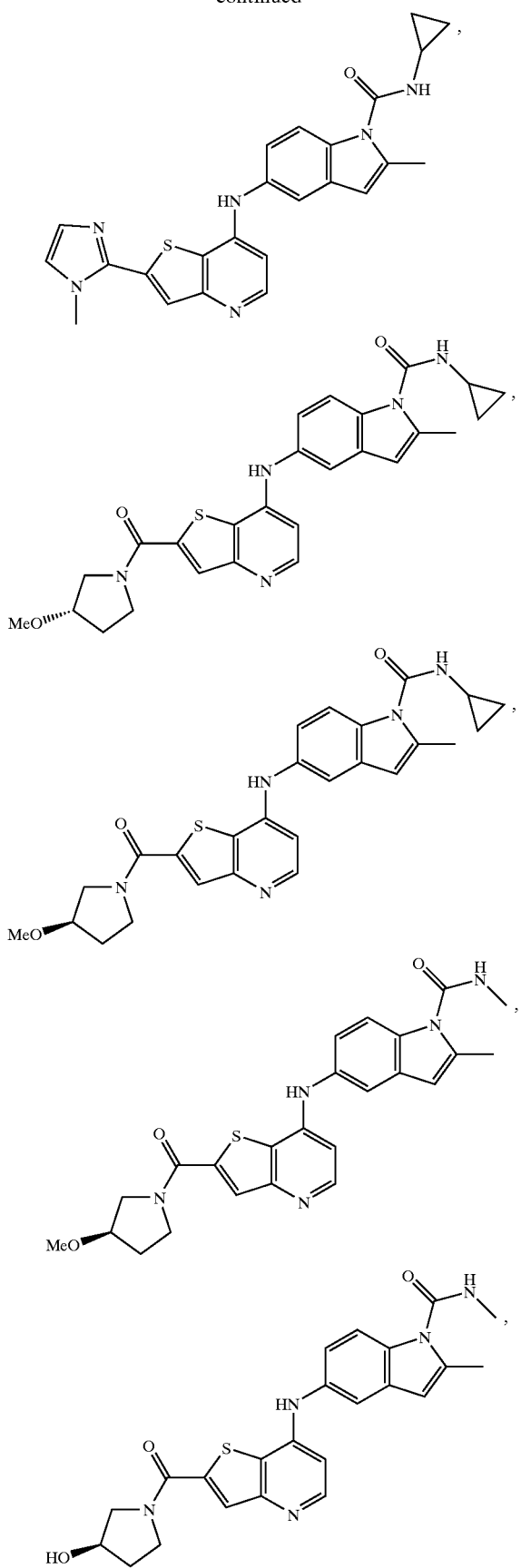
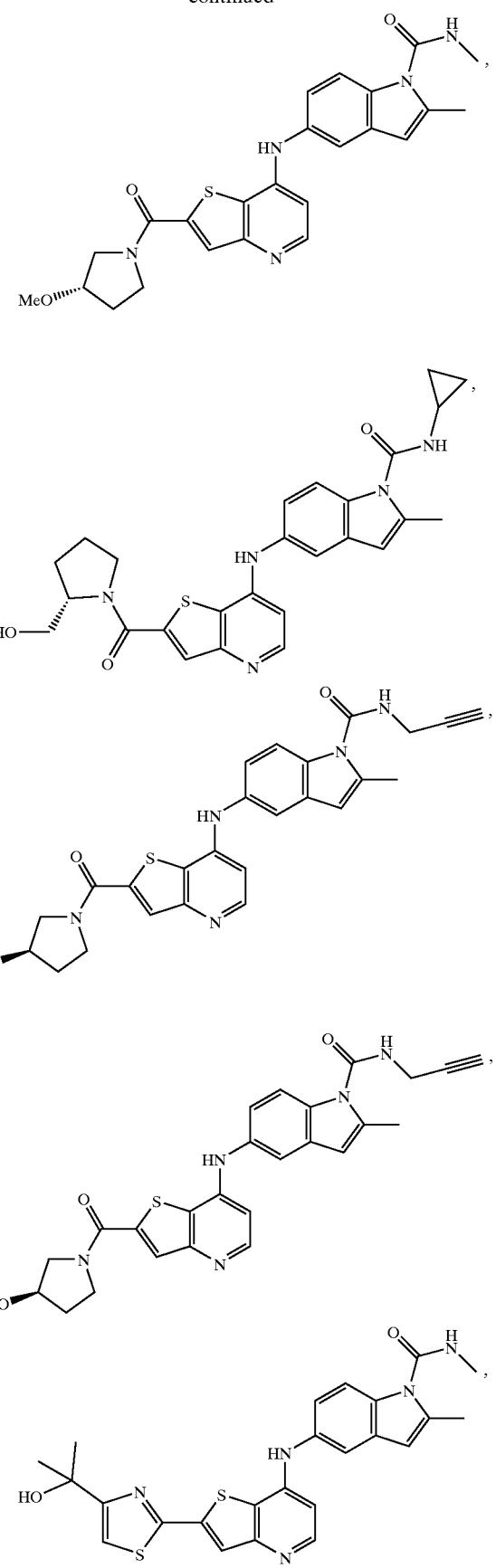

137
-continued
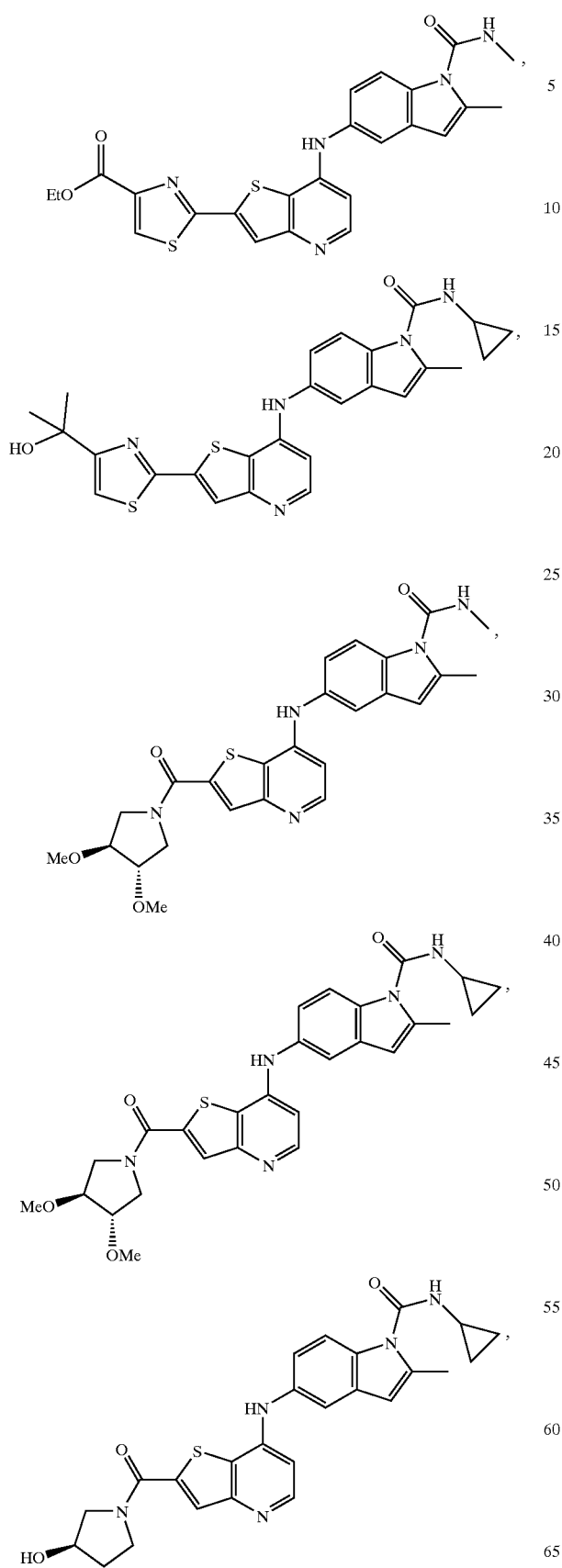
138
-continued
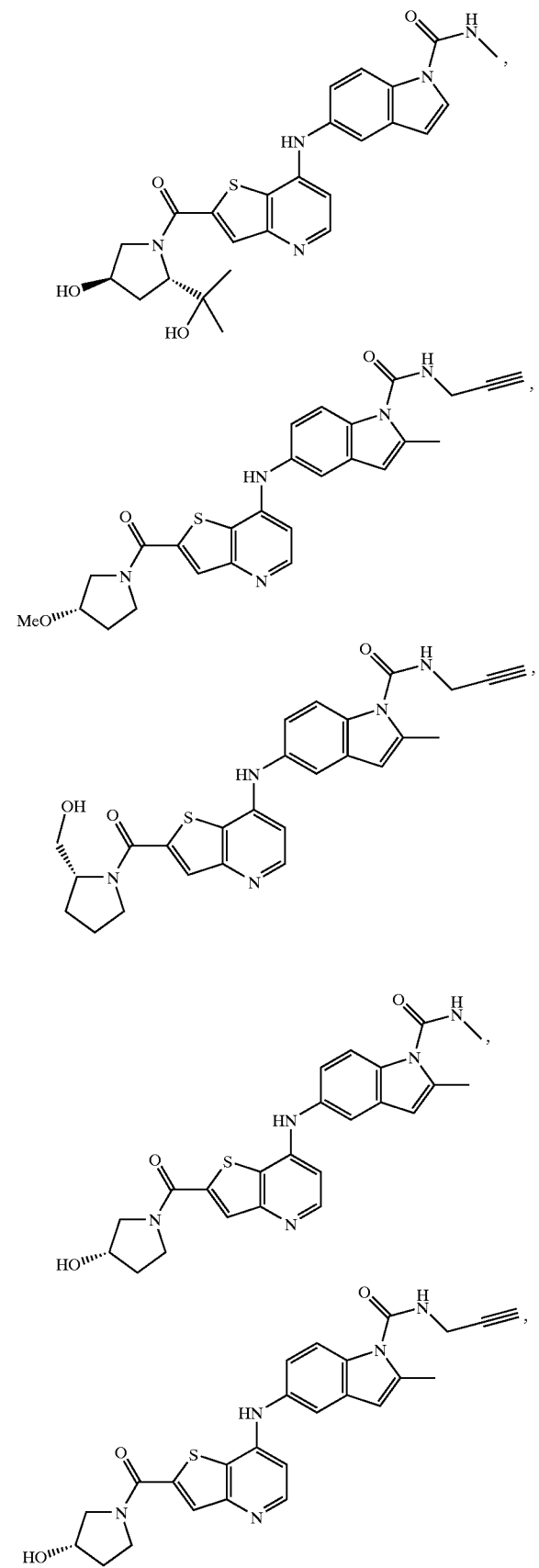

139
-continued
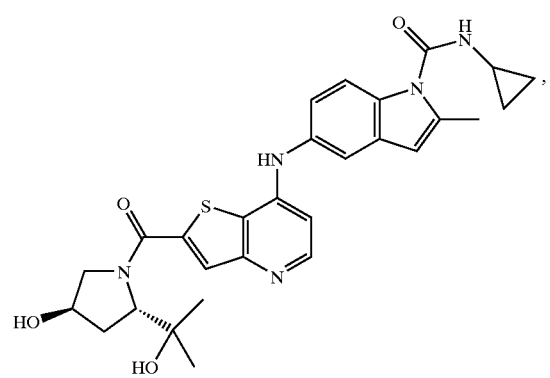
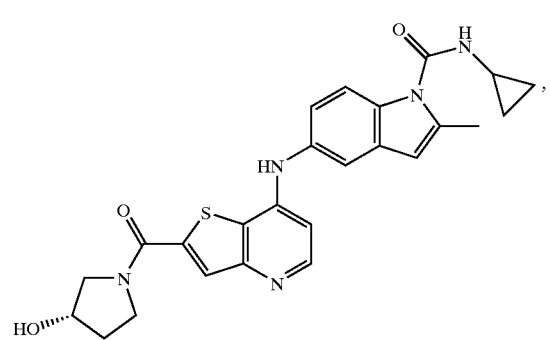
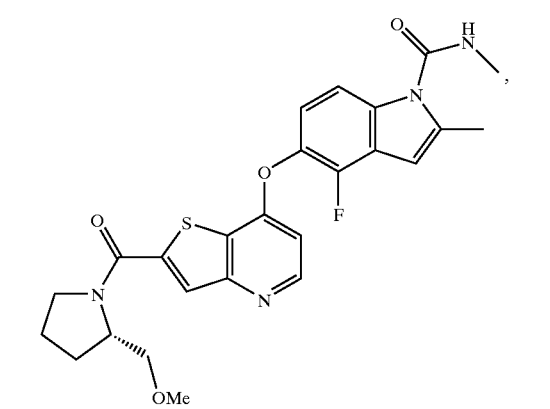
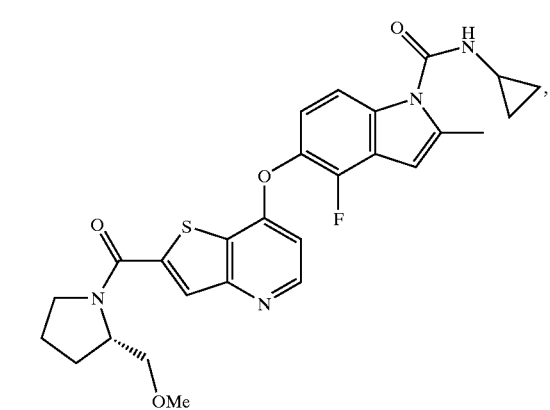
140
-continued
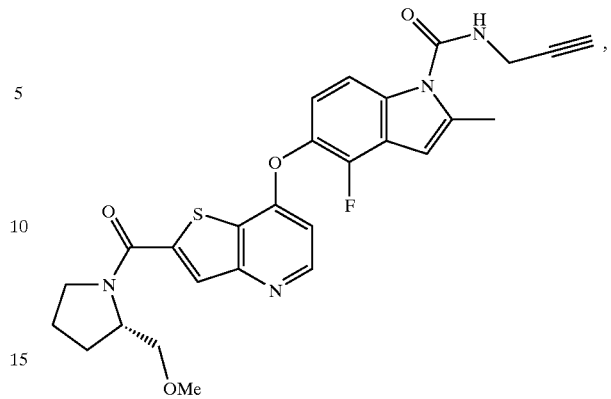
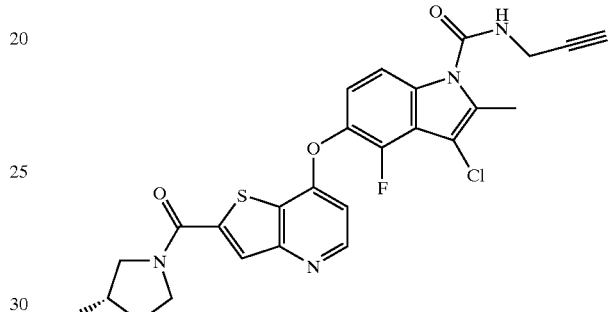
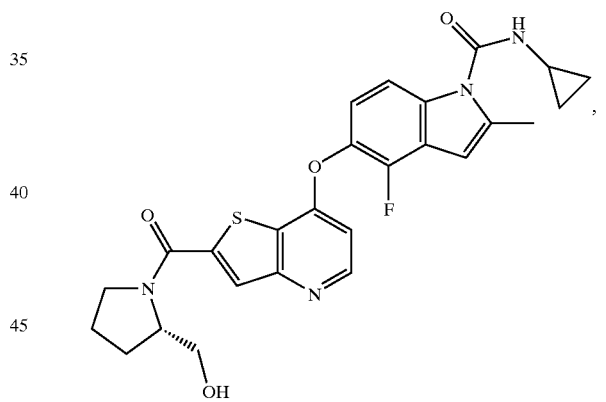
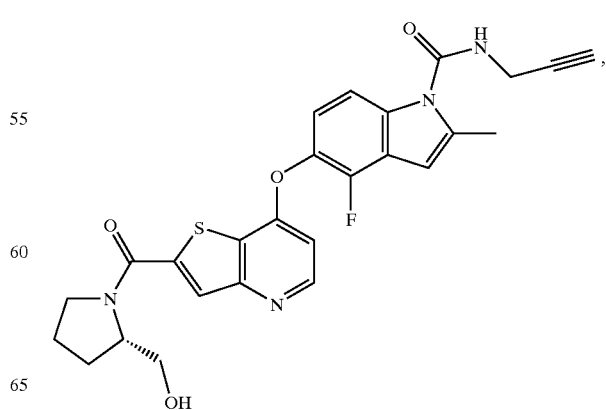

141
-continued
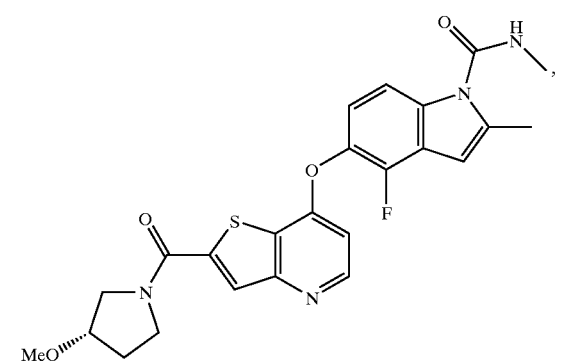
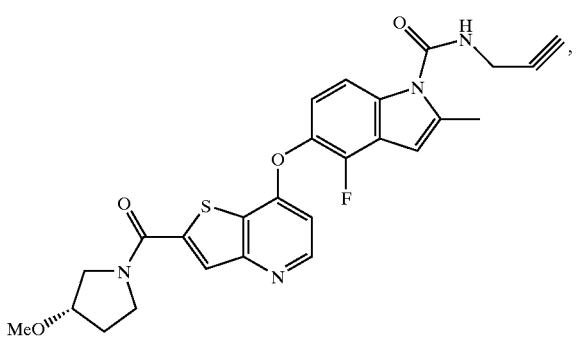
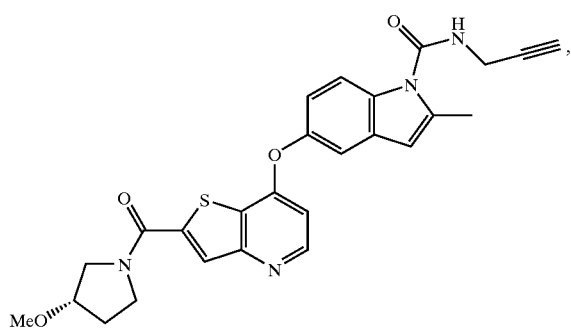
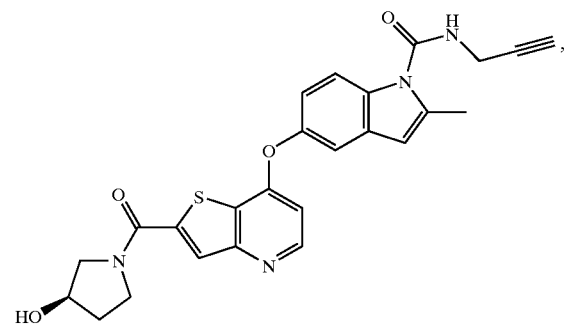
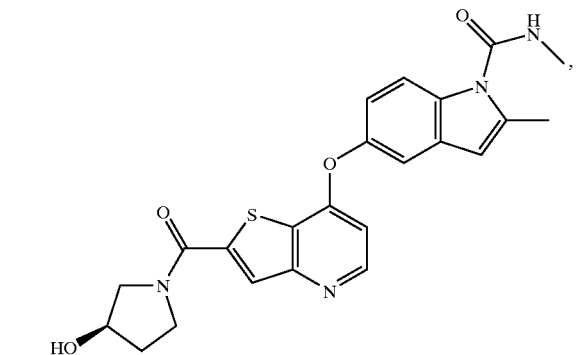
142
-continued
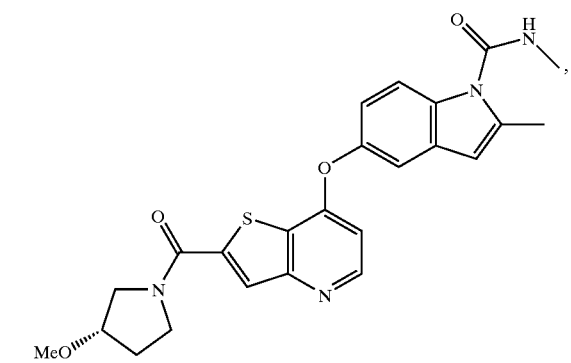
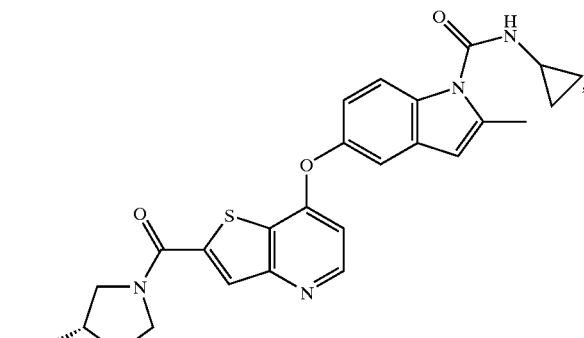
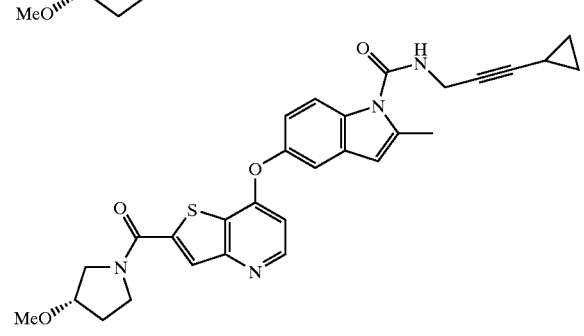
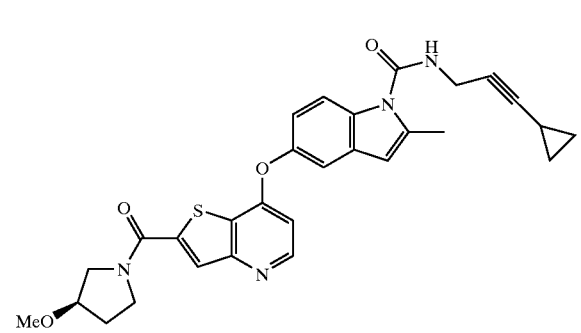
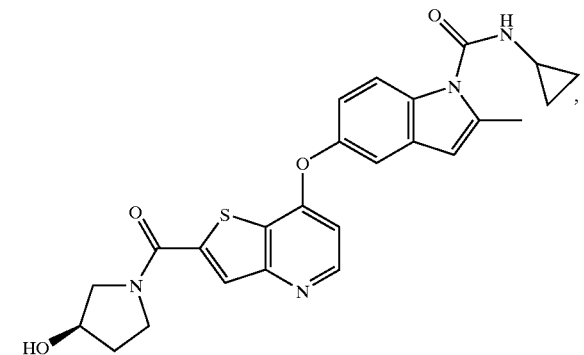

143
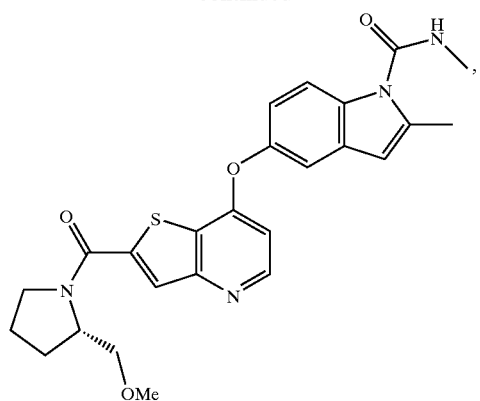
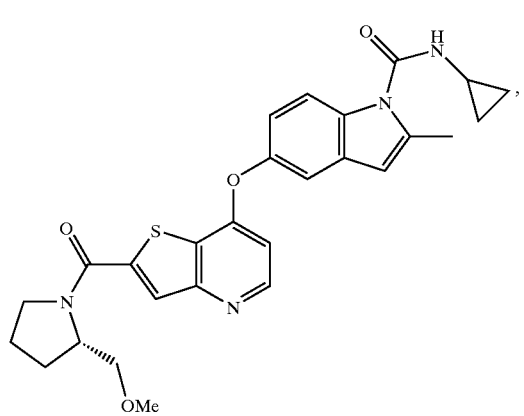
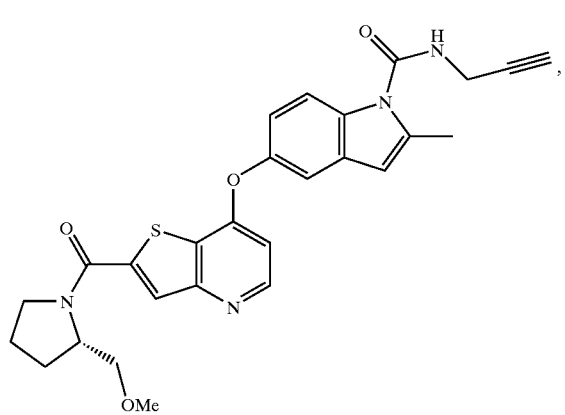
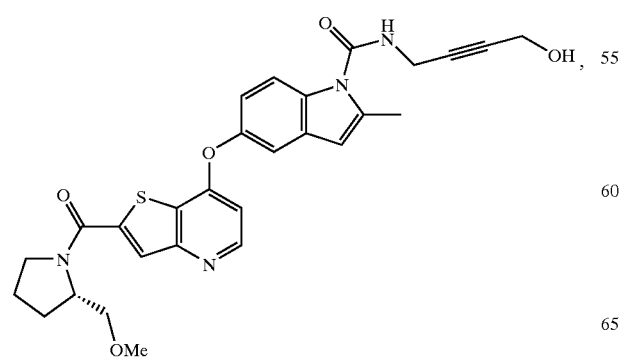
144
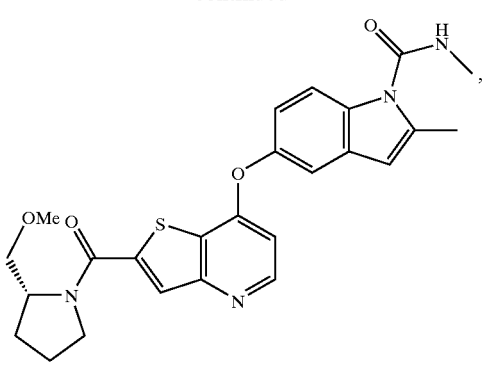
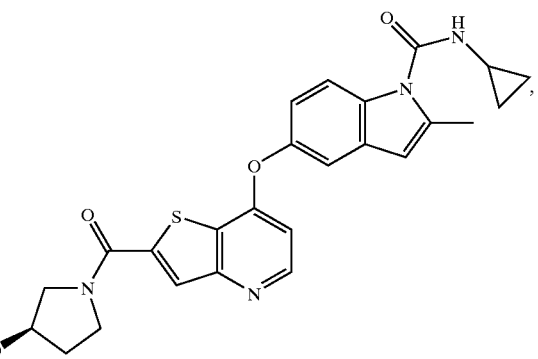

-continued

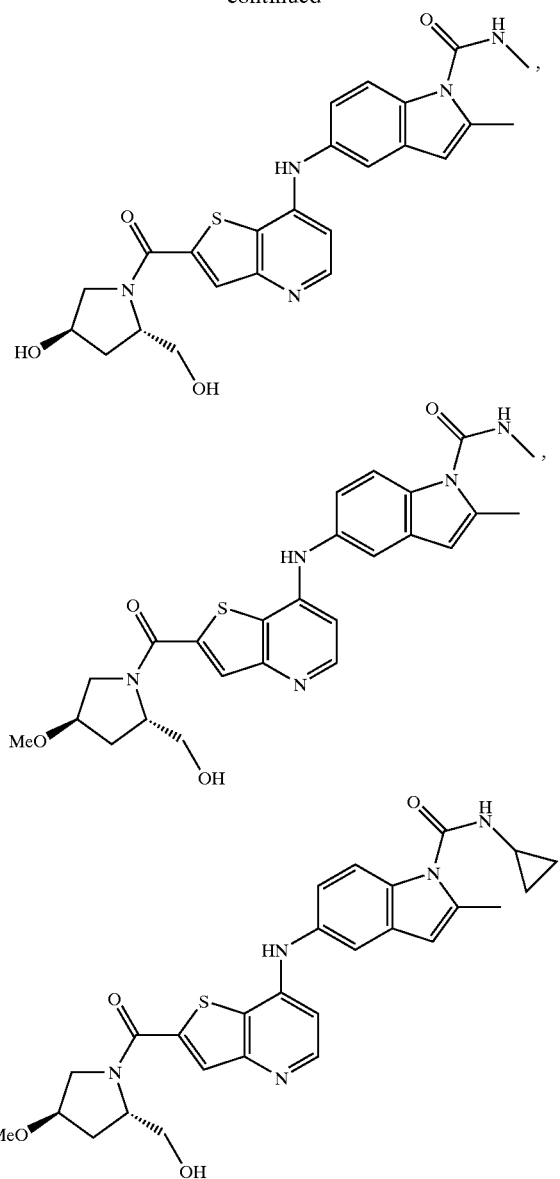

or prodrugs thereof, or pharmaceutically acceptable salts or solvates of said compounds and said prodrugs.

7. A compound represented by the formula I

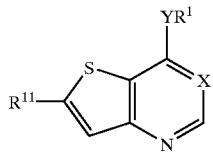

wherein
X is —CH—;
Y is —NH—, or —O—;
$R^1$ is an indole substituted at the N position by —C(O)NR$^6$R$^7$ or —C(O)NHCH$_2$—C≡CH, and is optionally further substituted with 1 to 5 $R^5$ substituents;
each $R^5$ is independently selected from halo, —C(O)OR$^8$, —C(O)NR$^6$R$^7$, $C_1$–$C_6$alkyl, —(CH$_2$)$_t$OR$^9$, and the alkyl moieties of the said $R^5$ groups are unsubstituted or substituted with —(CH$_2$)$_t$OR$^9$, wherein t is an integer from 0 to 6;
each $R^6$ and $R^7$ is independently selected from H, $C_1$–$C_6$ alkyl, $C_3$–$C_{10}$ cycloalkyl, —(CH$_2$)$_t$CN(CH$_2$)$_t$OR$^9$, and —(CH$_2$)$_t$CN(CH$_2$)$_t$R$^9$, and the alkyl and heterocyclic moieties of the said $R^6$ and $R^7$ groups are unsubstituted or substituted with cyano;
each $R^8$ is a $C_1$–$C_{10}$ alkyl;
each $R^9$ and $R^{10}$ is independently selected from H, —OR$^6$, $C_1$–$C_6$ alkyl; and,
$R_{11}$ is —C(O)NR$^{12}$R$^{13}$ or —(CH$_2$)$_t$(5 to 10 membered heterocyclic), wherein the heterocyclic is thiazolyl, imidazolyl, or pyrrolidinyl, and is optionally substituted by one or more $R^5$ groups;
each $R^{12}$ and $R^{13}$ is independently selected from H, $C_1$–$C_6$ alkyl, $C_3$–$C_{10}$ cycloalkyl, —(CH$_2$)$_t$(C$_3$–$C_{10}$ cycloalkyl), —(CH$_2$)$_t$(C$_6$–$C_{10}$ aryl), —CH$_2$)$_t$(5 to 10 membered heterocyclic), —(CH$_2$)$_t$O(CH$_2$)$_q$OR$^9$, and —(CH$_2$)$_t$OR$^9$, q is an integer from 2 to 6, and the alkyl, aryl and heterocyclic moieties of the said $R^{12}$ and $R^{13}$ groups are unsubstituted or substituted with one or more substituents independently selected from $R^5$;
or $R^{12}$ and $R^{13}$ are taken together with the nitrogen to which they are attached to form a pyrrolidinyl ring substituted with one or more $R^5$ substituents, where $R^{12}$ $R^{13}$ are not both bonded to the nitrogen directly through an oxygen wherein t is an integer from 0 to 6;
or pharmaceutically acceptable salts or solvates of said compounds and said prodrugs.

8. A compound represented by the formula III

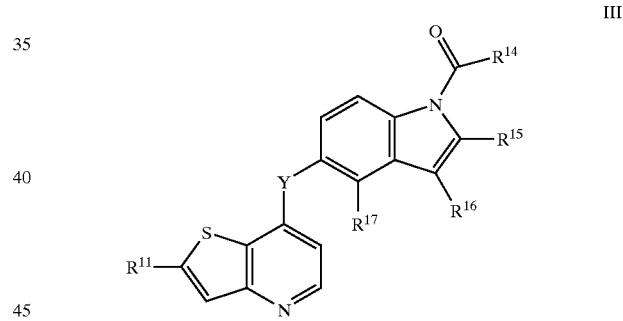

wherein
Y is —NH—, —O—;
$R^{14}$ is $C_1$–$C_6$ alkylamino, $C_3$–$C_{10}$ cycloalkylamino, or methylureido;
$R^{15}$, $R^{16}$ and $R^{17}$ are independently H or $C_1$–$C_6$ alkyl group; and
$R^{11}$ is a imidazolyl, thiazolyl, or pyrrolidinyl group unsubstituted or substituted by one or more groups selected from —C(O)OR$^8$, $C_1$–$C_6$ alkyl, and —(CH$_2$)$_t$OR$^9$, wherein t is an integer from 0 to 6;
each $R^8$ is independently selected from H, $C_1$–$C_{10}$ alkyl, $C_3$–$C_{10}$ cycloalkyl, —(CH$_2$)$_t$(C$_6$–$C_{10}$ aryl), and —(CH$_2$)$_t$(5 to 10 membered heterocyclic), wherein t is an integer from 0 to 6;
each $R^9$ independently selected from H, $C_1$–$C_6$ alkyl, and $C_3$–$C_{10}$ cycloalkyl;
pharmaceutically acceptable salts or solvates of said compounds.

* * * * *